US011746380B2

(12) United States Patent
Luca et al.

(10) Patent No.: US 11,746,380 B2
(45) Date of Patent: Sep. 5, 2023

(54) CLASSIFICATION AND PROGNOSIS OF CANCER

(71) Applicant: UNIVERSITY OF EAST ANGLIA, Norfolk (GB)

(72) Inventors: Bogdan-Alexandru Luca, Norfolk (GB); Vincent Moultion, Norfolk (GB); Daniel Simon Brewer, Norfolk (GB); Colin Stephen Cooper, Norfolk (GB)

(73) Assignee: UNIVERSITY OF EAST ANGLIA, Norfolk (GB)

(*) Notice: Subject to any disclaimer, the term of this patent is extended or adjusted under 35 U.S.C. 154(b) by 750 days.

(21) Appl. No.: 16/339,463

(22) PCT Filed: Oct. 5, 2017

(86) PCT No.: PCT/EP2017/075368
§ 371 (c)(1),
(2) Date: Apr. 4, 2019

(87) PCT Pub. No.: WO2018/065525
PCT Pub. Date: Apr. 12, 2018

(65) Prior Publication Data
US 2020/0263255 A1    Aug. 20, 2020

(30) Foreign Application Priority Data

Oct. 5, 2016    (GB) .................................. 1616912

(51) Int. Cl.
*C12Q 1/68*        (2018.01)
*C12Q 1/6886*      (2018.01)

(52) U.S. Cl.
CPC ...... *C12Q 1/6886* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| 6,351,666 | B1 | 2/2002  | Cuzick et al. |
| 7,914,988 | B1 | 3/2011  | Chudin et al. |
| 2005/0260572 | A1 | 11/2005 | Kato et al. |
| 2012/0053253 | A1 | 3/2012  | Stone et al. |
| 2014/0066323 | A1 | 3/2014  | Buerki et al. |

FOREIGN PATENT DOCUMENTS

| CA | 2915653 A1     | 10/2014 |
| WO | 2002/091211 A1 | 11/2002 |
| WO | 2003/041562 A2 | 5/2003  |
| WO | 2006/053328 A2 | 5/2006  |
| WO | 2008/103971 A2 | 8/2008  |
| WO | 2009/067655 A2 | 5/2009  |
| WO | 2011/085263 A2 | 7/2011  |
| WO | 2012/031008 A2 | 3/2012  |
| WO | 2014/012176 A1 | 1/2014  |
| WO | 2014/057279 A1 | 4/2014  |
| WO | 2014144657     | 9/2014  |
| WO | 2017/062505 A1 | 4/2017  |

OTHER PUBLICATIONS

Genbank TGM4 accession NM_003241 downloaded May 6 (Year: 2022).*
Taylor et al. (Cancer Cell 18:11-22) (Year: 2010).*
Taylor et al. (Cancer Cell 18:11-22 supplemental information inventory) (Year: 2010).*
Olmos, D., et al., "Prognostic value of blood mRNA expression signatures in castration-resistant prostate cancer: a prospective, two-stage study", Lancet Oncol, 2012, 13: 1114-24.
Rogers, S., et al., "The Latent Process Decomposition of cDNA Microarray Data Sets", IEEE/ACM Transactions on Computational Biology and Bioinformatics, 2005, 2(2): 143-156.
Carrivick, L., et al., "Identification of prognostic signatures in breast cancer microarray data using Bayesian techniques", J. R. Soc. Interface, 2006, 3: 367-381.
Cucchiara, V., et al., "Genomic Markers in Prostate Cancer Decision Making", European Urology, 2018, 73: 572-582.
Shi, T., et al., "Tumor classification by tissue microarray profiling: random forest clustering applied to renal cell carcinoma", Modern Pathology, 2005, 18: 547-557.
Algamal, Z.Y., et al., "Penalized logistic regression with the adaptive Lasso for gene selection in high-dimensional cancer classification", Expert Systems With Applications, 2015, 42: 9326-9332.
Ruiz De Porras, V., et al., "Expression patterns and prognostic value of Cyclin-dependent kinase 5 (Cdk5) in colorectal tumours", EACR24 Poster Sessions/European Journal of Cancer, 2016, 61(Suppl. 1): S204.
Cooper, C.S., et al., "Mechanisms of Disease: biomarkers and molecular targets from microarray gene expression studies in prostate cancer", Nature Clinical Practice Urology, 2007, 4(12): 677-687.
Perina, A., et al., "Biologically-aware Latent Dirichlet Allocation (BaLDA) for the Classification of Expression Microarray", PRIB, 2010, LNBI 6282: 230-241.
Zhang, X., et al., "Investigation of the molecular mechanisms underlying metastasis in prostate cancer by gene expression profiling". Experimental and Therapeutic Medicine, 2016, 12: 925-932.

(Continued)

*Primary Examiner* — Christopher M Gross
(74) *Attorney, Agent, or Firm* — Riverside Law LLP

(57) ABSTRACT

The present invention relates to the classification of cancers, in particular prostate cancers, using samples from patients. In particular, the invention provides methods for identifying potentially aggressive prostate cancers to determine which cancers are or will become aggressive (and hence require treatment) and which will remain indolent (and will therefore not require treatment). The present invention is therefore useful to identify patients with a poor prognosis. The specific population of cancer identified by the present invention is referred to herein as DESNT cancer. The invention also provides biomarker panels useful in the diagnosis and prognosis of cancer.

4 Claims, 22 Drawing Sheets

(56) References Cited

OTHER PUBLICATIONS

Figure 1:
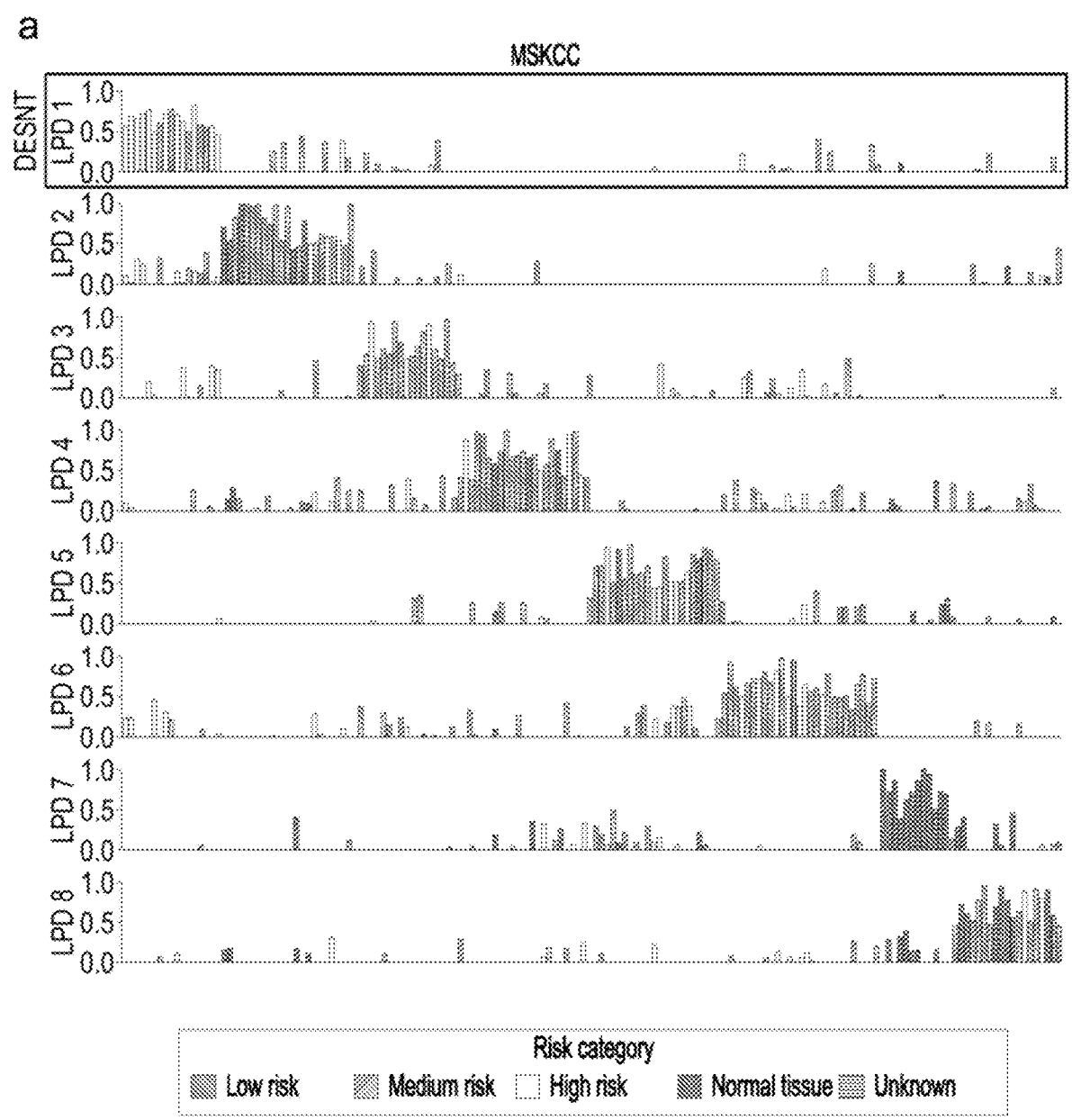
Figure 1:
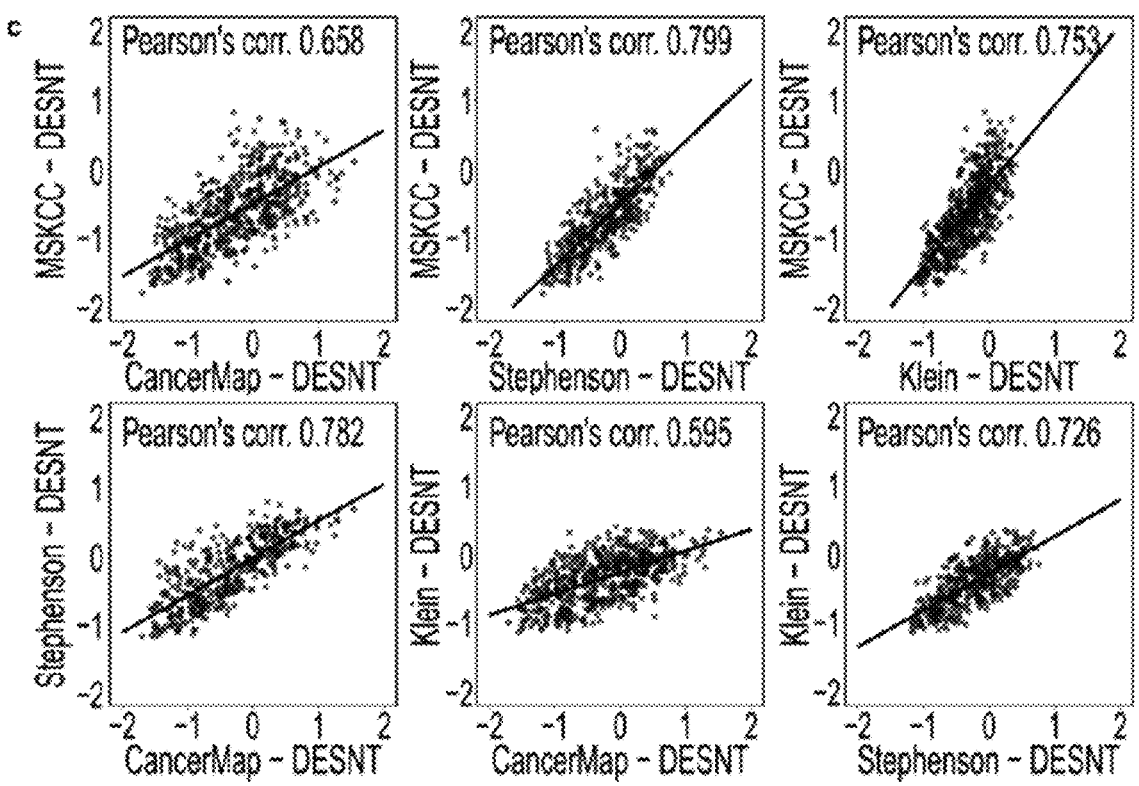
Figure 1:
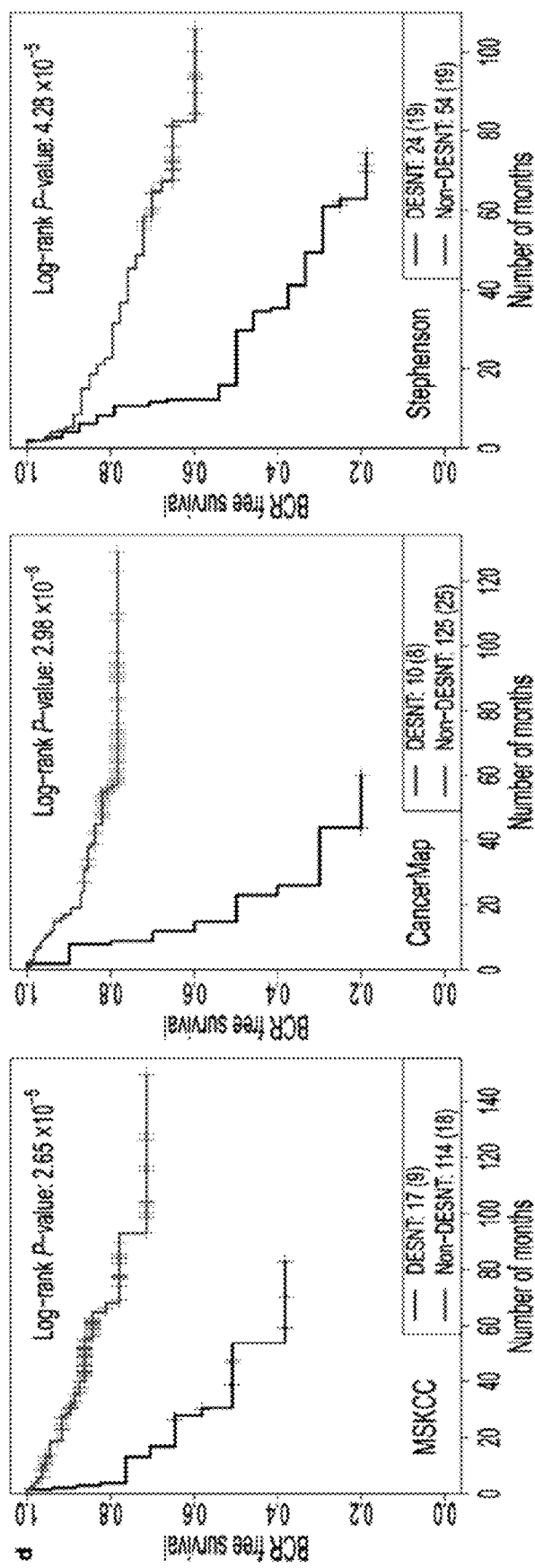

Kawamura, T., et al., "Cancer DNA Microarray Analysis Considering Multi-subclass with Graph-based Clustering Method", Journal of Bioscience and Bioengineering, 2008, 106(5): 442-448.

Tamura, K., et al., "Molecular Features of Hormone-Refractory Prostate Cancer Cells by Genome-Wide Gene Expression Profiles", Cancer Res, 2007, 67(11): 5117-5125.

Cuzick, J., et al., "Prognostic value of an RNA expression signature derived from cell cycle proliferation genes for recurrence and death from prostate cancer: A retrospective study in two cohorts". Lancet Oncol., 2011, 12(3): 245-255.

Erho, N., et al., "Discovery and Validation of a Prostate Cancer Genomic Classifier that Predicts Early Metastasis Following Radical Prostatectomy", PLOS One, 2013, 8(6): e66855, 1-12.

Knezevic, D., et al., "Analytical validation of the Oncotype DX prostate cancer assay—a clinical RT-PCR assay optimized for prostate needle biopsies", BMC Genomics, 2013, 14: 690.

Cuzick, J., et al., "Long-term outcome among men with conservatively treated localised prostate cancer", British Journal of Cancer, 2006, 95: 1186-1194.

Luca, B-A., et al., "DESNT: a Poor Prognosis Category of Human Prostate Cancer", Eur Urol Focus, 2018, 4(6):842-850.

Luca, B-A., et al., "A novel stratification framework for predicting outcome in patients with prostate cancer", British Journal of Cancer, 2020, 122: 1467-1476.

XP002355386—Affymetrix GeneChip, "Affymetrix GeneChip Human Genome U133 Array Set HG-U133A", Mar. 11, 2002, pp. 1-511.

\* cited by examiner

CLASSIFICATION AND PROGNOSIS OF CANCER

The present invention relates to the classification of cancers, in particular prostate cancers, using samples from patients. In particular, the invention provides methods for identifying potentially aggressive prostate cancers to determine which cancers are or will become aggressive (and hence require treatment) and which will remain indolent (and will therefore not require treatment). The present invention is therefore useful to identify patients with a poor prognosis. The specific population of cancer identified by the present invention is referred to herein as DESNT cancer.

A common method for the diagnosis of prostate cancer is the measure of prostate specific antigen (PSA) in blood. However, as many as 50-80% of PSA-detected prostate cancers are biologically irrelevant, that is, even without treatment, they would never have caused any symptoms. Radical treatment of early prostate cancer, with surgery or radiotherapy, should ideally be targeted to men with significant cancers, so that the remainder, with biologically 'irrelevant' disease, are spared the side-effects of treatment. Accurate prediction of individual prostate cancer behaviour at the time of diagnosis is not currently possible, and immediate radical treatment for most cases has been a common approach. Put bluntly, many men are left impotent or incontinent as a result of treatment for a 'disease' that would not have troubled them. A large number of prognostic biomarkers have been proposed for prostate cancer. A key question is whether these biomarkers can be applied to PSA-detected, early prostate cancer to distinguish the clinically significant cases from those with biologically irrelevant disease. Validated methods for detecting aggressive cancer early could lead to a paradigm-shift in the management of early prostate cancer.

A critical problem in the clinical management of prostate cancer is that it is highly heterogeneous. Accurate prediction of individual cancer behaviour is therefore not achievable at the time of diagnosis leading to substantial overtreatment. It remains an enigma that, in contrast to many other cancer types, stratification of prostate cancer based on unsupervised analysis of global expression patterns has not been possible: for breast cancer, for example, ERBB2 overexpressing, basal and luminal subgroups can be identified.

There remains in the art a need for a more reliable diagnostic test for prostate cancer and to better assist in distinguishing between aggressive cancer, which may require treatment, and non-aggressive cancer, which perhaps can be left untreated and spare the patient any side effects from unnecessary interventions.

The present invention provides an algorithm-based molecular diagnostic assay for predicting whether a patient is a member of a poor prognosis category of human prostate cancer designated DESNT. In some embodiments, the expression levels of certain genes (such as those listed in Table 2 or Table 3) may be used alone or in combination to predict whether the cancer is a DESNT cancer. The algorithm-based assay and associated information provided by the practice of the methods of the present invention facilitate optimal treatment decision making in prostate cancer. For example, such a clinical tool would enable physicians to identify patients who have a high risk of having aggressive disease and who therefore need radical and/or aggressive treatment.

The present inventors have applied a Bayesian clustering procedure called Latent Process Decomposition (LPD, Simon Rogers, Mark Girolami, Colin Campbell, Rainer Breitling, "The Latent Process Decomposition of cDNA Microarray Data Sets", IEEE/ACM Transactions on Computational Biology and Bioinformatics, vol. 2, no. 2, pp. 143-156, April-June 2005, doi:10.1109/TCBB.2005.29) identifying a common process, designated DESNT, in four independent prostate cancer transcriptome datasets. DESNT cancers are characterized by down-regulation of a core set of genes, many encoding proteins involved in the cytoskeleton machinery, ion transport and cell adhesion. For the three datasets with linked PSA failure data following prostatectomy patients with DESNT cancers exhibited a very poor outcome relative to non-DESNT patients ($p=2.65\times10^{-5}$, $p=7.74\times10^{-9}$, and $p=4.28\times10^{-5}$). DESNT cancers can therefore be considered aggressive prostate cancers, since they result in very poor outcomes for the patient. The results demonstrate the existence of a novel poor prognosis category of human prostate cancer, and assists in the targeting of therapy, helping avoid treatment-associated morbidity in men with indolent disease. Unlike in Rogers et al., the present inventors performed an analysis to determine the correlation of the groups with survival and to provide a definition of signature genes for each process. The inventors also conducted the analysis on a much larger set of cancers and multiple datasets and were surprisingly able, for the first time, to not only identify a process that is common across different datasets, but furthermore to invariably correlate this particular group with a poor cancer prognosis. The present inventors also discovered that the contribution of this process to a given expression profile can be used to determine the prognosis of the cancer, optionally in combination with other markers for prostate cancer such as tumour stage, Gleason score and PSA. Notably, the methods of the present invention are not simple hierarchical clustering methods, and allow a much more detailed and accurate analysis of patient samples that such prior art methods. For the first time, the present inventors have provided a method that allows a reliable prediction of cancer progression, whereas methods of the prior art could not be used to detect cancer progression, since there was nothing to indicate such a correlation could be made.

The present inventors also wished to develop a classifier that, unlike LPD, was not computer processing intensive and that could be applied to a wider range of datasets and to individual cancers. Therefore, the present invention also provides a method for identifying a gene signature that can be used in a random forest classification to identify DESNT cancers.

The present inventors have used additional mathematical techniques to provide further methods of prognosis and diagnosis, and also provide biomarkers and biomarker panels useful in identifying patients with a poor prognosis, As used herein, "DESNT" cancer refers to prostate cancer with a poor prognosis and one that requires treatment. "DESNT status" refers to whether or not the cancer is predicted to progress (or, for historical data, has progressed), hence a step of determining DESNT status refers to predicting whether or not a cancer will progress and hence require treatment. Progression may refer to elevated PSA, metastasis and/or patient death. The present invention is useful in identifying patients with a potentially poor prognosis and recommending them for treatment.

In a first aspect of the invention, there is provided a method of classifying cancer (such as prostate cancer), for example diagnosing aggressive cancer (such as aggressive prostate cancer) in a patient, or identifying a patient with a poor prognosis for cancer, (i.e. a patient with DESNT cancer) comprising:

a) determining the level of expression of a plurality of genes in a sample obtained from the patient to provide a patient expression profile;
b) conducting a statistical Bayesian clustering analysis or other clustering analyses on the patient expression profile and a reference dataset for the same plurality of genes from different patients;
c) optionally repeating the analysis step b) multiple times; and
d) classifying the cancer, determining whether the patient has cancer, or determining whether the patient has a poor prognosis (i.e. the patient has DESNT cancer).

This method and variants thereof are hereafter referred to as Method 1.

In a second aspect of the invention, there is provided a method of classifying prostate cancer, for example diagnosing aggressive prostate cancer in a patient, or identifying a patient with a poor prognosis for prostate cancer, (i.e. a patient with DESNT prostate cancer) comprising:
a) providing a reference dataset where DESNT status of each patient sample in the dataset is known (for example as determined by LPD analysis);
b) selecting from this dataset a plurality of genes, wherein the plurality of genes comprises at least 5, at least 10, at least 20, at least 30, at least 40 or at least 45 genes selected from the group listed in Table 2 or at least 5, at least 10, at least 15 or at least 20 genes selected from the group listed in Table 3;
c) optionally:
(i) determining the expression status of at least 1 further, different, gene in the patient sample as a control, wherein the control gene is not a gene listed in Table 2 or Table 3;
(ii) determining the relative levels of expression of the plurality of genes and of the control gene(s); and
d) using the expression status of those selected genes to apply a supervised machine learning algorithm (for example random forest analysis) on the reference dataset to obtain a predictor for DESNT cancer;
e) determining the expression status of the same plurality of genes in a sample obtained from the patient to provide a patient expression profile;
f) optionally normalising the patient expression profile to the reference dataset; and
g) applying the predictor to the patient expression profile to classify the cancer, determine the presence of aggressive cancer, or determining whether the patient has a poor prognosis (i.e. determine whether the patient's cancer is DESNT or non-DESNT).

This method and variants thereof are hereafter referred to as Method 2.

In a third aspect of the invention, there is provided a method of classifying cancer (such as prostate cancer), for example diagnosing aggressive cancer in a patient (such as aggressive prostate cancer), or identifying a patient with a poor prognosis for cancer, (i.e. a patient with DESNT cancer) comprising:
a) providing a reference dataset where DESNT status (i.e. cancer classification) of each patient sample in the dataset is known (for example as determined by LPD analysis);
b) selecting from this dataset of a plurality of genes;
c) using the expression status of those selected genes to apply a supervised machine learning algorithm (for example random forest analysis) on the dataset to obtain a predictor for DESNT cancers;
d) determining the expression status of the same plurality of genes in a sample obtained from the patient to provide a patient expression profile;
e) optionally normalising the patient expression profile to the reference dataset; and
f) applying the predictor to the patient expression profile to classify the cancer, determine the presence of aggressive cancer, or determining whether the patient has a poor prognosis (i.e. determine whether the patient's cancer is DESNT or non-DESNT).

This method and variants thereof are hereafter referred to as Method 3.

In a fourth aspect of the invention, there is provided a method of classifying prostate cancer, for example diagnosing aggressive cancer in a patient (such as aggressive prostate cancer), or identifying a patient with a poor prognosis for cancer, (i.e. a patient with DESNT cancer) comprising:
a) providing one or more reference datasets where DESNT status of each patient sample in the datasets is known (for example as determined by LPD analysis);
b) selecting from this dataset a plurality of genes whose expression statuses are known to vary between DESNT and non-DESNT cancer (for example a plurality of genes listed in Table 4, for example at least 100, at least 200, at least 300, at least 400, at least 500 or at least 1000 genes listed in Table 4);
c) applying a LASSO logistic regression model analysis on the selected genes to identify a subset of the selected genes that identify DESNT cancer;
d) using the expression status of this subset of selected genes to apply a supervised machine learning algorithm (for example random forest analysis) on the dataset to obtain a predictor for DESNT cancers;
e) determining the expression status of the subset of selected genes in a sample obtained from the patient to provide a patient expression profile;
f) optionally normalising the patient expression profile to the reference dataset(s); and
g) applying the predictor to the patient expression profile to classify the cancer, determine the presence of aggressive cancer, or determining whether the patient has a poor prognosis (i.e. determine whether the patient's cancer is DESNT or non-DESNT).

This method and variants thereof are hereafter referred to as Method 4.

In a fifth aspect of the invention, there is provided a biomarker panel comprising the genes listed in Table 2 as a predictor for the progression of cancer, or as a classifier of cancer. In particular, the genes listed in Table 2 can be used to predict progression of cancer (such as prostate cancer). Down-regulation of these genes is predictor of cancer progression. Generally, in embodiments of the invention, at least 5, at least 10, at least 20, at least 30 or at least 40 of the genes from Table 2 will be used. In some embodiments, all 45 genes from Table 2 will be used. This panel is therefore useful in diagnosing aggressive cancer in a patient, in particular aggressive prostate cancer, although progression of other cancer types can be predicted using the same biomarker panel.

In a sixth aspect of the invention, there is provided a biomarker panel comprising the genes listed in Table 3 as a predictor for the progression of cancer, or as a classifier of cancer. In particular, the genes listed in Table 3 can be used to predict progression of cancer. Generally, in embodiments of the invention, at least 5, at least 10, or at least 15 of the genes from Table 3 will be used. In some embodiments, all 20 genes from Table 3 will be used. This panel is of particular relevance to prostate cancer, and is therefore useful in predicting prostate cancer progression in a patient.

In a seventh aspect of the invention, there is provided a biomarker panel comprising the genes listed in Table 1 as a predictor for the progression of cancer, or as a classifier of cancer. In particular, the genes listed in Table 1 can be used to predict progression of cancer. Generally, in embodiments of the invention, at least 5, at least 10, or at least 15, at least 20, at least 50, at least 100, at least 200, at least 300 or at least 400 of the genes from Table 1 will be used. In some embodiments, all 500 genes from Table 1 will be used. This panel is of particular relevance to prostate cancer, and is therefore useful in predicting prostate cancer progression in a patient. The choice of genes used from Table 1 may be determined using a method as described herein. In some embodiments of the invention, a biomarker panel is generated according to a method of the invention involving determining predictors for cancer. Such an analysis can be done on any set of genes. Preferably the set of genes from which the biomarker panel is selected comprises at least 1000 randomly selected genes. In some embodiments, the genes are not housekeeping genes (for example none of the genes listed in Table 6).

The panels defined above may be referred to collectively herein as "the biomarker panels".

In a further aspect of the invention there is provided a method of diagnosing, screening or testing for cancer (such as prostate cancer), in particular aggressive or DESNT cancer (such as aggressive or DESNT prostate cancer), comprising detecting, in a sample, the level of expression of all or a selection of the genes from the biomarker panels. In some embodiments, the biological sample is a prostate tissue biopsy (such as a suspected tumour sample), saliva, a blood sample, or a urine sample. Preferably the sample is a tissue sample from a prostate biopsy, a prostatectomy specimen (removed prostate) or a TURP (transurethral resection of the prostate) specimen.

There is also provided one or more genes in the biomarker panels for use in diagnosing cancer (such as prostate cancer), in particular aggressive cancer (such as aggressive prostate cancer). There is also provided the use of one or more genes in the biomarker panels in methods of detecting or diagnosing such cancers, as well as methods of detecting or diagnosing such cancers using one or more genes in the biomarker panels.

There is also provided one or more genes in the biomarker panels for use in predicting progression of cancer (such as prostate cancer), in particular aggressive cancer (such as aggressive prostate cancer). There is also provided the use of one or more genes in the biomarker panel in methods of predicting progression of cancer, as well as methods of predicting cancer progression using one or more genes in the biomarker panels.

There is also provided one or more genes in the biomarker panels for use in classifying cancer (such as prostate cancer). There is also provided the use of one or more genes in the biomarker panel in classifying cancer, as well as methods of classifying cancer using one or more genes in the biomarker panels.

There is further provided a kit of parts for testing for prostate cancer comprising a means for detecting the level of expression of one or more genes in the biomarker panels in a biological sample. The kit may also comprise means for detecting the level of expression of one or more control genes not present in the biomarker panels.

There is also provided a method of distinguishing between aggressive and non-aggressive prostate cancer, comprising detecting the level of expression of one or more genes in the biomarker panels in a biological sample. Optionally the expression levels of each of the genes measured is compared with a reference. The reference may be a control or housekeeping gene. In some embodiments, the control genes are selected from the genes listed in Table 6 or Table 7. The control genes of Table 7 are of particular relevance to prostate cancer. The control genes of Table 6 are useful more broadly.

There is still further provided methods of diagnosing aggressive cancer, methods of classifying cancer, methods of prognosing cancer, and methods of predicting cancer progression comprising detecting the level of expression of one or more genes in the biomarker panels in a biological sample. Optionally the method further comprises comparing the expression levels of each of the quantified genes with a reference.

In a still further aspect of the invention there is provided a method of treating prostate cancer in a patient, comprising proceeding with treatment for prostate cancer if aggressive prostate cancer or cancer with a poor prognosis is diagnosed or suspected. In the invention, the patient has been diagnosed as having aggressive prostate cancer or as having a poor prognosis using one of the methods of the invention. In some embodiments, the method of treatment may be preceded by a method of the invention for diagnosing, classifying, prognosing or predicting progression of cancer (such as prostate cancer) in a patient, or a method of identifying a patient with a poor prognosis for prostate cancer, (i.e. identifying a patient with DESNT prostate cancer).

BRIEF DESCRIPTION OF THE FIGURES AND TABLES

FIG. 1. Latent Process Decomposition (LPD), gene correlations and clinical outcome.

Figure 2:
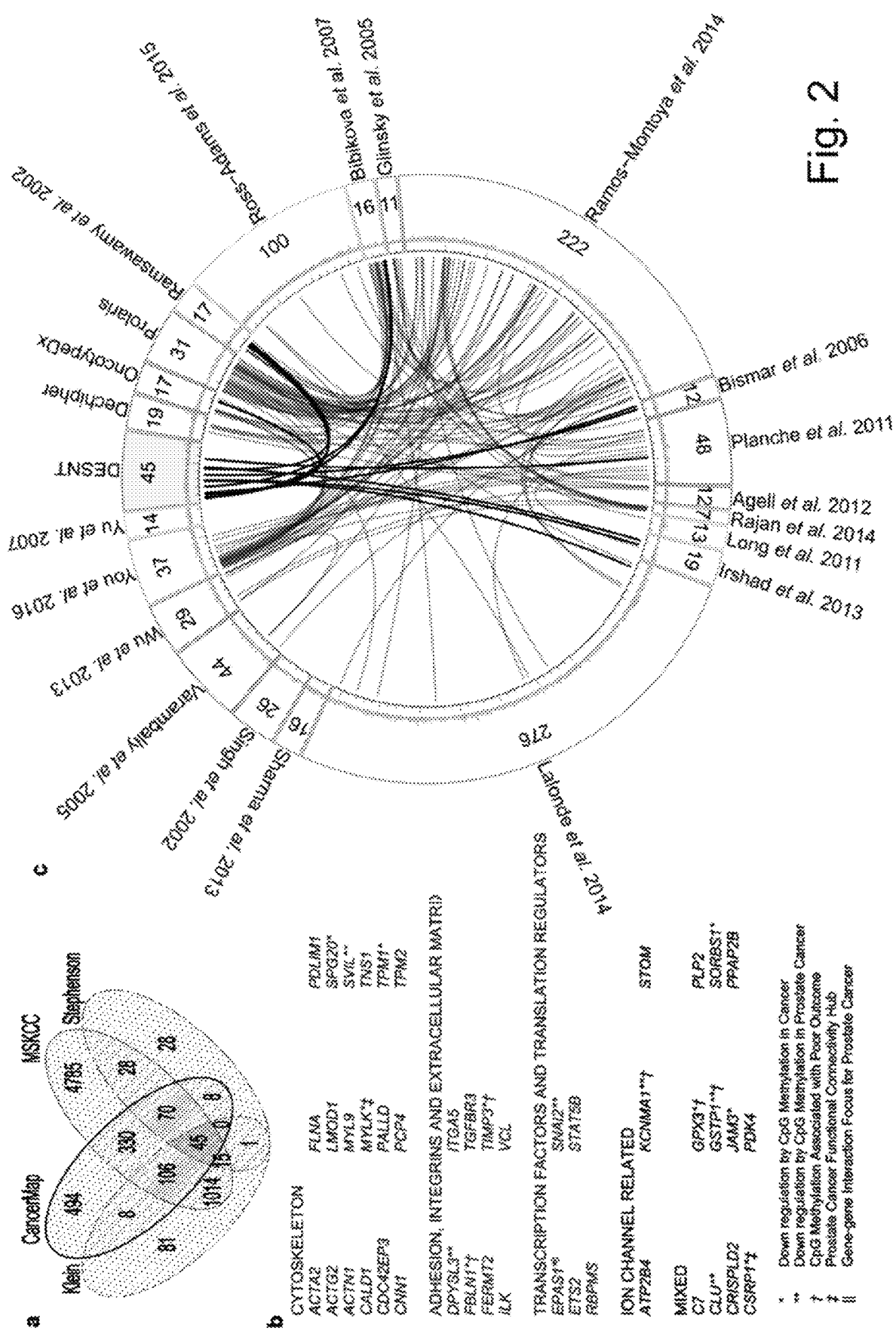

FIG. 2. Genes commonly down regulated in DESNT poor prognosis prostate cancer.

Figure 3:
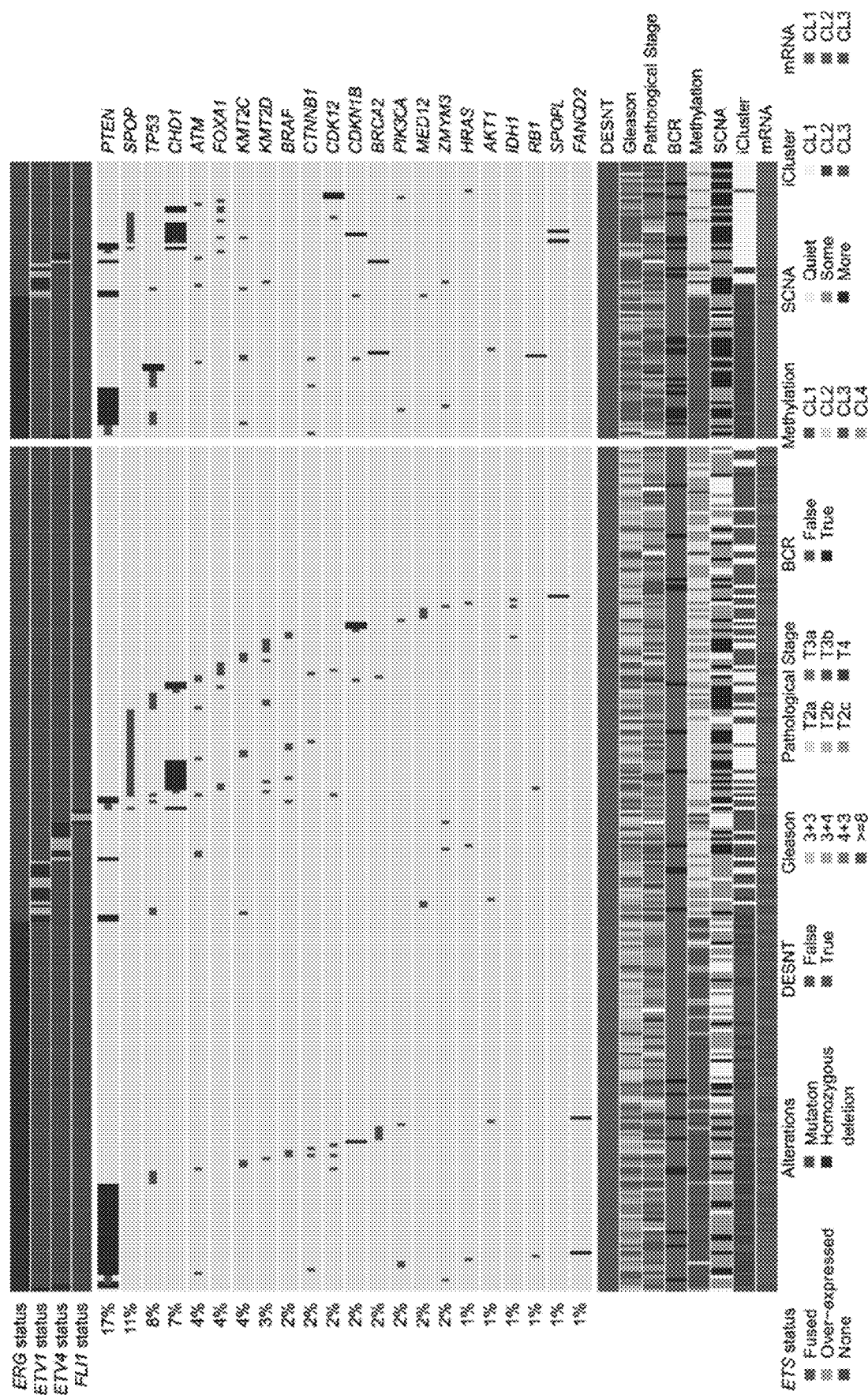

FIG. 3. Comparison of RF-DESNT and non-RF-DESNT cancers in The Cancer Genome Atlas dataset.

Figure 4:
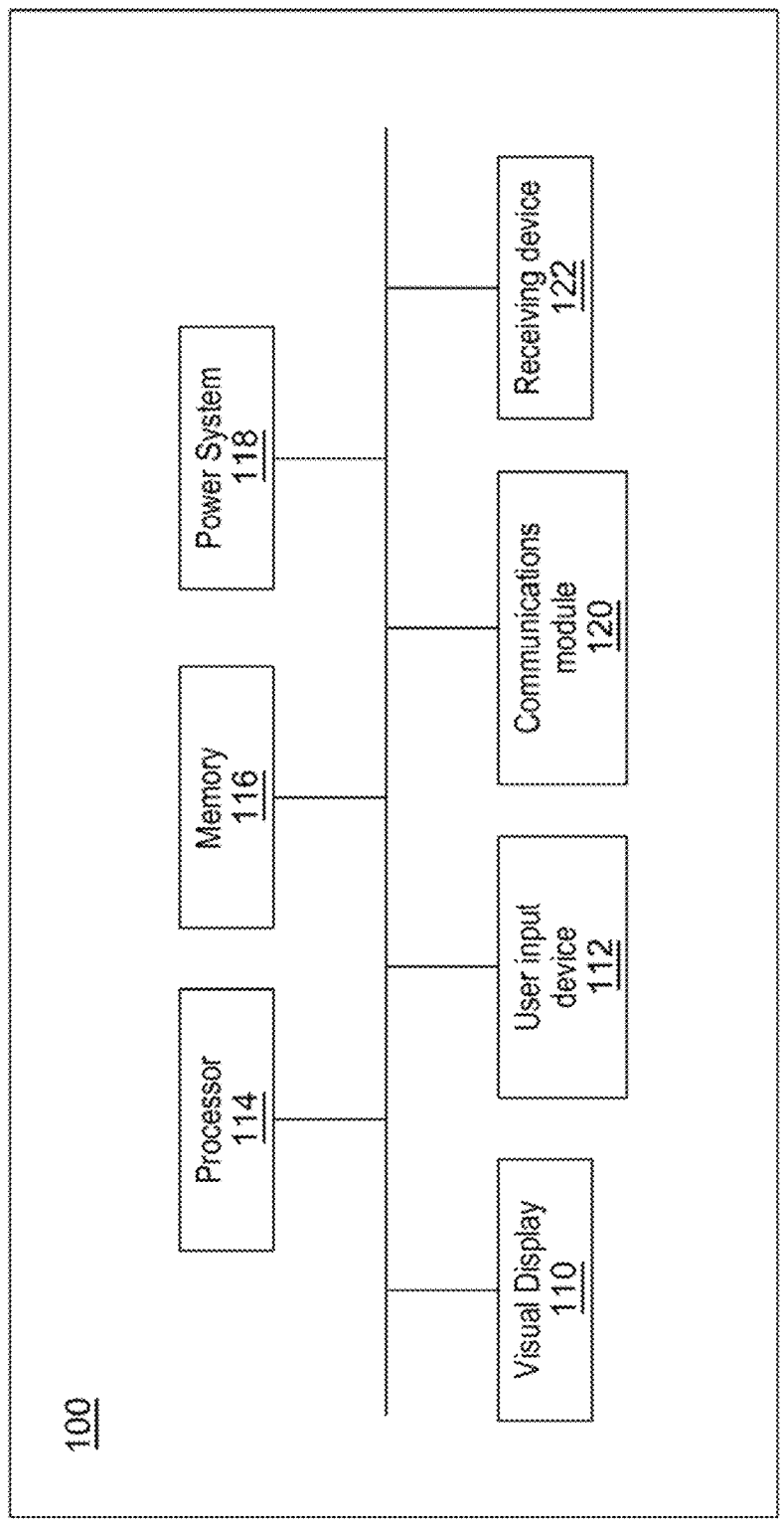

FIG. 4. Example computer apparatus.

Figure 5:
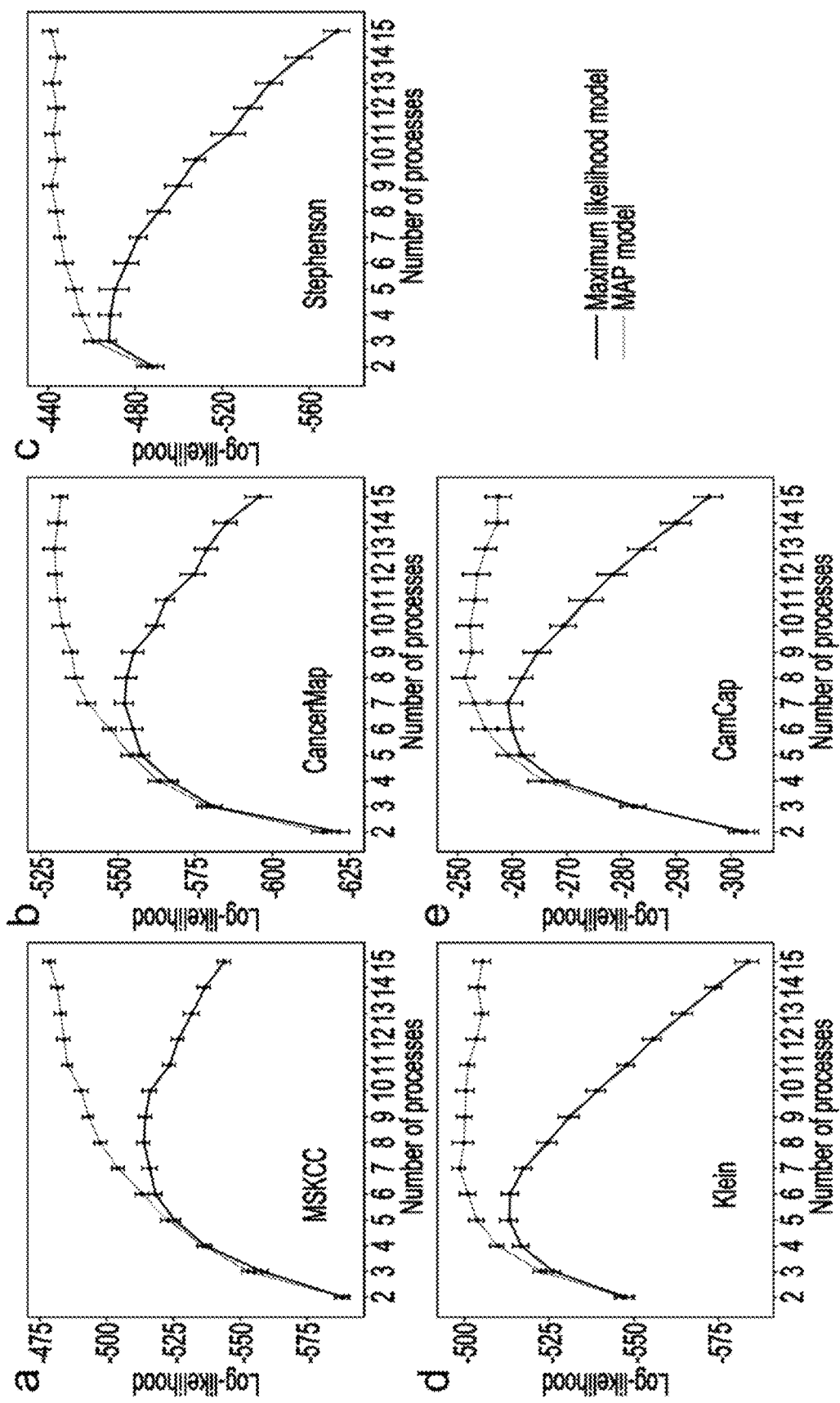

FIG. 5. Log-likelihood plots.

Figure 6:
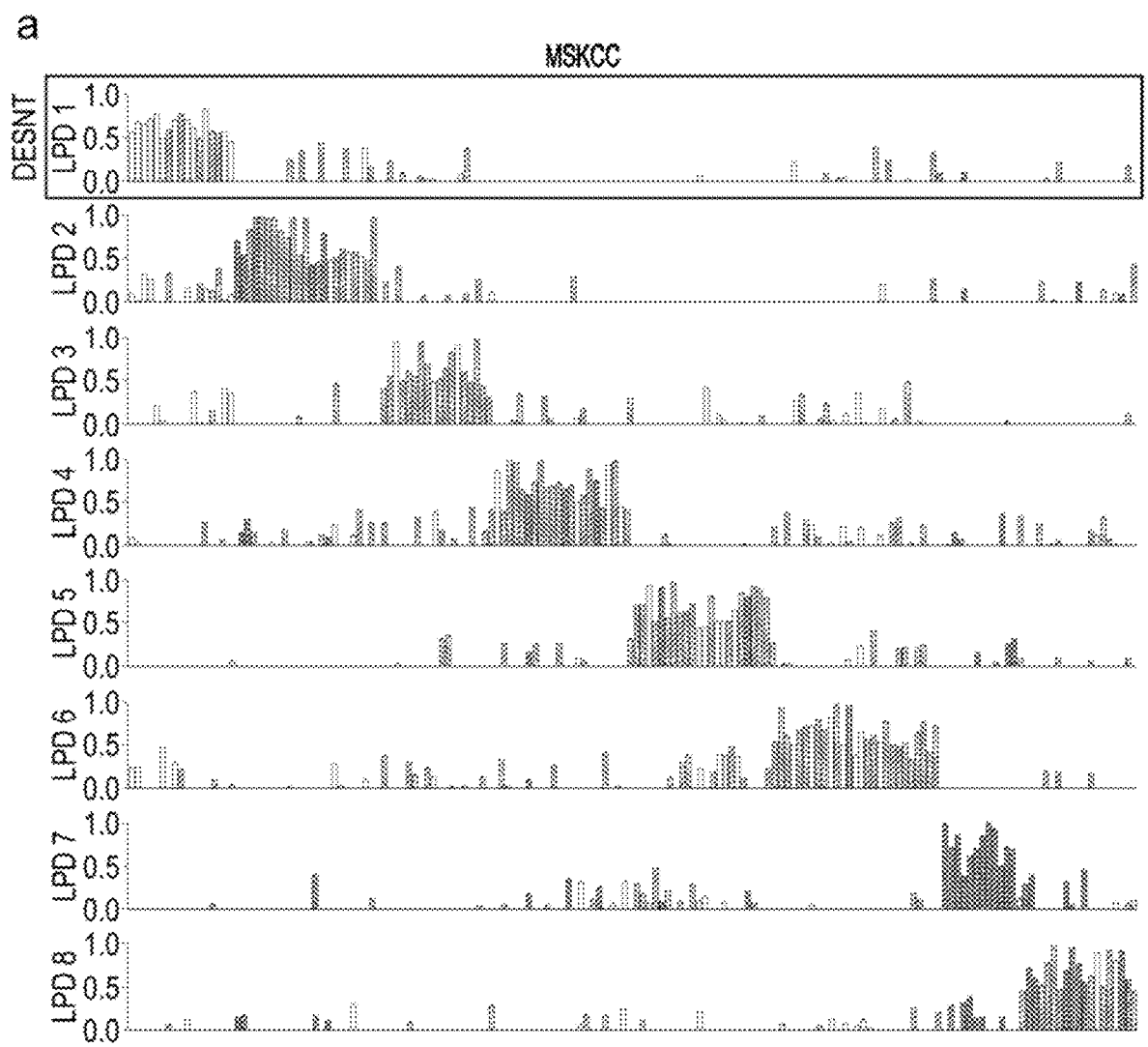
Figure 6:
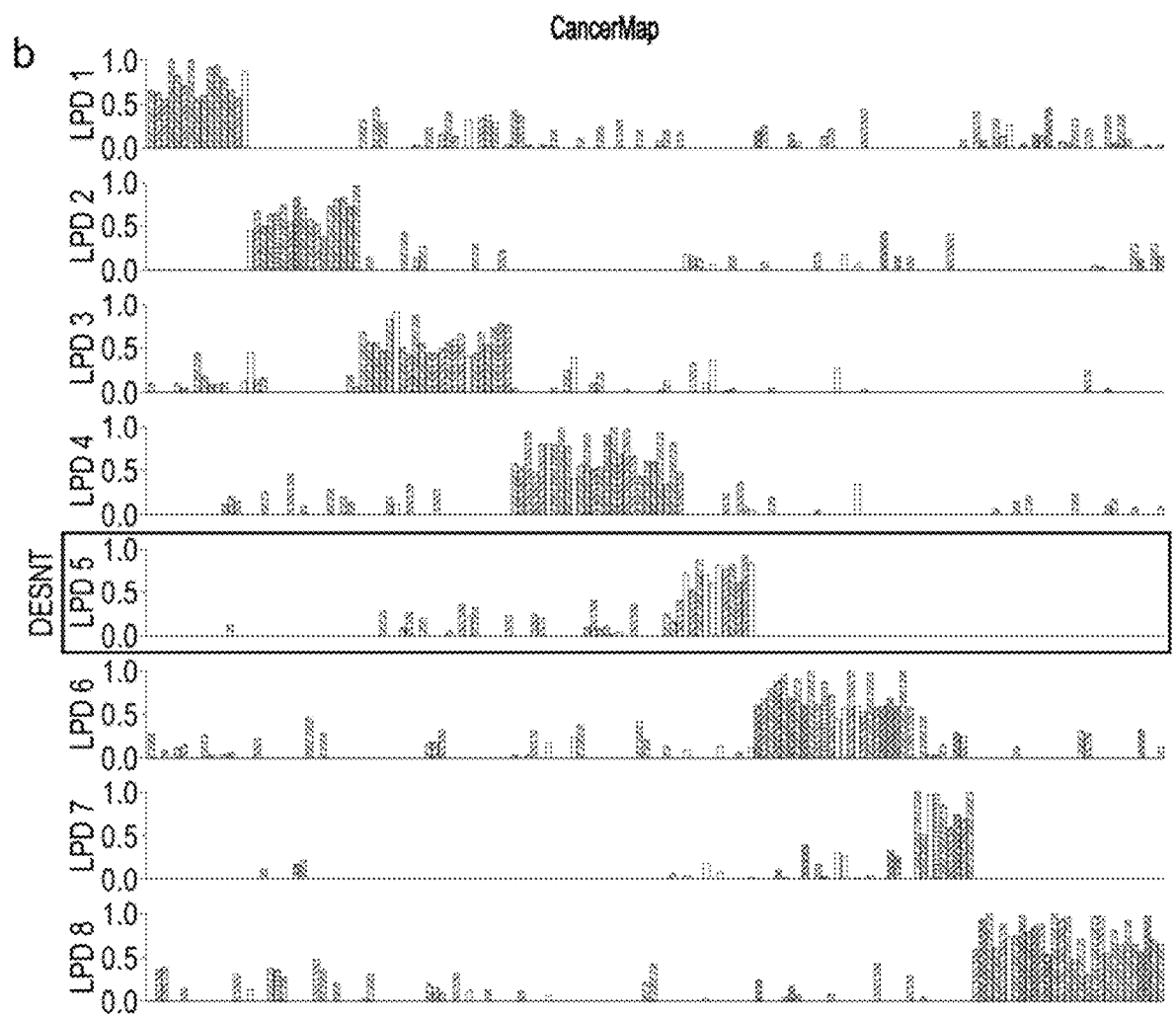
Figure 6:
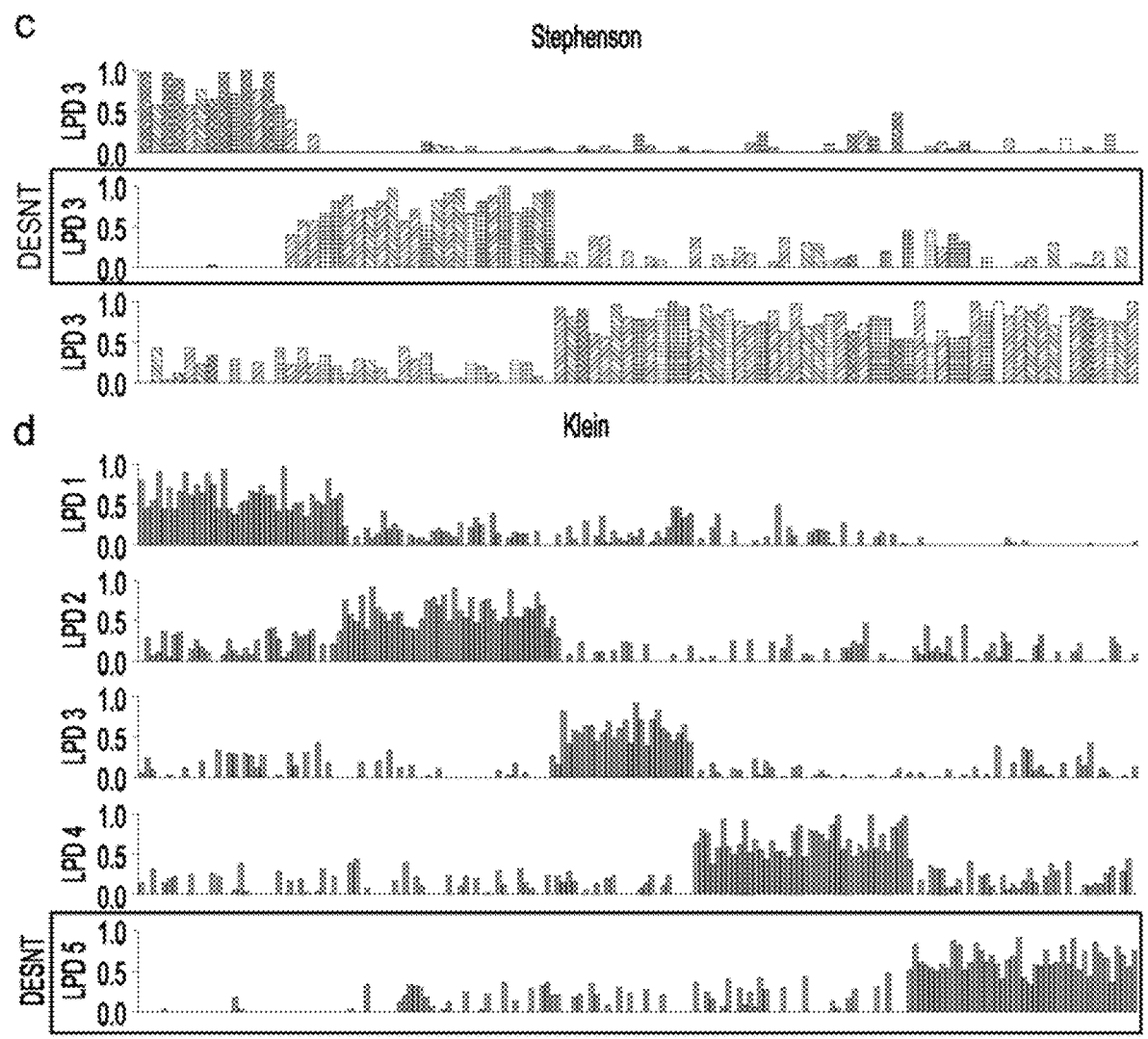
Figure 6:
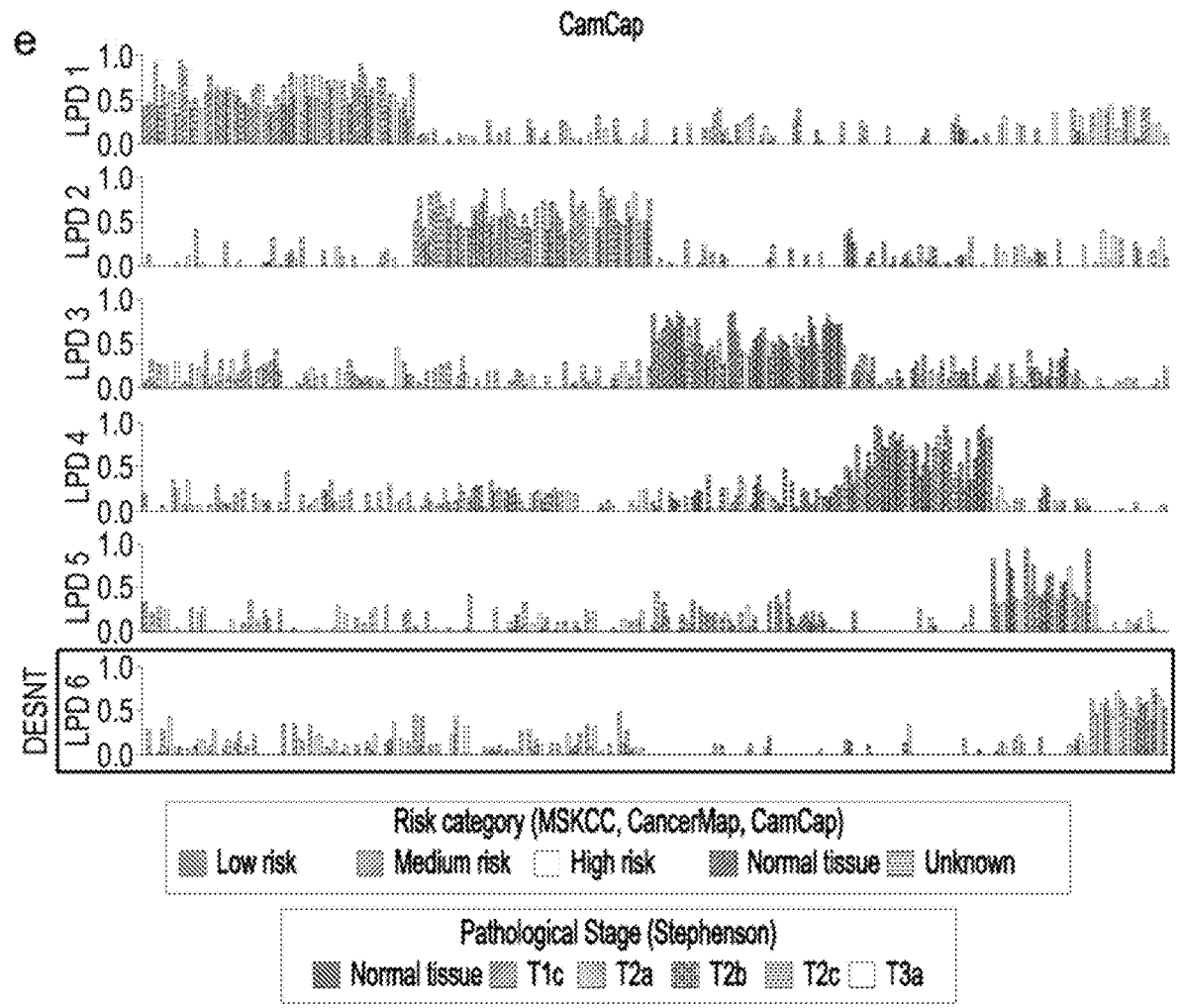

FIG. 6. Latent Process Decomposition (LPD) analysis of transcriptome datasets.

Figure 7:
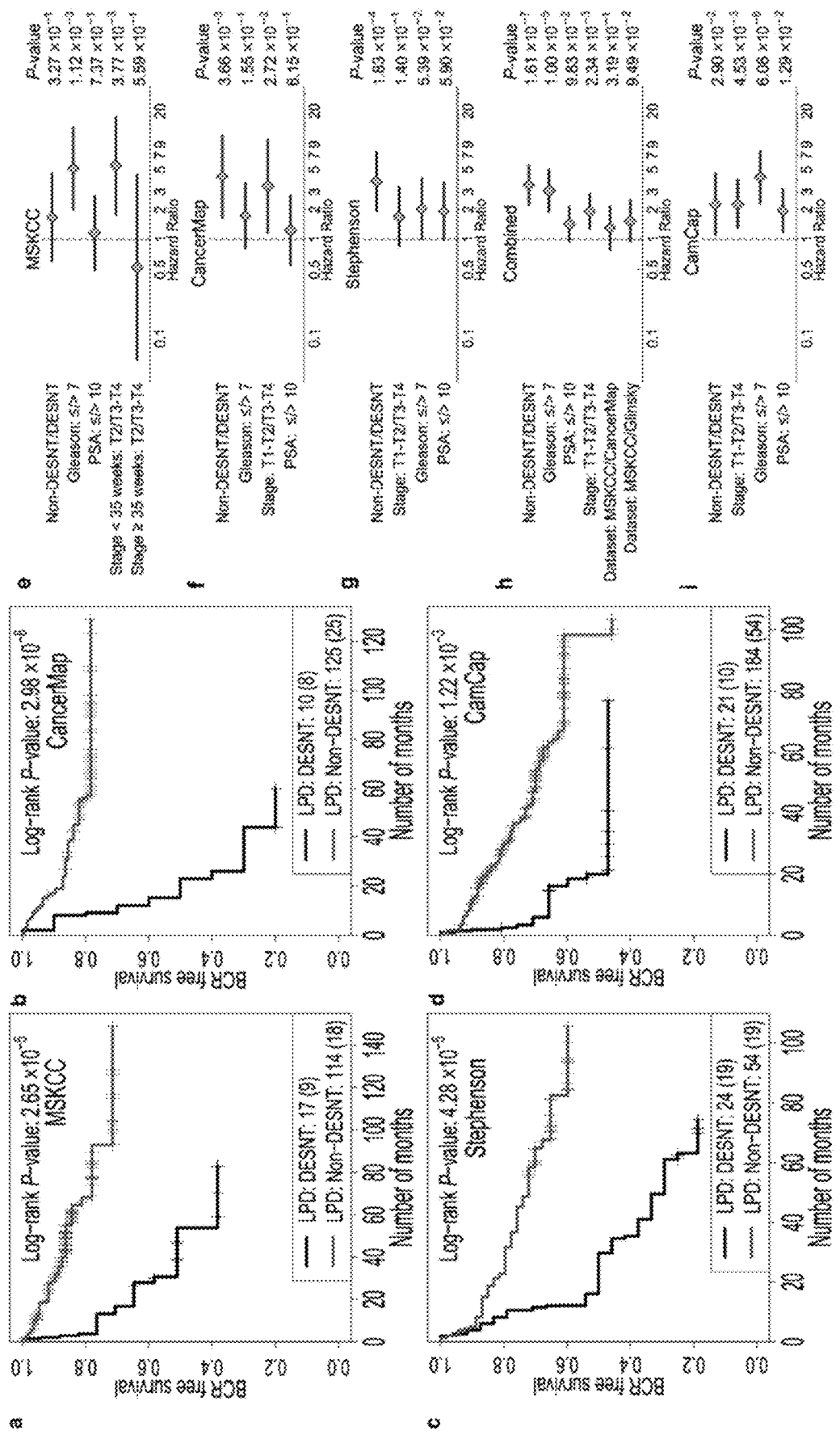

FIG. 7, Analysis of outcome for DESNT cancers identified by LPD.

Figure 8:
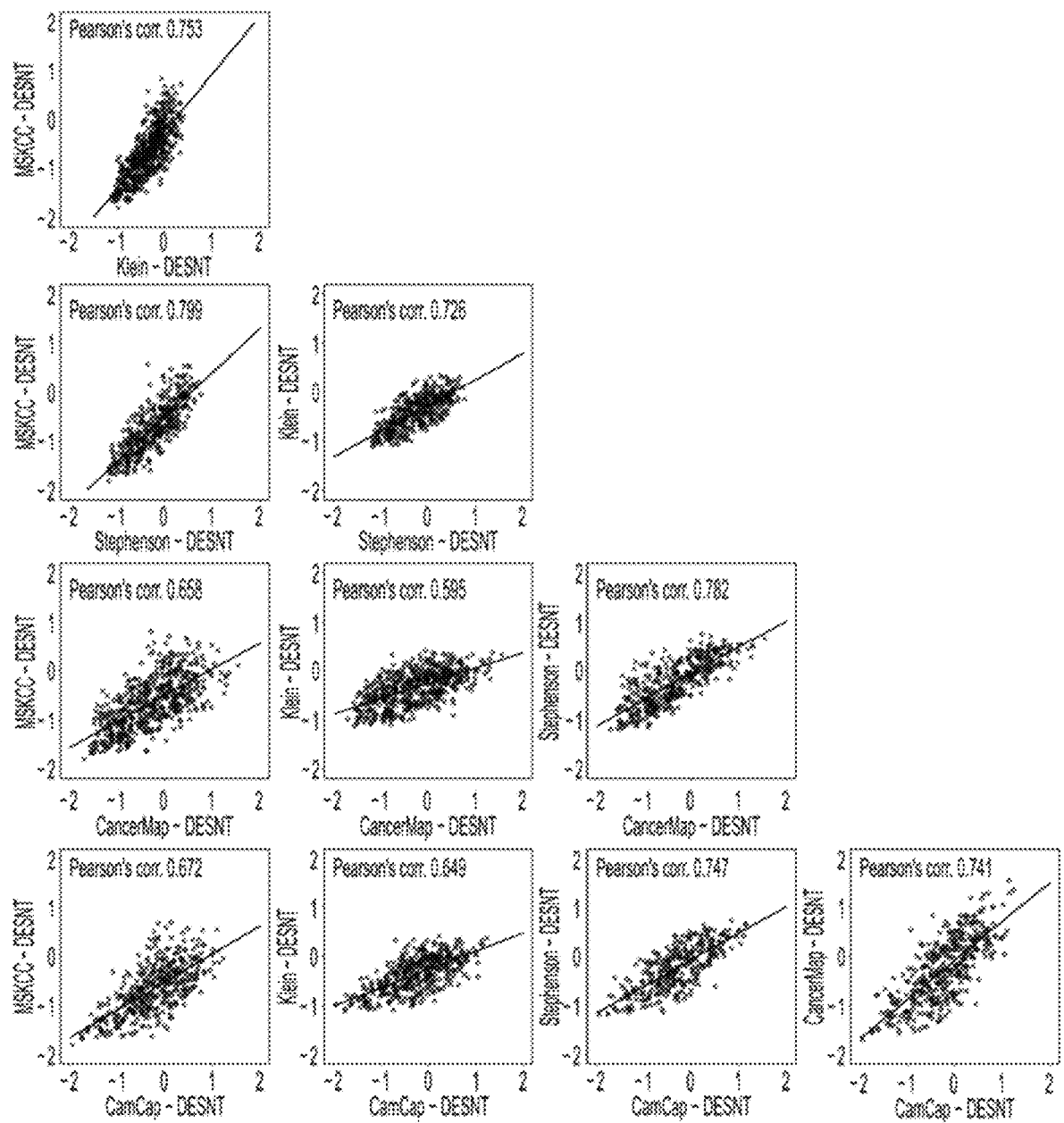

FIG. 8, Correlations of Gene Expression of DESNT cancers identified by LPD classification.

Figure 9:
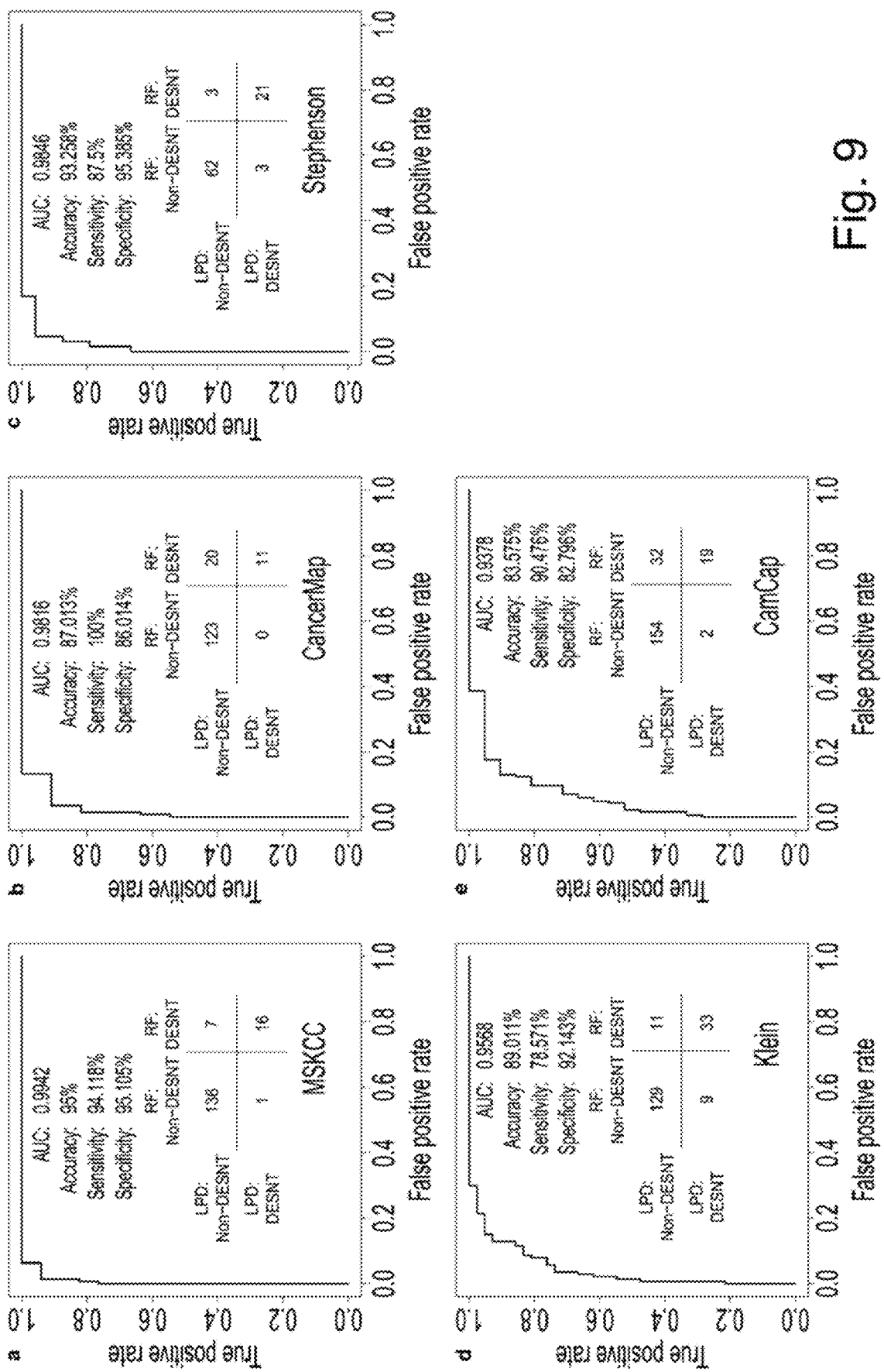

FIG. 9. Detection of DESNT cancers by RF classification using the 20 gene signature.

Figure 10:
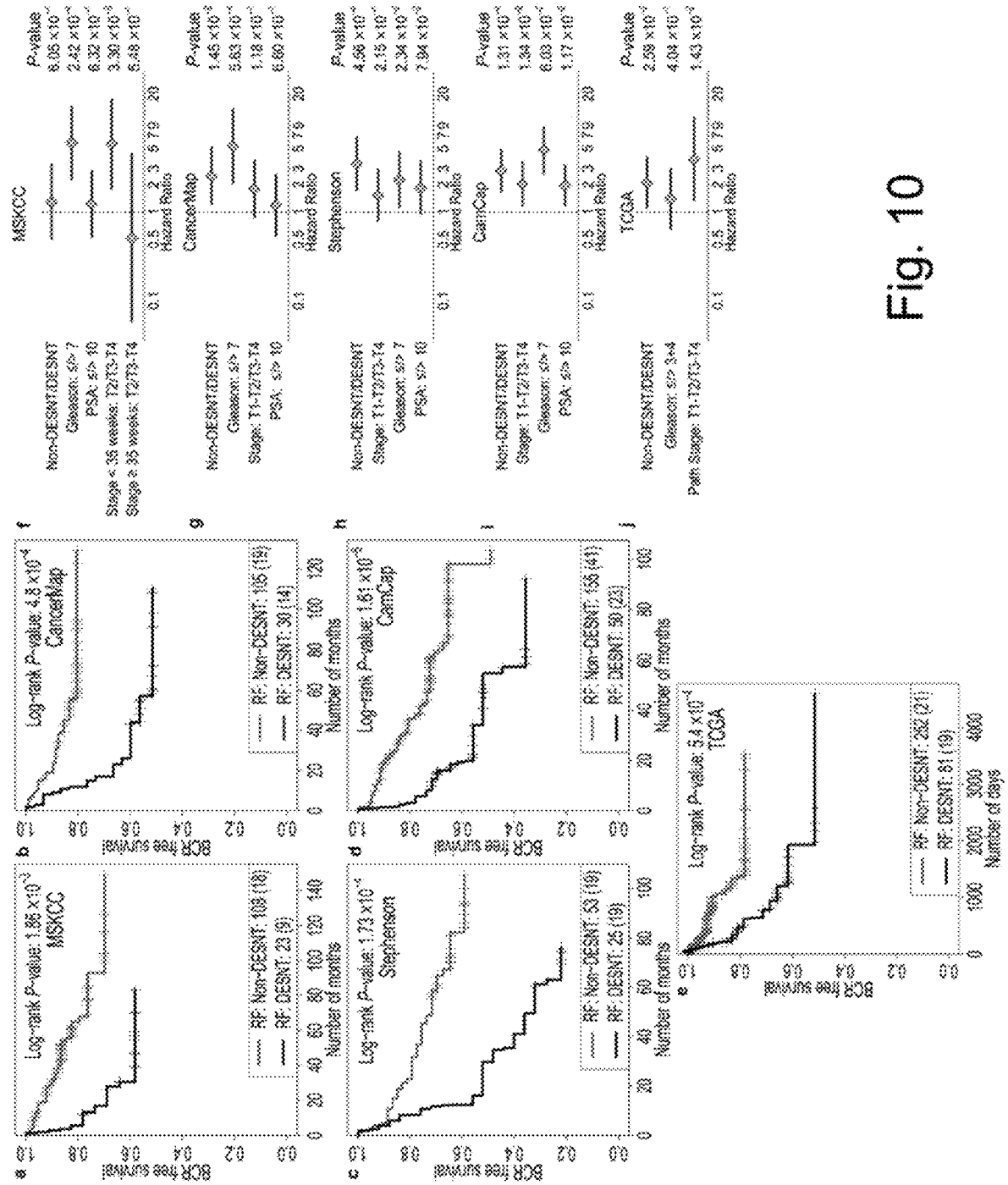

FIG. 10. Analysis of outcome for DESNT cancers identified by RF classification.

Figure 11:
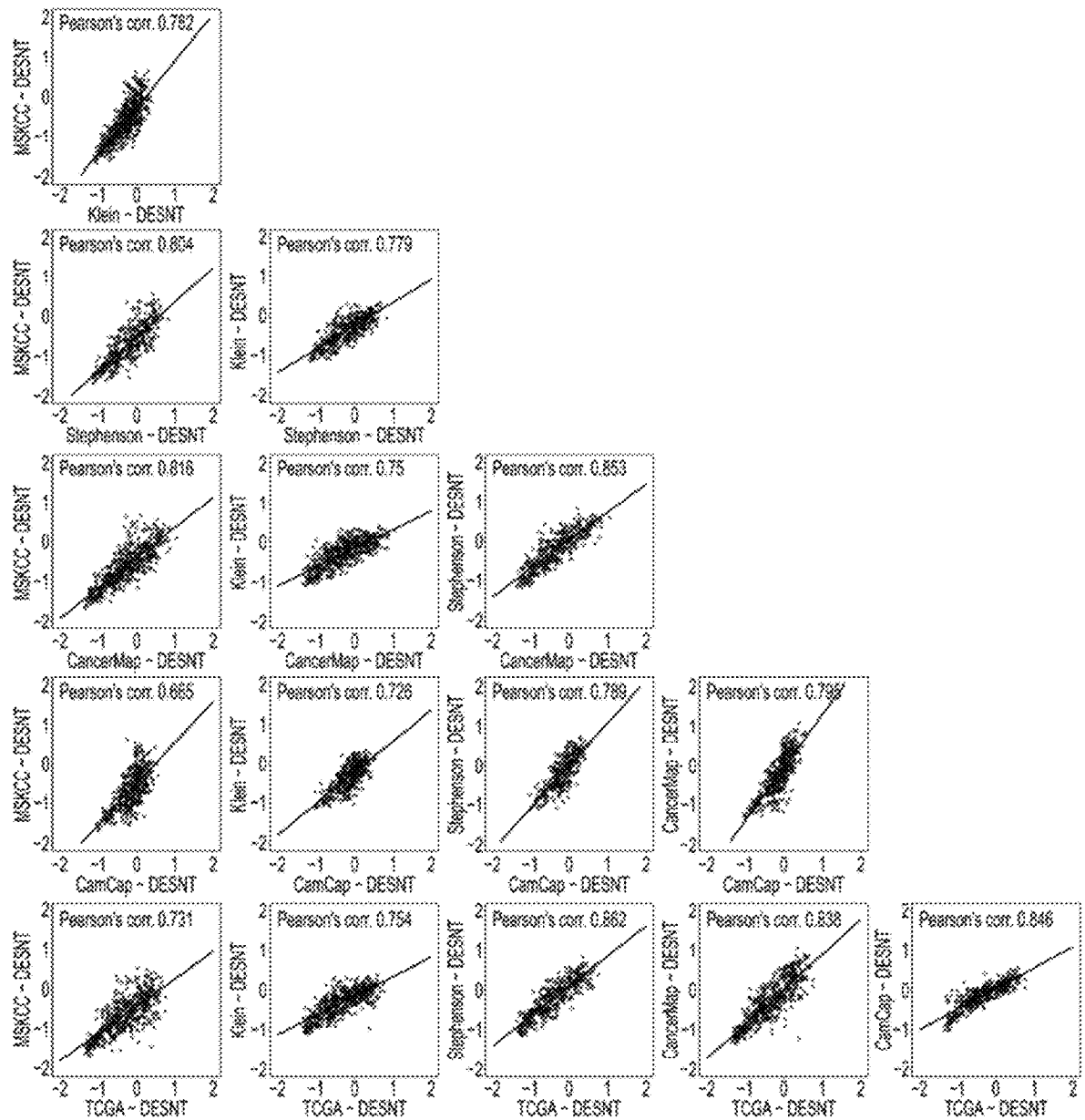

FIG. 11. Correlations of Gene Expression of DESNT cancers identified by RF classification.

Figure 12:
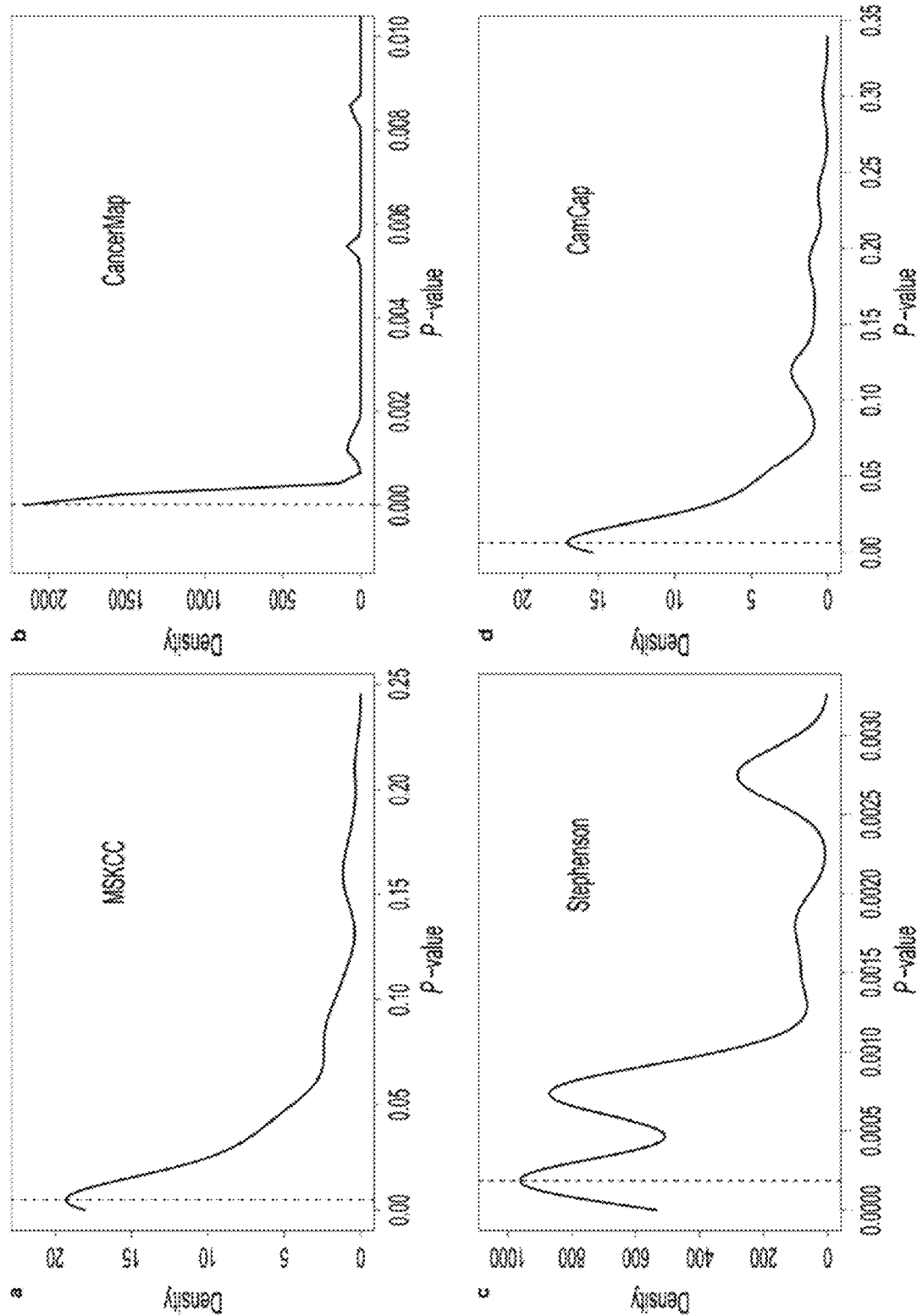

FIG. 12. Distribution of LPD runs.

Figure 13:
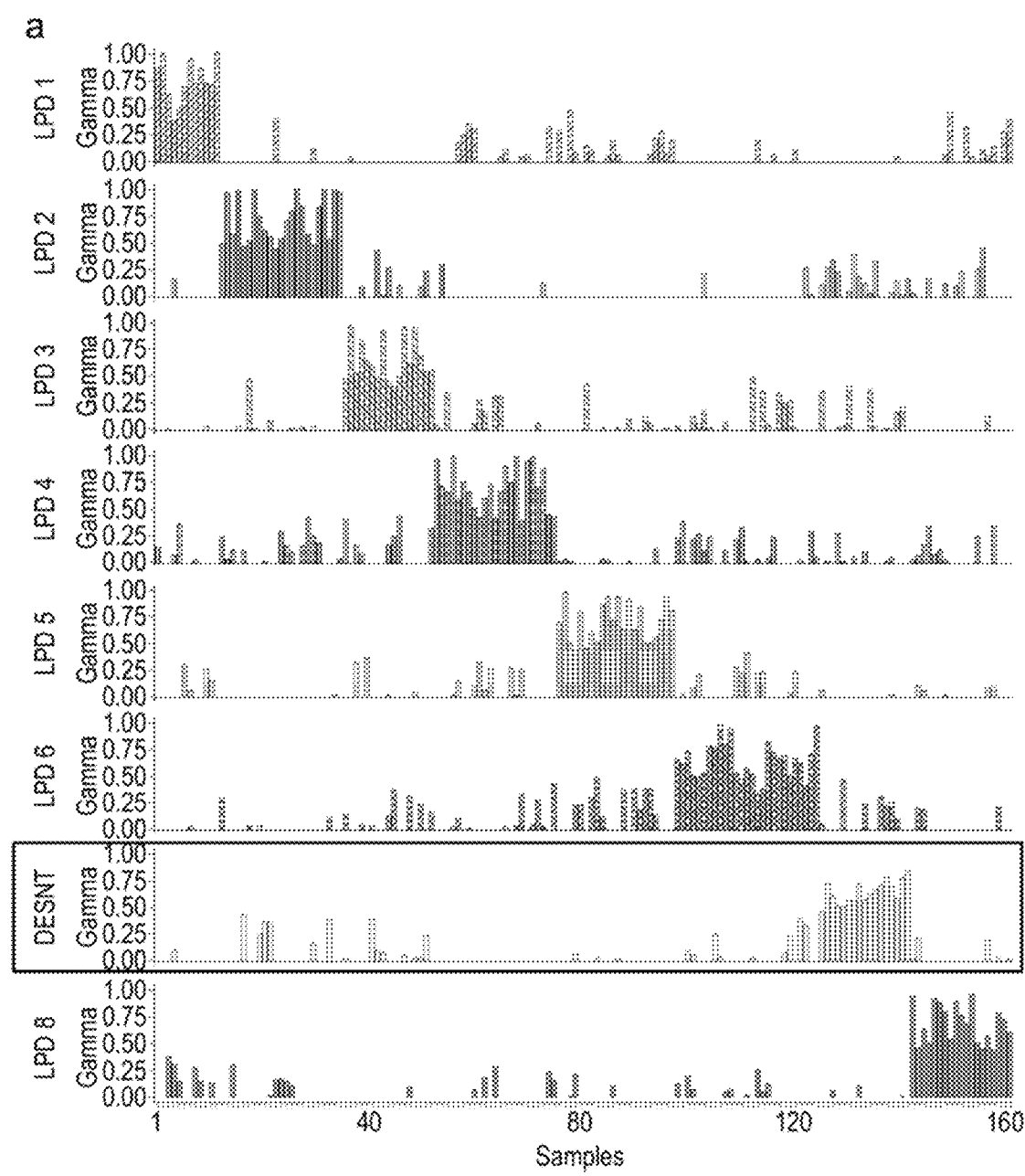
Figure 13:
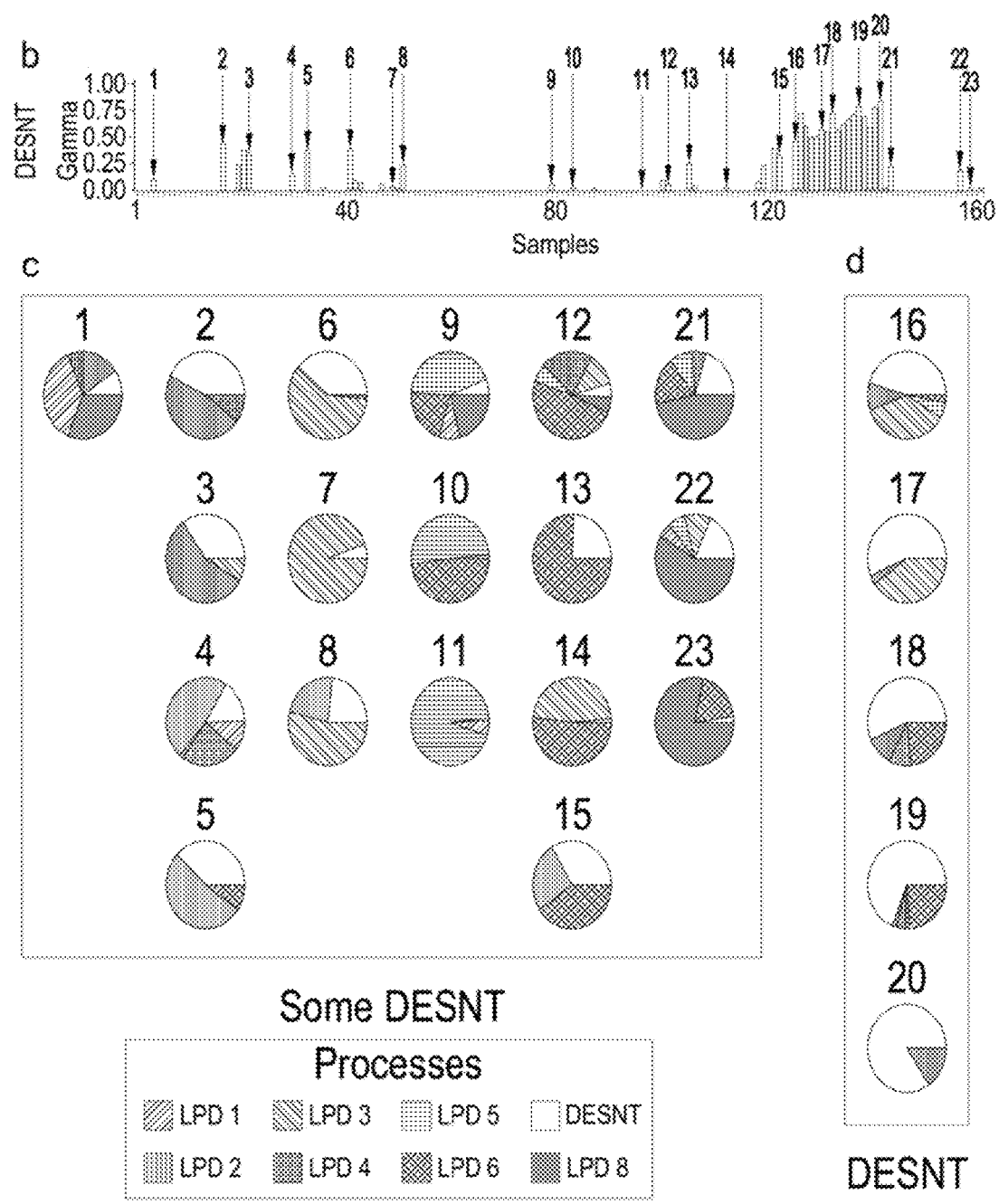

FIG. 13. LPD decomposition of the MSKCC dataset.

Figure 14:
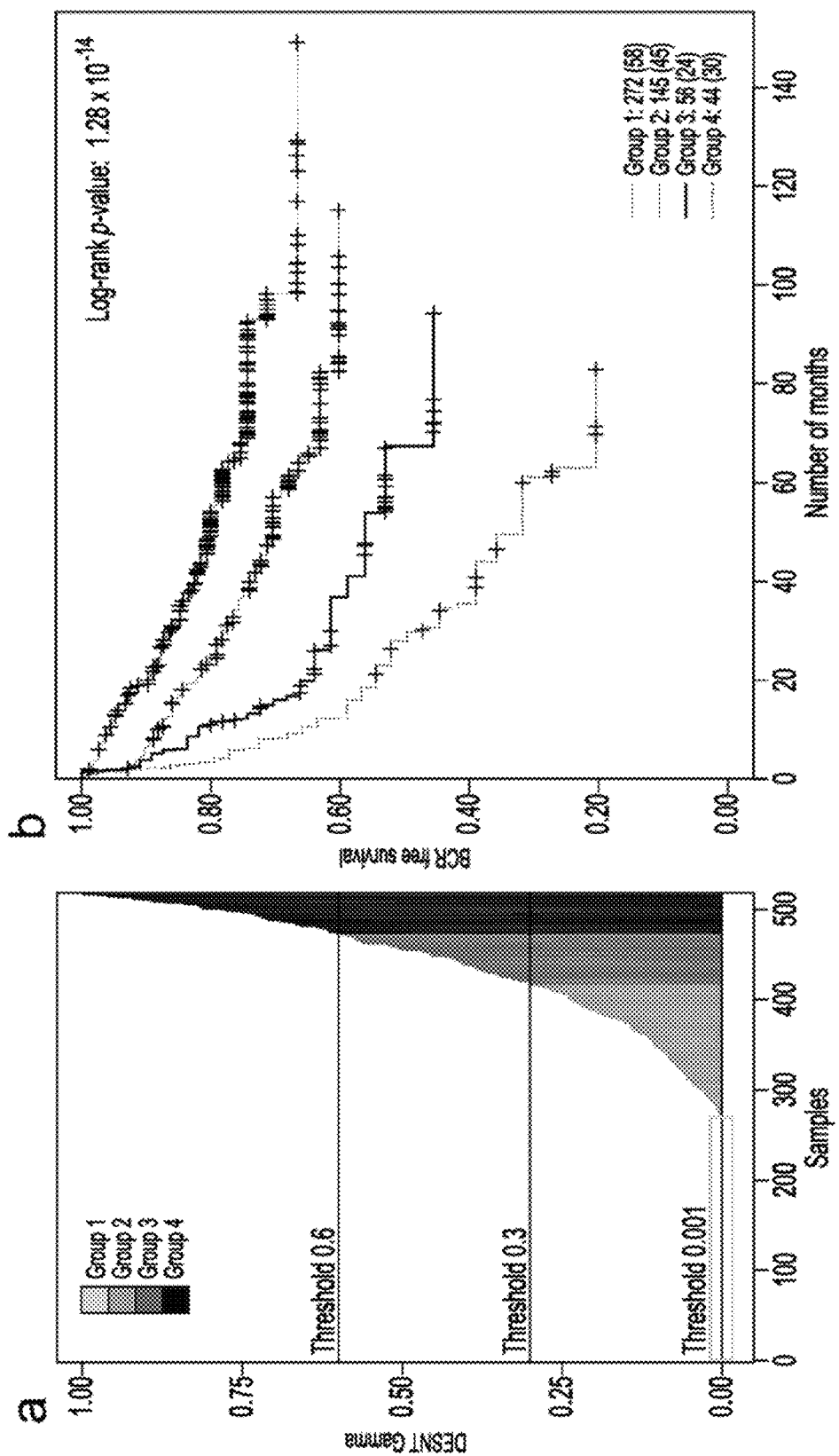

FIG. 14. Stratification of prostate cancer based on the percentage of DESNT cancer present.

Figure 15:
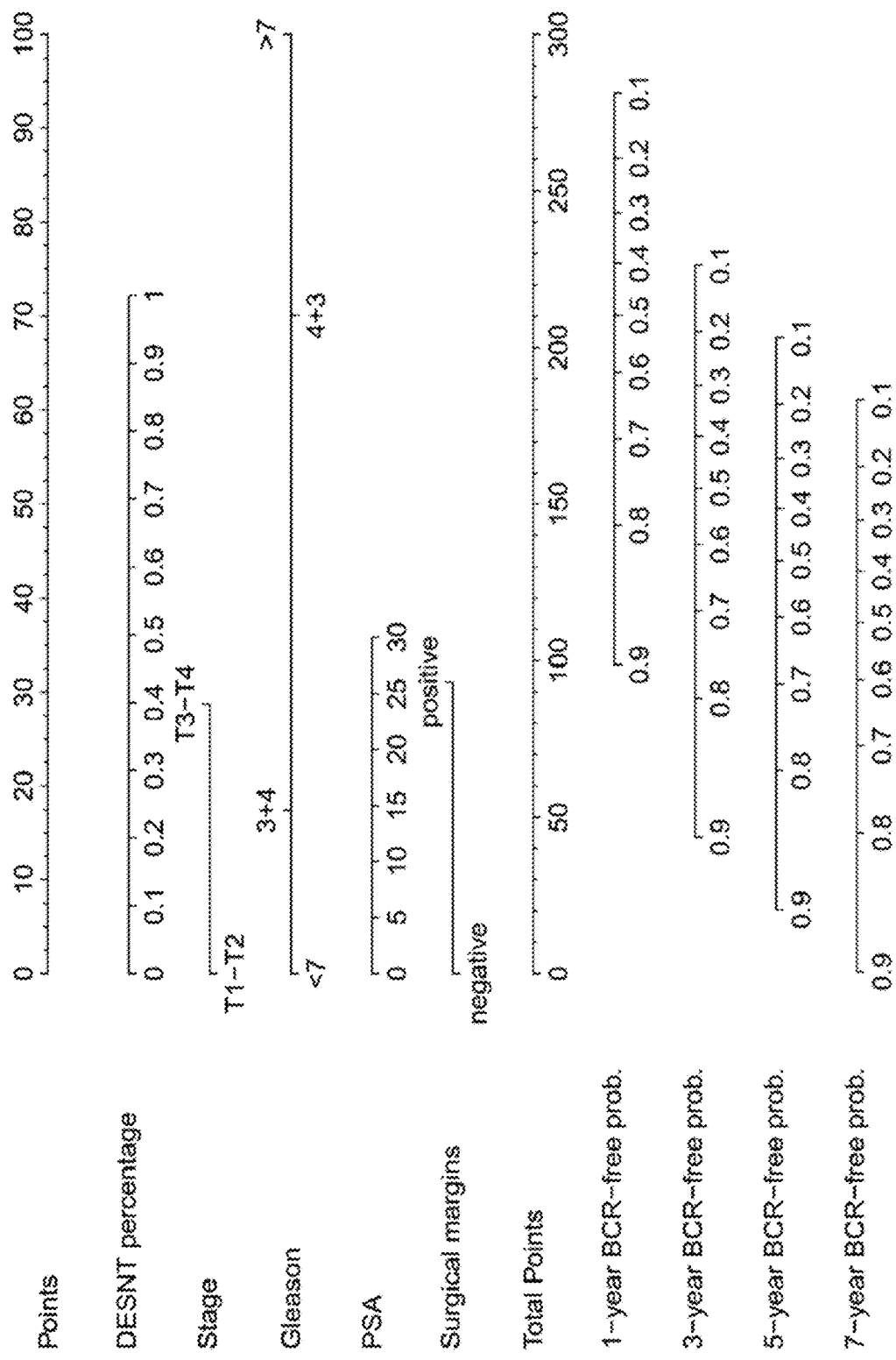

FIG. 15. Nomogram model developed to predict PSA free survival at 1, 3, 5 and 7 years for LPD.

Figure 16:
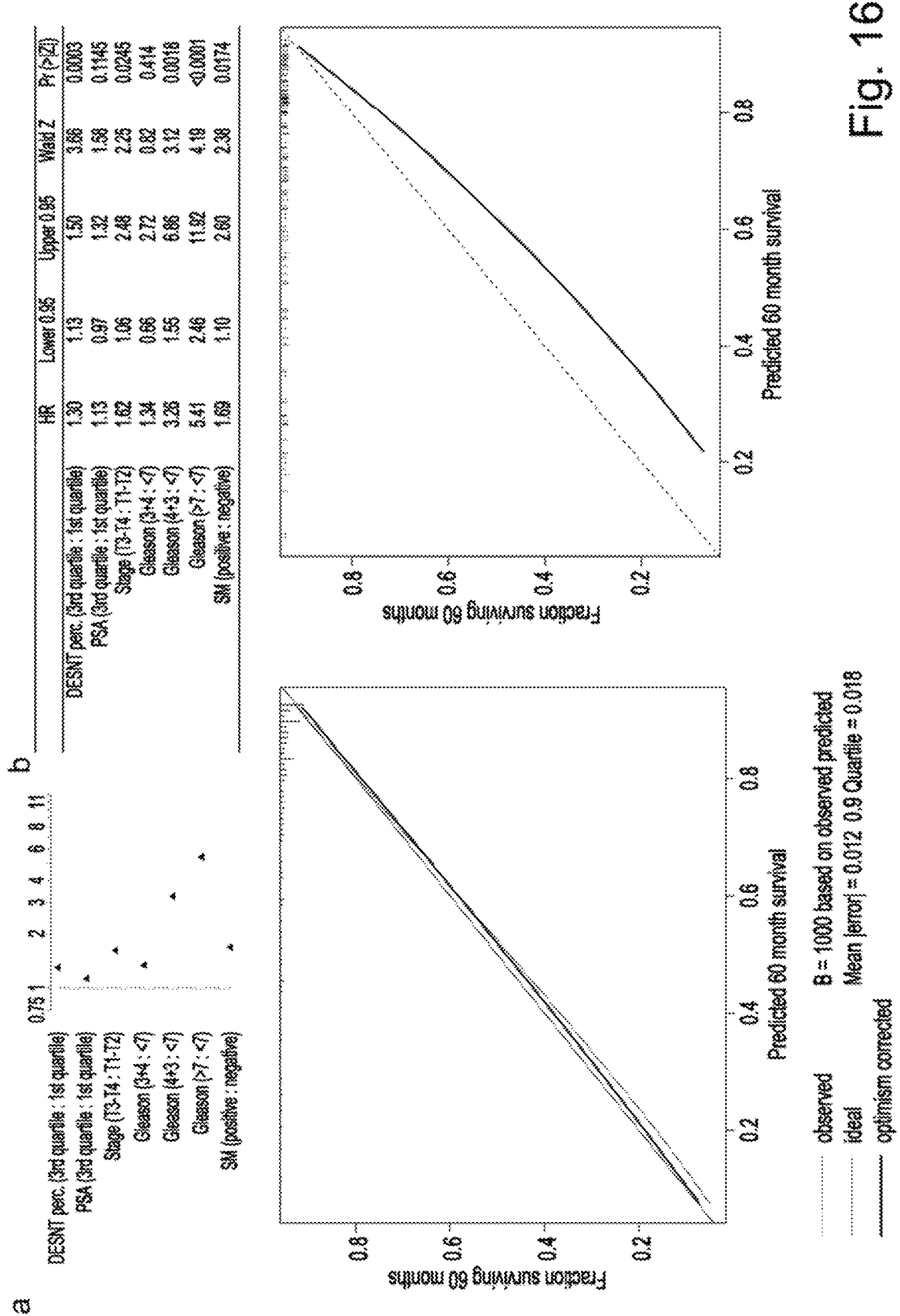

FIG. 16. Cox Model for LPD.

Table 1: 500 gene probes that vary most across prostate cancers.

Table 2: 45 commonly downregulated genes in 80/100 from CancerMap, Stephenson, MSKCC and Klein datasets.

Table 3: 20 random forest genes.

Table 4: 1669 genes that vary between DESNT and non-DESNT cancer.

Table 5: 35 commonly downregulated genes in 67/100 from CamCap, Stephenson, MSCKSS and Klein datasets.

Table 6: General control/housekeeping genes.

Table 7: Control/housekeeping genes for prostate cancer.

DETAILED DESCRIPTION OF THE INVENTION

The present invention provides methods, biomarker panels and kits useful in predicting cancer progression.

In one embodiment of the invention, there is provided a method of classifying cancer, diagnosing aggressive cancer, or identifying a patient with a poor prognosis for cancer, (i.e. a patient with DESNT cancer) comprising:
  a) determining the level of expression of a plurality of genes in a sample obtained from the patient to provide a patient expression profile;
  b) conducting a statistical Bayesian clustering analysis or other clustering analyses on the patient expression profile and a reference dataset for the same plurality of genes from different patients;
  c) optionally repeating the analysis step b) multiple times; and
  d) classifying the cancer, determining whether the patient has aggressive cancer, or determining whether the patient has a poor prognosis (i.e. the patient has DESNT cancer).

This method is of particular relevance to prostate cancer, but it can be applied to other cancers.

In embodiments where the analysis step b) of Method 1 is repeated, different initial random seeds may be used each time the analysis is run.

The step a) of Method 1 of determining the level of expression of a plurality of genes may be carried out on genes whose expression levels are known to vary across cancers. For example, the level of expression may be determined for at least 50, at least 100, at least 200 or most preferably at least 500 genes there are known to vary across cancers. The skilled person can determine which genes should be measured, for example using previously published dataset(s) for patients with cancer and choosing a group of genes whose expression levels vary across different cancer samples. In particular, the choice of genes is determined based on the amount by which their expression levels are known to vary across difference cancers.

Variation across cancers refers to variations in expression seen for cancers having the same tissue origin (e.g. prostate, breast, lung etc). For example, the variation in expression is a difference in expression that can be measured between samples taken from different patients having cancer of the same tissue origin. When looking at a selection of genes, some will have the same or similar expression across all samples. These are said to have little or low variance. Others have high levels of variation (high expression in some samples, low in others).

A measurement of how much the expression levels vary across prostate cancers can be determined in a number of ways known to the skilled person, in particular statistical analyses. For example, the skilled person may consider a plurality of genes in each of a plurality of cancer samples and select those genes for which the standard deviation or inter-quartile range of the expression levels across the plurality of samples exceeds a predetermined threshold. The genes can be ordered according to their variance across samples or patients, and a selection of genes that vary can be made. For example, the genes that vary the most can be used, such as the 500 genes showing the most variation. Of course, it is not vital that the genes that vary the most are always used. For example, the top 500 to 1000 genes could be used. Generally, the genes chosen will all be in the top 50% of genes when they are according to variance. What is important is the expression levels vary across the reference dataset. The selection of genes is without reference to clinical aggression. This is known as unsupervised analysis. The skilled person is aware how to select genes for this purpose.

Step b) requires the use of one or more reference datasets. Preparation of the reference datasets will generally not be part of the method, since reference datasets are available to the skilled person. When using a previously obtained reference dataset (or even a reference dataset obtained de novo in step b) of Method 1), normalisation of the levels of expression for the plurality of genes in the patient sample to the reference dataset may be required to ensure the information obtained for the patient sample was comparable with the reference dataset. Normalisation techniques are known to the skilled person, for example, Robust Multi-Array Average, Froze Robust Multi-Array Average or Probe Logarithmic Intensity Error when complete microarray datasets are available. Quantile normalisation can also be used. Normalisation may occur after the first expression profile has been combined with the reference dataset to provide a combined dataset that is then normalised.

Methods of normalisation generally involve correction of the measured levels to account for, for example, differences in the amount of RNA assayed, variability in the quality of the RNA used, etc, to put all the genes being analysed on a comparable scale. The control genes (also referred to as housekeeping genes) are useful as they are known not to differ in expression status under the relevant conditions (e.g. DESNT cancer). Exemplary housekeeping genes are known to the skilled person, and they include RPLP2, GAPDH, PGK1 Alas1, TBP1, HPRT, K-Alpha 1, and CLTC. In some embodiments, the housekeeping genes are those listed in Table 6 or Table 7. Table 7 is of particular relevance to prostate cancer. Preferred embodiments of the invention use at least 2 housekeeping genes for normalisation.

Step a) of Method 1 may involve a single expression profile from a single patient. Alternatively, two or more expression profiles from different patients undergoing diagnosis could be used. Such an approach is useful when diagnosing a number of patients simultaneously. The method may include a step of assigning a unique label to each of the patient expression profiles to allow those expression profiles to be more easily identified in the analysis step.

In some embodiments, in particular those relating to prostate cancer, the level of expression is determined for a plurality of genes selected from the list in Table 1.

In some embodiments, step a) of Method 1 involves determining the level of expression at least 20, at least 50, at least 100, at least 200 or at least 500 genes selected from the list in Table 1. As the number of genes increases, the accuracy of the test may also increase. In a preferred embodiment, at least all 500 genes are selected from the list in Table 1. However, the method does not need to be restricted to the genes of Table 1.

In some cases, information on the level of expression of many more genes may be obtained in step a) of Method 1, such as by using a microarray that determines the level of expression of a much larger number of genes. It is even possible to obtain the entire transcriptome. However, it is only necessary to carry out the subsequent analysis steps on a subset of genes whose expression levels are known to vary across prostate cancers. Preferably, the genes used will be those whose expression levels vary most across prostate cancers (i.e. expression varies according to cancer aggression), although this is not strictly necessary, provided the subset of genes is associated with differential expression levels across cancers (such as prostate cancers).

The actual genes on which the analysis is conducted will depend on the expression level information that is available, and it may vary from dataset to dataset. It is not necessary for this method step to be limited to a specific list of genes. However, the genes listed in Table 1 can be used.

Thus step a) of Method 1 may include the determination of a much larger number of genes that is needed for the rest of the method. The method may therefore further comprise a step of selecting, from the expression profile for the patient sample, a subset of genes whose expression level is known to vary across prostate cancers. Said subset may be the at least 20, at least 50, at least 100, at least 200 or at least 500 genes selected from Table 1.

In preferred embodiments, the Bayesian clustering analysis is a latent process decomposition (LPD) analysis. Such mathematical models are known to a person of skill in the art and are described in, for example, Simon Rogers, Mark Girolami, Colin Campbell, Rainer Breitling, "The Latent Process Decomposition of cDNA Microarray Data Sets", IEEE/ACM Transactions on Computational Biology and Bioinformatics, vol. 2, no. 2, pp. 143-156, April-June 2005, doi:10.1109/TCBB.2005.29. Alternative Bayesian clustering algorithms that could be used include: Dirichlet Process Mixture Models, Bayesian Hierarchical Clustering, Bayesian Multi-topic Microarray Analysis with Hyperparameter Reestimation, Bayesian Mixture Models, a Markov Chain Monte Carlo approach to LPD, or a marginalized variational Bayesian approach.

When an LPD analysis is carried out on the reference dataset, which includes, for a plurality of patients, information on the expression levels for a number of genes whose expression levels vary significantly across prostate cancers, it is possible to identify a population of patients that all exhibit DESNT (aggressive or poor prognosis) cancer. The LPD analysis groups the patients into "processes". The present inventors have surprisingly discovered that when the LPD analysis is carried out using genes whose expression levels are known to vary across prostate cancers, one particular patient population (or process) is identified that is substantially always associated with a negative outcome for the patient (i.e. a DESNT/aggressive cancer). Even more surprisingly, this process is present even across multiple different datasets.

In the development of the present invention, the inventors performed an LDP analysis using between 3 and 8 underlying processes contributing to the overall expression profile as indicated from log-likelihood plots (FIGS. 1b, 5). Following decomposition of each dataset, cancers were assigned to individual processes based on their highest $p_i$ value yielding the results shown in FIG. 1a and FIG. 6. $p_i$ is the contribution of each process i to the expression profile of an individual cancer: sum of $p_i$ over all processes=1. However, the highest pi value does not always need to be used and pi can be defined differently, and skilled person would be aware of possible variations. For example, pi can be at least 0.1, at least 0.2, at least 0.3, at least 0.4 or preferably at least 0.5.

Indeed, as demonstrated in Example 2, $p_i$ is a continuous variable and is a measure of the contribution of a given process to the expression profile of a given sample. The higher the contribution of the DESNT process (so the higher the value of $p_i$ for the DESNT process contributing to the expression profile for a given sample), the greater the chance the cancer will have a poor outcome. As demonstrated and indicated in Example 2, for a given sample, a number of different processes can contribute to an expression profile. It is not always necessary for the DESNT process to be the most dominant (i.e. to have to highest $p_i$ value of all the processes contributing to the expression profile) for a poor outcome to be predicted. However, the higher the $p_i$ value the worse the patient outcome; not only in reference to PSA but also metastasis and death are also more likely. In some embodiments, the contribution of the DESNT process to the overall expression profile for a given cancer may be determined when assessing the likelihood of a cancer being DESNT. In some embodiments, the prediction of cancer progression may be done in further combination with one or more of stage of the tumour, Gleason score and/or PSA score. Therefore, in some embodiments, the step of determining the cancer prognosis may comprise a step of determining the pi value for the DESNT process for the expression profile and, optionally, further determining the stage of the tumour, the Gleason score of the patient and/or PSA score of the patient.

In some embodiments, the step of grouping individual patient expression profiles comprises, for each expression profile, using the LDP analysis to determine the contribution ($p_i$) of each group to the overall expression profile for each patient expression profile (wherein the sum of all pi values for a given expression profile is 1). The patient expression profile may be assigned to an individual group according to the group that contributes the most to the overall expression profile (in other words, the patient expression profile is assigned to the group with the highest $p_i$ value). In some embodiments, each group is assigned either DESNT or a non-DESNT status. Cancer progression in the patient can be predicted according to the contribution ($p_i$ value) of the DESNT process to the overall expression profile. In some embodiments, DESNT cancer is predicted when the $p_i$ value for the DESNT process for the patient cancer sample is at least 0.1, at least 0.2, at least 0.3, at least 0.4 or at least 0.5.

In FIG. 1a, the "$p_i$" value is shown on the vertical axis. Each column represents as single patient. Following LPD of each dataset, cancers were assigned to individual processes based on their highest $p_i$ value yielding the results shown in this Figure. $p_i$ is the contribution of each process i to the expression profile of an individual cancer: sum of $p_i$ over all processes=1.

The reference dataset may have been obtained previously and, in general, the obtaining of these datasets is not part of the claimed method. However, in some embodiments, the method may further comprise obtaining the additional datasets for inclusion in the LPD analysis. The reference dataset is in the form of a plurality of expression profiles that comprises the same genes measured in the patient sample.

In any of the Methods described herein, there are four main ways in which it is possible to identify a DESNT cancer or a DESNT cancer group:
  (i) correlations of gene expression levels with DESNT cancer groups in another dataset or datasets;
  (ii) demonstration of overlaps of differentially expressed genes between DESNT and non-DESNT cancers with a core down-regulated gene set;
  (iii) its poorer clinical outcome; and
  (iv) LPD on a combined reference and unknown patient dataset with DESNT status assigned if the patient dataset clusters with the known DESNT group.

In the first (i) method, after the LPD analysis has been conducted, the patient samples are grouped together in different processes. For the patients in each process the level of expression for each gene is averaged. The averaged expression levels are then correlated with data from other datasets, where the presence of DESNT cancer is known. Hence the process in the new dataset associated with DESNT cancer can be determined. That new dataset can then be used in the method of the invention, since when the new dataset includes one or more unknown patient samples, a determination can be made as to whether the unknown patient sample(s) groups with the DESNT process or not (i.e. is assigned to the same process/group as the DESNT process/group). Alternatively, it is possible to correlate the expression of genes in the sample to the average gene expression level in the DESNT group. In this way, it is possible to carry out a correlation on a single unknown specimen.

In the second (ii) method, it is necessary to have a reference set of genes that is known to have altered expression (for example be down-regulated) in the DESNT cancer. This may have been obtained previously by conducting an LPD analysis on a plurality of datasets to determine the processes in each dataset. In that method, a common process can be identified based on gene correlations using the method described above. A subset of genes is identified that is consistently down-regulated in each expression profile of the DESNT process compared to non-DESNT processes of each dataset. In the analysis conducted by the present inventors, 45 genes were most commonly found to be downregulated in at least 80 out of 100 runs of the LPD analysis for each of 4 datasets analysed (Table 2). However, different genes might be identified if different datasets are used. It is likely there will be considerable overlap between the genes identified when different datasets are used. For example, in a second analysis performed by the investigators using a different combination of datasets 35 genes were found to be down regulated in at least 67 of 100 runs of the LPD analysis of each dataset (Table 5). There was a 27 gene overlap with the 45 commonly down-regulated genes identified in the first analysis.

Once the core down-regulated gene set is obtained, method (ii) can be carried out. In particular, DESNT cancer can be identified by demonstrating an overlap between the core down-regulated set of genes and the differentially expressed genes in one of the groups from the test dataset. "Overlap" may be 50%, 60%, 70%, 80%, 90% or 100% overlap. Preferably the overlap is at least 67%. The core down-regulated gene set may comprise at least 5, at least 10, at least 20, at least 30 or at least 40 genes. For example, the core down-regulated gene set may comprise the 45 genes of Table 1.

In one embodiment of the invention, there is therefore provided a method of classifying cancer, comprising comparing in a patient sample the level of expression of at least 5, at least 10, at least 20, at least 30, at least 40 or all 45 genes from Table 2 with the level of expression of the same genes in a healthy patient, or a patient not having aggressive or DESNT cancer. Alternatively, the method may comprise comparing in a patient sample the level of expression of at least 5, at least 10, at least 20, at least 30, or all 35 genes from Table 5. If the level of expression at least 50%, 60%, 70%, or 80% of genes in the patient sample is lower than in the control or reference genes, DESNT cancer is present and cancer progression is predicted.

When the new (test) dataset includes one or more unknown patient samples, a determination can be made as to whether the unknown patient sample(s) groups with the DESNT process or not.

In the third (iii) method, the DESNT cancer process identified by LPD is associated with poorer clinical outcome, for example patient death or cancer relapse when compared to non-DESNT cancer. Again, when the new (test) dataset includes one or more unknown patient samples, a determination can be made as to whether the unknown patient sample(s) groups with the DESNT process or not using this method (iii).

In the fourth (iv) method, it is not possible to run the LPD analysis on a single expression profile for the plurality of genes from a single patient sample and determine if that individual patient has DESNT cancer. Rather, in one method of the invention, it is necessary for the expression profile from the patient sample to be included in an analysis of a larger dataset. For example, step b) of Method 1 (the LPD analysis step) can therefore be conducted simultaneously on the patient expression profile and the reference dataset. In other words, the patient expression profile can be combined with the reference dataset prior to LPD analysis. If the additional patient sample groups with the DESNT cancer process, then the patient has DESNT cancer.

Thus, in one embodiment of the invention, the method comprises the steps of
  a) determining the level of expression of a plurality of genes in a sample obtained from the patient to provide a first expression profile;
  b) combining the first expression profile with a reference dataset, the reference dataset comprising expression profiles for the same plurality of genes obtained from different patients to obtain a combined dataset, optionally wherein the clinical outcome of the patients in the reference dataset is known;
  c) conducting an LPD analysis on the combined dataset;
  d) identifying a process (patient group) from the LPD analysis that is associated with DESNT cancer; and
  e) classifying the cancer or determining the presence or absence of DESNT cancer in the patient by determining whether or not the patient sample is in the process (patient group) associated with DESNT cancers.

As already noted, some of the methods of the invention can be carried out on multiple patient samples simultaneously. For example, level of expression of a plurality of genes in a sample may be determined in at least two samples obtained from at least two different patients to provide expression profiles for each patient.

The methods of the invention may also comprise assigning a unique label to the one or more patient expression profiles so they can be more easily identified during the analysis step.

In methods of the invention, identifying a process/patient group associated with DESNT cancer can be done using one of the first three methods mentioned above, specifically (i) correlation of gene expression levels with DESNT cancer groups in other datasets, (ii) demonstration of overlaps of differentially expressed genes between DESNT and non-DESNT cancers with a core down-regulated gene set, (iii) association with its poorer clinical outcome.

Assignment of an individual cancer as DESNT can be achieved using method (iv); carrying out LPD on a combined reference & patient dataset to determine if the patient dataset clusters with the known DESNT group. Method (iii) requires the clinical outcome of the patients in the reference dataset to be known.

By "clinical outcome" it is meant that for each patient in the reference dataset whether the cancer has progressed. For example, as part of an initial assessment, those patients may have prostate specific antigen (PSA) levels monitored. When it rises above a specific level, this is indicative of relapse and hence disease progression. Histopathological diagnosis may also be used. Spread to lymph nodes, and metastasis can also be used, as well as death of the patient from the cancer (or simply death of the patient in general) to define the clinical endpoint. Gleason scoring, cancer staging and multiple biopsies (such as those obtained using a coring method involving hollow needles to obtain samples) can be used. Clinical outcomes may also be assessed after treatment for prostate cancer. This is what happens to the patient in the long term. Usually the patient will be treated radically (prostatectomy, radiotherapy) to effectively remove or kill the prostate. The presence of a relapse or a subsequent rise in PSA levels (known as PSA failure) is indicative of progressed cancer. The DESNT cancer population identified using the method of the invention comprises a subpopulation of cancers that will progress more quickly.

Combinations of such methods (i), (ii) (iii) and (iv) may be used, and the skilled person is familiar with how to determine patient outcome for the patients in the reference dataset.

Accordingly, any of the methods of the invention may be carried out in patients in whom DESNT cancer is suspected. Importantly, the present invention allows a prediction of cancer progression before treatment of cancer is provided. This is particularly important for prostate cancer, since many patients will undergo unnecessary treatment for prostate cancer when the cancer would not have progressed even without treatment.

Additionally, the accuracy of the diagnosis can be increased by repeating the analysis, since the results of LPD can differ slightly each time the analysis is run even when the same data is being analysed. Often the variation is due to a different starting point of a random number generator (used as seed values) being used in each run of the LPD process and so even for a repeated run over the same dataset, multiple different outcomes can arise. Thus, carrying out the analysis a plurality of times and referring to the modal (most frequent) or mean (average) value can be beneficial. In some embodiments, the LPD analysis is carried out at least 2, 3, 5 or at least 20 times. In some embodiments, the analysis is carried out at least 50 times. In preferred embodiments, the analysis is carried out at least 100 times (i.e. it is repeated at least 99 times).

In embodiments where the analysis step is repeated, the step of determining whether the cancer is DESNT may require a comparison between the number of times the cancer is indicated as DESNT, and the number of times the cancer is indicated as non-DESNT (i.e. indolent or non-aggressive prostate cancer). For example, a determination that a patient has aggressive cancer may require the cancer to be DESNT in at least 50% of the analysis steps undertaken. In preferred embodiments, the cancer must be DESNT in at least 60%, or in more preferred embodiments, in at least 70%. In the most preferred embodiments, the cancer is DESNT in at least 67% of the analyses.

When the LPD analysis is undertaken, it splits the patients in the dataset being analysed into a number of processes (groups). In some embodiments of the invention, the step of determining whether a specific patient, whose clinical outcome is not known, has DESNT cancer requires the process (for example, the patient group associated with aggressive cancer) to be known. A patient sample added to the reference data set can then be present within the aggressive cancer (DESNT) group (or not, as the case may be) to determine whether the patient has aggressive cancer.

However, as noted above, it is not always necessary to know in advance the clinical outcome of the patients in the reference datasets. Either or both of these two methods for determining the presence of DESNT cancer can be used:
 (i) correlations of gene expression levels with DESNT cancer groups in other datasets; or
 (ii) demonstration of overlaps of differentially expressed genes between DESNT and non-DESNT cancers with a core down-regulated gene set.

The assignment of an individual cancer as DESNT can be achieved by carrying out LPD on a combined reference & patient dataset to determine if the patient dataset clusters with the known DESNT group.

Ideally, the presence or absence DESNT cancer in the reference datasets is determined using up to three of these methods:
 i. correlations of gene expression levels with DESNT cancer groups in another dataset or datasets,
 ii. demonstration of overlaps of differentially expressed genes between DESNT and non-DESNT cancers with a core down-regulated gene set,
 iii. correlation with clinical outcome.

The step of determining the level of expression of a plurality of genes in the patient sample can be done by any suitable means known to a person of skill in the art, such as those discussed elsewhere herein, or methods as discussed in any of Prokopec S D, Watson J D, Waggott D M, Smith A B, Wu A H, Okey A B et al. Systematic evaluation of medium-throughput mRNA abundance platforms. RNA 2013; 19: 51-62; Chatterjee A, Leichter A L, Fan V, Tsai P, Purcell R V, Sullivan M J et al. A cross comparison of technologies for the detection of microRNAs in clinical FFPE samples of hepatoblastoma patients. Sci Rep 2015; 5: 10438; Pollock J D. Gene expression profiling: methodological challenges, results, and prospects for addiction research. Chem Phys Lipids 2002; 121: 241-256; Mantione K J, Kream R M, Kuzelova H, Ptacek R, Raboch J, Samuel J M et al. Comparing bioinformatic gene expression profiling methods: microarray and RNA-Seq. Med Sci Monit Basic Res 2014; 20: 138-142; Casassola A, Brammer S P, Chaves M S, Ant J. Gene expression: A review on methods for the study of defense-related gene differential expression in plants. American Journal of Plant Research 2013; 4, 64-73; Ozsolak F, Milos P M. RNA sequencing: advances, challenges and opportunities. Nat Rev Genet 2011; 12: 87-98.

In embodiments of the invention, the analysis step in any of the methods can be computer implemented. The invention also provides a computer readable medium programmed to carry out any of the methods of the invention.

In a further embodiment of the invention, there is provided a method of classifying prostate cancer, for example diagnosing aggressive prostate cancer in a patient, or identifying a patient with a poor prognosis for prostate cancer, (i.e. a patient with DESNT prostate cancer) comprising:
 a) providing a reference dataset where DESNT status of each patient sample in the dataset is known (for example as determined by LPD analysis);
 b) selecting from this dataset a plurality of genes, wherein the plurality of genes comprises at least 5, at least 10, at least 20, at least 30, at least 40 or at least 45 genes selected from the group listed in Table 2 or at least 5, at least 10, at least 15 or at least 20 genes selected from the group listed in Table 3;

c) optionally:
(i) determining the expression status of at least 1 further, different, gene in the patient sample as a control, wherein the control gene is not a gene listed in Table 2 or Table 3;
(ii) determining the relative levels of expression of the plurality of genes and of the control gene(s); and d) using the expression status of those selected genes to apply a supervised machine learning algorithm (for example random forest analysis) on the dataset to obtain a predictor for DESNT cancer;

e) determining the expression status of the same plurality of genes in a sample obtained from the patient to provide a patient expression profile;

f) optionally normalising the patient expression profile to the reference dataset; and g) applying the predictor to the patient expression profile to classify the cancer, determine the presence of aggressive cancer, or determining whether the patient has a poor prognosis (i.e. determine whether the patient's cancer is DESNT or non-DESNT).

This method and variants thereof are hereafter referred to as Method 2. The genes of Table 2 were identified by the inventors by conducting an LPD analysis on multiple datasets and determining genes that were commonly down-regulated in the DESNT groups. The genes of Table 3 were identified by the inventors by conducting a LASSO analysis as described in Method 4.

In a preferred embodiment, the control genes used in step (i) are selected from the housekeeping genes listed in Table 6 or Table 7. Table 7 is particularly relevant to prostate cancer. In some embodiments of the invention, at least 1, at least 2, at least 5 or at least 10 housekeeping genes. Preferred embodiments use at least 2 housekeeping genes. Step (ii) above may comprise determining a ratio between the test genes and the housekeeping genes.

In a further method of the invention, there is provided a method of diagnosing aggressive cancer in a patient (such as aggressive prostate cancer), or identifying a patient with a poor prognosis for cancer, (i.e. a patient with DESNT cancer) comprising:

a) providing a reference dataset where DESNT status of each patient sample in the dataset is known (for example as determined by LPD analysis);
b) selecting from this dataset a plurality of genes;
c) using the expression status of those selected genes to apply a supervised machine learning algorithm (for example random forest analysis) on the dataset to obtain a predictor for DESNT cancers;
d) determining the expression status of the same plurality of genes in a sample obtained from the patient to provide a patient expression profile;
e) optionally normalising the patient expression profile to the reference dataset; and
f) applying the predictor to the patient expression profile to determine whether the patient's cancer is DESNT or non-DESNT.

This method and variants thereof are hereafter referred to as Method 3.

In an additional method of the invention, there is provided a method of diagnosing aggressive cancer in a patient (such as aggressive prostate cancer), or identifying a patient with a poor prognosis for cancer, (i.e. a patient with DESNT cancer) comprising:

a) providing one or more reference datasets where DESNT status of each patient sample in the datasets is known (for example as determined by LPD analysis);
b) selecting from this dataset a plurality of genes whose expression statuses are known to vary between DESNT and non-DESNT cancer (for example a plurality of genes listed in Table 4, for example at least 100, at least 200, at least 300, at least 400, at least 500, or at least 1000 genes listed in Table 4);
c) applying a LASSO logistic regression model analysis on the selected genes to identify a subset of the selected genes that [best] identify DESNT cancer;
d) using the expression status of this subset of selected genes to apply a supervised machine learning algorithm (for example random forest analysis) on the dataset to obtain a predictor for DESNT cancers;
e) determining the expression status of the subset of selected genes in a sample obtained from the patient to provide a patient expression profile;
f) optionally normalising the patient expression profile to the reference dataset(s); and
g) applying the optimal predictor to the patient expression profile to determine whether the patient's cancer is DESNT or non-DESNT.

This method and variants thereof are hereafter referred to as Method 4.

DESNT patient populations identified using methods involving Random Forest analysis are referred to as "RF-DESNT". DESNT patient populations identified using methods involving LPD analysis are referred to as "LPD-DESNT".

The presents inventors wished to develop a classifier that, unlike LPD, was not computer processing intensive and that could be applied to a wider range of datasets. Methods 2 to 4 provide such solutions, and can be used to predict cancer progression. Therefore, the present invention provides a method for identifying a gene signature that can be used in random forest classification to identify RF-DESNT cancers and predict cancer progression.

Supervised machine learning algorithms or general linear models are used to produce a predictor of DESNT status. The preferred approach is random forest analysis but alternatives such as support vector machines, neural networks, naive Bayes classifier, or nearest neighbour algorithms could be used. Such methods are known and understood by the skilled person.

Random forest analysis can be used to predict whether a cancer is DESNT or not. Methods 2 to 4 above require considerably less computing power than Method 1 and hence can be carried out more easily.

A random forest analysis is an ensemble learning method for classification, regression and other tasks, which operates by constructing a multitude of decision trees during training and outputting the class that is the mode of the classes (classification) or mean prediction (regression) of the individual decision trees. Accordingly, a random forest corrects for overfitting of data to any one decision tree.

A decision tree comprises a tree-like graph or model of decisions and their possible consequences, including chance event outcomes. Each internal node of a decision tree typically represents a test on an attribute or multiple attributes (for example whether an expression level of a gene in a cancer sample is above a predetermined threshold), each branch of a decision tree typically represents an outcome of a test, and each leaf node of the decision tree typically represents a class (classification) label.

In a random forest analysis, an ensemble classifier is typically trained on a training dataset (also referred to as a reference dataset) where the DESNT group, for example as determined by LPD, is known. The training produces a model that is a predictor for membership of DESNT or non-DESNT. The groups identified by RF can be referred to as RF-DESNT and RF-non-DESNT). Once trained the random forest classifier can then be applied to a dataset from an unknown sample. This step is deterministic i.e. if the classifier is subsequently applied to the same dataset repeatedly, it will consistently sort each cancer of the new dataset into the same class each time.

The ensemble classifier acts to classify each cancer sample in the new dataset as either a RF-DESNT cancer or a RF-non-DESNT cancer. Accordingly, when the random forest analysis is undertaken, the ensemble classifier splits the cancers in the dataset being analysed into a number of classes. The number of classes may be 2 (i.e. the ensemble classifier may group or classify the patients in the dataset into a DESNT class, or DESNT group, containing the DESNT cancers and a non-DESNT class, or non-DESNT group, containing other cancers).

Each decision tree in the random forest is an independent predictor that, given a cancer sample, assigns it to one of the classes which it has been trained to recognize, i.e. DESNT/non-DESNT. Each node of each decision tree comprises a test concerning one or more genes of the same plurality of genes as obtained in the cancer sample from the patient. Several genes may be tested at the node. For example, a test may ask whether the expression level(s) of one or more genes of the plurality of genes is above a predetermined threshold.

Variations between decision trees will lead to each decision tree assigning a sample to a class in a different way. The ensemble classifier takes the classification produced by all the independent decision trees and assigns the sample to the class on which the most decision trees agree.

The plurality of genes for which the level of expression is determined in step b) of Method 2, 3 or 4 (and on which the decisions of the random forest analysis are based) can be chosen using any suitable method. One possible method is to apply an LPD analysis or other Bayesian statistical analysis to a training dataset and determine the cancers that are assigned to the DESNT group/process. Then to select those genes that are shown to be consistently down-regulated in DESNT cancers compared to non-DESNT cancer. This down-regulation may be consistent across several different datasets on which LPD analysis has been conducted. In some embodiments, the plurality of genes used in step b) of Methods 2 3 and 4 comprises at least 5, at least 10, at least 15, at least 20, at least 30, at least 40 or at least 45 genes. In particular, the plurality of genes used in step b) of Method 2 and Method 3 comprises at least 5, at least 10, at least 15, at least 20, at least 30, at least 40, or all 45 genes listed in Table 2.

Another possible method (as in Method 4) is to perform a least absolute shrinkage and selection operator (LASSO) analysis on a training dataset and to select those genes that are found to best characterise DESNT membership. A logistic regression model is derived with a constraint on the coefficients such that the sum of the absolute value of the model coefficients is less than some threshold. This has the effect of removing genes that either don't have the ability to predict DESNT membership or are correlated with the expression of a gene already in the model. LASSO is a mathematical way of finding the genes that are most likely to distinguish the DESNT vs non-DESNT samples in a training or reference dataset. The subset of genes is step e) of Method 4 may comprise at least 5, at least 10, at least 15, or at least 20 genes. In a particular embodiment, steps a) and b) of Method 4 are not required, and instead the method can begin at step c) of Method 4 using at least 5, at least 10, at least 15 or at least 20 of the subset of genes identified in Table 3.

When devising Method 4, the present inventors carried out the following steps. As a starting point all genes with significantly altered expression in DESNT cancers (compared to Non-DESNT cancers) that were generally present in at least two of the five datasets analysed by the inventors (genes in total) were identified. A representative DESNT LPD classification for carrying out LASSO was chosen from the analysed MSKCC dataset. In practice, the DESNT classification used could use a representative run, selected for example by the mean p-value of some statistical test, or a summary of all the runs of some description, for example DESNT status is assigned to a sample if in at least 50% of runs it is assigned as DESNT.

A LASSO logistic regression model was used to predict DESNT membership in the MSKCC dataset leading to the selection of a set of 20 genes that characterized DESNT membership. These genes are listed in Table 3. Removal of these 20 genes from the 1669 gene and repetition of this procedure identified further sets of genes that could characterise DESNT memberships. Additional sets of genes could be obtained by carrying out the same analyses using other datasets that have been analysed by LPD as a starting point.

The invention provides a further list of genes that are associated with or predictive of DESNT cancer or cancer progression. For example, in one embodiment, a LASSO analysis can be used to provide an expression signature that is indicative or predictive of DESNT cancer, in particular DESNT prostate cancer. The expression signature may also be considered a biomarker panel, and comprises at least 5, at least 10, at least 12, at least 15 or all 20 genes selected from the group consisting of the genes listed in Table 3.

Note that in any methods of the invention, the statistical analysis can be conducted on the level of expression of the genes being analysed, or the statistical analysis can be conducted on a ratio calculated according to the relative level of expression of the genes and of any control genes.

For example, with reference to method 1, the method may comprise the steps of:
a) determining the level of expression of a plurality of genes in a sample obtained from the patient to provide a patient expression profile;
b) determining the expression status of at least 1 further, different, gene in the patient sample as a control, wherein the control genes are not any of the genes whose level of expression is determined in step a);
c) determining the relative levels of expression of the plurality of genes and of the control gene(s);
d) providing a reference dataset comprising expression profiles from different patients and determining the relative levels of expression of the same plurality of genes used in step a) and the same control gene or control genes used in step b);
e) conducting a statistical Bayesian clustering analysis or other clustering analyses on the relative expression levels obtained in steps c) and d);
f) optionally repeating the analysis step e) multiple times; and
g) classifying the cancer, determining whether the patient has cancer, or determining whether the patient has a poor prognosis (i.e. the patient has DESNT cancer).

With reference to method 2, the method may comprise the steps of:
a) providing a reference dataset where DESNT status of each patient sample in the dataset is known (for example as determined by LPD analysis);
b) selecting from this dataset a plurality of genes, wherein the plurality of genes comprises at least 5, at least 10, at least 20, at least 30, at least 40 or at least 45 genes selected from the group listed in Table 2 or at least 5, at least 10, at least 15 or at least 20 genes selected from the group listed in Table 3;
c) determining the expression status of at least 1 further, different, gene in the patient sample as a control;
d) determining the relative levels of expression of the plurality of genes and of the control gene(s);
e) using the relative levels of expression to apply a supervised machine learning algorithm (for example random forest analysis) on the reference dataset to obtain a predictor for DESNT cancer;
f) determining the relative levels of expression of the same plurality of genes and control genes in a sample obtained from the patient to provide a patient expression profile;
g) optionally normalising the patient expression profile to the reference dataset; and
h) applying the predictor to the patient expression profile to classify the cancer, determine the presence of aggressive cancer, or determining whether the patient has a poor prognosis (i.e. determine whether the patient's cancer is DESNT or non-DESNT).

With reference to method 3, the method may comprise the steps of:
a) providing a reference dataset where DESNT status (i.e. cancer classification) of each patient sample in the dataset is known (for example as determined by LPD analysis);
b) selecting from this dataset of a plurality of genes;
c) determining the expression status of at least 1 further, different, gene in the patient sample as a control;
d) determining the relative levels of expression of the plurality of genes and of the control gene(s);
e) using the relative expression levels of those selected genes to apply a supervised machine learning algorithm (for example random forest analysis) on the dataset to obtain a predictor for DESNT cancers;
f) providing a patient expression profile comprising the relative levels of expression in a sample obtained from the patient, wherein the relative levels of expression is obtained using the same plurality of genes selected in step b) and the same control gene(s) used in step d);
g) optionally normalising the patient expression profile to the reference dataset; and
h) applying the predictor to the patient expression profile to classify the cancer, determine the presence of aggressive cancer, or determining whether the patient has a poor prognosis (i.e. determine whether the patient's cancer is DESNT or non-DESNT).

With reference to method 4, the method may comprise the steps of:
a) providing one or more reference datasets where DESNT status of each patient sample in the datasets is known (for example as determined by LPD analysis);
b) selecting from this dataset a plurality of genes whose expression statuses are known to vary between DESNT and non-DESNT cancer (for example a plurality of genes listed in Table 4, for example at least 100, at least 200, at least 300, at least 400, at least 500 or at least 1000 genes listed in Table 4);
c) applying a LASSO logistic regression model analysis on the selected genes to identify a subset of the selected genes that identify DESNT cancer;
d) determining the expression status of at least 1 further, different, gene in the patient sample as a control;
e) determining the relative levels of expression of the subset of genes and of the control gene(s);
f) using the relative expression levels to apply a supervised machine learning algorithm (for example random forest analysis) on the dataset to obtain a predictor for DESNT cancers;
g) providing a patient expression profile comprising the relative levels of expression in a sample obtained from the patient, wherein the relative levels of expression are obtained using the same subset of genes selected in step c) and the same control gene(s) used in step e);
h) optionally normalising the patient expression profile to the reference dataset(s); and
i) applying the predictor to the patient expression profile to classify the cancer, determine the presence of aggressive cancer, or determining whether the patient has a poor prognosis (i.e. determine whether the patient's cancer is DESNT or non-DESNT).

In any of the above methods, the control gene or control genes may be selected from the genes listed in Table 6 or Table 7.

Datasets

The present inventors used MSKCC, CancerMap, Stephenson, CamCap and TOGA datasets in their analysis. However, other suitable datasets are and will become available skilled person. Generally, the datasets comprise a plurality of expression profiles from patient or tumour samples. The size of the dataset can vary. For example, the dataset may comprise expression profiles from at least 20, optionally at least 50, at least 100, at least 200, at least 300, at least 400 or at least 500 patient or tumour samples. Preferably the dataset comprises expression profiles from at least 500 patients or tumours.

In some embodiments, the methods of the invention use expression profiles from multiple datasets. For example, in some embodiments, the methods use expression profiles from at least 2 datasets, each data set comprising expression profiles from at least 250 patients or tumours.

The patient or tumour expression profiles may comprise information on the levels of expression of a subset of genes, for example at least 10, at least 40, at least 100, at least 500, at least 1000, at least 1500, at least 2000, at least 5000 or at least 10000 genes. Preferably, the patient expression profiles comprise expression data for at least 500 genes. In the analysis steps of the various Methods of the invention, any selection of a subset of genes will be taken from the genes present in the datasets.

Classification of Cancer

The methods and biomarkers disclosed herein are useful in classifying cancers according to their likelihood of progression (and hence are useful in the prognosis of cancer). The present invention is particularly focused on prostate cancer, but the methods can be used for other cancers. In particular, the list of genes in Table 2, for example, has been found to be indicative of progression of a range of cancers, including prostate cancer. Cancers that are likely or will progress are referred to by the inventors as DESNT cancers. References to DESNT cancer herein refer to cancers that are predicted to progress. References to DESNT status herein refer to an indicator of whether or not a cancer will progress. Aggressive cancers are cancers that progress.

Cancer types that can be classified according to methods of the invention include acute lymphoblastic leukemia, acute or chronic lymphocytic or granulocytic tumor, acute myeloid leukemia, acute promyelocytic leukemia, adenocarcinoma, adenoma, adrenal cancer, basal cell carcinoma, bone cancer, brain cancer, breast cancer, bronchi cancer, cervical dysplasia, chronic myelogenous leukemia, colon cancer, epidermoid carcinoma, Ewing's sarcoma, gallbladder cancer, gallstone tumor, giant cell tumor, glioblastoma multiforma, hairy-cell tumor, head cancer, hyperplasia, hyperplastic corneal nerve tumor, in situ carcinoma, intestinal ganglioneuroma, islet cell tumor, Kaposi's sarcoma, kidney cancer, larynx cancer, leiomyomater tumor, liver cancer, lung cancer, lymphomas, malignant carcinoid, malignant hypercalcemia, malignant melanomas, marfanoid habitus tumor, medullary carcinoma, metastatic skin carcinoma, mucosal neuromas, mycosis fungoide, myelodysplastic syndrome, myeloma, neck cancer, neural tissue cancer, neuroblastoma, osteogenic sarcoma, osteosarcoma, ovarian tumor, pancreas cancer, parathyroid cancer, pheochromocytoma, polycythemia vera, primary brain tumor, prostate cancer, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, or Wilm's tumor.

Of particular relevance to the present invention is prostate cancer, colorectal cancer and breast cancer.

References herein are made to "aggressive cancer" including "aggressive prostate cancer". Aggressive prostate cancer can be defined as a cancer that requires treatment to prevent, halt or reduce disease progression and potential further complications (such as metastases or metastatic progression). Ultimately, aggressive prostate cancer is prostate cancer that, if left untreated, will spread outside the prostate and may kill the patient. The present invention is useful in detecting some aggressive cancers, including aggressive prostate cancers.

Prostate cancer can be classified according to The American Joint Committee on Cancer (AJCC) tumour-nodes-metastasis (TNM) staging system. The T score describes the size of the main (primary) tumour and whether it has grown outside the prostate and into nearby organs. The N score describes the spread to nearby (regional) lymph nodes. The M score indicates whether the cancer has metastasised (spread) to other organs of the body:

T1 tumours are too small to be seen on scans or felt during examination of the prostate—they may have been discovered by needle biopsy, after finding a raised PSA level. T2 tumours are completely inside the prostate gland and are divided into 3 smaller groups:
  T2a—The tumour is in only half of one of the lobes of the prostate gland;
  T2b—The tumour is in more than half of one of the lobes;
  T2c—The tumour is in both lobes but is still inside the prostate gland.
T3 tumours have broken through the capsule (covering) of the prostate gland—they are divided into 2 smaller groups:
  T3a—The tumour has broken through the capsule (covering) of the prostate gland;
  T3b—The tumour has spread into the seminal vesicles.
T4 tumours have spread into other body organs nearby, such as the rectum (back passage), bladder, muscles or the sides of the pelvic cavity. Stage T3 and T4 tumours are referred to as locally advanced prostate cancer.

Lymph nodes are described as being 'positive' if they contain cancer cells. If a lymph node has cancer cells inside it, it is usually bigger than normal. The more cancer cells it contains, the bigger it will be:
  NX—The lymph nodes cannot be checked;
  N0—There are no cancer cells in lymph nodes close to the prostate;
  N1—There are cancer cells present in lymph nodes.
M staging refers to metastases (cancer spread):
  M0—No cancer has spread outside the pelvis;
  M1—Cancer has spread outside the pelvis;
  M1a—There are cancer cells in lymph nodes outside the pelvis;
  M1b—There are cancer cells in the bone;
  M1c—There are cancer cells in other places.

Prostate cancer can also be scored using the Gleason grading system, which uses a histological analysis to grade the progression of the disease. A grade of 1 to 5 is assigned to the cells under examination, and the two most common grades are added together to provide the overall Gleason score. Grade 1 closely resembles healthy tissue, including closely packed, well-formed glands, whereas grade 5 does not have any (or very few) recognisable glands. Scores of less than 6 have a good prognosis, whereas scores of 6 or more are classified as more aggressive. The Gleason score was refined in 2005 by the International Society of Urological Pathology and references herein refer to these scoring criteria (Epstein J I, Allsbrook W C Jr, Amin M B, Egevad L L; ISUP Grading Committee. The 2005 International Society of Urological Pathology (ISUP) Consensus Conference on Gleason grading of prostatic carcinoma. Am J Surg Pathol 2005; 29(9):1228-42). The Gleason score is detected in a biopsy, i.e. in the part of the tumour that has been sampled. A Gleason 6 prostate may have small foci of aggressive tumour that have not been sampled by the biopsy and therefore the Gleason is a guide. The lower the Gleason score the smaller the proportion of the patients will have aggressive cancer. Gleason score in a patient with prostate cancer can go down to 2, and up to 10. Because of the small proportion of low Gleasons that have aggressive cancer, the average survival is high, and average survival decreases as Gleason increases due to being reduced by those patients with aggressive cancer (i.e. there is a mixture of survival rates at each Gleason score).

Prostate cancers can also be staged according to how advanced they are. This is based on the TMN scoring as well as any other factors, such as the Gleason score and/or the PSA test. The staging can be defined as follows:
  Stage I:
  T1, N0, M0, Gleason score 6 or less, PSA less than 10 OR
  T2a, N0, M0, Gleason score 6 or less, PSA less than 10
  Stage IIA:
  T1, N0, M0, Gleason score of 7, PSA less than 20 OR
  T1, N0, M0, Gleason score of 6 or less, PSA at least 10 but less than 20: OR
  T2a or T2b, N0, M0, Gleason score of 7 or less, PSA less than 20
  Stage IIB:
  T2c, N0, M0, any Gleason score, any PSA OR
  T1 or T2, N0, M0, any Gleason score, PSA of 20 or more: OR
  T1 or T2, N0, M0, Gleason score of 8 or higher, any PSA
  Stage III:
  T3, N0, M0, any Gleason score, any PSA
  Stage IV:
  T4, N0, M0, any Gleason score, any PSA OR
  Any T, N1, M0, any Gleason score, any PSA: OR Any T, any N, M1, any Gleason score, any PSA In the present invention, an aggressive cancer is defined functionally or clinically: namely a cancer that can progress. This can be measured by PSA failure. When a patient has surgery or radiation therapy, the prostate cells are killed or removed. Since PSA is only made by prostate cells the PSA level in the patient's blood reduces to a very low or undetectable amount. If the cancer starts to recur, the PSA level increases and becomes detectable again. This is referred to as "PSA failure". An alternative measure is the presence of metastases or death as endpoints.

Increase in Gleason and stage as defined above can also be considered as progression. However, a DESNT characterisation is independent of Gleason, stage and PSA. It provides additional information about the development of aggressive cancer in addition to Gleason, stage and PSA. It is therefore a useful independent predictor of outcome. Nevertheless, DESNT status can be combined with Gleason, tumour stage and/or PSA.

Thus, the methods of the invention provide methods of classifying cancer, some methods comprising determining the expression level or expression status of a one or members of a biomarker panel. The panel of genes may be determined using a method of the invention. In some embodiments, the panel of genes may comprise at least 5, at least 10, at least 15 or all 20 of the genes listed in Table 3. The panel of genes may comprise at least 5, at least 10, at least 20, at least 30, at least 40 or all 45 genes listed in Table 2. Other biomarker panels of the invention, or those generated using methods of the invention, may also be used.

The cancer may be described as progressive when the status of one or more of those genes (for example at least 50%, at least 60%, at least 70%, at least 80%, at least 90%, at least 95% or 100% of the genes) is considered to have an abnormal status. An abnormal status can be defined as an expression status (for example as determined by the level of expression, by DNA methylation or other epigenetic factors) that differs from a healthy or non-progressive cancer state. This may be determined according to a previously determined reference expression status of the same genes being analysed, or may be achieved by determining the status of one or more control or housekeeping genes. Housekeeping genes are generally considered to be expressed at the same levels in progressed and non-progressed patients. Therefore, it is possible to determine the ratio of the test genes to your control genes. The ratio would be different in normal and progressed tissue. As noted above, the housekeeping genes of Table 6 or Table 7 can be used.

For example, in one embodiment, a cancer is defined as progressive or potentially/likely to be progressive when at least 50%, at least 60%, at least 70%, at least 80% or at least 90% of at least 15 genes listed in Table 3 are determined to have an abnormal expression status (for example at least 80% of at least 15 genes in Table 3). In another embodiment, a cancer is defined as progressive or potentially/likely to be progressive when at least 50%, at least 60%, at least 70%, at least 80% or at least 90% of at least 40 genes listed in Table 2 are determined to have an abnormal expression status (for example at least 80% of at least 40 genes in Table 2).

Determining the expression status of a gene may comprise determining the level of expression of the gene. Expression status and levels of expression as used herein can be determined by methods known the skilled person. For example, this may refer to the up or down-regulation of a particular gene or genes, as determined by methods known to a skilled person. Epigenetic modifications may be used as an indicator of expression, for example determining DNA methylation status, or other epigenetic changes such as histone marking, RNA changes or conformation changes. Epigenetic modifications regulate expression of genes in DNA and can influence efficacy of medical treatments among patients. Aberrant epigenetic changes are associated with many diseases such as, for example, cancer. DNA methylation in animals influences dosage compensation, imprinting, and genome stability and development. Methods of determining DNA methylation are known to the skilled person (for example methylation-specific PCR, matrix-assisted laser desorption/ionization time-of-flight mass spectrometry, use of microarrays, reduced representation bisulfate sequencing (RRBS) or whole genome shotgun bisulfate sequencing (WGBS). In addition, epigenetic changes may include changes in conformation of chromatin.

The expression status of a gene may also be judged examining epigenetic features. Modification of cytosine in DNA by, for example, methylation can be associated with alterations in gene expression. Other way of assessing epigenetic changes include examination of histone modifications (marking) and associated genes, examination of non-coding RNAs and analysis of chromatin conformation. Examples of technologies that can be used to examine epigenetic status are provided in the following publications:
1. Zhang, G. & Pradhan, S. Mammalian epigenetic mechanisms. IUBMB life (2014).
2. Grøb∴k, K. et al. A critical appraisal of tools available for monitoring epigenetic changes in clinical samples from patients with myeloid malignancies. Haematologica 97, 1380-1388 (2012).
3. Ulahannan, N. & Greally, J. M. Genome-wide assays that identify and quantify modified cytosines in human disease studies. Epigenetics Chromatin 8, 5 (2015).
4. Crutchley, J. L., Wang, X., Ferraiuolo, M. A. & Dostie, J. Chromatin conformation signatures: ideal human disease biomarkers? Biomarkers (2010).
5. Esteller, M. Cancer epigenomics: DNA methylomes and histone-modification maps. Nat. Rev. Genet. 8, 286-298 (2007).

If an expression status is found to be abnormal, this refers to a situation in which the biomarker's status in a particular sample differs from the status generally found in average samples (i.e. healthy samples or samples obtained from patients that do not have DESNT cancer). In the present invention, the presence of an abnormal expression status can be indicative of DESNT cancer. For example, an abnormal status might be determined using epigenetic factors or determining the level of gene expression (for example RNA level). With reference to the genes listed in Table 2, a decrease in gene expression or a change in expression status that results in a decrease in expression of that gene is indicative of DESNT cancer. Thus, the presence of an abnormal expression status in at least 5, at least 10, at least 20, at least 30, at least 40 or all 45 genes listed in Table 2 is indicative of DESNT cancer. Alternatively, a threshold may be determined by the skilled person that is an indicative measure of the expression status of at least 5, at least 10, at least 20, at least 30, at least 40 or all 45 genes listed in Table 2. If, for a given patient sample, the average expression status is below said threshold (due to a decrease in expression of one or more genes, or preferably the majority of the genes being analysed), this is indicative of DESNT cancer.

In some embodiments, a decrease in the expression status or level of expression of at least 5, at least 10, at least 20, at least 30, at least 40 or all 45 genes listed in Table 2 is indicative of DESNT cancer.

In some cases, a new biomarker panel may have been generated using the methods of the invention, and that used to classify cancer. For example, in a second analysis performed by the investigators using a different combination of datasets 35 genes were found to be down regulated in at least 67 of 100 runs of the LPD analysis of each dataset (Table 5). There was a 27 gene overlap with the 45 commonly down-regulated genes identified in the first analysis. Therefore, the biomarker panel may comprise at least 5, at least 10, at least 20, at least 30 or all 35 genes listed in table 5.

Usually, in order to determine if an expressions status is abnormal, it is necessary to include in the method a determination of the expression status of at least 1 control gene in the patient sample. Based on the expression status of the at least 1 control gene, an index value for the prognostic genes can be determined. If the index value is below a certain threshold, because of a decrease in expression of the prognostic genes, this is indicative of cancer progression or predictive of cancer progression (i.e. DESNT cancer). Said threshold is determined by normalising the expression levels of the prognostic genes using the 1 or more control genes and determining if at least 50%, at least 60%, at least 70%, at least 80%, at least 90% or at least 95% of the prognostic genes have a decreased expression level. In some embodiments, 100% of the prognostic genes having a decreased expression level is indicative or predictive of cancer progression (i.e. DESNT cancer).

In one embodiment of the invention, the method comprises:
a) enriching a biological sample for an analyte of interest (for example RNA, DNA or protein); and
b) determining the epigenetic status of the analyte of interest in the enriched sample.

Proteins can also be used to determine expression levels, and suitable method are known to the skilled person. This is also discussed further below.

Apparatus and Media

The present invention also provides an apparatus configured to perform any method of the invention.

FIG. 4 shows an apparatus or computing device 100 for carrying out a method as disclosed herein. Other architectures to that shown in FIG. 3 may be used as will be appreciated by the skilled person.

Referring to the Figure, the meter 100 includes a number of user interfaces including a visual display 110 and a virtual or dedicated user input device 112. The meter 100 further includes a processor 114, a memory 116 and a power system 118. The meter 100 further comprises a communications module 120 for sending and receiving communications between processor 114 and remote systems. The meter 100 further comprises a receiving device or port 122 for receiving, for example, a memory disk or non-transitory computer readable medium carrying instructions which, when operated, will lead the processor 114 to perform a method as described herein.

The processor 114 is configured to receive data, access the memory 116, and to act upon instructions received either from said memory 116, from communications module 120 or from user input device 112. The processor controls the display 110 and may communicate date to remote parties via communications module 120.

The memory 116 may comprise computer-readable instructions which, when read by the processor, are configured to cause the processor to perform a method as described herein.

The present invention further provides a machine-readable medium (which may be transitory or non-transitory) having instructions stored thereon, the instructions being configured such that when read by a machine, the instructions cause a method as disclosed herein to be carried out.

Other Methods and Uses of the Invention

The methods of the invention may be combined with a further test to further assist the diagnosis, for example a PSA test, a Gleason score analysis, or a determination of the staging of the cancer. In PSA methods, the amount of prostate specific antigen in a blood sample is quantified. Prostate-specific antigen is a protein produced by cells of the prostate gland. If levels are elevated in the blood, this may be indicative of prostate cancer. An amount that constitutes "elevated" will depend on the specifics of the patient (for example age), although generally the higher the level, the more like it is that prostate cancer is present. A continuous rise in PSA levels over a period of time (for example a week, a month, 6 months or a year) may also be a sign of prostate cancer. A PSA level of more than 4 ng/ml or 10 ng/ml, for example, may be indicative of prostate cancer, although prostate cancer has been found in patients with PSA levels of 4 or less.

In some embodiments of the invention, the methods are able to differentially diagnose aggressive cancer (such as aggressive prostate cancer) from non-aggressive cancer. This can be achieved by determining the DESNT status of the cancer. Alternatively or additionally, this may be achieved by comparing the level of expression found in the test sample for each of the genes being quantified with that seen in patients presenting with a suitable reference, for example samples from healthy patients, patients suffering from non-aggressive cancer, or using the control or housekeeping genes as discussed herein. In this way, unnecessary treatment can be avoided and appropriate treatment can be administered instead (for example antibiotic treatment for prostatitis, such as fluoxetine, gabapentin or amitriptyline, or treatment with an alpha reductase inhibitor, such as Finasteride).

In one embodiment of the invention, the method comprises the steps of:
1) detecting RNA in a biological sample obtained from a patient; and
2) quantifying the expression levels of each of the RNA molecules.

The RNA transcripts detected correspond to the biomarkers being quantified (and hence the genes whose expression levels are being measured). In some embodiments, the RNA being detected is the RNA (e.g. mRNA, lncRNA or small RNA) corresponding to at least 40 genes listed in Table 2 (optionally at least all of the genes listed in Table 2), or at least 15 genes listed in Table 3 (optionally all of the genes listed in Table 3). Such methods may be undertaken on a sample previously obtained from a patient, optionally a patient that has undergone a DRE to massage the prostate and increase the amount of RNA in the resulting sample. Alternatively, the method itself may include a step of obtaining a biological sample from a patient.

In one embodiment, the RNA transcripts detected correspond to a selection or all of the genes listed in Table 1. A subset of genes can then be selected for further analysis, such as LDP analysis.

In some embodiments of the invention, the biological sample may be enriched for RNA (or other analyte, such as protein) prior to detection and quantification. The step of enrichment is optional, however, and instead the RNA can be obtained from raw, unprocessed biological samples, such as whole urine. The step of enrichment can be any suitable pre-processing method step to increase the concentration of RNA (or other analyte) in the sample. For example, the step of enrichment may comprise centrifugation and filtration to remove cells from the sample.

In one embodiment of the invention, the method comprises:
a) enriching a biological sample for RNA by amplification, filtration or centrifugation, optionally wherein the biological sample has been obtained from a patient that has undergone DRE;
b) detecting RNA transcripts in the enriched sample; and
c) quantifying the expression levels of each of the detected RNA molecules.

The step of detection may comprise a detection method based on hybridisation, amplification or sequencing, or molecular mass and/or charge detection, or cellular phenotypic change, or the detection of binding of a specific molecule, or a combination thereof. Methods based on hybridisation include Northern blot, microarray, NanoString, RNA-FISH, branched chain hybridisation assay analysis, and related methods. Methods based on amplification include quantitative reverse transcription polymerase chain reaction (qRT-PCT) and transcription mediated amplification, and related methods. Methods based on sequencing include Sanger sequencing, next generation sequencing (high throughput sequencing by synthesis) and targeted RNAseq, nanopore mediated sequencing (MinION), Mass Spectrometry detection and related methods of analysis. Methods based on detection of molecular mass and/or charge of the molecule include, but is not limited to, Mass Spectrometry. Methods based on phenotypic change may detect changes in test cells or in animals as per methods used for screening miRNAs (for example, see Cullen & Arndt, *Immunol. Cell Biol.*, 2005, 83:217-23). Methods based on binding of specific molecules include detection of binding to, for example, antibodies or other binding molecules such as RNA or DNA binding proteins.

In some embodiments, the method may comprise a step of converting RNA transcripts into cDNA transcripts. Such a method step may occur at any suitable time in the method, for example before enrichment (if this step is taking place, in which case the enrichment step is a cDNA enrichment step), before detection (in which case the detection step is a step of cDNA detection), or before quantification (in which case the expression levels of each of the detected RNA molecules by counting the number of transcripts for each cDNA sequence detected).

Methods of the invention may include a step of amplification to increase the amount of RNA or cDNA that is detected and quantified. Methods of amplification include PCR amplification.

In some methods of the invention, detection and quantification of cDNA-binding molecule complexes may be used to determine gene expression. For example, RNA transcripts in a sample may be converted to cDNA by reverse-transcription, after which the sample is contacted with binding molecules specific for the genes being quantified, detecting the presence of a of cDNA-specific binding molecule complex, and quantifying the expression of the corresponding gene.

There is therefore provided the use of cDNA transcripts corresponding to one or more genes identified in the biomarker panels, for use in methods of detecting, diagnosing or determining the prognosis of prostate cancer, in particular prostate cancer.

Once the expression levels are quantified, a diagnosis of cancer (in particular aggressive prostate cancer) can be determined. The methods of the invention can also be used to determine a patient's prognosis, determine a patient's response to treatment or to determine a patient's suitability for treatment for cancer, since the methods can be used to predict cancer progression.

The methods may further comprise the step of comparing the quantified expression levels with a reference and subsequently determining the presence or absence of cancer, in particular aggressive prostate cancer.

Analyte enrichment may be achieved by any suitable method, although centrifugation and/or filtration to remove cell debris from the sample may be preferred. The step of obtaining the RNA from the enriched sample may include harvesting the RNA from microvesicles present in the enriched sample.

The step of sequencing the RNA can be achieved by any suitable method, although direct RNA sequencing, RT-PCR or sequencing-by-synthesis (next generation, or NGS, high-throughput sequencing) may be preferred. Quantification can be achieved by any suitable method, for example counting the number of transcripts identified with a particular sequence. In one embodiment, all the sequences (usually 75-100 base pairs) are aligned to a human reference. Then for each gene defined in an appropriate database (for example the Ensembl database) the number of sequences or reads that overlap with that gene (and don't overlap any other) are counted. To compare a gene between samples it will usually be necessary to normalise each sample so that the amount is the equivalent total amount of sequenced data. Methods of normalisation will be apparent to the skilled person.

As would be apparent to a person of skill in the art, any measurements of analyte concentration may need to be normalised to take in account the type of test sample being used and/or and processing of the test sample that has occurred prior to analysis.

The level of expression of a gene can be compared to a control to determine whether the level of expression is higher or lower in the sample being analysed. If the level of expression is higher in the sample being analysed relative to the level of expression in the sample to which the analysed sample is being compared, the gene is said to be up-regulated. If the level of expression is lower in the sample being analysed relative to the level of expression in the sample to which the analysed sample is being compared, the gene is said to be down-regulated.

In embodiments of the invention, the levels of expression of genes can be prognostic. As such, the present invention is particularly useful in distinguishing prostate cancers requiring intervention (aggressive prostate cancer), and those not requiring intervention (indolent or non-aggressive prostate cancer), avoiding the need for unnecessary procedures and their associated side effects. The most likely use of the present invention will be the use of the 500 gene panel to determine if an additional patient sample is DESNT by LPD analysis, the use of the 45 gene panel to determine if a patent is DESNT by measuring down-regulation of genes in the patient sample, and use of the 20 gene panel by RF analysis.

In some embodiments of the invention, the biomarker panels may be combined with another test such as the PSA test, PCA3 test, Prolaris, or Oncotype DX test. Other tests may be a histological examination to determine the Gleason score, or an assessment of the stage of progression of the cancer.

In a still further embodiment of the invention there is provided a method for determining the suitability of a patient for treatment for prostate cancer, comprising classifying the cancer according to a method of the invention, and deciding whether or not to proceed with treatment for prostate cancer if cancer progression is diagnosed or suspected, in particular if aggressive prostate cancer is diagnosed or suspected.

There is also provided a method of monitoring a patient's response to therapy, comprising classifying the cancer according to a method of the invention using a biological sample obtained from a patient that has previously received therapy for prostate cancer (for example chemotherapy and/or radiotherapy). In some embodiments, the method is repeated in patients before and after receiving treatment. A decision can then be made on whether to continue the therapy or to try an alternative therapy based on the comparison of the levels of expression. For example, if DESNT cancer is detected or suspected after receiving treatment, alternative treatment therapies may be used. The method can be repeated to see if the treatment is successful at downgrading a patient's cancer from DESNT to non-DESNT.

In one embodiment, there is therefore provided a method comprising:
 a) conducting a diagnostic method of the invention of a sample obtained from a patient to determine the presence or absence of a DESNT cancer (such as DESNT prostate cancer);
 b) providing treatment for cancer where DESNT cancer is found or suspected;
 c) subsequently conducting a diagnostic method of the invention of a further sample obtained from a patient to determine the presence or absence of a DESNT cancer; and
 d) maintaining, changing or withdrawing the therapy for cancer.

In some embodiments of the invention, the methods and biomarker panels of the invention are useful for individualising patient treatment, since the effect of different treatments can be easily monitored, for example by measuring biomarker expression in successive urine samples following treatment. The methods and biomarkers of the invention can also be used to predict the effectiveness of treatments, such as responses to hormone ablation therapy.

In another embodiment of the invention there is provided a method of treating or preventing cancer in a patient (such as aggressive prostate cancer), comprising conducting a diagnostic method of the invention of a sample obtained from a patient to determine the presence or absence of a DESNT cancer, and, if DESNT cancer is detected or suspected, administering cancer treatment. Methods of treating prostate cancer may include resecting the tumour and/or administering chemotherapy and/or radiotherapy to the patient.

The methods of treating cancer of the present invention are particularly useful in the treatment of aggressive prostate cancer. In some embodiments, the methods of treatment are performed on patients who have been identified as having DESNT cancer.

If possible, treatment for prostate cancer involves resecting the tumour or other surgical techniques. For example, treatment may comprise a radical or partial prostatectomy, trans-urethral resection, orchiectomy or bilateral orchiectomy. Treatment may alternatively or additionally involve treatment by chemotherapy and/or radiotherapy. Chemotherapeutic treatments include docetaxel, abiraterone or enzalutamide. Radiotherapeutic treatments include external beam radiotherapy, pelvic radiotherapy, post-operative radiotherapy, brachytherapy, or, as the case may be, prophylactic radiotherapy. Other treatments include adjuvant hormone therapy (such as androgen deprivation therapy, cryotherapy, high-intensity focused ultrasound, immunotherapy, brachytherapy and/or administration of bisphosphonates and/or steroids.

In another embodiment of the invention, there is provided a method identifying a drug useful for the treatment of cancer, comprising:
 a) conducting a diagnostic method of the invention of a sample obtained from a patient to determine the presence or absence of a DESNT cancer;
 b) administering a candidate drug to the patient;
 c) subsequently conducting a diagnostic method of the invention on a further sample obtained from a patient to determine the presence or absence of a DESNT cancer; and
 d) comparing the finding in step (a) with the finding in step (c), wherein a reduction in the prevalence or likelihood of DESNT cancer identifies the drug candidate as a possible treatment for cancer.

Biological Samples

Methods of the invention may comprise steps carried out on biological samples. The biological sample that is analysed may be a urine sample, a semen sample, a prostatic exudate sample, or any sample containing macromolecules or cells originating in the prostate, a whole blood sample, a serum sample, saliva, or a biopsy (such as a prostate tissue sample or a tumour sample). Most commonly for prostate cancer the biological sample is from a prostate biopsy, prostatectomy or TURP. The method may include a step of obtaining or providing the biological sample, or alternatively the sample may have already been obtained from a patient, for example in ex vivo methods. The samples are considered to be representative of the level of expression of the relevant genes in the potentially cancerous prostate tissue, or other cells within the prostate, or microvesicles produced by cells within the prostate or blood or immune system. Hence the methods of the present invention may use quantitative data on RNA produced by cells within the prostate and/or the blood system and/or bone marrow in response to cancer, to determine the presence or absence of prostate cancer.

The methods of the invention may be carried out on one test sample from a patient. Alternatively, a plurality of test samples may be taken from a patient, for example at least 2, 3, 4 or 5 samples. Each sample may be subjected to a separate analysis using a method of the invention, or alternatively multiple samples from a single patient undergoing diagnosis could be included in the method.

Further Analytical Methods Used in the Invention

The level of expression of a gene or protein from a biomarker panel of the invention can be determined in a number of ways. Levels of expression may be determined by, for example, quantifying the biomarkers by determining the concentration of protein in the sample, if the biomarkers are expressed as a protein in that sample. Alternatively, the amount of RNA or protein in the sample (such as a tissue sample) may be determined. Once the level of expression has been determined, the level can optionally be compared to a control. This may be a previously measured level of expression (either in a sample from the same subject but obtained at a different point in time, or in a sample from a different subject, for example a healthy subject or a subject with non-aggressive cancer, i.e. a control or reference sample) or to a different protein or peptide or other marker or means of assessment within the same sample to determine whether the level of expression or protein concentration is higher or lower in the sample being analysed. Housekeeping genes can also be used as a control. Ideally, controls are a protein or DNA marker that generally does not vary significantly between samples.

Other methods of quantifying gene expression include RNA sequencing, which in one aspect is also known as whole transcriptome shotgun sequencing (WTSS). Using RNA sequencing it is possible to determine the nature of the RNA sequences present in a sample, and furthermore to quantify gene expression by measuring the abundance of each RNA molecule (for example, mRNA or microRNA transcripts). The methods use sequencing-by-synthesis approaches to enable high throughout analysis of samples.

There are several types of RNA sequencing that can be used, including RNA PolyA tail sequencing (there the polyA tail of the RNA sequences are targeting using polyT oligonucleotides), random-primed sequencing (using a random oligonucleotide primer), targeted sequence (using specific oligonucleotide primers complementary to specific gene transcripts), small RNA/non-coding RNA sequencing (which may involve isolating small non-coding RNAs, such as microRNAs, using size separation), direct RNA sequencing, and real-time PCR. In some embodiments, RNA sequence reads can be aligned to a reference genome and the number of reads for each sequence quantified to determine gene expression. In some embodiments of the invention, the methods comprise transcription assembly (de-novo or genome-guided).

RNA, DNA and protein arrays (microarrays) may be used in certain embodiments. RNA and DNA microarrays comprise a series of microscopic spots of DNA or RNA oligonucleotides, each with a unique sequence of nucleotides that are able to bind complementary nucleic acid molecules. In this way the oligonucleotides are used as probes to which the correct target sequence will hybridise under high-stringency condition. In the present invention, the target sequence can be the transcribed RNA sequence or unique section thereof, corresponding to the gene whose expression is being detected. Protein microarrays can also be used to directly detect protein expression. These are similar to DNA and RNA microarrays in that they comprise capture molecules fixed to a solid surface.

Capture molecules include antibodies, proteins, aptamers, nucleic acids, receptors and enzymes, which might be preferable if commercial antibodies are not available for the analyte being detected. Capture molecules for use on the arrays can be externally synthesised, purified and attached to the array. Alternatively, they can be synthesised in-situ and be directly attached to the array. The capture molecules can be synthesised through biosynthesis, cell-free DNA expression or chemical synthesis. In-situ synthesis is possible with the latter two.

Once captured on a microarray, detection methods can be any of those known in the art. For example, fluorescence detection can be employed. It is safe, sensitive and can have a high resolution. Other detection methods include other optical methods (for example colorimetric analysis, chemiluminescence, label free Surface Plasmon Resonance analysis, microscopy, reflectance etc.), mass spectrometry, electrochemical methods (for example voltammetry and amperometry methods) and radio frequency methods (for example multipolar resonance spectroscopy).

Methods for detection of RNA or cDNA can be based on hybridisation, for example, Northern blot, Microarrays, NanoString, RNA-FISH, branched chain hybridisation assay, or amplification detection methods for quantitative reverse transcription polymerase chain reaction (qRT-PCR) such as TaqMan, or SYBR green product detection. Primer extension methods of detection such as: single nucleotide extension, Sanger sequencing. Alternatively, RNA can be sequenced by methods that include Sanger sequencing, Next Generation (high throughput) sequencing, in particular sequencing by synthesis, targeted RNAseq such as the Precise targeted RNAseq assays, or a molecular sensing device such as the Oxford Nanopore MinION device. Combinations of the above techniques may be utilised such as Transcription Mediated Amplification (TMA) as used in the Gen-Probe PCA3 assay which uses molecule capture via magnetic beads, transcription amplification, and hybridisation with a secondary probe for detection by, for example chemiluminescence.

RNA may be converted into cDNA prior to detection. RNA or cDNA may be amplified prior or as part of the detection.

The test may also constitute a functional test whereby presence of RNA or protein or other macromolecule can be detected by phenotypic change or changes within test cells. The phenotypic change or changes may include alterations in motility or invasion.

Commonly, proteins subjected to electrophoresis are also further characterised by mass spectrometry methods. Such mass spectrometry methods can include matrix-assisted laser desorption/ionisation time-of-flight (MALDI-TOF).

MALDI-TOF is an ionisation technique that allows the analysis of biomolecules (such as proteins, peptides and sugars), which tend to be fragile and fragment when ionised by more conventional ionisation methods. Ionisation is triggered by a laser beam (for example, a nitrogen laser) and a matrix is used to protect the biomolecule from being destroyed by direct laser beam exposure and to facilitate vaporisation and ionisation. The sample is mixed with the matrix molecule in solution and small amounts of the mixture are deposited on a surface and allowed to dry. The sample and matrix co-crystallise as the solvent evaporates.

Additional methods of determining protein concentration include mass spectrometry and/or liquid chromatography, such as LC-MS, UPLC, a tandem UPLC-MS/MS system, and ELISA methods. Other methods that may be used in the invention include Agilent bait capture and PCR-based methods (for example PCR amplification may be used to increase the amount of analyte).

Methods of the invention can be carried out using binding molecules or reagents specific for the analytes (RNA molecules or proteins being quantified). Binding molecules and reagents are those molecules that have an affinity for the RNA molecules or proteins being detected such that they can form binding molecule/reagent-analyte complexes that can be detected using any method known in the art. The binding molecule of the invention can be an oligonucleotide, or oligoribonucleotide or locked nucleic acid or other similar molecule, an antibody, an antibody fragment, a protein, an aptamer or molecularly imprinted polymeric structure, or other molecule that can bind to DNA or RNA. Methods of the invention may comprise contacting the biological sample with an appropriate binding molecule or molecules. Said binding molecules may form part of a kit of the invention, in particular they may form part of the biosensors of in the present invention.

Aptamers are oligonucleotides or peptide molecules that bind a specific target molecule. Oligonucleotide aptamers include DNA aptamer and RNA aptamers. Aptamers can be created by an in vitro selection process from pools of random sequence oligonucleotides or peptides. Aptamers can be optionally combined with ribozymes to self-cleave in the presence of their target molecule. Other oligonucleotides may include RNA molecules that are complimentary to the RNA molecules being quantified. For example, polyT oligos can be used to target the polyA tail of RNA molecules.

Aptamers can be made by any process known in the art. For example, a process through which aptamers may be identified is systematic evolution of ligands by exponential enrichment (SELEX). This involves repetitively reducing the complexity of a library of molecules by partitioning on the basis of selective binding to the target molecule, followed by re-amplification. A library of potential aptamers is incubated with the target protein before the unbound members are partitioned from the bound members. The bound members are recovered and amplified (for example, by polymerase chain reaction) in order to produce a library of reduced complexity (an enriched pool). The enriched pool is used to initiate a second cycle of SELEX. The binding of subsequent enriched pools to the target protein is monitored cycle by cycle. An enriched pool is cloned once it is judged that the proportion of binding molecules has risen to an adequate level. The binding molecules are then analysed individually. SELEX is reviewed in Fitzwater & Polisky (1996) *Methods Enzymol*, 267:275-301.

Antibodies can include both monoclonal and polyclonal antibodies and can be produced by any means known in the art. Techniques for producing monoclonal and polyclonal antibodies which bind to a particular protein are now well developed in the art. They are discussed in standard immunology textbooks, for example in Roitt et al., Immunology, second edition (1989), Churchill Livingstone, London. The antibodies may be human or humanised, or may be from other species. The present invention includes antibody derivatives that are capable of binding to antigens. Thus, the present invention includes antibody fragments and synthetic constructs. Examples of antibody fragments and synthetic constructs are given in Dougall et al. (1994) *Trends Biotechnol*, 12:372-379. Antibody fragments or derivatives, such as Fab, F(ab')2 or Fv may be used, as may single-chain antibodies (scAb) such as described by Huston et al. (993) *Int Rev Immunol*, 10:195-217, domain antibodies (dAbs), for example a single domain antibody, or antibody-like single domain antigen-binding receptors. In addition, antibody fragments and immunoglobulin-like molecules, peptidomimetics or non-peptide mimetics can be designed to mimic the binding activity of antibodies. Fv fragments can be modified to produce a synthetic construct known as a single chain Fv (scFv) molecule. This includes a peptide linker covalently joining VH and VL regions which contribute to the stability of the molecule.

Other synthetic constructs include CDR peptides. These are synthetic peptides comprising antigen binding determinants. These molecules are usually conformationally restricted organic rings which mimic the structure of a CDR loop and which include antigen-interactive side chains. Synthetic constructs also include chimeric molecules. Synthetic constructs also include molecules comprising a covalently linked moiety which provides the molecule with some desirable property in addition to antigen binding. For example, the moiety may be a label (e.g. a detectable label, such as a fluorescent or radioactive label), a nucleotide, or a pharmaceutically active agent.

In those embodiments of the invention in which the binding molecule is an antibody or antibody fragment, the method of the invention can be performed using any immunological technique known in the art. For example, ELISA, radio immunoassays or similar techniques may be utilised. In general, an appropriate autoantibody is immobilised on a solid surface and the sample to be tested is brought into contact with the autoantibody. If the cancer marker protein recognised by the autoantibody is present in the sample, an antibody-marker complex is formed. The complex can then be directed or quantitatively measured using, for example, a labelled secondary antibody which specifically recognises an epitope of the marker protein. The secondary antibody may be labelled with biochemical markers such as, for example, horseradish peroxidase (HRP) or alkaline phosphatase (AP), and detection of the complex can be achieved by the addition of a substrate for the enzyme which generates a colorimetric, chemiluminescent or fluorescent product. Alternatively, the presence of the complex may be determined by addition of a marker protein labelled with a detectable label, for example an appropriate enzyme. In this case, the amount of enzymatic activity measured is inversely proportional to the quantity of complex formed and a negative control is needed as a reference to determining the presence of antigen in the sample. Another method for detecting the complex may utilise antibodies or antigens that have been labelled with radioisotopes followed by a measure of radioactivity. Examples of radioactive labels for antigens include $^3$H, $^{14}$C and $^{125}$I.

The method of the invention can be performed in a qualitative format, which determines the presence or absence of a cancer marker analyte in the sample, or in a quantitative format, which, in addition, provides a measurement of the quantity of cancer marker analyte present in the sample. Generally, the methods of the invention are quantitative. The quantity of biomarker present in the sample may be calculated using any of the above described techniques. In this case, prior to performing the assay, it may be necessary to draw a standard curve by measuring the signal obtained using the same detection reaction that will be used for the assay from a series of standard samples containing known amounts or concentrations of the cancer marker analyte. The quantity of cancer marker present in a sample to be screened can then extrapolated from the standard curve.

Methods for determining gene expression as used in the present invention therefore include methods based on hybridization analysis of polynucleotides, methods based on sequencing of polynucleotides, proteomics-based methods, reverse transcription PCR, microarray-based methods and immunohistochemistry-based methods. References relating to measuring gene expression are also provided above.

Kit of Parts and Biosensors

In a still further embodiment of the invention there is provided a kit of parts for predicting cancer progression (detecting DESNT cancer) comprising a means for quantifying the expression or concentration of the biomarkers of the invention, or means of determining the expression status of the biomarkers of the invention. The means may be any suitable detection means. For example, the means may be a biosensor, as discussed herein. The kit may also comprise a container for the sample or samples and/or a solvent for extracting the biomarkers from the biological sample. The kit may also comprise instructions for use.

In some embodiments of the invention, there is provided a kit of parts for classifying cancer (for example, determining the likelihood of cancer progression) comprising a means for detecting the expression status (for example level of expression) of the biomarkers of the invention. The means for detecting the biomarkers may be reagents that specifically bind to or react with the biomarkers being quantified. Thus, in one embodiment of the invention, there is provided a method of diagnosing prostate cancer comprising contacting a biological sample from a patient with reagents or binding molecules specific for the biomarker analytes being quantified, and measuring the abundance of analyte-reagent or analyte-binding molecule complexes, and correlating the abundance of analyte-reagent or analyte-binding molecule complexes with the level of expression of the relevant protein or gene in the biological sample.

For example, in one embodiment of the invention, the method comprises the steps of:
a) contacting a biological sample with reagents or binding molecules specific for one or more of the biomarkers of the invention;
b) quantifying the abundance of analyte-reagent or analyte-binding molecule complexes for the biomarkers; and
c) correlating the abundance of analyte-reagent or analyte-binding molecule complexes with the expression level of the biomarkers in the biological sample.

The method may further comprise the step of d) comparing the expression level of the biomarkers in step c) with a reference to classify the status of the cancer, in particular to determine the likelihood of cancer progression and hence the requirement for treatment (aggressive prostate cancer). Of course, in some embodiments, the method may additionally comprise conducting a statistical analysis, such as those described in the present invention. The patient can then be treated accordingly. Suitable reagents or binding molecules may include an antibody or antibody fragment, an oligonucleotide, an aptamer, an enzyme, a nucleic acid, an organelle, a cell, a biological tissue, imprinted molecule or a small molecule. Such methods may be carried out using kits of the invention.

The kit of parts may comprise a device or apparatus having a memory and a processor. The memory may have instructions stored thereon which, when read by the processor, cause the processor to perform one or more of the methods described above. The memory may further comprise a plurality of decision trees for use in the random forest analysis.

The kit of parts of the invention may be a biosensor. A biosensor incorporates a biological sensing element and provides information on a biological sample, for example the presence (or absence) or concentration of an analyte. Specifically, they combine a biorecognition component (a bioreceptor) with a physiochemical detector for detection and/or quantification of an analyte (such as RNA or a protein).

The bioreceptor specifically interacts with or binds to the analyte of interest and may be, for example, an antibody or antibody fragment, an enzyme, a nucleic acid (such as an aptamer), an organelle, a cell, a biological tissue, imprinted molecule or a small molecule. The bioreceptor may be immobilised on a support, for example a metal, glass or polymer support, or a 3-dimensional lattice support, such as a hydrogel support.

Biosensors are often classified according to the type of biotransducer present. For example, the biosensor may be an electrochemical (such as a potentiometric), electronic, piezoelectric, gravimetric, pyroelectric biosensor or ion channel switch biosensor. The transducer translates the interaction between the analyte of interest and the bioreceptor into a quantifiable signal such that the amount of analyte present can be determined accurately. Optical biosensors may rely on the surface plasmon resonance resulting from the interaction between the bioreceptor and the analyte of interest. The SPR can hence be used to quantify the amount of analyte in a test sample. Other types of biosensor include evanescent wave biosensors, nanobiosensors and biological biosensors (for example enzymatic, nucleic acid (such as RNA or an aptamer), antibody, epigenetic, organelle, cell, tissue or microbial biosensors).

The invention also provides microarrays (RNA, DNA or protein) comprising capture molecules (such as RNA or DNA oligonucleotides) specific for each of the biomarkers being quantified, wherein the capture molecules are immobilised on a solid support. The microarrays are useful in the methods of the invention.

In one embodiment of the invention, there is provided a method of classifying prostate cancer comprising determining the expression level of one or more of the biomarkers of the invention, and optionally comparing the so determined values to a reference.

The biomarkers that are analysed can be determined according to the Methods of the invention. Alternatively, the biomarker panels provided herein can be used. At least 15 (preferably all 20) of the genes listed in Table 3 are useful in classifying prostate cancer. At least 40 (preferably all 45) of the genes listed in Table 2 are useful in classifying several different types of cancer and determining the likelihood of progression, including the classification of prostate cancer.

Features for the second and subsequent aspects of the invention are as for the first aspect of the invention mutatis mutandis.

The present invention shall now be further described with reference to the following examples, which are present for the purposes of illustration only and are not to be construed as being limiting on the invention.

In the Examples, reference is made to a number of Figures, as follows:

FIG. 1. Latent Process Decomposition (LPD), gene correlations and clinical outcome. a, LPD analysis of Affymetrix expression data from the MSKCC datasets divided the samples into eight processes, each represented here by a bar chart. Samples are represented in all eight processes and height of each bar corresponds to the proportion ($p_i$) of the signature that can be assigned to each LPD process. Samples are assigned to the LPD group in which they exhibit the highest value of $p_i$. LPD was performed using the 500 gene probes with the greatest variation in expression between samples in the MSKCC dataset. The process containing DESNT cancers is indicated. b, List of datasets used in LPD analysis. The unique number of primary cancer and normal specimens used in LPD are indicated. FF, fresh frozen specimen; FFPE, formalin-fixed paraffin embedded specimen. The CancerMap and CamCap were not independent having 40 cancers in common. Clinical and molecular details for the CancerMap dataset are given in Supplementary Information Table 2 and Supplementary Data 1. c, Correlations of average levels of gene expression between cancers designated as DESNT. All six comparisons for the MSKCC, CancerMap, Stephenson and Klein datasets are shown. The expression levels of each gene have been normalised across all samples to mean 0 and standard deviation 1. d, Kaplan-Meier PSA failure plots for the MSKCC, CancerMap and Stephenson datasets. The number of cancers in each group is indicated in the bottom right corner of each Kaplan-Meier plot. The number of patients with PSA failure is indicated in parentheses.

FIG. 2. Genes commonly down regulated in DESNT poor prognosis prostate cancer. a, Number of genes with significantly altered expression in DESNT cancers compared to non-DESNT cancers (P<0.01 after correction for False Discovery Rate). 45 genes had lower expression in DESNT cancers in all four expression microarray datasets, based on a stringency requirement of being down-regulated in at least 80 of 100 independent LPD runs. b, List of the 45 genes according to biological grouping. Encoded protein functions are shown in Supplementary Information Table 3. Although some of the 45 genes are preferentially expressed in stromal tissue we found no correlation between stromal content and clinical outcome in both the CancerMap and CamCap patient series, where data on cellular composition were available. When patients were stratified into two groups (above and below median stromal content) Kaplan-Meier plots failed to show outcome difference for both the CancerMap (Log-rank test, p=0.159) and CamCap (p=0.261) patient series. c. Relationship between the genes in published poor prognosis signatures for prostate cancer and the DESNT classification for human prostate cancer, represented as a circos plot. Links to the 45 commonly down-regulated genes are shown in brown.

FIG. 3. Comparison of RF-DESNT and non-RF-DESNT cancers in The Cancer Genome Atlas dataset. A 20-gene random forest (RF) classifier was used to identify DESNT cancers (designated RF-DESNT cancers). The types of genetic alteration are shown for each gene (mutations, fusions, deletions, and overexpression). Clinical parameters including biochemical recurrence (BCR) are represented at the bottom together with groups for iCluster, methylation, somatic copy number alteration (SVNA) and mRNA[7,20]. When mutations and homozygous deletions for each gene were combined RF-DESNT cancers contained an excess of genetic alterations in BRCA2 (P=0.021, $\chi^2$ test) and TP53 (P=0.0038), but after correcting for multiple testing these differences were not significant (P>0.05).

FIG. 5. Log-likelihood plots. The log-likelihood (vertical axis) versus number of processes (horizontal-axis) using the MAP solution (upper curve) and maximum likelihood solution (lower curve) for each dataset. For the maximum likelihood model, the peak in log-likelihood indicates the number of processes to use. For the MAP model, a Bayesian prior is used to penalize construction of an over-complex model. The log-likelihood rises to a plateau after which no further gain is to be made indicating the maximum number of processes that should be used.

FIG. 6. Latent Process Decomposition (LPD) analysis of transcriptome datasets. The MSKCC, Stephenson, CancerMap, CamCap and Klein datasets were each decomposed into the optimal number of processes indicated from their log-likelihood plot (FIG. 5). A single sample is represented across all processes and height of each bar corresponds to the proportion ($p_i$) of the signature that can be attributed to each LPD process. Samples are assigned to the LPD group in which they exhibit the highest value of $p_i$. For the MSKCC, CancerMap, and CamCap datasets red, blue and green denote cancers with different risks of progression based on clinical parameters as defined in the Methods. For the Stephenson dataset only pathological stage is indicated because some of the parameters required for designation into the three risk groups are missing. Clinical data from the Klein dataset is not publically available. For each dataset, the process containing DESNT cancers is indicated. Log-likelihood plots and LPD decompositions were performed using the 500 gene loci whose expression varied most in the MSKCC dataset.

FIG. 7. Analysis of outcome for DESNT cancers identified by LPD. (a-d) Kaplan-Meier PSA failure plots for the MSKCC (a), CancerMap (b), Stephenson (c), and CamCap (d) datasets. For each dataset, the cancers assigned to the DESNT process by LPD are comparing to the remaining cancers. The number of cancers in each group is indicated in the bottom right corner of each plot. The number of cancers with PSA failure is indicated in parentheses. The Kaplan-Meier plot shown represents the most frequent (mode) p-value from 100 LPD runs each performed using randomly chosen seed parameters (FIG. 12). (e-i) Multivariate analyses were performed as described in the Methods for the MSKCC (e), CancerMap (f), and Stephenson (g) datasets. For (h) multivariate analyses were performed on the combined MSKCC, CancerMap, and Stephenson datasets. (i), Multivariate analyses performed on the CamCap dataset. CamCap was analysed separately because of the 40 cancer overlap with the CancerMap dataset. Pathological Stage covariates for MSKCC and Stephenson datasets did not meet the proportional hazards assumptions of the Cox model and have been modelled as time-dependent variables, as described in the Methods.

FIG. 8. Correlations of Gene Expression of DESNT cancers identified by LPD classification. Correlations (corr.) of average levels of gene expression between cancers assigned to the DESNT process using LPD from each of the MSKCC, CancerMap, Stephenson, Klein and CamCap datasets. Data from the 500 genetic loci whose expression levels varied most in MSKCC dataset and that were used for LPD are shown. The expression levels of each gene have been normalised across all samples to mean 0 and standard deviation 1. All ten possible comparisons are presented.

FIG. 9. Detection of DESNT cancers by RF classification using the 20 gene signature. A random forest classification was performed using the signature of 20 genes identified in lasso regression analysis of the 1669 genes with significantly altered expression in DESNT cancers in at least two of the five datasets: MSKCC, CancerMap, Stephenson, Klein, and CamCap. For each dataset the reference used were the cancers for the DESNT group corresponding to the modal p-value shown in FIG. 12. The figure shows the AUC, Accuracy, Sensitivity and Specificity for each prediction. A grid showing the number of false-positive (top right) and false-negative (bottom left) assignments is shown for each dataset.

FIG. 10. Analysis of outcome for DESNT cancers identified by RF classification. (a-e) Kaplan-Meier PSA failure plots for the MSKCC (a), CancerMap (b), Stephenson (c), CamCap (d) and TOGA (e) datasets. For each dataset, the cancers assigned to DESNT using the 20 gene RF classifier are comparing to the remaining cancers. The number of cancers in each group is indicated in the bottom right corner of each plot. The number of cancers with PSA failure is indicated in parentheses. Multivariate analyses were performed as described in the Methods for the MSKCC (f), CancerMap (g), Stephenson (h), CamCap (i) and TOGA (j) datasets. Pathological Stage covariates for MSKCC and Stephenson datasets did not meet the proportional hazards assumptions of the Cox model and have been modelled as time-dependent variables, as described in the Methods.

FIG. 11. Correlations of Gene Expression of DESNT cancers identified by RF classification. Correlations of average levels of gene expression between cancers assigned to the DESNT process using RF classification from each of the MSKCC, CancerMap, Stephenson, Klein, CamCap and TOGA datasets. Data from the 500 loci whose expression levels varied most in MSKCC dataset and that were used for LPD are shown. The expression levels of each gene have been normalised across all samples to mean 0 and standard deviation 1. All 15 possible comparisons are presented. For each dataset similar correlations between DESNT processes identified by LPD and RF were observed (data not shown).

FIG. 12. Distribution of LPD runs. The distribution of the PSA failure log-rank p-values of 100 LPD restarts with random seeds, for the datasets (a) MSKCC, (b) CancerMap, (c) CamCap and (d) Stephenson. Examples of Kaplan-Meier plots corresponding to modal log-rank p values are shown in FIG. 1d and FIG. 7a-d.

FIG. 13. LPD decomposition of the MSKCC dataset. (a) Samples are represented in all eight processes and height of each bar corresponds to the proportion (Gamma, vertical axis) of the signature that can be assigned to each LPD process. The seventh row illustrates the percentage of the DESNT expression signature identified in each sample. (b) Bar chart showing the proportion of DESNT cancer present in each sample. (c,d) Pie Charts showing the composition of individual cancers. DESNT is in red. Other LPD groups are represented by different colours as indicated in the key. The numbers next the pie chart indicates which cancer it represents from the bar chart above. Individual cancers were assigned as a "DESNT cancer" when the DESNT signature was the most abundant; examples are shown in the left box (DESNT). Many other cancers contain a smaller proportion of DESNT cancer (d) and are predicted also to have a poor outcome: examples shown in larger box (c, Some DESNT).

FIG. 14. Stratification of prostate cancer based on the percentage of DESNT cancer present. For these analyses the data from the MSKCC, CancerMap, CamCap and Stephenson datasets were combined (n=517). (a) Plot showing the contribution of DESNT cancer to each cancer and the division into 4 groups. Group 1 samples have less than 0.1% DESNT cancer. (b) Kaplan-Meier plot showing the Biochemical Recurrence (BCR) free survival based on proportion of DESNT cancer present as determined by LPD. Number of cancers in each Group are indicated (bottom right) and the number of PCR failures in each group are show in parentheses. The definition of Groups 1-4 is shown in FIG. 2a. Cancers with Gamma values up to 30% DESNT (Group 2) exhibited poorer clinical outcome (X2-test, p=0.015) compared to cancers lacking DESNT (<0.1%). Cancers with the intermediate (0.3 to 0.6) and high (>0.6) values of Gamma also exhibited significantly worse outcome (respectively P=2.69×10-6 and P=2.22×10-14 compare to cancers lacking DESNT. The combined Log-rank p value=1.28×10-14.

FIG. 15. Nomogram model developed to predict PSA free survival at 1, 3, 5 and 7 years for LPD. Assessing a single patient each clinical variable has a corresponding point score (top scales). The point scores for each variable are added to produce a total points score for each patient. The predicted probability of PSA free survival at 1, 3, 5 and 7 years can be determined by drawing a vertical line from the total points score to the probability scales below.

FIG. 16. Cox Model for LPD. (a) graphical representation of HR for each covariate and 95% confidence intervals of HR. (b) HR, 95% CI and Wald test statistics of the Cox model. (c) Calibration plots for the internal validation of the nomogram, using 1000 bootstrap resamples. Solid black line represents the apparent performance of the nomogram, blue line the bias-corrected performance and dotted line the ideal performance. (d) Calibration plots for the external validation of the nomogram using the CamCap dataset. Solid line corresponds to the observed performance and dotted line to the ideal performance.

EXAMPLES

Example 1

A critical problem in the clinical management of prostate cancer is that it is highly heterogeneous[1,2]. Accurate prediction of individual cancer behavior is therefore not achievable at the time of diagnosis leading to substantial overtreatment[3,4]. It remains an enigma that, in contrast to breast cancers, unsupervised analyses of global expression profiles has not defined robust categories of prostate cancer with distinct clinical outcomes[6,7]. In the current study the application of an unsupervised Bayesian procedure called Latent Process Decomposition[8] (LPD) identifies a common process in four independent prostate cancer transcriptome datasets. Cancers assigned to this process (designated DESNT cancers) are characterized by low expression of a core set of 45 genes, many encoding proteins involved in the cytoskeleton machinery, ion transport and cell adhesion. For the three datasets with linked PSA failure data following prostatectomy, patients with DESNT cancer exhibited very poor outcome relative to other patients (P=2.65×10$^{-5}$, P=4.28× 10$^{-5}$, and P=2.98×10$^{-8}$). Analysis of prostate cancers annotated in The Cancer Genome Atlas using a random forest classifier failed to reveal links between DESNT cancers and the presence of any particular class of genetic mutation, including ETS-gene status. Our results demonstrate the existence of a poor prognosis category of human prostate cancer and will assist in the targeting of therapy, helping avoid treatment-associated morbidity in men with indolent disease.

Most expression-based prognostic signatures for prostate cancer have in common that they were derived using supervised steps, involving either comparisons of aggressive and non-aggressive disease[9,10] or the selection of genes representing specific biological functions[11-14]. Alternatively expression biomarkers may be linked to the presence of somatic copy number variations (SCNVs)[7]. LPD, based on the latent Dirichlet allocation method[15], examines the structure of a dataset in the absence of knowledge of clinical outcome or biological role[8]. In contrast to standard unsupervised clustering models (e.g. k-means and hierarchical clustering) individual cancers are not assigned to a single cluster: instead gene expression levels in each cancer are modeled via combinations of latent processes. This type of analysis should be particularly suitable for prostate cancer where the composition of individual cancers can be highly heterogeneous[16,17] and where a single specimen may contain more than one contributing lineage[15-20]. LPD has been previously used to confirm the presence of basal and ERBB2 overexpressing subgroups in breast cancer datasets[5], and to show that patients with advanced prostate cancer can be stratified into two clinically distinct categories[21].

Four independent transcriptome datasets (designated MSKCC[6], CancerMap, Klein[22], and Stephenson[23], FIG. 1b) obtained from prostatectomy specimens were analyzed. LPD was performed using between 3 and 8 underlying processes contributing to the overall expression profile as indicated from log-likelihood plots (FIG. 1b, FIG. 5). Following decomposition of each dataset, cancers were assigned to individual latent processes based on their highest $p_i$ value yielding the results shown in FIG. 1a and FIG. 6. p is the contribution of each process i to the expression profile of an individual cancer: sum of $p_i$ over all processes=1. Searching for relationships between the decompositions one process was identified that, based on correlations of gene expression levels, appeared to be common across all four datasets (FIG. 1c). To further investigate this association, for each dataset, we identified genes that were expressed at significantly lower or higher levels (P<0.01 after correction for False Discovery Rate) in the cancers assigned to this process compared to all other cancers from the same dataset. This unveiled a shared set of 45 genes all with lower expression (FIG. 2a, Extended Data Table 1). Many of the proteins encoded by these 45 core genes are components of the cytoskeleton or regulate its dynamics, while others are involved in cell adhesion and ion transport (FIG. 2b). Eleven of the 45 genes were members of published prognostic signatures for prostate cancer (FIG. 2c, Supplementary Data 1). For example MYLK, ACTG2, and CNN1 are down-regulated in a signature for cancer metastasis[24], while lower expression of TMP2 is associated with poorer outcome as part of the Oncotype DX signature[25]. The cancers assigned to this common process are referred to as "DESNT" (latin DEScenduNT, they descend).

Using linked clinical data available for the MSKCC expression dataset the inventors found that patients with DESNT cancer exhibited extremely poor outcome when compared to patients assigned to other processes (P=2.65× $10^{-5}$, Log-rank test, FIG. 1d). Validation was provided in two further datasets where PSA failure data following prostatectomy was available (FIG. 1d): for both the Stephenson and CancerMap datasets patients with DESNT cancer exhibited very poor outcome (P=4.28×$10^{-5}$ and P=2.98×$10^{-8}$ respectively). In multivariate analysis including Gleason sum, Stage and PSA assignment as a DESNT cancer was an independent predictor of poor outcome in the Stephenson and CancerMap datasets (P=1.83×$10^{-4}$ and P=3.66×$10^{-3}$, Cox regression model) but not in the MSKCC dataset (P=0.327) (Table 8, FIG. 7). When the three datasets were combining the independent predictive value of DESNT membership was P=1.61×$10^{-7}$ (FIG. 7), compared to P=1.00×$10^{-5}$ for Gleason Sum. The poor prognosis DESNT process was also identified in the CamCap dataset[7] (Table 8, FIGS. 7 and 8), which was excluded from the from the above analysis because it was not independent: there a substantial overlap with cancers included in CancerMap (FIG. 1b).

The inventors wished to develop a classifier that, unlike LPD, was not computer processing intensive and that could be applied both to a wider range of datasets and to individual cancers. 1669 genes with significantly altered expression between DESNT and non-DESNT cancers in at least two datasets were selected for analysis. A LASSO logistic regression model was used to identify genes that were the best predictors of DESNT membership in the MSKCC dataset leading to the selection of a set of 20 genes (Extended Data Table 2), which had a one gene overlap (ACTG2) to the 45 genes with significantly lower expression in DESNT cancers. Using random forest (RF) classification these 20 genes provided high specificity and sensitivity for predicting that individual cancers were DESNT in both the MSKCC training dataset and in three validation datasets (FIG. 9). For the two validation datasets (Stephenson and CancerMap) with linked PSA failure data the predicted cancer subgroup exhibited poorer clinical outcome in both univariate and multivariate analyses, in agreement with the results observed using LPD (Table 8, FIG. 10). When RF classification was applied to RNAseq data from 333 prostate cancers annotated by The Cancer Genome Atlas (TCGA)[20] a patient subgroup was identified that was confirmed as DESNT based on: (i) correlations of gene expression levels with DESNT cancer groups in other datasets (FIG. 11); (ii) demonstration of overlaps of differentially expressed genes between DESNT and non-DESNT cancers with the core down-regulated gene set (45/45 genes); and (iii) its poorer clinical outcome (P=5.4×$10^{-4}$) compared to non-DESNT patients (Table 8, FIG. 10e).

For the TCGA dataset we failed to find correlations between assignment as a DESNT cancer and the presence of any specific genetic alteration (P>0.05 after correction for False Discovery Rate, $\chi^2$ test, FIG. 3). Of particular note, there was no correlation to ETS-gene status (P, =0.136, $\chi^2$ test, FIG. 3). A lack of correlation between DESNT cancers and ERG-gene rearrangement, determined using the fluorescence in situ hybridization break-apart assay[26], was confirmed using CancerMap samples (LPD-DESNT, P=0.549; RF-DESNT, P=0.2623, $\chi^2$ test: DESNT cancers identified by LPD and by RF approaches are referred to respectively as LPD-DESNT and RF-DESNT). These observations are consistent with the lack of correlation between ERG status and clinical outcome[27]. Since ETS-gene alteration, found in around half of prostate cancer[20,26], is considered to be an early step in prostate cancer development[17,28] it is likely that changes involved in the generation of DESNT cancer represent a later event that is common to both ETS-positive and ETS-negative cancers.

For RF-DESNT cancers in the TGCA series some of the 45 core genes exhibited altered levels of CpG gene methylation compared to non-RF-DESNT cancers (Supplementary Information Table 1) suggesting a possible role in controlling gene expression. Supporting this idea, for sixteen of the 45 core genes, epigenetic down regulation in human cancer has been previously reported including six genes in prostate cancer (CLU, DPYSL3, GSTP1, KCNMA1, SNAI2, and SVIL) (FIG. 2b, Extended Data Table 1). CpG methylation of five of the genes (FBLN1, GPX3, GSTP1, KCNMA1, TIMP3) has previously been linked to cancer aggression. The down-regulation of genes determining cytoskeleton structure and involved in cell adhesion in DESNT cancers would argue against the contributions of amoeboid-type movement and mesenchymal migration in determining cancer aggression, but could reflect collective migration or expansive growth phenotypes[29].

Evidence from The European Randomized study of Screening for Prostate Cancer demonstrates that PSA screening can reduce mortality from prostate cancer by 21%[30]. However, a critical problem with PSA screening is that it leads to the detection of up to 50% of cancers that are clinically irrelevant[3,4]: that is cancers that would never have caused symptoms in a man's lifetime in the absence of screening. In our study application of LPD to prostate cancer transcriptome datasets has revealed the existence of a novel poor prognosis category of prostate cancer common across all prostatectomy series examined. The DESNT cancer category was detected using data generated by several different platforms (Illumina HT12 v4 BeadChip array, RNAseq, Affymetrix arrays) and from both frozen and formalin fixed tissue. Classification of a cancer as DESNT should significantly enhance the ability to identify patients whose cancers will progress. In turn this will allow the targeting of radiotherapy, surgery and chemotherapy to men with more aggressive disease helping avoid the side effects of treatment, including impotence, in men with irrelevant cancers.

Methods

The CancerMap Dataset

Fresh prostate cancer specimens were obtained from a systematic series of patients who had undergone a prostatectomy at the Royal Marsden NHS Foundation Trust and Addenbrooke's Hospital, Cambridge. The relevant local Research Ethics Committee approved was obtained for this study. Frozen prostate slices at were collected[31] and RNAs were prepared[7,32] as described previously.

Expression profiles were determined as previously described[32] using 1.0 Human Exon ST arrays (Affymetrix, Santa Clara, Calif., USA) according to the manufacturer's instructions. The Affymetrix GeneChip® Whole Transcript Sense Target Labelling Assay was used to generate amplified and biotinylated sense-strand DNA targets from the entire expressed genome (1.5 µg of total RNA) without bias. Manufacturer's instructions were followed for the hybridization, washing and scanning steps. Arrays were hybridized by rotating them at 60 rpm in the Affymetrix Gene Chip hybridization oven at 45° C. for 16 h. After hybridization, the arrays were washed in the Affymetrix GeneChip Fluidics station FS 450. The arrays were scanned using the Affymetrix Gene Chip scanner 3000 7G system. Data is available from the Gene Expression Omnibus: GSE (data to be released on publication).

Risk of Progression Categories

Prostatectomy risk of progression categories were defined based on the UK International Cancer Genome Consortium stratification of for prostate cancer (Chris Foster, personal communication).

| Low risk | PSA <= 10 ng/ml AND (Gleason = 3 + 3 OR (Gleason = 3 + 4 AND no extra capsular extension)) |
| --- | --- |
| Medium risk | 10 ng/ml < PSA <= 20 ng/ml OR (Gleason = 4 + 3 AND no extra capsular extension) OR (Gleason = 3 + 4 AND extra capsular extension) |
| High risk | PSA > 20 ng/ml OR Gleason sum > 7 OR (Gleason = 4 + 3 AND extra capsular extension) OR Seminal vesicle invasion |

Additional Transcriptome Datasets

Five prostate cancer microarray datasets were analysed that will be referred to as: MSKCC, CancerMap, CamCap, Stephenson and Klein. All data analysed was from radical prostatectomy specimens. The MSKCC dataset contains 370 Affymetrix Human Exon 1.0 ST Array experiments (GEO: GSE21034)[6]. 50 microarrays were removed corresponding to cell-lines, xenografts and metastatic tissue. The remaining 320 microarrays represents 160 replicates from primary tumour and normal tissue samples: only one dataset from each sample was used in LPD analyses. The Stephenson dataset contains data from 78 cancers and 11 normal prostate samples obtained using Affymetrix U133A human gene arrays[23]. Klein consists of 182 formalin-fixed and paraffin-embedded (FFPE) primary tumour samples analysed with Affymetrix Human Exon 1.0 ST Arrays (GEO: GSE62667)[22]. The CamCap dataset used in our study was produced combining Illumine HumanHT-12 V4.0 expression beadchip (bead microarray) datasets (GEO: GSE70768 and GSE70769) obtained from two prostatectomy series (Cambridge and Stockholm) and consisted of 147 cancer and 73 normal samples[7]. The CamCap and CancerMap datasets have in common 40 patients and thus are not independent. One RNAseq dataset consisting of 333 prostate cancers from The Cancer Genome Atlas was analysed which is referred to as TCGA[20]. The counts per gene supplied by TCGA were used.

Data Processing

Gene-level and exon-level expression signal estimates were derived from CEL files generated from Affymetrix GeneChip Exon 1.0 ST arrays using the robust multiarray analysis algorithm[33] implemented in the Affymetrix Expression Console software package. For the bead microarray datasets pre-normalised data was used and annotated to UCSC hg19 using illuminaHumanv4.db R annotation package. Poor quality probes ("Bad" and "No match" probes) were removed. The pre-normalised Stephenson dataset was annotated using the hgu133a.db R package. When necessary, dataset/centre batch effects were adjusted for using the ComBat algorithm[34] implemented in the sva R package.

Latent Process Decomposition

Latent process decomposition (LPD)[8,35], an unsupervised Bayesian approach, was used to classify samples into subgroups called processes. As in Rogers et al.[35] the 500 probesets with greatest variance across the MSKCC dataset were selected for use in LPD. These probesets map to 492 genes. For each dataset all probes that map to these genes were used in LPD analyses (CancerMap: 507, CamCap:483, Stephenson: 609).

LPD can objectively assess the most likely number of processes. The inventors assessed the hold-out validation log-likelihood of the data computed at various number of processes and used a combination of both the uniform (equivalent to a maximum likelihood approach) and non-uniform (MAP approach) priors to choose the number of processes. For the MAP approach the mean parameter of the model is set to 0.1, as it has been previously observed that the value used had little impact on the results, and the variance parameter set to the value of the prior that corresponds to the maximum log-likelihood, i.e. −0.5 for MSKCC, −0.5 for CancerMap, −0.05 for CamCap, −0.75 for Stephenson and −0.3 for Klein.

For robustness, the inventors restarted LPD 100 times with different seeds, for each dataset. Out of the 100 runs the inventors selected a representative run that was used for subsequent analysis. The representative run, was the run with the survival log-rank p-value closest to the mode. For the Klein dataset, for which do not have clinical data was not available, the hold-out log-likelihood from LPD was used instead.

Statistical Tests

All statistical tests were performed in R version 3.2.2 (r-project.org/). Correlations between the expression profiles between two datasets for a particular gene set and sample subgroup were calculated as follows:

1. For each gene one probeset is selected at random;
2. For each probeset its distribution is transformed across all samples to a standard normal distribution;
3. The average expression for each probeset across the samples in the subgroup is determined, to obtain an expression profile for the subgroup; and
4. The Pearson's correlation between the expression profiles of the subgroups in the two datasets is determined.

Differentially expressed probesets were identified using a moderated t-test implemented in the limma R package[36]. Genes are considered significantly differentially expressed if the adjusted p-value was below 0.01 (p values adjusted using the False Discovery Rate).

Survival analyses were performed using Cox proportional hazards models and Kaplan-Meier estimator, with biochemical recurrence after prostatectomy as the end point. When several samples per patient were available, only the sample with the highest proportion of tumour tissue was used. Expression profiles from normal tissue were not included. Multivariate survival analyses were performed with the clinical covariates Gleason grade (≤7 and >7), pathological stage (T1/T2 and T3/T4) and PSA levels (≤10 and >10). The inventors modelled the variables that did not satisfy the proportional hazards assumption (T-stage in MSKCC), as a product of the variable with the heavyside function:

$$g(t) = \begin{cases} 1, & \text{if } t \geq t_0 \\ 0, & \text{otherwise} \end{cases}$$

where $t_0$ is a time threshold. The multiplication of a predictor with the heavyside function, divides the predictor into time intervals for which the extended Cox model computes different hazard ratios.

Driving an Optimal Predictor of DESNT Membership

To derive an optimal predictor of DESNT membership the datasets were prepared so that they were comparable: probes were only retained if the associated gene was found in every microarray platform, only one randomly chosen probe was retained per gene and the batch effects adjusted using the ComBat algorithm[34]. The MSKCC dataset was used as the training set and other datasets as test sets. Gene selection was performed using regularized general linear model approach (LASSO) implemented in the glmnet R package[37], starting with all genes that were significantly up or down regulated in DESNT in at least two of the total of five microarray dataset (1669 genes). LASSO was run 100 times and only genes that were selected in at least 25% of runs were retained. The optimal predictor was then derived using the random forest model[38] implemented in the randomForest R package[39]. Default parameters were used, apart from the number of trees were set to 10001 and the class size imbalance was adjusted for by down-sampling the majority class to the frequency of the minority class.

Example 2

Presence of DESNT Signature Predicts Poor Clinical Outcome.

In previous studies optimal decomposition of expression microarray datasets was performed using between 3 and 8 underlying processes. An illustration of the decomposition of the MSKCC dataset into 8 processes is shown in FIG. 13a where each process is represented by a bar chart. Samples are represented in all eight processes and height of each bar corresponds to the proportion (Gamma or pi) of the signature that can be assigned to each LPD process. LPD Process 7 illustrates the percentage of the DESNT expression signature identified in each sample, with individual cancer being assigned as a "DESNT cancer" when the DESNT signature was the most abundant as shown in FIGS. 13b and 13d. Based on PSA failure patients with DESNT cancers always exhibited poorer outcome, relative to other cancers in the same dataset. The implication is that it is the presence of regions of cancer containing the DESNT signature that conferred poor outcome. This model predicts that cancers containing smaller contribution of DESNT signature, such as those shown in FIG. 13c for the MSKCC dataset, should also exhibit poorer outcome.

To increase the power to test this prediction data from cancers from the MSKCC, CancerMap, Stephenson, and CamCap were combined (n=515). Treating the proportion of expression assigned to the DESNT process (Gamma) as a continuous variable the inventors found that it had a significant association with PSA recurrence (P=2.66×10$^{-15}$, HR=1.5, 95% CI=[1.35, 1.66], Cox proportional hazard regression model). Outcome became worse as Gamma increased. This is illustrated by dividing the cancers into four groups based on the proportion of the DESNT process present (FIG. 14a), then PSA failure free survival is as follows (FIG. 14b); (i) no DESNT cancer, 74.4% at 70 months; (ii) less than 0.3 Gamma, 63.1% at 70 months; (iii) 0.3 to 0.6 Gamma, 45.5% at 70 months and (iv) >0.60 Gamma, 20.4% at 70 months (FIG. 14b). Overall 47% of cancers contained at least some DESNT cancer (FIG. 14a).

Nomogram for DESNT Predicting PSA Failure

The proportion of DESNT cancer was combined with other clinical variables (Gleason grade, PSA levels, pathological stage and the surgical margins status) in a Cox proportional hazards model and fitted to a combine dataset of 330 cancers. DESNT Gamma was an independent predictor of worse clinical outcome (P=3×10$^{-4}$, HR=1.30, 95% CI=[1.13, 1.50]), FIG. 16a,b) along with Gleason grade=4+3 (P=1.8×10$^{-3}$, HR=3.26, 95% CI=[1.55, 6.86]), Gleason grade>7 (P<1×10$^{-4}$, HR=5.41, 95% CI=[2.46, 11.92]) pathological stage (P=2.45×10$^{-2}$, HR=1.62, 95% CI=[1.06, 2.48]), and positive surgical margins (P=1.74× 10$^{-2}$, HR=1.69, 95% CI=[1.10, 2.60]). PSA level as a predictor was below our threshold of statistical significance (P=0.1145, HR=1.13, 95% CI=[0.97, 1.32]). Using this survival model a nomogram for use of DESNT cancer together with other variables was devised (FIG. 15, FIG. 16) to predict the risk of biochemical recurrence at 1, 3, 5 and 7 years following prostatectomy. At internal validation, the nomogram obtained a bootstrap-corrected C-index of 0.761, and at external validation, on the CamCap dataset, a C-index of 0.799.

TABLES

TABLE 1

500 GENE PROBES THAT VARY IN EXPRESSION MOST ACROSS THE MSKCC DATASET

| HGNC symbol | Accession ID |
| --- | --- |
| TGM4 | NM_003241 |
| RLN1 | NM_006911 |
| ORM1 | NM_000607 |
| OLFM4 | NM_006418 |
| OR51E2 | NM_030774 |
| SERPINB11 | NM_080475 |
| CRISP3 | NM_006061 |
| TDRD1 | NM_198795 |
| SLC14A1 | NM_001128588 |
| IGJ | NM_144646 |
| ERG | NM_001136154 |
| GDEP | NR_026555 |
| TMEFF2 | NM_016192 |
| CST1 | NM_001898 |
| LTF | NM_002343 |
| AMACR | NM_014324 |
| SERPINA3 | NM_001085 |
| NEFH | NM_021076 |
| ACSM1 | NM_052956 |
| OR51E1 | NM_152430 |
| MT1G | NM_005950 |
| ANKRD36B | NM_025190 |
| LOC100510059 | XM_003120411 |
| PLA2G2A | NM_000300 |
| TARP | NM_001003799 |
| REXO1L1 | NM_172239 |
| ANPEP | NM_001150 |
| HLA-DRB5 | NM_002125 |
| PLA2G7 | NM_001168357 |
| NCAPD3 | NM_015261 |
| OR51F2 | NM_001004753 |
| SPINK1 | NM_003122 |
| RCN1 | NM_002901 |
| CP | NM_000096 |
| SMU1 | NM_018225 |
| ACTC1 | NM_005159 |
| AGR2 | NM_006408 |
| SLC26A4 | NM_000441 |
| IGKC | BC032451 |
| MYBPC1 | NM_002465 |
| NPY | NM_000905 |
| PI15 | NM_015886 |
| SLC22A3 | NM_021977 |
| PIGR | NM_002644 |

TABLE 1-continued

500 GENE PROBES THAT VARY IN EXPRESSION MOST ACROSS THE MSKCC DATASET

| HGNC symbol | Accession ID |
|---|---|
| APOD | NM_001647 |
| HPGD | NM_000860 |
| LEPREL1 | NM_018192 |
| LCE1D | NM_178352 |
| GSTM5 | NM_000851 |
| SLC30A4 | NM_013309 |
| SEMA3D | NM_152754 |
| CACNA2D1 | NM_000722 |
| GPR116 | NM_015234 |
| C7orf63 | NM_001039706 |
| FAM198B | NM_001128424 |
| SCD | NM_005063 |
| NR4A2 | NM_006186 |
| ARG2 | NM_001172 |
| ZNF385B | NM_152520 |
| RGS1 | NM_002922 |
| DNAH5 | NM_001369 |
| NPR3 | NM_000908 |
| RAB3B | NM_002867 |
| CHRDL1 | NM_145234 |
| ZNF208 | NM_007153 |
| MBOAT2 | NM_138799 |
| ATF3 | NM_001040619 |
| ST6GAL1 | NM_173216 |
| GDF15 | NM_004864 |
| ANXA1 | NM_000700 |
| FOLH1 | NM_004476 |
| C4B | NM_001002029 |
| ELOVL2 | NM_017770 |
| GSTM1 | NM_000561 |
| GLIPR1 | NM_006851 |
| C3 | NM_000064 |
| MYO6 | NM_004999 |
| ORM2 | NM_000608 |
| RAET1L | NM_130900 |
| PCDHB3 | NM_018937 |
| C1orf150 | ENST00000366488 |
| ALOX15B | NM_001141 |
| LSAMP | NM_002338 |
| SLC15A2 | NM_021082 |
| PCP4 | NM_006198 |
| MCCC2 | NM_022132 |
| GCNT1 | NM_001097634 |
| C5orf23 | BC022250 |
| SCGB1D2 | NM_006551 |
| CXCL2 | NM_002089 |
| AFF3 | NM_001025108 |
| ATP1B1 | NM_001677 |
| GJA1 | NM_000165 |
| PLA1A | NM_015900 |
| MPPED2 | NM_001584 |
| AMD1 | NM_001634 |
| EMP1 | NM_001423 |
| PRR16 | NM_016644 |
| CNN1 | NM_001299 |
| GHR | NM_000163 |
| ALDH1A1 | NM_000689 |
| TRIM29 | NM_012101 |
| IFNA17 | NM_021268 |
| TAS2R4 | NM_016944 |
| SEPP1 | NM_001093726 |
| GREM1 | NM_013372 |
| RASD1 | NM_016084 |
| C1S | NM_201442 |
| CLSTN2 | NM_022131 |
| DMXL1 | NM_005509 |
| HIST1H2BC | NM_003526 |
| NRG4 | NM_138573 |
| ARL17A | NM_001113738 |
| GRPR | NM_005314 |
| PART1 | NR_024617 |
| CYP3A5 | NR_033807 |
| KCNC2 | NM_139136 |
| SERPINE1 | NM_000602 |
| SLC6A14 | NM_007231 |
| EIF4A1 | NM_001416 |
| MYOF | NM_013451 |
| PHOSPHO2 | NM_001008489 |
| GCNT2 | NM_145649 |
| AOX1 | NM_001159 |
| CCDC80 | NM_199511 |
| ATP2B4 | NM_001001396 |
| UGDH | NM_003359 |
| GSTM2 | NM_000848 |
| MEIS2 | NM_172316 |
| RGS2 | NM_002923 |
| PRKG2 | NM_006259 |
| FIBIN | NM_203371 |
| FDXACB1 | NM_138378 |
| SOD2 | NM_001024465 |
| SEPT7 | NM_001788 |
| PTPRC | NM_002838 |
| GABRP | NM_014211 |
| CBWD3 | NM_201453 |
| TOR1AIP2 | NM_022347 |
| TRPC4 | NM_016179 |
| RAB27A | NM_004580 |
| CD69 | NM_001781 |
| RPL17 | NM_000985 |
| PSCA | NM_005672 |
| ATRNL1 | NM_207303 |
| MYOCD | NM_001146312 |
| MS4A8B | NM_031457 |
| TNS1 | NM_022648 |
| BAMBI | NM_012342 |
| IGF1 | NM_001111283 |
| RALGAPA1 | NM_014990 |
| S100A10 | NM_002966 |
| PMS2CL | NR_002217 |
| MMP2 | NM_004530 |
| SLC8A1 | NM_021097 |
| OAS2 | NM_002535 |
| ARRDC3 | NM_020801 |
| AMY2B | NM_020978 |
| SPARCL1 | NM_001128310 |
| IQGAP2 | NM_006633 |
| ACAD8 | NM_014384 |
| LPAR3 | NM_012152 |
| HIGD2A | NM_138820 |
| NUCB2 | NM_005013 |
| HLA-DPA1 | NM_033554 |
| SLITRK6 | NM_032229 |
| MME | NM_007288 |
| RBPMS | L17325 |
| HLA-DRB1 | NM_002124 |
| FOLH1 | NM_001193471 |
| LUZP2 | NM_001009909 |
| MSMB | NM_002443 |
| GSTT1 | NM_000853 |
| MMP7 | NM_002423 |
| ODZ1 | NM_001163278 |
| ACTB | NM_001101 |
| SPON2 | NM_012445 |
| SLC38A11 | NM_173512 |
| FOS | NM_005252 |
| OR51T1 | NM_001004759 |
| HLA-DMB | NM_002118 |
| KRT15 | NM_002275 |
| ITGA8 | NM_003638 |
| CXADR | NM_001338 |
| LYZ | NM_000239 |
| CEACAM20 | NM_001102597 |
| C8orf4 | NM_020130 |
| DPP4 | NM_001935 |
| PGC | NM_002630 |
| C15orf21 | NR_022014 |
| CHORDC1 | NM_012124 |
| LRRN1 | NM_020873 |
| MT1M | NM_176870 |
| EPHA6 | NM_001080448 |

TABLE 1-continued

500 GENE PROBES THAT VARY IN EXPRESSION MOST ACROSS THE MSKCC DATASET

| HGNC symbol | Accession ID |
|---|---|
| PDE11A | NM_001077197 |
| TMSB15A | NM_021992 |
| LYPLA1 | NM_006330 |
| FOSB | NM_006732 |
| F5 | NM_000130 |
| C15orf48 | NM_032413 |
| MIPEP | NM_005932 |
| HSD17B6 | NM_003725 |
| SLPI | NM_003064 |
| CD38 | NM_001775 |
| MMP23B | NM_006983 |
| OR51A7 | NM_001004749 |
| CFB | NM_001710 |
| CCL2 | NM_002982 |
| POTEM | NM_001145442 |
| TPMT | NM_000367 |
| FAM3B | NM_058186 |
| FLRT3 | NM_198391 |
| ATP8A2 | NM_016529 |
| PRIM2 | NM_000947 |
| ADAMTSL1 | NM_001040272 |
| NELL2 | NM_001145108 |
| RPS4Y1 | NM_001008 |
| CD24 | NM_013230 |
| GOLGA6L9 | NM_198181 |
| ZFP36 | NM_003407 |
| TRIB1 | NM_025195 |
| BNIP3 | NM_004052 |
| KL | NM_004795 |
| PDE5A | NM_001083 |
| DCN | NM_001920 |
| LDHB | NM_001174097 |
| PCDHB5 | NM_015669 |
| ACADL | NM_001608 |
| ZNF99 | NM_001080409 |
| CPNE4 | NM_130808 |
| CCDC144B | NR_036647 |
| SLC26A2 | NM_000112 |
| CYP1B1 | NM_000104 |
| SELE | NM_000450 |
| CLDN1 | NM_021101 |
| KRT13 | NM_153490 |
| SFRP2 | NM_003013 |
| SLC25A33 | NM_032315 |
| HSD17B11 | NM_016245 |
| HSD17B13 | NM_178135 |
| UGT2B4 | NM_021139 |
| CTGF | NM_001901 |
| SCIN | NM_001112706 |
| C10orf81 | NM_001193434 |
| CYR61 | NM_001554 |
| PRUNE2 | NM_015225 |
| IFI6 | NM_002038 |
| MYH11 | NM_022844 |
| PPP1R3C | NM_005398 |
| KCNH8 | NM_144633 |
| ZNF615 | NM_198480 |
| ERV3 | NM_001007253 |
| F3 | NM_001993 |
| TTN | NM_133378 |
| LYRM5 | NM_001001660 |
| FMOD | NM_002023 |
| NEXN | NM_144573 |
| IL28A | NM_172138 |
| FHL1 | NM_001159702 |
| CXCL10 | NM_001565 |
| CXCR4 | NM_001008540 |
| OR51L1 | NM_001004755 |
| SLC12A2 | NM_001046 |
| AGAP11 | NM_133447 |
| SLC27A2 | NM_003645 |
| AZGP1 | NM_001185 |
| VCAN | NM_004385 |
| ERAP2 | NM_022350 |
| KRT17 | NM_000422 |
| SLC2Al2 | NM_145176 |
| CCL4 | NM_002984 |
| RPF2 | NM_032194 |
| SLC45A3 | NM_033102 |
| SEC11C | NM_033280 |
| IFIT1 | NM_001548 |
| PAK1IP1 | NM_017906 |
| HIST1H3C | NM_003531 |
| ERRFI1 | NM_018948 |
| ADAMTS1 | NM_006988 |
| TRIM36 | NM_018700 |
| FLNA | NM_001456 |
| CCND2 | NM_001759 |
| IFIT3 | NM_001031683 |
| FN1 | NM_212482 |
| PRY | NM_004676 |
| HSPB8 | NM_014365 |
| CD177 | NM_020406 |
| TP63 | NM_003722 |
| IFI44 | NM_006417 |
| COL12A1 | NM_004370 |
| EDNRA | NM_001957 |
| PCDHB2 | NM_018936 |
| HLA-DRA | NM_019111 |
| TUBA3E | NM_207312 |
| ASPN | NM_017680 |
| FAM127A | NM_001078171 |
| DMD | NM_000109 |
| DHRS7 | NM_016029 |
| ANO7 | NM_001001891 |
| MEIS1 | NM_002398 |
| TSPAN1 | NM_005727 |
| CNTN1 | NM_001843 |
| TRIM22 | NM_006074 |
| GSTA2 | NM_000846 |
| SORBS1 | NM_001034954 |
| GPR81 | NM_032554 |
| CSRP1 | NM_004078 |
| C3orf14 | AF236158 |
| TPM2 | NM_003289 |
| REPS2 | NM_004726 |
| EAF2 | NM_018456 |
| CAV1 | NM_001172895 |
| PRUNE2 | NM_015225 |
| TMEM178 | NM_152390 |
| MFAP4 | NM_001198695 |
| SYNM | NM_145728 |
| EFEMP1 | NM_004105 |
| RND3 | NM_005168 |
| SCNN1A | NM_001038 |
| B3GNT5 | NM_032047 |
| LMOD1 | NM_012134 |
| UBC | NM_021009 |
| LMO3 | NM_018640 |
| LOX | NM_002317 |
| NFIL3 | NM_005384 |
| C11orf92 | NR_034154 |
| C11orf48 | NM_024099 |
| BCAP29 | NM_018844 |
| EPCAM | NM_002354 |
| PTGDS | NM_000954 |
| ASB5 | NM_080874 |
| TUBA1B | NM_006082 |
| SERHL | NR_027786 |
| ITGA5 | NM_002205 |
| SPARC | NM_003118 |
| C7 | NM_000587 |
| NTN4 | NM_021229 |
| FAM36A | NM_198076 |
| CNTNAP2 | NM_014141 |
| SC4MOL | NM_006745 |
| CH17-189H20.1 | AK000992 |
| TRGC2 | ENST00000427089 |
| RAP1B | NM_015646 |
| SLC4A4 | NM_001098484 |

TABLE 1-continued

500 GENE PROBES THAT VARY IN EXPRESSION MOST ACROSS THE MSKCC DATASET

| HGNC symbol | Accession ID |
|---|---|
| LCE2D | NM_178430 |
| EGR1 | NM_001964 |
| MT1L | NR_001447 |
| SCUBE2 | NM_020974 |
| FAM55D | NM_001077639 |
| PDK4 | NM_002612 |
| CXCL13 | NM_006419 |
| CACNA1D | NM_000720 |
| GPR160 | NM_014373 |
| CPM | NM_001874 |
| PTGS2 | NM_000963 |
| TSPAN8 | NM_004616 |
| BMP5 | NM_021073 |
| GOLGA8A | NR_027409 |
| OR4N2 | NM_001004723 |
| FAM135A | NM_001105531 |
| DYNLL1 | NM_001037494 |
| DSC3 | NM_024423 |
| C4orf3 | NM_001001701 |
| HIST1H2BK | NM_080593 |
| LCN2 | NM_005564 |
| STEAP4 | NM_024636 |
| RPS27L | NM_015920 |
| TRPM8 | NM_024080 |
| ID2 | NM_002166 |
| LUM | NM_002345 |
| EDNRB | NM_001122659 |
| PGM5 | NM_021965 |
| SFRP4 | NM_003014 |
| STEAP1 | NM_012449 |
| FADS2 | NM_004265 |
| CXCL11 | NM_005409 |
| CWH43 | NM_025087 |
| SNRPN | BC043194 |
| GPR110 | NM_153840 |
| THBS1 | NM_003246 |
| SPOCK1 | NM_004598 |
| GSTP1 | NM_000852 |
| OAT | NM_000274 |
| HIST2H2BF | NM_001024599 |
| ACSM3 | NM_005622 |
| GLB1L3 | NM_001080407 |
| SLC5A1 | NM_000343 |
| OR4N4 | NM_001005241 |
| MAOB | NM_000898 |
| BZW1 | NM_014670 |
| GENSCAN00000007309 | GENSCAN00000007309 |
| IFI44L | NM_006820 |
| KRT5 | NM_000424 |
| SCN7A | NM_002976 |
| GOLM1 | NM_016548 |
| HIST4H4 | NM_175054 |
| IL7R | NM_002185 |
| CSGALNACT1 | NM_018371 |
| A2M | NM_000014 |
| LRRC9 | AK128037 |
| ARHGEF38 | NM_017700 |
| ACSL5 | NM_016234 |
| SGK1 | NM_001143676 |
| TMEM45B | NM_138788 |
| AHNAK2 | NM_138420 |
| NEDD8 | NM_006156 |
| GREB1 | NM_014668 |
| UBQLN4 | NM_020131 |
| SDHC | NM_003001 |
| TCEAL2 | NM_080390 |
| SLC18A2 | NM_003054 |
| HIST1H2BE | NM_003523 |
| RARRES1 | NM_206963 |
| PLN | NM_002667 |
| OGN | NM_033014 |
| GPR110 | NM_025048 |
| CLGN | NM_001130675 |
| NIPAL3 | NM_020448 |
| ACTG2 | NM_001615 |
| RCAN3 | NM_013441 |
| KLK11 | NM_001167605 |
| HMGCS2 | NM_005518 |
| EML5 | NM_183387 |
| EDIL3 | NM_005711 |
| PIGH | NM_004569 |
| GLYATL1 | NM_080661 |
| FGFR2 | NM_000141 |
| SNAI2 | NM_003068 |
| CALCRL | NM_005795 |
| MON1B | NM_014940 |
| PVRL3 | NM_015480 |
| VGLL3 | NM_016206 |
| SULF1 | NM_001128205 |
| LIFR | NM_002310 |
| SH3RF1 | AB062480 |
| C12orf75 | NM_001145199 |
| GNPTAB | NM_024312 |
| CALM2 | NM_001743 |
| KLF6 | NM_001300 |
| C7orf58 | NM_024913 |
| RDH11 | NM_016026 |
| NR4A1 | NM_002135 |
| RWDD4 | NM_152682 |
| ABCC4 | NM_005845 |
| ZNF91 | NM_003430 |
| GABRE | NM_004961 |
| SLC16A1 | NM_001166496 |
| DEGS1 | NM_003676 |
| CLDN8 | NM_199328 |
| HAS2 | NM_005328 |
| ODC1 | NM_002539 |
| REEP3 | NM_001001330 |
| LYRM4 | AF258559 |
| PPFIA2 | NM_003625 |
| PGM3 | NM_015599 |
| ZDHHC8P1 | NR_003950 |
| C6orf72 | AY358952 |
| HIST1H2BD | NM_138720 |
| TES | NM_015641 |
| PDE8B | NM_003719 |
| DNAJB4 | NM_007034 |
| RGS5 | NM_003617 |
| EPHA3 | NM_005233 |
| COX7A2 | NR_029466 |
| MT1H | NM_005951 |
| HIST2H2BE | NM_003528 |
| TGFB3 | NM_003239 |
| VEGFA | NM_001025366 |
| CRISPLD2 | NM_031476 |
| TFF1 | NM_003225 |
| LOC100128816 | AY358109 |
| SYT1 | NM_001135805 |
| CPE | NM_001873 |
| LOC286161 | AK091672 |
| NAALADL2 | NM_207015 |
| TMPRSS2 | NM_001135099 |
| SERPINF1 | NM_002615 |
| EPHA7 | NM_004440 |
| SDAD1 | NM_018115 |
| SOX14 | NM_004189 |
| RPL35 | NM_007209 |
| HSPA1B | NM_005346 |
| MSN | NM_002444 |
| MTRF1L | NM_019041 |
| PTN | NM_002825 |
| CAMKK2 | NM_006549 |
| RBM7 | NM_016090 |
| OR52H1 | NM_001005289 |
| C1R | NM_001733 |
| CHRNA2 | NM_000742 |
| MRPL41 | NM_032477 |
| PROM1 | NM_001145847 |
| LPAR6 | NM_005767 |
| SAMHD1 | NM_015474 |

TABLE 1-continued

500 GENE PROBES THAT VARY IN EXPRESSION MOST ACROSS THE MSKCC DATASET

| HGNC symbol | Accession ID |
|---|---|
| SCNN1G | NM_001039 |
| DNAJC10 | NM_018981 |
| MOXD1 | NM_015529 |
| HIST1H2BG | NM_003518 |
| ID1 | NM_181353 |
| SEMA3C | NM_006379 |

TABLE 2

45 GENES COMMONLY DOWNREGULATED IN THE MSKCC, KLEIN, CANCERMAP AND STEPHENSON DATASETS (AT LEAST 80/100 LPD RUNS)

| | | | | | |
|---|---|---|---|---|---|
| C7 | CSRP1 | GPX3 | EPAS1 | CRISPLD2 | PCP4 |
| JAM3 | FBLN1 | LMOD1 | CNN1 | ETS2 | ACTN1 |
| MYLK | ATP2B4 | SPG20 | CLU | ILK | CDC42EP3 |
| ACTG2 | PPAP2B | STOM | GSTP1 | MYL9 | SORBS1 |
| STAT5B | PLP2 | ITGA5 | TIMP3 | PALLD | PDK4 |
| TPM2 | RBPMS | TNS1 | SVIL | FERMT2 | |
| FLNA | CALD1 | SNAI2 | TPM1 | TGFBR3 | |
| KCNMA1 | ACTA2 | PDLIM1 | DPYSL3 | VCL | |

TABLE 3

20 GENES IDENTFIED BY LASSO ANLAYSIS FROM THE 1669 GENES IDENTIFED IN TABLE 4

| | | | | |
|---|---|---|---|---|
| DST | CYP27A1 | SP100 | ALDH2 | MME |
| CHRDL1 | RND3 | PARM1 | WDR59 | S100A13 |
| THSD4 | ACTG2 | ZNF532 | LDHB | MSRA |
| GSTM4 | PLEKHA6 | DLG5 | CDK6 | EPHX2 |

TABLE 4

1669 GENES THAT EXHIBIT SIGNIFICANTLY DIFFERENT EXPRESSION BETWEEN DESNT AND NON-DESNT CANCERS IN AT LEAST TWO DATASETS

| | | | | | | | |
|---|---|---|---|---|---|---|---|
| LPP | CX3CL1 | NSFL1C | PFKFB3 | USP11 | CCND2 | CLIC4 | |
| UGP2 | RGL1 | CCDC69 | PER3 | DLD | FBXO7 | DKC1 | |
| MFN2 | ATAD1 | TRIM29 | RFWD2 | C11orf54 | S100A13 | WLS | |
| UTY | CHD1 | EIF5 | AOC3 | ATP2B4 | SQRDL | EMP2 | |
| SPRY1 | ZNF589 | STMN1 | ATF3 | FBXO18 | COPZ2 | SLC2A5 | |
| CTNNB1 | SETD5 | MITF | GON4L | WSB1 | ALDH3A2 | FBXW4 | |
| CAT | ABR | TNKS | TMF1 | ST8SIA1 | TPP2 | GALM | |
| MBTPS1 | WDR19 | MSRB2 | NR4A1 | ID1 | FAM129A | ECHDC2 | |
| SLC38A2 | ZCCHC11 | MBNL2 | SPTBN1 | CASC3 | PCDH9 | ACTA2 | |
| CCT3 | STK24 | TRIP11 | FLOT1 | RBMS3 | FHL2 | MADD | |
| ITSN1 | PI4KA | PIAS2 | DGKA | SPG11 | WIPF1 | EYA4 | |
| SCYL3 | NFAT5 | RYK | VCL | CCDC121 | RBPMS | DLX1 | |
| TPST1 | CAPNS1 | GPR161 | TFDP 1 | SERINC3 | SIK2 | FAM198B | |
| MGP | METTL3 | ACTC1 | PREX2 | RBBP6 | ACOX1 | TAB2 | |
| SMC1A | RFC2 | BRE | PRRG4 | CRTAP | LYST | SMARCA2 | |
| KCNMB1 | SNAI2 | ZC3H18 | ANKRD12 | NUB1 | PPIC | TCF7L2 | |
| LMBRD1 | ANKRD34B | SLC1A1 | APEX1 | FOXN3 | NCOA1 | FBLN1 | |
| TJP2 | SF3A1 | GABBR1 | MEF2A | AMT | CNOT1 | SET | |
| DVL2 | ATP2A2 | PPP1R10 | PI15 | EPS15 | LONRF3 | PPAP2B | |
| IL4R | CDK5RAP2 | ROCK2 | LARGE | MATR3 | UBE2E3 | CDH11 | |
| FBXO32 | DHX9 | RARA | PARP6 | SKP2 | ILF3 | SP110 | |
| RAB2A | STAU1 | SVIL | ANXA7 | TUBB | WAC | CAST | |
| ZMYND8 | MAPKAPK2 | PMP22 | PDSS2 | PEX10 | LRP1 | EP400 | |
| MTMR9 | ATP10D | KIF1B | LRPPRC | RAB27A | TCF12 | AFF1 | |
| GLIPR2 | USP9X | PBRM1 | COX7A1 | LASP1 | TSPAN13 | PCBP1 | |
| GLT8D1 | SLC41A1 | ANAPC1 | NUP214 | NRBP1 | AIMP2 | | |
| CLK1 | METTL7A | LGALS3BP | WDR11 | YTHDC1 | CDC45 | GNG12 | |
| CDC5L | LTBP1 | PRMT1 | SFXN3 | HEG1 | KLF3 | FAM13B | |
| POGZ | BNC2 | BAG3 | SON | MORF4L2 | LRP10 | ADAMTS1 | |
| PRDM2 | EPC2 | ACSS3 | TRAF3IP2 | AMFR | SERPING1 | EFEMP1 | |
| PER1 | RUVBL1 | MSN | PKP1 | COX11 | GPM6B | GTF2I | |
| GCNT2 | PARM1 | PPP1R15A | UBR2 | STARD13 | PCDH7 | MANBAL | |
| SLC22A17 | VEZF1 | FGA | MXI1 | RBMS1 | FYTTD1 | SSTR1 | |
| APP | MYLK | MYH11 | STAT3 | ROBO1 | AMMECR1 | TEAD1 | |
| DMD | ZYG11B | CDH7 | MTUS1 | VSIG2 | WDFY3 | RBAK | |
| KCTD9 | SH3RF1 | TCF20 | HEPH | TRERF1 | NDRG2 | SORBS2 | |
| CUL3 | VPS13D | C2orf43 | DNAJB5 | FAF1 | ATOX1 | BIN1 | |
| ADRA1A | MDH1 | POPDC2 | TGFBI | WHSC1L1 | PITPNC1 | HSPB1 | |
| SCMH1 | APCDD1 | LRPAP1 | PDLIM4 | C9orf72 | PPP1R15B | PPARD | |
| ZNF483 | AHNAK2 | ARID1B | AGL | SYNE1 | U5P25 | C9orf3 | |
| NAMPT | ACTR3 | ERC1 | ELF1 | GAB1 | EXOSC10 | NID1 | |
| ITGB4 | CBX7 | LIMK2 | CELF2 | PINK1 | ZNF207 | SF3B1 | |
| SMC6 | LEPREL1 | DYRK1A | MEIS2 | PLD3 | PDS5A | FAM124A | |
| NBEAL1 | MT1M | HIPK1 | TP53BP1 | TRPM7 | IRF2BP2 | RNF213 | |
| EPB41L5 | TSPYL2 | TTC17 | PTGDS | NF1 | MED13 | LPAR1 | |
| TMEM51 | RHOT1 | JAZF1 | NBAS | ASAP1 | DDX42 | PDE8A | |
| IGF1R | DYNLT1 | SMAD3 | TACC2 | CLSPN | KPNA6 | TNPO1 | |
| SYNM | HERC4 | PRKCD | CELF1 | CAP2 | MPHOSPH8 | TSPAN18 | |
| MYL9 | SERPINB1 | SMG6 | SLC37A3 | RNF185 | PYGL | UST | |

TABLE 4-continued

1669 GENES THAT EXHIBIT SIGNIFICANTLY DIFFERENT EXPRESSION
BETWEEN DESNT AND NON-DESNT CANCERS IN AT LEAST TWO DATASETS

| | | | | | | |
|---|---|---|---|---|---|---|
| UBA6 | HSPA9 | PDZRN4 | DICER1 | SEC31A | KCNAB1 | SAP130 |
| HSD17B11 | DPYSL3 | VWA5A | TP53INP2 | CLU | CTSB | ALAS1 |
| DDX17 | PELI1 | PDGFC | SS18 | MAPKAP1 | STOM | FST |
| MYADM | ARSJ | UNG | ST5 | SNX2 | EGFR | CLASP1 |
| SMURF2 | PSIP1 | CCNL1 | FLNA | PARP14 | RB1 | ELOVL6 |
| ZFP36L1 | PPFIBP1 | PRICKLE2 | DHX8 | KHDRBS3 | TLN1 | DDX24 |
| YY1AP1 | AGPAT1 | JAK2 | CAV1 | RAPH1 | NEO1 | CD99L2 |
| FN1 | SETD3 | DCN | CPT1A | SMNDC1 | TLE4 | PRUNE2 |
| PPFIBP2 | BRIX1 | VPS45 | TGFB3 | CCNI | LMNA | SLK |
| UBE4B | GSTP1 | IP6K2 | BTBD7 | USO1 | TTC14 | ENSA |
| APOBEC3C | WBP5 | HFE | ATP12A | DNAH10 | THOC2 | GBP1 |
| PDS5B | SLC25A23 | CSDE1 | NCOA7 | CTDSP2 | LATS1 | PTEN |
| DDR2 | FAM65A | TMLHE | C16orf45 | CEBPB | ANG | HP1BP3 |
| WDR1 | DYM | SPATS2L | C7 | VEGFA | PRPF4B | TBX3 |
| COL4A6 | MAP1B | MED13L | PSMC4 | AKAP11 | MON2 | TIMP3 |
| SH3BP5 | PAXIP1 | STAT5B | PIK3C3 | ZC3H7A | PLCL1 | CDC73 |
| NEBL | MYOCD | CLIP1 | RCAN3 | KIAA0513 | ACSS2 | ZYX |
| ARHGEF7 | CDKL5 | NUP98 | BPTF | PDCD6IP | LPHN2 | DLG1 |
| DST | NSF | NIPAL3 | ZMYM4 | RTN4 | KIAA1109 | EFS |
| KPNA1 | ITM2C | CYB5B | UBQLN1 | ASPH | TRIM38 | TTLL7 |
| DIP2C | CREG1 | EP841L1 | APOL1 | MLXIP | NCK1 | SH3BGRL |
| MSRB3 | NUCKS1 | TOPBP1 | ZEB2 | FAM114A1 | PITRM1 | PSMD1 |
| NHS | BAZ1B | PDK4 | PJA2 | PLEKHO1 | RBM3 | ADHFE1 |
| ZNF460 | LMOD1 | TNFRSF1A | UTP14A | ARIH1 | NFX1 | ZRANB2 |
| JPH2 | CACNA1D | CAPN7 | OGN | NFIX | ORMDL1 | WRNIP1 |
| MTMR3 | HIF1A | ANXA11 | CDK4 | YWHAB | TMEM43 | AKAP7 |
| SLIT2 | PAN3 | CACHD1 | PIK3R1 | ROR2 | NID2 | CSRNP1 |
| CCDC91 | UACA | MCAM | CXCL12 | TCIRG1 | NHLRC2 | FREM2 |
| YEATS2 | BACH1 | TPM1 | MAEA | SCP2 | PALLD | MAP1LC3B |
| SYNE2 | MAP4K4 | HBP1 | ZBTB20 | MATN2 | ASXL2 | ATF6 |
| GEM | MKX | DZIP1 | NOL8 | LMO3 | DES | LMO4 |
| SLC10A7 | PAPD4 | CBLB | CD81 | SLC7A8 | MAPKAPK5 | SLC16A2 |
| PTGS2 | PDGFRA | PCNA | CDC42BPB | ZFYVE9 | UBR4 | KPNB1 |
| USP24 | RSPO3 | ACOX2 | NIPBL | PDE5A | MSMB | TNFRSF19 |
| C1S | AP281 | EIF4A2 | ANO5 | FERMT2 | TNFRSF10B | UBE3C |
| ANGPT1 | SRI | NFATC3 | DUOX1 | PDLIM3 | IK | LIMA1 |
| AFF3 | PSMA4 | B4GALT5 | BCLAF1 | TSC22D3 | TUBB6 | EPAS1 |
| MAP3K4 | NT5C2 | POLDIP3 | SMG7 | PTPRA | PHF21A | MARK3 |
| MME | MIER1 | TOP2A | QKI | MRPL10 | SLC8A1 | CYP27A1 |
| RHOJ | DCAF7 | THBS1 | PCM1 | SEMA3C | ACIN1 | NDEL1 |
| CHRDL1 | FGFR2 | NSD1 | MKL2 | DCBLD1 | APBB1 | NUMB |
| AASS | TRIM33 | GGA2 | VAPA | MAX | ZNF516 | TMBIM1 |
| INO80 | PCP4 | CWC27 | CMIP | KIF20A | CLIC6 | RELA |
| FBXO11 | IER3 | FAM127B | STAT2 | CLK4 | DEDD | PIK3CA |
| PDK2 | ABCC13 | LITAF | RCC2 | FLOT2 | AFAP1L2 | MACF1 |
| DMXL2 | AKAP13 | TRIP6 | ETS2 | TGFBR2 | TPR | PRNP |
| MEIS1 | F5 | RDH10 | TRIP12 | RALGAPA2 | USH2A | CTNS |
| RPRD2 | EPHX2 | PTK2 | LRRN1 | THSD4 | TEX2 | PER2 |
| NXF1 | CHMP1A | ITSN2 | SETBP1 | SNX9 | CPE | TTLL13 |
| RICTOR | CPM | FBXO17 | LRCH2 | IREB2 | ATP1A1 | HS18P3 |
| TTBK2 | ALMS1 | VAMP3 | MAPK14 | GPX3 | ITIH5 | DHX36 |
| DDHD2 | YAP1 | OGDHL | CSNK1D | PSME1 | DDX3Y | TMEM185A |
| NUP153 | SRPX | TNRC6A | ZFP36 | PPFIA1 | ARHGAP1 | USP48 |
| SNRNP200 | PGM5 | HOXD10 | SSX2IP | MY06 | COL6A1 | ADH5 |
| LONRF1 | IGF1 | UBE2C | PYGM | GJA1 | PTK2B | PRKAR1A |
| KANK1 | CMBL | ITGB1 | BAZ2B | REST | ILK | PRPF8 |
| HECTD1 | B3GALT2 | UBR3 | ABI2 | CALU | LRP6 | PIGT |
| ABHD6 | ATP8B1 | MAGI2 | TOMM34 | OLFML3 | ITGB8 | PLP2 |
| DSTN | PARD3 | PRPF3 | HSPB6 | XRN2 | BCAS1 | ATG9A |
| KDM3B | MTMR8 | ATP6V0E1 | ID4 | S100A16 | RALGAPB | ABI1 |
| COL6A3 | ZNF451 | CCDC80 | GDAP1 | EIF4EBP2 | ITGB3 | LSAMP |
| KLHL5 | RC3H2 | ITPK1 | RYBP | LDHB | AKT3 | DOPEY1 |
| TAGLN | IFI16 | MAPK1IP1L | TIMP2 | SLMO2 | TRMU | ETV5 |
| PKN2 | MMP19 | FLNC | RNF217 | SPAG9 | KAT2B | NKAIN1 |
| TCERG1 | YPEL5 | DO CK1 | CCT6A | PUM2 | OGDH | NFE2L1 |
| ADAR | VPS37A | KANK2 | CCNT2 | YWHAH | IARS | USP34 |
| REV1 | NUDT5 | STARD4 | KDM3A | ZNF655 | YME1L1 | CASP14 |
| SORT1 | STK4 | CKAP5 | CDKN1B | TCF21 | KIF2A | CYB5R2 |
| DDX198 | ANXA4 | ATF7IP | HLF | IL17RA | ZMYND11 | ROCK1 |
| CFL2 | ARHGAP26 | RAB7A | MYH9 | STXBP1 | ATG2B | PPP1R12A |
| CDK12 | TIMP1 | ENAH | SCARA3 | SDCCAG8 | TIMELESS | DKK3 |
| RGN | SKP1 | NPC2 | LRP2 | DDX3X | SEC248 | SBNO1 |
| MPDZ | GPBP1 | BOD1 | CHST3 | SCAMPI | CAV2 | PCNX |
| SLC1A5 | ANXA2 | GSTM4 | OTUB1 | C11orf57 | DCBLD2 | SPEG |
| MAP4 | ANKRD17 | AQR | LGALS1 | EFTUD1 | CDC42SE2 | ZNF234 |
| LCLAT1 | FOXO4 | IVNS1ABP | NR2C2 | TOR1AIP1 | KCNJ8 | CYB5R3 |
| LIX1L | BCOR | SORBS3 | AXIN2 | C16orf62 | NISCH | KCNMA1 |

TABLE 4-continued

1669 GENES THAT EXHIBIT SIGNIFICANTLY DIFFERENT EXPRESSION
BETWEEN DESNT AND NON-DESNT CANCERS IN AT LEAST TWO DATASETS

| | | | | | | |
|---|---|---|---|---|---|---|
| DPT | PPP1R38 | SPTA1 | SESTD 1 | GMPR | CNOT4 | RAB11FIP2 |
| FAM127A | TIA1 | CALD1 | CIZ1 | GDPD1 | SNX33 | CHMP2B |
| OTUD4 | NVL | EML4 | NCK2 | OPA1 | ITPR2 | KLHDC2 |
| EPS15L1 | HADHA | ARHGAP17 | NIN | VDAC3 | ARHGAP10 | USP30 |
| ARL6IP1 | LRRC41 | GADD45B | CD59 | RNF216 | CDC42EP3 | HOOK3 |
| BIN3 | AES | KCTD10 | PARN | MPZL2 | CD74 | SMAD4 |
| CNN2 | GSTM2 | EDARADD | TSPAN31 | ZSCAN18 | TMED10 | HPS1 |
| AFF4 | SMARCA5 | CTSA | FOSL2 | CASP7 | DIXDC1 | CLCN6 |
| ADCY5 | CYP20A1 | WDR26 | GSTK1 | FMNL2 | LRRC16A | SERINC1 |
| RDX | VAMP2 | CTTNBP2NL | RASA1 | NPHP3 | SKIL | SSFA2 |
| RABGAP1L | LDB3 | MAF | TNRC6B | GNAO1 | GGT7 | RNF121 |
| RAD50 | PRKCB | SYTL4 | YTHDC2 | GCLC | FLII | CEP350 |
| EAF2 | ATM | TMEM63A | PTPLA | ARRB1 | MAT2A | TAPBP |
| FYCO1 | S100A6 | NFKBIZ | PAK1IP1 | LGALS3 | BCL6 | MEF2C |
| RBM4 | CYTH3 | TNC | CDC27 | RUFY3 | N48P2L2 | MTPAP |
| MKLN1 | DEK | CAPRIN1 | COMMD6 | NPAS2 | CD47 | CD44 |
| TRA2B | ATF2 | BCL7B | MID2 | MAML2 | PEA15 | VILL |
| EXOC4 | MAPK10 | ADCY8 | SRGN | NUFIP2 | RRM1 | NFIB |
| DIRAS2 | MBNL1 | R3HDM1 | LIMS2 | REL | GLI3 | CD40 |
| TUBA1A | ALDH1A2 | FNBP1L | NETO2 | MRVI1 | GLG1 | PUS7 |
| EEA1 | MRAS | TTLL5 | GIT2 | SUPT4H1 | SUN1 | UTP18 |
| CA11 | REXO2 | ZCCHC24 | GNL2 | GATAD2B | PDHA1 | PTPRG |
| AKT2 | RIC3 | FAT1 | COMMD1 | MSL2 | KIF16B | KLF4 |
| ACOX3 | AUTS2 | DHX15 | ARID4B | MFAP4 | ARPP19 | TBC1D14 |
| MLLT10 | PSAP | TBC1D1 | EFHD2 | AOX1 | GAS1 | PSMC5 |
| HNRNPU | CUL1 | MAN1A2 | EIF4G2 | SOS1 | STRN3 | DYNC1H1 |
| ATXN2 | SORBS1 | TTC28 | CSTB | ZNF280D | GPR124 | RBM23 |
| TSHZ3 | EXOC7 | CALCOCO2 | MMP2 | MAPK1 | OAZ1 | RRAS |
| ELP3 | PPARGC1A | HK1 | ZEB1 | TBC1D5 | NFKBIA | CEP120 |
| GNS | DMTF1 | DIP2B | ARNT | SCPEP1 | SCN7A | STAM2 |
| EP300 | PTPN14 | STK38L | HELZ | BBS2 | DOCK9 | DUSP1 |
| FGF2 | ATP2B1 | CPEB3 | EGR1 | AFTPH | USP4 | RHOA |
| DLG5 | GIGYF2 | PARVA | CHD9 | GAS6 | SMARCC2 | CDC42BPA |
| TBL1X | GSTM5 | SCRN1 | NEU1 | PRPSAP1 | PAICS | SUPT16H |
| PTPRM | ACO1 | SMURF1 | STAT6 | IL13RA1 | TGFB1I1 | TRAK2 |
| RHOBTB3 | STXBP6 | EIF5B | MEF2D | BHLHE40 | MED21 | PRRG1 |
| GGCT | SERPINH1 | MCL1 | CHMP1B | UCK2 | STX12 | ASH1L |
| CLINT1 | SMAD2 | RBL2 | TNKS2 | FXYD6 | TMEM165 | ATP8B2 |
| LAPTM4A | ATL3 | SMC5 | TOP1 | AP3B1 | NT5DC3 | KIAA1033 |
| ANO4 | CREB3L2 | ASAP2 | SETX | LBR | CALCOCO1 | LAMP1 |
| ZNFX1 | ABCC9 | LRCH3 | PSME4 | MTOR | NR4A3 | TRPC4 |
| CDC42EP4 | FOSB | PTRF | ZC3H13 | GLIPR1 | CDC42EP5 | NR4A2 |
| PLSCR1 | COQ10B | TPM2 | ANPEP | FRMD6 | NCAPD2 | POLR2A |
| IFI35 | CHRM1 | NEIL3 | ACACB | SETD2 | DNAJB1 | CNN3 |
| HNRNPM | ITM2B | ZNF611 | SEC63 | PRKDC | EIF4G3 | VIM |
| PCDH15 | ALOX15B | INO80D | C1R | RIN2 | GNAI2 | IMMT |
| BBX | TMEM55A | NFIA | STXBP3 | SLFN5 | SPATA6 | PAGE4 |
| EXOC1 | ERAP1 | PRPS2 | JARID2 | JAM3 | EPHA3 | ARHGAP20 |
| A2M | DNAJC13 | PIBF1 | CDC37L1 | TBCK | ZNF396 | GALNT8 |
| ASCC3 | ITCH | RARS2 | DAB2 | ARL6IP5 | TBCEL | SLMAP |
| TGFBR1 | DAAM2 | HMGXB4 | SOS2 | IDE | FUBP1 | FBN1 |
| CORO1C | LARP6 | TSC1 | TECPR2 | RBBP7 | PHF11 | NEXN |
| GNAL | IFNAR1 | NEK7 | GPATCH8 | TACC1 | ATP1A2 | PUM1 |
| GTF3C2 | FAM160B1 | IDS | SLC39A14 | BTG2 | APOOL | EPRS |
| IL6ST | LAMB2 | FAM107B | SH3PXD2B | VPS39 | NCBP1 | MORC3 |
| TTLL4 | KIF15 | SUPT6H | ZNF384 | AHCYL1 | NOTCH2 | TGFBR3 |
| TNRC6C | IP08 | EARS2 | AP3D1 | KRT15 | STX6 | SECISBP2L |
| SAT2 | WNK1 | ANKRD40 | JMJD1C | TEP1 | CALM1 | UBP1 |
| HIPK3 | PLXDC2 | IRS1 | COL6A2 | WDR12 | SENP7 | KBTBD2 |
| PHF1 | CD63 | ADD1 | TCEAL2 | COPS3 | PYGB | SBF2 |
| TSG101 | STAT5A | DENND4A | STAM | BNIP2 | TRAPPC10 | PBX1 |
| EYA1 | HDDC2 | NNT | EMP3 | PNMA1 | KLF9 | HERPUD2 |
| C15orf41 | NPTN | RND3 | SHKBP1 | FBXO31 | ZNF3 | SWAP70 |
| DENND5A | SMOC1 | FNBP1 | TRIO | ROS1 | SLC18A2 | AHR |
| PPIP5K2 | HSPB8 | DUSP3 | FHL1 | LDB1 | HIST1H4C | RASD2 |
| TTLL3 | ITGA7 | PLEKHA6 | SIN3A | FAM20B | MRGPRF | RAB8B |
| SMTN | EZH1 | CAP1 | MYO1D | PLEK2 | KHDRBS1 | MY09A |
| PRKD1 | PDE4D | PHF3 | JUN | DERA | LSM14A | XPO7 |
| GPRC5B | KRT23 | CHURC1 | ENTPD4 | COPA | SLC12A4 | KCNS3 |
| PRKACA | SPON1 | LNPEP | ACADVL | CSRP1 | M6PR | DDX1 |
| HERC1 | C10orf76 | CAPZB | VPS53 | MYCBP2 | POLR2B | ANXA1 |
| ZZEF1 | ZNF318 | PCDH18 | HEXB | C11orf30 | OTUD5 | CYR61 |
| SNTB2 | PHC3 | KIF4A | UBE2E1 | PRPSAP2 | SPRY2 | RGS2 |
| RBM5 | AMOT | SNRNP40 | USP14 | TGFB2 | TMEM109 | ARRDC3 |
| WWTR1 | STAG1 | CST3 | TINAGL1 | MYO1C | SPTAN1 | REV3L |
| DAAM1 | ARPC2 | CSNK2B | PRPF18 | ANTXR2 | PLEKHA5 | OSMR |
| GSN | AGFG1 | LDB2 | PKD2 | ITGA9 | SAMD8 | SLC15A2 |

TABLE 4-continued

1669 GENES THAT EXHIBIT SIGNIFICANTLY DIFFERENT EXPRESSION
BETWEEN DESNT AND NON-DESNT CANCERS IN AT LEAST TWO DATASETS

| | | | | | | |
|---|---|---|---|---|---|---|
| C2orf88 | TMEM59 | RLF | UBAP1 | PDE11A | TMEM220 | REPS1 |
| GPRASP1 | STX7 | SMG1 | TNS1 | RAF1 | XRCC5 | PPWD1 |
| CDKAL1 | VPS4B | DCUN1D4 | GNG2 | PTN | FNBP4 | TMEM35 |
| SLC25A12 | ITGA5 | BIRC6 | KIF14 | DARS | UFC1 | TBC1D23 |
| PCGF5 | DAPK3 | EMP1 | RBPMS2 | TEAD3 | CTGF | MSRA |
| KIF5B | ZHX2 | KRT5 | PPP1R7 | ZFR | NPAT | ABCB11 |
| ARMCX1 | KIAA0430 | PRDM8 | SLC4A7 | PSMB7 | CISD1 | ACTN1 |
| SNX19 | JAK1 | RHOB | DRAM2 | SMARCA4 | CNPY2 | CD38 |
| WBP2 | MED12 | PTTG1IP | EHD2 | TCF4 | SEC24A | QRICH1 |
| PHIP | RNF38 | ITGA1 | STRBP | TRPS1 | FOXJ3 | SP100 |
| KLF8 | ALDH2 | SPEN | NPR2 | DEPDC1B | TMEM47 | CYLD |
| TET2 | XYLB | CDK6 | MYL6 | UBAP2L | EXT1 | TRO |
| MIB1 | SIDT1 | EPHB6 | XRN1 | TLE2 | PAK3 | CD46 |
| SRD5A2 | ZFAND 5 | PPP3CB | RAP1A | TCF25 | IGFBP5 | OSBPL9 |
| PDLIM1 | SPARCL1 | MTMR12 | PITPNB | CYC1 | CNOT6 | NCKAP1 |
| GDAP2 | USP53 | ZNF185 | DCP1A | PLAGL1 | FABP3 | SOD2 |
| DCTN1 | ACTG2 | FAM160B2 | VAMP5 | MTR | TP63 | PTP4A2 |
| BMPR2 | SPOP | SF3B3 | VPS13C | SMAD9 | SHISA5 | CHD2 |
| CCDC25 | WDR59 | BIRC5 | CREBBP | LZTFL1 | SERPINF1 | SPOCK3 |
| ITPR1 | LAMA4 | MXRA5 | CAMK2G | FCHSD2 | ZNF148 | G3BP1 |
| GTF3C3 | MCC | EHBP1 | CNN1 | SOX4 | CRIM1 | PREPL |
| ETV6 | DPYD | AEBP2 | MAP3K7 | CREB1 | MAN2A1 | FUBP3 |
| TBC1D9B | ASB2 | ZFC3H1 | MYOF | HNRNPA2B1 | QSER1 | RSRC2 |
| ARFGEF2 | ZBTB4 | IQGAP1 | SGCB | PIP4K2A | MPPED2 | SMARCA1 |
| SEC23A | CHMP7 | BOC | NFYC | UBC | RCBTB2 | AP1G1 |
| PHACTR2 | VPS41 | SPRED1 | IL1R1 | RQCD1 | AKIRIN2 | PPP1CB |
| CRISPLD2 | CRY2 | FZD7 | ARHGEF12 | SLC22A3 | GABARAPL1 | MAP4K5 |
| ADSL | FGFR1 | GNG4 | DCUN1D1 | FASTKD2 | STK38 | GALC |
| XPC | ASNS | CTNNA1 | RNF11 | SENP6 | KDSR | FNDC3B |
| NFE2L2 | GABARAPL2 | ERBB2IP | RARRES1 | ESYT2 | GBF1 | PPIL4 |
| CDS2 | TRIP13 | SYNRG | CYP3A5 | RABGAP1 | SHOC2 | ZNF532 |
| HUWE1 | EDNRA | DDX5 | PTPRK | STIM1 | EPCAM | MARVELD1 |
| AHI1 | ABCA8 | EPB41L2 | CCDC88A | GRAMD3 | TRIP10 | SLAIN2 |
| YPEL3 | AZGP1 | SLC14A1 | SCAPER | NCAPG2 | NEK1 | RAB3GAP2 |
| KDM2A | DCAF8 | MYO15B | ZNF638 | FAM69A | | |
| RAD54L2 | RIMKLB | CRTC3 | WFDC2 | L3MBTL4 | | |

TABLE 5

35 GENES COMMONLY DOWNREGULATED IN
THE MSKCC, KLEIN, CAMCAP AND STEPHENSON
DATASETS (AT LEAST 67/100 LPD RUNS)

35 genes 67 of 100

| | | | | | |
|---|---|---|---|---|---|
| ACTN1 | ANXA2 | HSPB8 | ILK | CSRP1 | FERMT2 |
| ATP2B4 | ACTG2 | PCP4 | MYLK | CNN1 | JAM3 |
| LMOD1 | TPM2 | SORBS1 | MYH11 | DPYSL3 | VCL |
| LPAR1 | MYL9 | STOM | FBLN1 | KCNMA1 | PALLD |
| GSTP1 | C7 | TGFB3 | RND3 | CXCL12 | ITGA5 |
| PTRF | ACTA2 | TGFBR3 | FZD7 | FLNA | |

TABLE 6

Example Control Genes: House Keeping Control genes

| | | | | | |
|---|---|---|---|---|---|
| HPRT | 18S rRNA | RPL9 | PFKP | H2A.X | RPL23a |
| 82M | 28s rRNA | SRP14 | EF-1d | IMP | RPL37 |
| TBP | PBGD | RPL24 | IMPDH1 | accession number X56932 | RPS11 |
| GAPDH | ACTB | RPL22 | IDH2 | | RPS3 |
| ALAS1 | UBC | RPS29 | KGDHC | ODC-AZ | SDHB |
| RPLP2 | rb 23kDa | RPS16 | SRF7 | PDHA1 | SNRPB |
| KLK3_ex2-3 | TUBA1 | RPL4 | RPLP0 | PLA2 | SDH |
| KLK3_ex1-2 | RPS9 | RPL6 | ALDOA | PMI1 | TCP20 |
| SDH1 | TFR | OAZ1 | COX !V | SRP75 | CLTC |
| GPI | RPS13 | RPS12 | AST | RPL3 | |
| PSMB2 | RPL27 | LDHA | MDH | RPL32 | |

TABLE 6-continued

Example Control Genes: House Keeping Control genes

| | | | | |
|---|---|---|---|---|
| PSMB4 | RPS20 | PGAM1 | EIF4A1 | RPL7a |
| RAB7A | RPL30 | PGK1 | FH | RNAP II |
| REEP5 | RPL13A | VIM | ATP5F1 | RPL10 |

TABLE 7

Example Control Genes: Prostate specific control transcripts

| | | | | | |
|---|---|---|---|---|---|
| KLK2 | PCGEM1 | TGM4 | PSCA | HOXB13 | SPINK1 |
| KLK3 | PCA3 | RLN1 | NKX3.1 | PMEPA1 | |
| KLK4 | TMPRSS2 | ACPP | SPDEF | PAP | |
| FOLH1(PSMA) | TMPRSS2/ERG | PTI-1 | PMA | STEAP1 | |

TABLE 8

Poor clinical outcome of patients with DESNT cancers

Latent Process Decomposition

| Dataset | Univariate p-value | Multivariate p-value |
|---|---|---|
| MSKCC | $2.65 \times 10^{-5}$ | $3.27 \times 10^{-1}$ |
| CancerMap | $2.98 \times 10^{-8}$ | $3.66 \times 10^{-3}$ |
| Stephenson | $4.28 \times 10^{-5}$ | $1.21 \times 10^{-4}$ |
| CamCap | $1.22 \times 10^{-3}$ | $2.90 \times 10^{-2}$ |

TABLE 8-continued

Poor clinical outcome of patients with DESNT cancers

Random Forest

| Dataset | Univariate p-value | Multivariate p-value |
|---|---|---|
| MSKCC | $1.85 \times 10^{-3}$ | $6.05 \times 10^{-1}$ |
| CancerMap | $4.80 \times 10^{-4}$ | $1.45 \times 10^{-2}$ |
| Stephenson | $1.75 \times 10^{-4}$ | $4.56 \times 10^{-4}$ |
| CamCap | $1.61 \times 10^{-5}$ | $1.31 \times 10^{-4}$ |
| TCGA | $5.41 \times 10^{-4}$ | $2.59 \times 10^{-2}$ |

For each dataset comparisons were made between PSA failures reported for DESNT and non-DESNT cancers. LPD, Latent Process Decomposition; RF, Random Forest. For LPD the log-rank P-values represent the modal LPD run selected from the 100 independent LPD runs as described in the Methods. For multivariate analyses Gleason, PSA at diagnosis and Pathological Stage are included for all datasets with the exception of the TCGA dataset where only Gleason and Clinical Stage data were available. The full analyses are presented in FIG. 7.

EXTENDED DATA TABLES

EXTENDED DATA TABLE 1

Genes with altered expression in the DESNT cancer group.

| Gene | MSKCC | CancerMap | Stephenson | Klein |
|---|---|---|---|---|
| ACTA2 | 100 | 92 | 100 | 98 |
| ACTG2 | 100 | 98 | 100 | 98 |
| ACTN1 | 100 | 92 | 100 | 100 |
| *ATP2B4* | 100 | 92 | 100 | 100 |
| C7 | 100 | 89 | 100 | 100 |
| CALD1 | 100 | 92 | 92 | 100 |
| CDC42EP3 | 100 | 92 | 100 | 95 |
| CLU** | 100 | 92 | 100 | 100 |
| CNN1 | 100 | 92 | 100 | 98 |
| CRISPLD2 | 100 | 92 | 100 | 98 |
| CSRP1*‡ | 100 | 93 | 100 | 100 |
| DPYSL3** | 100 | 92 | 100 | 86 |
| EPAS1*|| | 100 | 92 | 100 | 100 |
| ETS2 | 100 | 92 | 100 | 100 |
| FBLN1*† | 100 | 92 | 100 | 100 |
| FERMT2 | 100 | 92 | 100 | 100 |
| FLNA | 100 | 92 | 100 | 98 |
| GPX3*† | 100 | 92 | 100 | 100 |
| GSTP1**† | 100 | 92 | 100 | 81 |
| ILK | 100 | 92 | 100 | 100 |
| ITGA5 | 100 | 92 | 100 | 100 |
| JAM3* | 92 | 85 | 100 | 100 |
| *KCNMA1***‡ | 100 | 92 | 100 | 99 |
| LMOD1 | 100 | 92 | 100 | 91 |
| MYL9 | 100 | 92 | 100 | 98 |
| MYLK*‡ | 100 | 92 | 100 | 98 |
| PALLD | 100 | 92 | 100 | 100 |
| PCP4 | 100 | 92 | 100 | 100 |
| PDK4 | 100 | 83 | 100 | 96 |
| PDLIM1 | 100 | 91 | 100 | 81 |
| PLP2 | 100 | 92 | 100 | 100 |
| PPAP2B | 100 | 92 | 100 | 100 |
| RBPMS | 100 | 92 | 100 | 100 |
| SNAI2** | 100 | 93 | 100 | 91 |
| SORBS1* | 100 | 92 | 100 | 98 |
| SPG20* | 100 | 92 | 100 | 100 |
| STAT5B | 100 | 92 | 100 | 100 |
| *STOM* | 100 | 92 | 100 | 100 |
| SVIL** | 100 | 83 | 100 | 100 |
| TGFBR3 | 100 | 92 | 93 | 87 |
| TIMP3*† | 100 | 92 | 100 | 97 |
| TNS1 | 100 | 92 | 100 | 100 |
| TPM1* | 100 | 92 | 100 | 100 |
| TPM2 | 100 | 92 | 100 | 80 |
| VCL | 100 | 92 | 100 | 100 |

For each dataset the genes with significantly altered expression ($p < 0.05$) in the DESNT cancer group compared to the non-DESNT group were calculated: p-values were corrected for multiple testing. LPD was re-run 100 times for each dataset using different randomly chosen seed values. The results for the 45 genes that had altered expression in at least 80/100 runs for all four datasets are listed. The precise number of runs in which each gene has significantly altered expression is presented. All genes were down regulated in the DESNT cancer group. The emphases represent genes whose products are components of or linked to the: Cytoskeleton (bold); Adhesion, Integrins and Extracellular Matrix (underlined), Transcription Factors and Translational Regulators (double underlined), and Ion Channels (dashed underlined). Symbols: *Down regulation by CpG Methylation in Cancer; **Down regulation by CpG Methylation in Prostate Cancer; †CpG Methylation Associated with Poor Outcome; ‡Prostate Cancer Functional Connectivity Hub; and || Gene-gene Interaction Focus for Prostate Cancer.

EXTENDED DATA TABLE 2

Twenty gene random forest classifier.

| Gene | Variable Importance |
|---|---|
| DST | 2.146140965 |
| CHRDL1 | 1.758974273 |
| THSD4 | 1.561264948 |
| GSTM4 | 1.550345548 |
| CYP27A1 | 1.408713974 |
| RND3 | 1.339094656 |
| ACTG2 | 1.304989674 |
| PLEKHA6 | 0.735553263 |
| SP100 | 0.680938431 |
| PARM1 | 0.671688267 |
| ZNF532 | 0.630661162 |
| DLG5 | 0.492853186 |
| ALDH2 | 0.481637788 |
| WDR59 | 0.467824475 |
| LDHB | 0.449345969 |
| CDK6 | 0.351043941 |
| MME | 0.275274353 |
| S100A13 | 0.250416073 |
| MSRA | 0.229702526 |
| EPHX2 | 0.213536527 |

A list of 1669 genes with significantly altered expression in DESNT cancers in at least two of the five datasets (MSKCC, CancerMap, Stephenson, Klein, and CamCap) was used as a starting point. Applying a lasso logistic regression model to predict DESNT membership in the MSKCC dataset leading to the selection of a set of 20 genes shown in this table. For each gene, its importance as a variable when performing random forest classification is also recorded.

SUPPLEMENTARY INFORMATION TABLES

SUPPLEMENTARY INFORMATION TABLE 1

Differential methylation. The differential methylation between DENST and non-DESNT cancers identified in the TCGA dataset is presented. DESNT cancer were identified using the 20-gene signature show in Extended Data Table 2 using random forest classification. We then applied a method to detect Differentially Methylated Regions (DMR) implemented in the R package "methyAnalysis" (bioconductor.org/packages/release/bioc/html/methyAnalysis.html). The significant results are listed.

| Chr | Start | End | Num. Probes | Gene Symbol | Distance TSS* | Promoter | Min P-value | Min P-adjust |
|---|---|---|---|---|---|---|---|---|
| 1 | 56992372 | 56992372 | 1 | PPAP2B | 52885 | FALSE | 1.71E−28 | 4.92E−27 |
| 1 | 92197531 | 92197531 | 1 | TGFBR3 | 130072 | FALSE | 1.56E−12 | 7.59E−12 |
| 1 | 92295946 | 92295946 | 1 | TGFBR3 | 31657 | FALSE | 3.72E−16 | 2.56E−15 |
| 1 | 203598330 | 203599089 | 7 | ATP2B4 | 2415 | FALSE | 7.48E−25 | 1.23E−23 |
| 1 | 203605590 | 203605590 | 1 | ATP2B4 | 9675 | FALSE | 1.34E−26 | 2.70E−25 |
| 1 | 203670963 | 203671140 | 2 | ATP2B4 | 19093 | FALSE | 1.44E−39 | 4.05E−37 |
| 10 | 29923736 | 29924258 | 3 | SVIL | 0 | TRUE | 1.11E−29 | 4.22E−28 |
| 10 | 29936149 | 29948428 | 3 | SVIL | 76302 | FALSE | 2.48E−35 | 3.09E−33 |
| 10 | 29981216 | 29981216 | 1 | SVIL | 43514 | FALSE | 4.12E−21 | 4.57E−20 |
| 10 | 79150517 | 79150517 | 1 | KCNMA1 | 247060 | FALSE | 3.38E−22 | 4.17E−21 |
| 10 | 79396584 | 79396793 | 3 | KCNMA1 | 784 | FALSE | 1.08E−12 | 5.32E−12 |
| 10 | 97049610 | 97049610 | 1 | PDLIM1 | 1295 | FALSE | 2.64E−29 | 8.99E−28 |
| 10 | 97169147 | 97175479 | 4 | SORBS1 | 6351 | FALSE | 1.75E−33 | 1.31E−31 |
| 11 | 67350976 | 67350976 | 1 | GSTP1 | −90 | TRUE | 1.65E−14 | 9.79E−14 |
| 11 | 67351271 | 67352041 | 6 | GSTP1 | 205 | FALSE | 1.03E−36 | 1.92E−34 |
| 11 | 134020750 | 134020750 | 1 | JAM3 | 81930 | FALSE | 4.58E−28 | 1.29E−26 |
| 12 | 54811762 | 54812085 | 3 | ITGA5 | 965 | FALSE | 4.27E−27 | 9.99E−26 |
| 13 | 36919344 | 36919960 | 6 | SPG20 | 686 | FALSE | 8.29E−18 | 6.41E−17 |
| 14 | 69443362 | 69443362 | 1 | ACTN1 | 921 | FALSE | 5.45E−35 | 6.12E−33 |
| 15 | 63345124 | 63345124 | 1 | TPM1 | 4488 | FALSE | 1.25E−12 | 6.11E−12 |
| 16 | 84870066 | 84870203 | 2 | CRISPLD2 | 16479 | FALSE | 1.14E−25 | 2.00E−24 |
| 16 | 84918794 | 84918851 | 2 | CRISPLD2 | 65207 | FALSE | 7.28E−18 | 5.79E−17 |
| 2 | 46526843 | 46527098 | 2 | EPAS1 | 2302 | FALSE | 7.50E−10 | 3.02E−09 |
| 2 | 218767655 | 218767655 | 1 | TNS1 | 881 | FALSE | 9.13E−16 | 6.24E−15 |
| 20 | 35169380 | 35169594 | 3 | MYL9 | −293 | TRUE | 6.90E−31 | 3.09E−29 |
| 22 | 45899736 | 45899736 | 1 | FBLN1 | 1017 | FALSE | 6.75E−35 | 6.89E−33 |
| 3 | 123339417 | 123339568 | 2 | MAK | 0 | TRUE | 9.65E−23 | 1.27E−21 |
| 3 | 123414733 | 123414733 | 1 | MAK | 5623 | FALSE | 1.68E−32 | 1.18E−30 |
| 3 | 123535716 | 123535716 | 1 | MAK | 14614 | FALSE | 1.31E−33 | 1.23E−31 |
| 3 | 123602485 | 123602485 | 1 | MAK | 664 | FALSE | 3.14E−32 | 2.07E−30 |
| 4 | 169664785 | 169664785 | 1 | PALLD | 112017 | FALSE | 2.54E−26 | 4.99E−25 |
| 4 | 169737224 | 169737224 | 1 | PALLD | 184456 | FALSE | 1.02E−26 | 2.12E−25 |
| 4 | 169754328 | 169754534 | 2 | PALLD | 1172 | FALSE | 9.98E−11 | 4.27E−10 |
| 4 | 169770092 | 169770092 | 1 | PALLD | 16936 | FALSE | 2.81E−24 | 4.37E−23 |
| 5 | 40933444 | 40982092 | 2 | C7 | 23845 | FALSE | 3.70E−10 | 1.51E−09 |
| 7 | 134575145 | 134575524 | 5 | CALD1 | 110981 | FALSE | 1.24E−22 | 1.62E−21 |
| 7 | 134626083 | 134626083 | 1 | CALD1 | 8344 | FALSE | 1.31E−15 | 8.70E−15 |
| 8 | 27468981 | 27469186 | 3 | CLU | 82 | FALSE | 7.22E−28 | 1.84E−26 |
| 8 | 30243241 | 30243260 | 2 | RBPMS | 1297 | FALSE | 2.72E−15 | 1.74E−14 |
| 8 | 30254923 | 30254923 | 1 | RBPMS | 12979 | FALSE | 8.21E−29 | 2.56E−27 |
| 8 | 30290489 | 30290489 | 1 | RBPMS | 48545 | FALSE | 2.39E−11 | 1.06E−10 |
| 8 | 30419935 | 30419935 | 1 | RBPMS | 84620 | FALSE | 6.82E−32 | 4.25E−30 |
| X | 153598077 | 153598077 | 1 | FLNA | 4929 | FALSE | 1.28E−10 | 5.39E−10 |

SUPPLEMENTARY INFORMATION TABLE 2

Clinical characteristics of the CancerMap dataset

| | Category | Count/Median (Range) |
|---|---|---|
| Patients | | 154 |
| Age at prostatectomy | | 62 (21-74) |
| PSA at prostatectomy | | 7.9 (2.4-40) |
| Follow up time (months) | | 56 (1-129) |
| Recurrence Event | Yes | 35 |
| | No | 102 |
| | Unknown | 17 |
| Gleason | 6 | 40 |
| | 7 (3 + 4) | 83 |
| | 7 (4 + 3) | 20 |
| | 8 | 4 |
| | 9 | 7 |
| Stage | T1c | 1 |
| | T2a | 6 |
| | T2b | 3 |
| | T2c | 49 |
| | T2x | 26 |
| | T3a | 50 |
| | T3b | 17 |
| | T4x | 2 |

SUPPLEMENTARY INFORMATION TABLE 3

Functions of differentially expressed genes.
List of the 45 genes commonly down-regulated in DESNT cancers identified in the MSKCC, Stephenson, CancerMap, and Klein datasets.

| Gene | Identity | Notes |
| --- | --- | --- |
| ACTA2 | Smooth muscle actin alpha 2 | Actin cytoskeleton and cell motility; marker for myofibroblasts |
| ACTG2 | Smooth muscle actin gamma 2 | Cytoskeletal component, involved in cell motility-expression is actually widespread. |
| ACTN1 | Actinin alpha 1 | Alpha actinin is an actin-binding protein with multiple roles in different cell types. In nonmuscle cells, the cytoskeletal isoform is found along microfilament bundles and adherens-type junctions, where it is involved in binding actin to the membrane. In contrast, skeletal, cardiac, and smooth muscle isoforms are localized to the Z-disc and analogous dense bodies, where they help anchor the myofibrillar actin filaments. This gene encodes a nonmuscle, cytoskeletal, alpha actinin isoform and maps to the same site as the structurally similar erythroid beta spectrin gene.[2] |
| ATP2B4 | ATPase plasma membrane Ca2+ transporting 4 | Intracellular Ca homeostasis |
| C7 | complement component 7 | Complement system activation; poteintial link to adhesion via vitronectin receptor |
| CALD1 | Caldesmon | calmodulin- and actin-binding protein that plays an essential role in the regulation of smooth muscle and nonmuscle contraction |
| CDC42EP3 | | Binds to and negatively regulates CDC42, small GTPase involved in actin filament assembly in filopodia |
| CLU | Clusterin | CLU is a molecular chaperone responsible for aiding protein folding of secreted proteins; clearance of cellular debris and apoptosis |
| CNN1 | calponin 1 | calponin 1 functions as an inhibitory regulator of smooth muscle contractility through inhibiting actomyosin interactions.[2][23][24]In this regulation, binding of Ca$^{2+}$-calmodulin and PKC phosphorylation dissociate calponin 1 from the actin filament and facilitate smooth muscle contraction.[25] |
| CRISPLD2 | Cysteine-rich secretory protein LCCL domain-containing 2 | Secretory protein; aka late gestation lung-1. Involved in regulation of cell migration |
| CSRP1 | cysteine and glycine rich protein 1 | CSRP1 is a member of the CSRP family of genes encoding a group of LIM domain proteins, which may be involved in regulatory processes important for development and cellular differentiation. The LIM/double zinc-finger motif found in CRP1 is found in a group of proteins with critical functions in gene regulation, cell growth, and somatic differentiation Other genes in the family include CSRP2 and CSRP3.[3] |
| DPYSL3 | dihydro-pyrimidinase like 3 | Putative tumour suppressor; stabilizer of focal adhesion complexes-link to cell migration |
| EPAS1 | Endothelial PAS domain-containing protein 1 (EPAS1, also known as hypoxia-inducible factor-2alpha (HIF-2alpha)) | HIF2-alpha-a key transcription factor regulating cellular responses to hypoxia |
| ETS2 | Ets-2 | Member of the c-Ets family of transcription factors |
| FBLN1 | fibulin 1 | Fibulin-1 is a secreted glycoprotein that is found in association with extracellular matrix structures including fibronectin-containing fibers, elastin-containing fibers and basement membranes. Fibulin-1 binds to a number of extracellular matrix constituents including fibronectin,[3] nidogen-1, and the proteoglycan, versican.[3][4] Fibulin-1 is also a blood protein capable of binding to fibrinogen.[5] |
| FERMT2 | fermitin family member 2 | FERMT2 is a component of extracellular matrix structures in mammalian cells and is required for proper control of cell shape change.[4] |
| FLNA | filamin A | Actin-binding protein, or filamin, is a 280-kD protein that crosslinks actin filaments into orthogonal networks in cortical cytoplasm and participates in the anchoring of membrane proteins for the actin cytoskeleton. Remodeling of the cytoskeleton is central to the modulation of cell shape and migration. Filamin A, encoded by the FLNA gene, is a widely expressed protein that regulates reorganization of the actin cytoskeleton by interacting with integrins, transmembrane receptor complexes, and second messengers.[supplied by OMIM][3] |
| GPX3 | Glutathione peroxidase-3 | Aka Plasma, or Extracellular glutathione peroxidase; involved in detoxification of hydrogen peroxide |
| GSTP1 | Glutathione transferase Pi 1 | Glutathione S-transferases (GSTs) are a family of enzymes that play an important role in detoxification by catalyzing the conjugation of many hydrophobic and electrophilic compounds with reduced glutathione. |
| ILK | Integrin-linked kinase | Associates with beta-1 integrin, role in adhesion, migration survival etc |
| ITGA5 | Integrin alpha-5 | With integrin beta 1 constitutes fibronectin receptor; involved in adhesion, migration, signallingh |
| JAM3 | Junctional adhesion molecule-3 | Aka JAM-C; Cell-cell interactions via tight junctions; important in platelet-leukocyte interactions, via Mac-1 |
| KCNMA1 | Calcium-activated potassium channel subunit alpha-1 | Voltage-gated potassium channel |

SUPPLEMENTARY INFORMATION TABLE 3-continued

Functions of differentially expressed genes.
List of the 45 genes commonly down-regulated in
DESNT cancers identified in the MSKCC,
Stephenson, CancerMap, and Klein datasets.

| Gene | Identity | Notes |
|---|---|---|
| LMOD1 | Leiomodin-1 | Smooth muscle actin and tropomyosin-binding |
| MYL9 | Myosin light chain 9 | Muscle contraction, binds Ca and acted on by MLCK |
| MYLK | Myosin light chain kinase | MLCK; Ca/Calmodulin-dependent |
| PALLD | Palladin | Palladin is a component of actin-containing microfilaments that control cell shape, adhesion, and contraction.[4] |
| PCP4 | Purkinje cell protein-4 | PCP4 accelerates both the association and dissociation of calcium ($Ca^{2+}$) with calmodulin(CaM), which is postulated to influence the activity of CaM-dependent enzymes, especially CaM kinase II (CaMK-II) |
| PDK4 | Pyruvate dehydrogenase lipoamide kinase isozyme 4, mitochondrial | Regulation of krebs cycle; located in the matrix of the mitochondria and inhibits the pyruvate dehydrogenase complex by phosphorylating one of its subunits, reducing the conversion of pyruvate to acetyl-CoA |
| PDLIM1 | PDZ and LIM domain protein 1 | Binds to alpha actinin-1 and actin filaments, regulating cell migration |
| PLP2 | Proteolipid protein 2 | Interaction with chemokine resptor CCR1 and regulation of cell migration |
| PPAP2B | Lipid phosphate phosphohydrolase 3 | member of the phosphatidic acid phosphatase (PAP) family. PAPs convert phosphatidic acid to diacylglycerol, and function in de novo synthesis of glycerolipids as well as in receptor-activated signal transduction mediated by phospholipase D. |
| RBPMS | RNA-binding protein with multiple splicing | a member of the RRM family of RNA-binding proteins: regulates development of gastrointestinal smooth muscle. |
| SNAI2 | Zinc finger protein SNAI2 | member of the Snail family of C2H2-type zinc finger transcription factors. The encoded protein acts as a transcriptional repressor that binds to E-box motifs and is also likely to repress E-cadherin transcription in breast carcinoma. |
| SORBS1 | CAP/Ponsin protein, also known as Sorbin and SH3 domain-containing 1 | CAP/Ponsin is part of a small family of adaptor proteins that regulate cell adhesion, growth factor signaling protein and cytoskeletal formation |
| SPG20 | Spartin | protein may be involved in endosomal trafficking, microtubule dynamics, or both functions |
| STAT5B | Signal transducer and activator of transcription 5B | Transcription factor that mediates the signal transduction triggered by various cell ligands, such as IL2, IL4, CSF1, and different growth hormones |
| STOM | Stomatin also known as human erythrocyte integral membrane protein band 7 | Integral membrane protein, regulator of ion channels |
| SVIL | Supervilin | Actin-binding protein that also has nuclear localization signal; Its function may include recruitment of actin and other cytoskeletal proteins into specialized structures at the plasma membrane and in the nuclei of growing cells |
| TGFBR3 | Betaglycan TGFbeta Receptor III | Betaglycan also known as Transforming growth factor beta receptor III (TGFBR3), is a cell-surface chondroitin sulfate/heparan sulfate proteoglycan >300 kDa in molecular weight. Betaglycan binds to various members of the TGF-beta superfamily of ligands via its core protein, and bFGF via its heparan sulfate chains. It is not involved directly in TGF-beta signal transduction but by binding to various member of the TGF-beta superfamily at the cell surface it acts as a reservoir of ligand for TGF-beta receptors.[1][2] |
| TIMP3 | Tissue inhibitor of metalloproteinase-3 | A negative regulator of MMPs and also certain other ADAM and ADAMTS metalloproteinases; involved in regulation of ECM remodelling and cell signalling |
| TNS1 | Tensin-1 | A cytoskeletal regulator found in focal adhesions, crosslinks actin filaments and has SH2 domain so probaly involved in cell signalling; a recent paper on it positively regulating RhoA |
| TPM1 | Tropomyosin alpha-1 chain | actin-binding protein involved in the contractile system of striated and smooth muscles and the cytoskeleton of non-muscle cells |
| TPM2 | β-Tropomyosin, also known as tropomyosin beta chain | β-tropomyosin is striated muscle-specific coiled coil dimer that functions to stabilize actin filaments and regulate muscle contraction. |
| VCL | Vinculin | vinculin is a membrane-cytoskeletal protein in focal adhesion plaques that is involved in linkage of integrin adhesion molecules to the actin cytoskeleton |

SUPPLEMENTARY DATA

Supplementary Data 1: Clinical and molecular characteristics of samples in the CancerMap dataset.

| Row | Sample ID | Donor ID | Batch | Material_Type | Extraction_Method | Centre | ERG_FISH_status | Tumour_percentage | Ethnicity |
|---|---|---|---|---|---|---|---|---|---|
| 1 | TB08.0234_v1 | TB08.0234 | CamFinal | Normal | Qiagen miRNA kit | Cambridge | | 0 | White-British |
| 2 | TB08.0234_v3 | TB08.0234 | CamFinal | Normal | Qiagen miRNA kit | Cambridge | | 0 | White-British |

Supplementary Data 1: Clinical and molecular characteristics of samples in the CancerMap dataset.

| Row | Sample ID | Donor ID | Batch | Material_Type | Extraction_Method | Centre | ERG_FISH_status | Tumour_percentage | Ethnicity |
|---|---|---|---|---|---|---|---|---|---|
| 3 | TB08.0262_v3 | TB08.0262 | CamFinal | Tumour | Qiagen miRNA kit | Cambridge | 2N | 75 | White-British |
| 4 | TB08.0268_v3 | TB08.0268 | CamFinal | Low Tumour | Qiagen miRNA kit | Cambridge | 2N | 5 | White-British |
| 5 | TB08.0271_v1 | TB08.0271 | CamFinal | Low Tumour | Qiagen miRNA kit | Cambridge | 2N | 10 | White British |
| 6 | TB08.0311_v2 | TB08.0311 | CamFinal | Tumour | Qiagen miRNA kit | Cambridge | MixedEdel | 33 | White-British |
| 7 | TB08.0311_v3 | TB08.0311 | CamFinal | Low Tumour | Qiagen miRNA kit | Cambridge | Edel | 10 | White-British |
| 8 | TB08.0327_v1 | TB08.0327 | CamFinal | Tumour | Qiagen miRNA kit | Cambridge | Edel | 30 | White-British |
| 9 | TB08.0341_v1 | TB08.0341 | CamFinal | Normal | Qiagen miRNA kit | Cambridge |  | 0 | White-British |
| 10 | TB08.0341_v5 | TB08.0341 | CamFinal | Tumour | Qiagen miRNA kit | Cambridge | 2N | 25 | White-British |
| 11 | TB08.0359_v16 | TB08.0359 | CamFinal | Normal | Qiagen miRNA kit | Cambridge |  | 0 | White-British |
| 12 | TB08.0359_v2 | TB08.0359 | CamFinal | Stroma | Qiagen miRNA kit | Cambridge | 2N | 0 | White-British |
| 13 | TB08.0368_v14 | TB08.0368 | CamFinal | Normal | Qiagen miRNA kit | Cambridge | Esplit | 0 |  |
| 14 | TB08.0429_v7 | TB08.0429 | CamFinal | Low Tumour | Qiagen miRNA kit | Cambridge |  | 3 | White-British |
| 15 | TB08.0489_v5 | TB08.0489 | CamFinal | Normal | Qiagen miRNA kit | Cambridge |  | 0 | White-British |
| 16 | TB08.0489_v13 | TB08.0489 | CamFinal | Tumour | Qiagen miRNA kit | Cambridge | Esplit | 30 | White-British |
| 17 | TB08.0501_v8 | TB08.0501 | CamFinal | Tumour | Qiagen miRNA kit | Cambridge | 2N | 33 | White-British |
| 18 | TB08.0519_v14 | TB08.0519 | CamFinal | Tumour | Qiagen miRNA kit | Cambridge | Edel | 75 | Turkish |
| 19 | TB08.0533_v6 | TB08.0533 | CamFinal | Tumour | Qiagen miRNA kit | Cambridge | 2N | 50 | White-British |
| 20 | TB08.0588_v1 | TB08.0588 | CamFinal | Tumour | Qiagen miRNA kit | Cambridge | MixedEsplit | 40 | White-British |
| 21 | TB08.0589_v1 | TB08.0589 | CamFinal | Tumour | Qiagen miRNA kit | Cambridge | 2N | 36 | White-British |
| 22 | TB08.0589_v2 | TB08.0589 | CamFinal | Low Tumour | Qiagen miRNA kit | Cambridge | MixedPloidy | 10 | White-British |
| 23 | TB08.0589_v4 | TB08.0589 | CamFinal | Stroma | Qiagen miRNA kit | Cambridge | 2N | 0 | White-British |
| 24 | TB08.0589_v5 | TB08.0589 | CamFinal | Low Tumour | Qiagen miRNA kit | Cambridge | MixedPloidy | 8 | White-British |
| 25 | TB08.0598_v12 | TB08.0598 | CamFinal | Tumour | Qiagen miRNA kit | Cambridge | 2N | 45 | White-British |
| 26 | TB08.0609_v11 | TB08.0609 | CamFinal | Low Tumour | Qiagen miRNA kit | Cambridge | MixedRearrangement | 15 | White-British |
| 27 | TB08.0667_v9 | TB08.0667 | CamFinal | Tumour | Qiagen miRNA kit | Cambridge | 2N | 40 | White-British |
| 28 | TB08.0667_v6 | TB08.0667 | CamFinal | Stroma | Qiagen miRNA kit | Cambridge |  | 0 | White-British |
| 29 | TB08.0689_v14 | TB08.0689 | CamFinal | Tumour | Qiagen miRNA kit | Cambridge | MixedRearrangement | 40 | White-British |
| 30 | TB08.0689_v15 | TB08.0689 | CamFinal | Tumour | Qiagen miRNA kit | Cambridge | MixedEdel | 70 | White-British |
| 31 | TB08.0689_v2 | TB08.0689 | CamFinal | Tumour | Qiagen miRNA kit | Cambridge | Esplit | 21 | White-British |
| 32 | TB08.0689_v8 | TB08.0689 | CamFinal | Tumour | Qiagen miRNA kit | Cambridge | 2N | 33 | White-British |
| 33 | TB08.0691_v13 | TB08.0691 | CamFinal | Tumour | Qiagen miRNA kit | Cambridge | MixedEsplit | 50 | White-British |
| 34 | TB08.0716_v18 | TB08.0716 | CamFinal | Stroma | Qiagen miRNA kit | Cambridge | 2N | 0 | White-British |
| 35 | TB08.0719_v11 | TB08.0719 | CamFinal | Tumour | Qiagen miRNA kit | Cambridge | 2N | 50 | White-British |
| 36 | TB08.0731_v13 | TB08.0731 | CamFinal | Low Tumour | Qiagen miRNA kit | Cambridge | Esplit | 3 | White-British |
| 37 | TB08.0816_v2 | TB08.0816 | CamFinal | Low Tumour | Qiagen miRNA kit | Cambridge | Edel | 18 | White-British |
| 38 | TB08.0817_v14 | TB08.0817 | CamFinal | Tumour | Qiagen miRNA kit | Cambridge | MixedPloidy | 34 | White-British |
| 39 | TB08.0848_v10 | TB08.0848 | CamFinal | Tumour | Qiagen miRNA kit | Cambridge | Esplit | 35 | White-Other |
| 40 | TB08.0869_v4 | TB08.0869 | CamFinal | Low Tumour | Qiagen miRNA kit | Cambridge | MixedRearrangement | 5 | White-British |
| 41 | TB08.0869_v6 | TB08.0869 | CamFinal | Low Tumour | Qiagen miRNA kit | Cambridge | MixedEsplit | 15 | White-British |
| 42 | TB08.0869_v7 | TB08.0869 | CamFinal | Low Tumour | Qiagen miRNA kit | Cambridge | MixedEsplit | 15 | White-British |
| 43 | TB08.0870_v18 | TB08.0870 | CamFinal | Low Tumour | Qiagen miRNA kit | Cambridge | MixedPloidy | 8 | Black or Black British-Caribbean |
| 44 | TB08.0872_v2 | TB08.0872 | CamFinal | Tumour | Qiagen miRNA kit | Cambridge | MixedRearrangement | 20 | White-Other |
| 45 | TB08.0877_v19 | TB08.0877 | CamFinal | Tumour | Qiagen miRNA kit | Cambridge | Edel | 40 | White-British |
| 46 | TB08.0879_v11 | TB08.0879 | CamFinal | Low Tumour | Qiagen miRNA kit | Cambridge | Edel | 5 | White-British |
| 47 | TB08.0884_v2 | TB08.0884 | CamFinal | Normal | Qiagen miRNA kit | Cambridge | 2N | 0 | White-British |
| 48 | TB08.0927_v5 | TB08.0927 | CamFinal | Tumour | Qiagen miRNA kit | Cambridge | 2N | 20 | White-British |
| 49 | TB08.0943_v7 | TB08.0943 | CamFinal | Stroma | Qiagen miRNA kit | Cambridge | 2N | 0 | White-British |
| 50 | TB08.0958_v12 | TB08.0958 | CamFinal | Tumour | Qiagen miRNA kit | Cambridge | 2Edel | 55 | White-British |
| 51 | TB08.0958_v13 | TB08.0958 | CamFinal | Tumour | Qiagen miRNA kit | Cambridge | MixedRearrangement | 45 | White-British |
| 52 | TB08.0973_v9 | TB08.0973 | CamFinal | Tumour | Qiagen miRNA kit | Cambridge | 2N | 23 | White-British |
| 53 | TB08.0978_v7 | TB08.0978 | CamFinal | Tumour | Qiagen miRNA kit | Cambridge | MixedPloidy | 20 | White-British |
| 54 | TB08.0978_v8 | TB08.0978 | CamFinal | Tumour | Qiagen miRNA kit | Cambridge | 2N | 45 | White-British |
| 55 | TB08.0978_v9 | TB08.0978 | CamFinal | Tumour | Qiagen miRNA kit | Cambridge | 2N | 29 | White-British |
| 56 | TB08.0986_v2 | TB08.0986 | CamFinal | Tumour | Qiagen miRNA kit | Cambridge | MixedEsplit | 38 | White-British |
| 57 | TB08.0987_v6 | TB08.0987 | CamFinal | Tumour | Qiagen miRNA kit | Cambridge | 2N | 49 | White-British |
| 58 | TB08.0993_v12 | TB08.0993 | CamFinal | Low Tumour | Qiagen miRNA kit | Cambridge | MixedRearrangement | 4 | White-British |
| 59 | TB08.0997_v6 | TB08.0997 | CamFinal | Stroma | Qiagen miRNA kit | Cambridge |  | 0 | White-British |
| 60 | TB08.0999_v11 | TB08.0999 | CamFinal | Tumour | Qiagen miRNA kit | Cambridge | 2N | 30 | White-British |
| 61 | TB08.0999_v2 | TB08.0999 | CamFinal | Tumour | Qiagen miRNA kit | Cambridge | MixedRearrangement | 48 | White-British |
| 62 | TB08.1015_v10 | TB08.1015 | CamFinal | Tumour | Qiagen miRNA kit | Cambridge | MixedEdel | 78 | White-British |
| 63 | TB08.1015_v11 | TB08.1015 | CamFinal | Tumour | Qiagen miRNA kit | Cambridge | MixedEdel | 78 | White-British |
| 64 | TB08.1015_v9 | TB08.1015 | CamFinal | Tumour | Qiagen miRNA kit | Cambridge | MixedEdel | 50 | White-British |
| 65 | TB08.1019_v1 | TB08.1019 | CamFinal | Low Tumour | Qiagen miRNA kit | Cambridge | MixedRearrangement | 10 | White-British |
| 66 | TB08.1019_v14 | TB08.1019 | CamFinal | Low Tumour | Qiagen miRNA kit | Cambridge | 2Esplit | 10 | White-British |
| 67 | TB08.1019_v15 | TB08.1019 | CamFinal | Tumour | Qiagen miRNA kit | Cambridge | MixedRearrangement | 20 | White-British |
| 68 | TB08.1019_v2 | TB08.1019 | CamFinal | Tumour | Qiagen miRNA kit | Cambridge | MixedRearrangement | 30 | White-British |
| 69 | TB08.1026_v17 | TB08.1026 | CamFinal | Tumour | Qiagen miRNA kit | Cambridge | 2N | 78 | White-British |
| 70 | TB08.1044_v7 | TB08.1044 | CamFinal | Tumour | Qiagen miRNA kit | Cambridge | 2N | 40 | White-British |
| 71 | TB08.1053_v5 | TB08.1053 | CamFinal | Tumour | Qiagen miRNA kit | Cambridge | MixedRearrangement | 48 | White-British |
| 72 | TB08.1063_v16 | TB08.1063 | CamFinal | Tumour | Qiagen miRNA kit | Cambridge | MixedRearrangement | 50 | White-British |
| 73 | TB08.1063_v8 | TB08.1063 | CamFinal | Tumour | Qiagen miRNA kit | Cambridge | 2N | 31 | White-British |
| 74 | TB08.1083_v3 | TB08.1083 | CamFinal | Tumour | Qiagen miRNA kit | Cambridge | 2Esplit | 33 | White-British |
| 75 | TB08.1116_v2 | TB08.1116 | CamFinal | Low Tumour | Qiagen miRNA kit | Cambridge | MixedRearrangement | 15 | White-British |
| 76 | TB08.1116_v3 | TB08.1116 | CamFinal | Tumour | Qiagen miRNA kit | Cambridge | MixedEsplit | 56 | White-British |

Supplementary Data 1: Clinical and molecular characteristics of samples in the CancerMap dataset.

| Row | Sample ID | Donor ID | Batch | Material_Type | Extraction_Method | Centre | ERG_FISH_status | Tumour_percentage | Ethnicity |
|---|---|---|---|---|---|---|---|---|---|
| 77 | TB08.1116_v9 | TB08.1116 | CamFinal | Tumour | Qiagen miRNA kit | Cambridge | MixedRearrangement | 30 | White-British |
| 78 | TB08.1159_v2 | TB08.1159 | CamFinal | Normal | Qiagen miRNA kit | Cambridge | Edel | 0 | White-British |
| 79 | TB08.0601_v16 | TB08.0601 | CamFinal | Normal | Qiagen miRNA kit | Cambridge | | | White-British |
| 80 | TB09.0217_v16 | TB09.0217 | CamFinal | Tumour | Qiagen miRNA kit | Cambridge | Edel | 63 | White-British |
| 81 | TB09.0217_v7 | TB09.0217 | CamFinal | Tumour | Qiagen miRNA kit | Cambridge | MixedPloidy | 28 | White-British |
| 82 | TB09.0219_v13 | TB09.0219 | CamFinal | Low Tumour | Qiagen miRNA kit | Cambridge | 2N | 10 | White-British |
| 83 | TB09.0219_v2 | TB09.0219 | CamFinal | Low Tumour | Qiagen miRNA kit | Cambridge | MixedRearrangement | 11 | White-British |
| 84 | TB09.0219_v21 | TB09.0219 | CamFinal | Tumour | Qiagen miRNA kit | Cambridge | Esplit | 57 | White-British |
| 85 | TB09.0219_v8 | TB09.0219 | CamFinal | Low Tumour | Qiagen miRNA kit | Cambridge | 2N | 4 | White-British |
| 86 | TB09.0238_v12 | TB09.0238 | CamFinal | Stroma | Qiagen miRNA kit | Cambridge | 2N | 0 | White-British |
| 87 | TB09.0238_v18 | TB09.0238 | CamFinal | Tumour | Qiagen miRNA kit | Cambridge | MixedRearrangement | 50 | White-British |
| 88 | TB09.0238_v5 | TB09.0238 | CamFinal | Tumour | Qiagen miRNA kit | Cambridge | 2N | 25 | White-British |
| 89 | TB09.0272_v6 | TB09.0272 | CamFinal | Tumour | Qiagen miRNA kit | Cambridge | Esplit | 65 | White-British |
| 90 | TB09.0272_v7 | TB09.0272 | CamFinal | Tumour | Qiagen miRNA kit | Cambridge | 2N | 35 | White-British |
| 91 | TB09.0295_v2 | TB09.0295 | CamFinal | Tumour | Qiagen miRNA kit | Cambridge | 2N | 70 | White-British |
| 92 | TB09.0413_v11 | TB09.0413 | CamFinal | Tumour | Qiagen miRNA kit | Cambridge | 2N | 68 | Black or Black British-Caribbean |
| 93 | TB09.0413_v8 | TB09.0413 | CamFinal | Low Tumour | Qiagen miRNA kit | Cambridge | MixedPloidy | 5 | Black or Black British-Caribbean |
| 94 | TB09.0443_v3 | TB09.0443 | CamFinal | Low Tumour | Qiagen miRNA kit | Cambridge | Edel | 2 | White-British |
| 95 | TB09.0443_v8 | TB09.0443 | CamFinal | Tumour | Qiagen miRNA kit | Cambridge | 2N | 65 | White-British |
| 96 | TB09.0448_v8 | TB09.0448 | CamFinal | Tumour | Qiagen miRNA kit | Cambridge | MixedPloidy | 33 | White-British |
| 97 | TB09.0462_v7 | TB09.0462 | CamFinal | Low Tumour | Qiagen miRNA kit | Cambridge | MixedEsplit | 8 | White-British |
| 98 | TB09.0471_v11 | TB09.0471 | CamFinal | Tumour | Qiagen miRNA kit | Cambridge | Edel | 20 | White-British |
| 99 | TB09.0504_v4 | TB09.0504 | CamFinal | Tumour | Qiagen miRNA kit | Cambridge | 2N | 50 | White-British |
| 100 | TB09.0550_v15 | TB09.0550 | CamFinal | Tumour | Qiagen miRNA kit | Cambridge | MixedEsplit | 55 | White-British |
| 101 | TB09.0606_v3 | TB09.0606 | CamFinal | Low Tumour | Qiagen miRNA kit | Cambridge | MixedPloidy | 18 | White-British |
| 102 | TB09.0706_v5 | TB09.0706 | CamFinal | Tumour | Qiagen miRNA kit | Cambridge | Esplit | 54 | White-British |
| 103 | TB09.0720_v19 | TB09.0720 | CamFinal | Tumour | Qiagen miRNA kit | Cambridge | Edel | 23 | White-British |
| 104 | TB09.0721_v14 | TB09.0721 | CamFinal | Low Tumour | Qiagen miRNA kit | Cambridge | MixedPloidy | 10 | White-British |
| 105 | TB09.0721_v15 | TB09.0721 | CamFinal | Low Tumour | Qiagen miRNA kit | Cambridge | RG | 3 | White-British |
| 106 | TB09.0725_v9 | TB09.0725 | CamFinal | Tumour | Qiagen miRNA kit | Cambridge | 2N | 68 | White-British |
| 107 | TB09.0774_v1 | TB09.0774 | CamFinal | Stroma | Qiagen miRNA kit | Cambridge | Esplit | 0 | White-British |
| 108 | TB09.0774_v15 | TB09.0774 | CamFinal | Low Tumour | Qiagen miRNA kit | Cambridge | 2N | 10 | White-British |
| 109 | TB09.0850_v2 | TB09.0850 | CamFinal | Low Tumour | Qiagen miRNA kit | Cambridge | MixedEsplit | 5 | White-British |
| 110 | TB09.0962_v13 | TB09.0962 | CamFinal | Tumour | Qiagen miRNA kit | Cambridge | MixedPloidy | 23 | White-British |
| 111 | TB09.0962_v16 | TB09.0962 | CamFinal | Tumour | Qiagen miRNA kit | Cambridge | Esplit | 75 | White-British |
| 112 | NP1 | ICR_38 | 1208 | Normal | Trizol | ICR | 2N | 0 | White-British |
| 113 | NP10 | ICR_47 | 309 | Normal | Trizol | ICR | 2N | 0 | White-British |
| 114 | NP11 | ICR_50 | 309 | Normal | Trizol | ICR | 2N | 0 | White-British |
| 115 | NP12 | ICR_58 | 309 | Normal | Trizol | ICR | 2N | 0 | White-British |
| 116 | NP14 | ICR_35 | 309 | Normal | Trizol | ICR | 2N | 0 | White-British |
| 117 | NP15 | ICR_65 | 309 | Normal | Trizol | ICR | 2N | 0 | White-British |
| 118 | NP16 | ICR_69 | 309 | Normal | Trizol | ICR | 2N | 0 | Black or Black British-African |
| 119 | NP17 | ICR_51 | 509 | Normal | Trizol | ICR | 2N | 0 | |
| 120 | NP18 | ICR_66 | 509 | Stroma | Trizol | ICR | 2N | 0 | White-British |
| 121 | NP19 | ICR_73 | 509 | Stroma | Trizol | ICR | 2N | 0 | White-British |
| 122 | NP2 | ICR_37 | 1208 | Normal | Trizol | ICR | 2N | 0 | White-British |
| 123 | NP20 | ICR_57 | 509 | Normal | Trizol | ICR | 2N | 0 | White-British |
| 124 | NP21 | ICR_56 | 509 | Stroma | Trizol | ICR | 2N | 0 | White-British |
| 125 | NP4 | ICR_47 | 1208 | Normal | Trizol | ICR | 3N | 0 | White-British |
| 126 | NP5 | ICR_59 | 1208 | Normal | Trizol | ICR | 2N | 0 | White-British |
| 127 | NP8 | ICR_34 | 309 | Normal | Trizol | ICR | 2N | 0 | White-British |
| 128 | NP9 | ICR_54 | 309 | Normal | Trizol | ICR | 2N | 0 | White-Other |
| 129 | PRC140 | ICR_20 | 509 | Low Tumour | Trizol | ICR | Esplit | 10 | White-British |
| 130 | PRC101 | ICR_28 | 908 | Tumour | RNAeasyPlus | ICR | Edel | 40 | White-British |
| 131 | PRC102 | ICR_44 | 908 | Tumour | Trizol | ICR | 2N | 60 | White-British |
| 132 | PRC103 | ICR_34 | 908 | Tumour | RNAeasyPlus | ICR | 2N | 20 | White-British |
| 133 | PRC105 | ICR_43 | 908 | Tumour | RNAeasyPlus | ICR | 2N | 45 | White-Other |
| 134 | PRC106 | ICR_54 | 908 | Low Tumour | RNAeasyPlus | ICR | 2N | 15 | White-Other |
| 135 | PRC109 | ICR_54 | 1008 | Tumour | Trizol | ICR | Edel | 60 | White-British |
| 136 | PRC10 | ICR_49 | 507 | Tumour | Trizol | ICR | Edel | | White-British |
| 137 | PRC110 | ICR_22 | 1008 | Tumour | Trizol | ICR | 2Edel | 55 | White-British |
| 138 | PRC111 | ICR_49 | 1008 | Tumour | Trizol | ICR | 2N | 20 | White-British |
| 139 | PRC112 | ICR_49 | 1008 | Normal | Trizol | ICR | 2N | 0 | White-Other |
| 140 | PRC113 | ICR_60 | 1008 | Tumour | Trizol | ICR | 2N | 70 | White-British |
| 141 | PRC114 | ICR_63 | 1008 | Tumour | Trizol | ICR | 2Esplit | 40 | White-British |
| 142 | PRC115 | ICR_41 | 1008 | Tumour | Trizol | ICR | 2Esplit | 30 | White-British |
| 143 | PRC116 | ICR_41 | 1008 | Tumour | Trizol | ICR | MixedRearrangement | 50 | White-British |
| 144 | PRC117 | ICR_17 | 1008 | Tumour | Trizol | ICR | Esplit | 20 | White-British |
| 145 | PRC118 | ICR_17 | 1008 | Tumour | Trizol | ICR | 2N | 90 | White-British |
| 146 | PRC119 | ICR_50 | 1008 | Tumour | Trizol | ICR | Edel | 30 | White-British |
| 147 | PRC11 | ICR_59 | 507 | Tumour | Trizol | ICR | Edel | 60 | White-British |
| 148 | PRC122 | ICR_4 | 1008 | Low Tumour | Trizol | ICR | Esplit | 3 | White-British |

Supplementary Data 1: Clinical and molecular characteristics of samples in the CancerMap dataset.

| Row | Sample ID | Donor ID | Batch | Material_Type | Extraction_Method | Centre | ERG_FISH_status | Tumour_percentage | Ethnicity |
|---|---|---|---|---|---|---|---|---|---|
| 149 | PRC123 | ICR_17 | 1008 | Low Tumour | Trizol | ICR | 2N | 5 | |
| 150 | PRC124 | ICR_40 | 1008 | Tumour | Trizol | ICR | 2N | 20 | White-British |
| 151 | PRC125 | ICR_61 | 1208 | Tumour | Trizol | ICR | 2N | 45 | |
| 152 | PRC126 | ICR_40 | 1208 | Tumour | Trizol | ICR | 2Edel | 70 | White-British |
| 153 | PRC127 | ICR_48 | 1208 | Tumour | Trizol | ICR | Edel | 50 | White-British |
| 154 | PRC128 | ICR_48 | 1208 | Low Tumour | Trizol | ICR | 2Esplit | 15 | White-British |
| 155 | PRC129 | ICR_55 | 1208 | Tumour | Trizol | ICR | 2Esplit | 70 | White-British |
| 156 | PRC12 | ICR_55 | 507 | Tumour | Trizol | ICR | | 85 | White-British |
| 157 | PRC130 | ICR_25 | 1208 | Tumour | Trizol | ICR | 2N | 70 | White-British |
| 158 | PRC133 | ICR_58 | 309 | Tumour | Trizol | ICR | MixedPloidy | 90 | White-British |
| 159 | PRC134 | ICR_35 | 309 | Normal | Trizol | ICR | MixedPloidy | 0 | White-British |
| 160 | PRC135 | ICR_35 | 309 | Tumour | Trizol | ICR | 2Esplit | 60 | White-British |
| 161 | PRC136 | ICR_68 | 309 | Tumour | Trizol | ICR | MixedPloidy | 70 | White-British |
| 162 | PRC137 | ICR_71 | 309 | Tumour | Trizol | ICR | 2N | 30 | White-British |
| 163 | PRC138 | ICR_65 | 309 | Tumour | Trizol | ICR | 2N | 60 | Black or Black British-African |
| 164 | PRC139 | ICR_69 | 309 | Tumour | Trizol | ICR | 2N | 70 | Black or Black British-African |
| 165 | PRC13 | ICR_69 | 507 | Tumour | Trizol | ICR | 2Edel | 25 | White-British |
| 166 | PRC141 | ICR_2 | 509 | Tumour | Trizol | ICR | Edel | 60 | White-Other |
| 167 | PRC142 | ICR_68 | 509 | Normal | Trizol | ICR | 2N | 0 | White-British |
| 168 | PRC143 | ICR_67 | 509 | Low Tumour | Trizol | ICR | Edel | 5 | White-British |
| 169 | PRC144 | ICR_73 | 509 | Tumour | Trizol | ICR | 2N | 70 | White-British |
| 170 | PRC145 | ICR_57 | 509 | Low Tumour | Trizol | ICR | NG | 5 | White-British |
| 171 | PRC146 | ICR_45 | ICRFinal | Low Tumour | Trizol | ICR | 2N | 2 | White-British |
| 172 | PRC147 | ICR_56 | ICRFinal | Low Tumour | Trizol | ICR | MixedEdel | 5 | White-British |
| 173 | PRC148 | ICR_70 | ICRFinal | Tumour | Trizol | ICR | 2N | 35 | White-British |
| 174 | PRC149 | ICR_70 | ICRFinal | Low Tumour | Trizol | ICR | MixedPloidy | 5 | White-British |
| 175 | PRC14 | ICR_39 | 507 | Normal | Trizol | ICR | 2N | 0 | White-Other |
| 176 | PRC150 | ICR_72 | ICRFinal | Tumour | Trizol | ICR | Esplit | 30 | White-British |
| 177 | PRC151 | ICR_7 | ICRFinal | Tumour | Trizol | ICR | 2N | 50 | White-British |
| 178 | PRC152 | ICR_53 | ICRFinal | Low Tumour | Trizol | ICR | 2N | 15 | White-British |
| 179 | PRC153 | ICR_64 | ICRFinal | Tumour | Trizol | ICR | 2N | 20 | White-British |
| 180 | PRC154 | ICR_33 | ICRFinal | Tumour | Trizol | ICR | MixedPloidy | 65 | |
| 181 | PRC155 | ICR_33 | ICRFinal | Tumour | Trizol | ICR | 2N | 65 | White-British |
| 182 | PRC156 | ICR_1 | ICRFinal | Tumour | Trizol | ICR | Edel | 50 | White-Other |
| 183 | PRC157 | ICR_62 | ICRFinal | Tumour | Trizol | ICR | 2N | 85 | White-British |
| 184 | PRC158 | ICR_74 | ICRFinal | Tumour | Trizol | ICR | MixedPloidy | 70 | White-British |
| 185 | PRC159 | ICR_8 | ICRFinal | Tumour | Trizol | ICR | 4N | 40 | White-Other |
| 186 | PRC15 | ICR_80 | 507 | Normal | Trizol | ICR | 2N | 0 | White-British |
| 187 | PRC160 | ICR_79 | ICRFinal | Tumour | Trizol | ICR | 2N | 75 | White-Other |
| 188 | PRC161 | ICR_23 | ICRFinal | Tumour | Trizol | ICR | 2N | 60 | White-British |
| 189 | PRC162 | ICR_76 | ICRFinal | Tumour | Trizol | ICR | Esplit | 50 | White-British |
| 190 | PRC163 | ICR_80 | ICRFinal | Tumour | Trizol | ICR | 2N | 50 | White-British |
| 191 | PRC164 | ICR_81 | ICRFinal | Tumour | Trizol | ICR | Esplit | 40 | White-Irish |
| 192 | PRC165 | ICR_73 | ICRFinal | Tumour | Trizol | ICR | Edel | 30 | White-Other |
| 193 | PRC166 | ICR_3 | ICRFinal | Tumour | Trizol | ICR | Edel | 65 | White-British |
| 194 | PRC167 | ICR_36 | ICRFinal | Tumour | Trizol | ICR | Esplit | 70 | White-British |
| 195 | PRC168 | ICR_19 | ICRFinal | Tumour | Trizol | ICR | Edel | 70 | White-British |
| 196 | PRC169 | ICR_78 | ICRFinal | Low Tumour | Trizol | ICR | Esplit | 10 | White-British |
| 197 | PRC16 | ICR_77 | 507 | Normal | Trizol | ICR | | 0 | White-British |
| 198 | PRC17 | ICR_75 | 507 | Low Tumour | Trizol | ICR | Esplit | 10 | White-British |
| 199 | PRC18 | ICR_6 | 507 | Tumour | Trizol | ICR | | | White-British |
| 200 | PRC19 | ICR_25 | 507 | Low Tumour | Trizol | ICR | | 5 | White-British |
| 201 | PRC1 | ICR_27 | 507 | Tumour | Trizol | ICR | Edel | 45 | White-British |
| 202 | PRC20 | ICR_2 | 507 | Low Tumour | Trizol | ICR | Esplit | 15 | |
| 203 | PRC21 | ICR_82 | 507 | Low Tumour | Trizol | ICR | 2Esplit | 15 | |
| 204 | PRC22 | ICR_82 | 507 | Normal | Trizol | ICR | | 0 | White-British |
| 205 | PRC23 | ICR_24 | 507 | Normal | Trizol | ICR | | 0 | White-British |
| 206 | PRC24 | ICR_26 | 507 | Tumour | Trizol | ICR | 2Edel | 30 | White-British |
| 207 | PRC25 | ICR_12 | 507 | Tumour | Trizol | ICR | Edel | 35 | White-British |
| 208 | PRC26 | ICR_29 | 507 | Low Tumour | Trizol | ICR | 2N | 15 | White-British |
| 209 | PRC27 | ICR_30 | 407 | Tumour | Trizol | ICR | | 50 | Black or Black British-Caribbean |
| 210 | PRC28 | ICR_13 | 407 | Low Tumour | Trizol | ICR | | 5 | White-British |
| 211 | PRC29 | ICR_15 | 407 | Low Tumour | Trizol | ICR | MixedPloidy | 15 | White-British |
| 212 | PRC2 | ICR_18 | 507 | Low Tumour | Trizol | ICR | Edel | 10 | White-Other |
| 213 | PRC30 | ICR_7 | 407 | Tumour | Trizol | ICR | Edel | | White-British |
| 214 | PRC31 | ICR_22 | 507 | Low Tumour | Trizol | ICR | | 5 | White-British |
| 215 | PRC32 | ICR_14 | 507 | Low Tumour | Trizol | ICR | | 5 | White-Other |
| 216 | PRC34 | ICR_21 | 407 | Normal | Trizol | ICR | 2N | 0 | White-Irish |
| 217 | PRC35 | ICR_5 | 407 | Normal | Trizol | ICR | Edel | 0 | White-Irish |
| 218 | PRC36 | ICR_5 | 407 | Low Tumour | Trizol | ICR | Edel | 5 | White-British |
| 219 | PRC38 | ICR_12 | 407 | Low Tumour | Trizol | ICR | Edel | 15 | White-British |
| 220 | PRC39 | ICR_11 | 407 | Low Tumour | Trizol | ICR | | 10 | White-British |

-continued

Supplementary Data 1: Clinical and molecular characteristics of samples in the CancerMap dataset.

| Row | Sample ID | Donor ID | Batch | Material_Type | Extraction_Method | Centre | ERG_FISH_status | Tumour_percentage | Ethnicity |
|---|---|---|---|---|---|---|---|---|---|
| 221 | PRC3 | ICR_32 | 507 | Tumour | Trizol | ICR | Edel | 50 | White-British |
| 222 | PRC40 | ICR_9 | 407 | Tumour | Trizol | ICR | Edel | 70 | White-British |
| 223 | PRC42 | ICR_20 | 407 | Low Tumour | Trizol | ICR | Edel | 5 | White-British |
| 224 | PRC45 | ICR_10 | 407 | Normal | Trizol | ICR | | 0 | White-British |
| 225 | PRC4 | ICR_14 | 507 | Tumour | Trizol | ICR | 2Esplit | 25 | White-British |
| 226 | PRC5 | ICR_16 | 507 | Low Tumour | Trizol | ICR | Esplit | 3 | White-British |
| 227 | PRC6 | ICR_23 | 507 | Tumour | Trizol | ICR | | 80 | White-British |
| 228 | PRC7 | ICR_10 | 507 | Tumour | Trizol | ICR | | 50 | White-British |
| 229 | PRC8 | ICR_23 | 507 | Tumour | Trizol | ICR | | 80 | White-British |
| 230 | PRC9 | ICR_31 | 507 | Tumour | Trizol | ICR | | 30 | White-British |
| 231 | ST1 | ICR_48 | 1208 | Stroma | Trizol | ICR | Edel | 0 | White-British |
| 232 | ST2 | ICR_46 | ICRFinal | Stroma | Trizol | ICR | 2N | 0 | White-British |
| 233 | ST3 | ICR_52 | ICRFinal | Stroma | Trizol | ICR | 2N | 0 | White-British |
| 234 | ST4 | ICR_66 | ICRFinal | Stroma | Trizol | ICR | 2N | 0 | White-British |
| 235 | ST5 | ICR_76 | ICRFinal | Stroma | Trizol | ICR | 2N | 0 | White-Other |

Note this table has been divided to enable the information to be presented in this application. Each row comprises the columns Row, Sample ID, Donor ID, Batch, Material Type, Extraction Method, Centre, ERG FISH status, Tumour percentage, Ethnicity, Age at Diagnosis, Pathology Stage, Pathology sub stage, PSA pre-prostatectomy, Gleason Score, Margins, Extra Capsular Extension, BCR FreeTime months, BCR Event and ICGC category.

| Row | Sample ID | Age_at_Diagnosis | Pathology_Stage | Pathology_sub_stage | PSA_pre_prostatectomy | Gleason_Score | Margins | Extra_Capsular_Extension | BCR_FreeTime_months | BCR_Event | ICGC_category |
|---|---|---|---|---|---|---|---|---|---|---|---|
| 1 | TB08.0234_v1 | 64 | T2 | b | 5.80 | 3 + 5 | negative margins | N | 66.00 | FALSE | normal |
| 2 | TB08.0234_v3 | 64 | T2 | b | 5.80 | 3 + 5 | negative margins | N | 66.00 | FALSE | normal |
| 3 | TB08.0262_v3 | 69 | T3 | a | 8.30 | 3 + 4 | Positive circumferential | Y | 65.00 | FALSE | cat_1 |
| 4 | TB08.0268_v3 | 56 | T3 | a | 8.70 | 3 + 4 | Positive circumferential | Y | 59.00 | FALSE | cat_1 |
| 5 | TB08.0271_v1 | 74 | T2 | x | 15.40 | 3 + 4 | Negative | N | 73.00 | FALSE | cat_2 |
| 6 | TB08.0311_v2 | 69 | T3 | a | 15.30 | 3 + 4 | Positive base | Y | 64.00 | FALSE | cat_2 |
| 7 | TB08.0311_v3 | 69 | T3 | a | 15.30 | 3 + 4 | Positive base | Y | 64.00 | FALSE | cat_2 |
| 8 | TB08.0327_v1 | 57 | T2 | x | 4.80 | 3 + 4 | Negative | N | 64.00 | FALSE | cat_1 |
| 9 | TB08.0341_v1 | 57 | T2 | x | 5.10 | 3 + 4 | negative margins | N | 6.00 | TRUE | normal |
| 10 | TB08.0341_v5 | 57 | T2 | x | 5.10 | 3 + 4 | negative margins | N | 6.00 | TRUE | cat_1 |
| 11 | TB08.0359_v16 | 63 | T2 | a | 9.90 | 3 + 4 | positive Apex margin | N | 2.00 | TRUE | normal |
| 12 | TB08.0359_v2 | 63 | T2 | a | 9.90 | 3 + 4 | positive Apex margin | N | 2.00 | TRUE | cat_1 |
| 13 | TB08.0368_v14 | 71 | T3 | b | | 4 + 3 | positive apex & circumferential margin | Y | 34.00 | FALSE | unknown |
| 14 | TB08.0429_v7 | 72 | T3 | b | 9.20 | 3 + 4 | positive circumferential margin | Y | 3.00 | FALSE | normal |
| 15 | TB08.0489_v5 | 62 | T3 | a | 5.30 | 4 + 3 | negative margins | Y | 49.00 | FALSE | normal |
| 16 | TB08.0489_v13 | 62 | T3 | a | 5.30 | 4 + 3 | negative margins | Y | 49.00 | FALSE | cat_2 |
| 17 | TB08.0501_v8 | 64 | T3 | a | 20.50 | 3 + 4 | Negative | Y | 76.00 | FALSE | cat_3 |
| 18 | TB08.0519_v14 | 55 | T4 | x | 9.80 | 5 + 4 | positive apex | | | | cat_3 |
| 19 | TB08.0S33_v6 | 65 | T3 | a | 5.80 | 3 + 4 | negative margins | Y | 62.00 | FALSE | cat_1 |
| 20 | TB08.0588_v1 | 55 | T3 | a | 13.90 | 3 + 4 | Negative | Y | 55.00 | TRUE | cat_2 |
| 21 | TB08.0589_v1 | 66 | T4 | x | 5.17 | 5 + 4 | Positive base | Y | 2.00 | TRUE | cat_3 |
| 22 | TB08.0589_v2 | 66 | T4 | x | 5.17 | 5 + 4 | Positive base | Y | 2.00 | TRUE | cat_3 |
| 23 | TB08.0589_v4 | 66 | T4 | x | 5.17 | 5 + 4 | Positive base | Y | 2.00 | TRUE | cat_3 |
| 24 | TB08.0589_v5 | 66 | T4 | x | 5.17 | 5 + 4 | Positive base | Y | 2.00 | TRUE | cat_3 |
| 25 | TB08.0598_v12 | 65 | T2 | x | 8.80 | 3 + 4 | negative margins | N | 61.00 | FALSE | cat_1 |
| 26 | TB08.0609_v11 | 66 | T2 | x | 11.40 | 4 + 3 | Negative | N | 34.00 | FALSE | cat_2 |
| 27 | TB08.0667_v9 | 57 | T2 | x | 7.80 | 3 + 3 | negative margins | N | 42.00 | FALSE | cat_1 |
| 28 | TB08.0667_v6 | 57 | T2 | x | 7.80 | 3 + 3 | negative margins | N | 42.00 | FALSE | normal |
| 29 | TB08.0689_v14 | 51 | T2 | x | 8.80 | 3 + 3 | Negative | N | 60.00 | FALSE | cat_1 |
| 30 | TB08.0689_v15 | 51 | T2 | x | 8.80 | 3 + 3 | Negative | N | 60.00 | FALSE | cat_1 |
| 31 | TB08.0689_v2 | 51 | T2 | x | 8.80 | 3 + 3 | Negative | N | 60.00 | FALSE | cat_1 |
| 32 | TB08.0689_v8 | 51 | T2 | x | 8.80 | 3 + 3 | Negative | N | 60.00 | FALSE | cat_1 |
| 33 | TB08.0691_v13 | 69 | T3 | a | 9.40 | 3 + 4 | Negative | Y | 8.00 | TRUE | cat_1 |
| 34 | TB08.0716_v18 | 64 | T3 | a | 8.90 | 3 + 4 | negative margins | Y | 60.00 | FALSE | cat_1 |
| 35 | TB08.0719_v11 | 62 | T2 | x | 6.50 | 3 + 3 | positive circumferential margin | N | 60.00 | FALSE | cat_1 |
| 36 | TB08.0731_v13 | 59 | T3 | a | 7.90 | 3 + 4 | Negative | Y | 61.00 | FALSE | cat_1 |
| 37 | TB08.0816_v2 | 63 | T3 | a | 10.40 | 3 + 4 | negative margins | Y | 60.00 | FALSE | cat_2 |
| 38 | TB08.0817_v14 | 62 | T3 | a | 10.40 | 3 + 4 | Negative | Y | 24.00 | TRUE | cat_2 |
| 39 | TB08.0848_v10 | 63 | T3 | a | 4.90 | 4 + 3 | negative margins | Y | 55.00 | FALSE | cat_2 |
| 40 | TB08.0869_v4 | 58 | T2 | x | 40.00 | 3 + 3 | Negative | N | 19.00 | TRUE | cat_3 |
| 41 | TB08.0869_v6 | 58 | T2 | x | 40.00 | 3 + 3 | Negative | N | 19.00 | TRUE | cat_3 |
| 42 | TB08.0869_v7 | 58 | T2 | x | 40.00 | 3 + 3 | Negative | N | 19.00 | TRUE | cat_3 |
| 43 | TB08.0870_v18 | 71 | T3 | b | 8.20 | 3 + 4 | Negative | Y | 1.00 | TRUE | cat_1 |
| 44 | TB08.0872_v2 | 63 | T2 | c | 7.50 | 3 + 3 | Negative | N | 56.00 | FALSE | cat_1 |
| 45 | TB08.0877_v19 | 61 | T2 | x | 8.70 | 3 + 3 | Negative | N | 49.00 | FALSE | cat_1 |
| 46 | TB08.0879_v11 | 62 | T3 | a | 8.40 | 4 + 3 | Negative | Y | 60.00 | FALSE | cat_2 |
| 47 | TB08.0884_v2 | 46 | T2 | x | 2.40 | 3 + 4 | negative margins | N | 61.00 | FALSE | cat_1 |

-continued

| Row | Sample ID | Age_at_Diagnosis | Pathology_Stage | Pathology_sub_stage | PSA_pre_prostatectomy | Gleason_Score | Margins | Extra_Capsular_Extension | BCR_FreeTime_months | BCR_Event | ICGC_category |
|---|---|---|---|---|---|---|---|---|---|---|---|
| 48 | TB08.0927_v5 | 59 | T2 | c | 9.30 | 3 + 3 | positive Apex margin | N | 59.00 | FALSE | cat_1 |
| 49 | TB08.0943_v7 | 56 | T3 | a | 3.40 | 3 + 4 | positive base margin | Y | 53.00 | FALSE | cat_1 |
| 50 | TB08.0958_v12 | 42 | T2 | x | 11.80 | 3 + 3 | Negative | N | 43.00 | FALSE | cat_2 |
| 51 | TB08.0958_v13 | 42 | T2 | x | 11.80 | 3 + 3 | Negative | N | 43.00 | FALSE | cat_2 |
| 52 | TB08.0973_v9 | 68 | T2 | c | 6.40 | 3 + 4 | negative margins | N | 58.00 | FALSE | cat_1 |
| 53 | TB08.0978_v7 | 64 | T3 | a | 12.00 | 3 + 4 | Negative | Y | 58.00 | FALSE | cat_2 |
| 54 | TB08.0978_v8 | 64 | T3 | a | 12.00 | 3 + 4 | Negative | Y | 58.00 | FALSE | cat_2 |
| 55 | TB08.0978_v9 | 64 | T3 | a | 12.00 | 3 + 4 | Negative | Y | 58.00 | FALSE | cat_2 |
| 56 | TB08.0986_v2 | 56 | T3 | a | 15.50 | 3 + 4 | Positive base | Y | 58.00 | FALSE | cat_2 |
| 57 | TB08.0987_v6 | 54 | T3 | a | 12.00 | 3 + 4 | positive circumferential margin | Y | 58.00 | FALSE | cat_2 |
| 58 | TB08.0993_v12 | 66 | T2 | c | 7.70 | 4 + 3 | Negative | N | 60.00 | FALSE | cat_2 |
| 59 | TB08.0997_v6 | 62 | T3 | a | 7.00 | 4 + 3 | positive Apex margin | Y | 58.00 | FALSE | normal |
| 60 | TB08.0999_v11 | 67 | T3 | a | 9.20 | 3 + 4 | Negative | Y | 52.00 | FALSE | cat_1 |
| 61 | TB08.0999_v2 | 67 | T3 | a | 9.20 | 3 + 4 | Negative | Y | 52.00 | FALSE | cat_1 |
| 62 | TB08.1015_v10 | 63 | T3 | a | 8.00 | 3 + 5 | Negative | Y | 12.00 | TRUE | cat_3 |
| 63 | TB08.1015_v11 | 63 | T3 | a | 8.00 | 3 + 5 | Negative | Y | 12.00 | TRUE | cat_3 |
| 64 | TB08.1015_v9 | 63 | T3 | a | 8.00 | 3 + 5 | Negative | Y | 12.00 | TRUE | cat_3 |
| 65 | TB08.1019_v1 | 59 | T3 | a | 5.00 | 3 + 4 | Negative | Y | 68.00 | FALSE | cat_1 |
| 66 | TB08.1019_v14 | 59 | T3 | a | 5.00 | 3 + 4 | Negative | Y | 68.00 | FALSE | cat_1 |
| 67 | TB08.1019_v15 | 59 | T3 | a | 5.00 | 3 + 4 | Negative | Y | 68.00 | FALSE | cat_1 |
| 68 | TB08.1019_v2 | 59 | T3 | a | 5.00 | 3 + 4 | Negative | Y | 68.00 | FALSE | cat_1 |
| 69 | TB08.1026_v17 | 61 | T3 | a | 8.40 | 3 + 4 | negative margins | Y | 57.00 | TRUE | cat_1 |
| 70 | TB08.1044_v7 | 71 | T3 | a | 7.90 | 3 + 4 | Positive base & circumferential | Y | 59.00 | FALSE | cat_1 |
| 71 | TB08.1053_v5 | 71 | T3 | a | 17.00 | 3 + 4 | Negative | Y | 57.00 | FALSE | cat_2 |
| 72 | TB08.1063_v16 | 67 | T3 | a | 5.80 | 4 + 3 | Positive base & circumferential | Y | 38.00 | TRUE | cat_2 |
| 73 | TB08.1063_v8 | 67 | T3 | a | 5.80 | 4 + 3 | Positive base & circumferential | Y | 38.00 | TRUE | cat_2 |
| 74 | TB08.1083_v3 | 64 | T3 | a | 7.30 | 3 + 3 | negative margins | Y | 57.00 | FALSE | cat_1 |
| 75 | TB08.1116_v2 | 61 | T3 | a | 6.00 | 3 + 4 | Negative | Y | 42.00 | FALSE | cat_1 |
| 76 | TB08.1116_v3 | 61 | T3 | a | 6.00 | 3 + 4 | Negative | Y | 42.00 | FALSE | cat_1 |
| 77 | TB08.1116_v9 | 61 | T3 | a | 6.00 | 3 + 4 | Negative | Y | 42.00 | FALSE | cat_1 |
| 78 | TB08.1159_v2 | 56 | T2 | a | 7.90 | 3 + 3 | negative margins | N | 56.00 | FALSE | cat_1 |
| 79 | TB08.0601_v16 | 66 | T2 | x | 8.28 | 3 + 3 | negative margins | N | 68.00 | FALSE | normal |
| 80 | TB09.0217_v16 | 63 | T3 | a | 11.50 | 3 + 4 | Positive base | Y | 12.00 | TRUE | cat_2 |
| 81 | TB09.0217_v7 | 63 | T3 | a | 11.50 | 3 + 4 | Positive base | Y | 12.00 | TRUE | cat_2 |
| 82 | TB09.0219_v13 | 62 | T3 | a | 17.30 | 3 + 4 | Negative | Y | 16.00 | TRUE | cat_2 |
| 83 | TB09.0219_v2 | 62 | T3 | a | 17.30 | 3 + 4 | Negative | Y | 16.00 | TRUE | cat_2 |
| 84 | TB09.0219_v21 | 62 | T3 | a | 17.30 | 3 + 4 | Negative | Y | 16.00 | TRUE | cat_2 |
| 85 | TB09.0219_v8 | 62 | T3 | a | 17.30 | 3 + 4 | Negative | Y | 16.00 | TRUE | cat_2 |
| 86 | TB09.0238_v12 | 66 | T3 | a | 9.60 | 3 + 4 | Negative | Y | 54.00 | FALSE | cat_1 |
| 87 | TB09.0238_v18 | 66 | T3 | a | 9.60 | 3 + 4 | Negative | Y | 54.00 | FALSE | cat_1 |
| 88 | TB09.0238_v5 | 66 | T3 | a | 9.60 | 3 + 4 | Negative | Y | 54.00 | FALSE | cat_1 |
| 89 | TB09.0272_v6 | 62 | T3 | a | 12.00 | 3 + 4 | Negative | Y | 58.00 | FALSE | cat_2 |
| 90 | TB09.0272_v7 | 62 | T3 | a | 12.00 | 3 + 4 | Negative | Y | 58.00 | FALSE | cat_2 |
| 91 | TB09.0295_v2 | 64 | T3 | b | 22.60 | 3 + 4 | positive apex | | | | cat_3 |
| 92 | TB09.0413_v11 | 48 | T3 | a | 5.30 | 4 + 3 | Negative | Y | 45.00 | TRUE | cat_2 |
| 93 | TB09.0413_v8 | 48 | T3 | a | 5.30 | 4 + 3 | Negative | Y | 45.00 | TRUE | cat_2 |
| 94 | TB09.0443_v3 | 41 | T3 | a | 16.20 | 3 + 4 | Negative | Y | 51.00 | FALSE | cat_2 |
| 95 | TB09.0443_v8 | 41 | T3 | a | 16.20 | 3 + 4 | Negative | Y | 51.00 | FALSE | cat_2 |
| 96 | TB09.0448_v8 | 70 | T2 | c | 4.68 | 3 + 4 | Negative | N | 19.00 | TRUE | cat_1 |
| 97 | TB09.0462_v7 | 56 | T3 | a | 5.80 | 3 + 4 | Negative | Y | 57.00 | FALSE | cat_1 |
| 98 | TB09.0471_v11 | 54 | T2 | c | 5.80 | 3 + 3 | negative margins | N | 54.00 | FALSE | cat_1 |
| 99 | TB09.0504_v4 | 60 | T2 | a | 5.10 | 3 + 5 | Negative | N | 51.00 | FALSE | cat_3 |
| 100 | TB09.0550_v15 | 47 | T3 | a | 11.50 | 3 + 4 | Negative | Y | 51.00 | FALSE | cat_2 |
| 101 | TB09.0606_v3 | 64 | T3 | b | 10.00 | 4 + 5 | Negative | Y | 15.00 | TRUE | cat_3 |
| 102 | TB09.0706_v5 | 63 | T3 | a | 7.30 | 3 + 4 | Negative | Y | 17.00 | TRUE | cat_1 |
| 103 | TB09.0720_v19 | 67 | T2 | x | 8.90 | 3 + 3 | negative margins | N | 50.00 | FALSE | cat_1 |
| 104 | TB09.0721_v14 | 58 | T2 | c | 4.00 | 3 + 3 | Negative | N | 10.00 | TRUE | cat_1 |
| 105 | TB09.0721_v15 | 58 | T2 | c | 4.00 | 3 + 3 | Negative | N | 10.00 | TRUE | cat_1 |
| 106 | TB09.0725_v9 | 64 | T2 | x | 10.70 | 3 + 4 | negative margins | N | 49.00 | FALSE | cat_2 |
| 107 | TB09.0774_v1 | 64 | T2 | c | 6.40 | 3 + 4 | Negative | N | 49.00 | FALSE | cat_1 |
| 108 | TB09.0774_v15 | 64 | T2 | c | 6.40 | 3 + 4 | Negative | N | 49.00 | FALSE | cat_1 |
| 109 | TB09.0850_v2 | 21 | T3 | a | 5.70 | 3 + 4 | Negative | Y | 56.00 | FALSE | cat_1 |
| 110 | TB09.0962_v13 | 65 | T2 | x | 6.20 | 3 + 3 | Negative | N | 48.00 | FALSE | cat_1 |
| 111 | TB09.0962_v16 | 65 | T2 | x | 6.20 | 3 + 3 | Negative | N | 48.00 | FALSE | cat_1 |
| 112 | NP1 | 66 | T2 | a | 9.80 | 3 + 3 | Negative | No | 95.00 | FALSE | cat_1 |
| 113 | NP10 | 60 | T3 | b | 15.00 | 4 + 3 | Positive circumferential | Unknown | 55.00 | FALSE | normal |
| 114 | NP11 | 61 | T2 | c | 6.90 | 3 + 4 | Negative | No | 72.00 | FALSE | normal |
| 115 | NP12 | 65 | T2 | c | 7.40 | 4 + 3 | Negative | No | 15.00 | TRUE | normal |
| 116 | NP14 | 72 | T2 | x | 11.10 | 3 + 4 | Positive circumferential | Unknown | 59.00 | FALSE | normal |
| 117 | NP15 | 64 | T2 | c | 6.10 | 3 + 4 | Positive apex | No | 51.00 | FALSE | normal |
| 118 | NP16 | 53 | T2 | c | 11.10 | 3 + 3 | Negative | No | 48.00 | FALSE | normal |

-continued

| Row | Sample ID | Age_at_Diagnosis | Pathology_Stage | Pathology_sub_stage | PSA_pre_prostatectomy | Gleason_Score | Margins | Extra_Capsular_Extension | BCR_FreeTime_months | BCR_Event | ICGC_category |
|---|---|---|---|---|---|---|---|---|---|---|---|
| 119 | NP17 | 58 | T2 | c | 4.70 | 3 + 4 | Positive circumferential | No | 60.00 | FALSE | cat_1 |
| 120 | NP18 | 60 | T2 | c | 16.90 | 3 + 4 | Positive circumferential | No | 69.00 | FALSE | normal |
| 121 | NP19 | 60 | T3 | b | 8.00 | 4 + 5 | Positive circumferential | Yes | 6.00 | TRUE | cat_3 |
| 122 | NP2 | 53 | T3 | a | | 3 + 4 | Positive circumferential | Yes | 76.00 | FALSE | unknown |
| 123 | NP20 | 68 | T2 | c | 7.10 | 3 + 4 | Negative | No | 61.00 | FALSE | normal |
| 124 | NP21 | 66 | T2 | c | 6.10 | 3 + 4 | | No | 63.00 | FALSE | normal |
| 125 | NP4 | 60 | T3 | b | 15.00 | 4 + 3 | Positive circumferential | Unknown | 55.00 | FALSE | cat_2 |
| 126 | NP5 | 61 | T2 | c | 3.10 | 3 + 3 | Negative | No | 68.00 | FALSE | cat_1 |
| 127 | NP8 | 59 | T2 | c | 7.70 | 3 + 4 | Negative | No | 55.00 | FALSE | normal |
| 128 | NP9 | 62 | T2 | c | 7.60 | 3 + 5 | Negative | Unknown | 68.00 | FALSE | normal |
| 129 | PRC140 | 71 | T2 | b | 6.30 | 4 + 3 | Negative | No | 57.00 | FALSE | cat_2 |
| 130 | PRC101 | 55 | T2 | c | 4.75 | 3 + 4 | Negative | Unknown | 64.00 | FALSE | cat_1 |
| 131 | PRC102 | 59 | T2 | c | 7.70 | 3 + 4 | Negative | No | 55.00 | FALSE | cat_1 |
| 132 | PRC103 | 61 | T2 | c | 4.00 | 3 + 4 | Negative | No | 72.00 | FALSE | cat_1 |
| 133 | PRC105 | 62 | T2 | c | 7.60 | 3 + 5 | Negative | Unknown | 68.00 | FALSE | cat_3 |
| 134 | PRC106 | 62 | T2 | c | 7.60 | 3 + 5 | Negative | Unknown | 68.00 | FALSE | cat_3 |
| 135 | PRC109 | 62 | T3 | b | 12.40 | 3 + 4 | Positive apex & circumferential | No | 47.00 | FALSE | cat_2 |
| 136 | PRC10 | 58 | T2 | c | 6.60 | 3 + 3 | | Unknown | 3.00 | TRUE | cat_1 |
| 137 | PRC110 | 62 | T3 | b | 12.40 | 3 + 4 | Positive apex & circumferential | No | 47.00 | FALSE | cat_2 |
| 138 | PRC111 | 62 | T3 | b | 12.40 | 3 + 4 | Positive apex & circumferential | No | 47.00 | FALSE | cat_2 |
| 139 | PRC112 | 68 | T2 | c | 6.40 | 3 + 4 | Positive apex | No | 39.00 | FALSE | cat_1 |
| 140 | PRC113 | 49 | T2 | c | 8.90 | 3 + 4 | Negative | No | 43.00 | FALSE | cat_1 |
| 141 | PRC114 | 40 | T2 | c | 8.40 | 3 + 4 | Negative | No | 16.00 | FALSE | cat_1 |
| 142 | PRC115 | 40 | T2 | c | 8.40 | 3 + 4 | Negative | No | 16.00 | FALSE | cat_1 |
| 143 | PRC116 | 61 | T2 | c | 7.90 | 3 + 4 | Negative | Unknown | 69.00 | FALSE | cat_1 |
| 144 | PRC117 | 61 | T2 | c | 7.90 | 3 + 4 | Negative | Unknown | 69.00 | FALSE | cat_1 |
| 145 | PRC118 | 61 | T2 | c | 6.90 | 3 + 4 | Negative | No | 72.00 | FALSE | cat_1 |
| 146 | PRC119 | 61 | T2 | c | 3.10 | 3 + 3 | Negative | No | 68.00 | FALSE | cat_1 |
| 147 | PRC11 | 58 | T2 | x | 4.10 | 3 + 3 | Positive circumferential | No | 93.00 | FALSE | cat_1 |
| 148 | PRC122 | 61 | T2 | c | 7.90 | 3 + 4 | Negative | Unknown | 69.00 | FALSE | cat_1 |
| 149 | PRC123 | 55 | T3 | a | 3.30 | 3 + 4 | Positive complex | Yes | 71.00 | FALSE | cat_2 |
| 150 | PRC124 | 61 | T3 | a | 6.40 | 3 + 4 | Negative | No | 49.00 | FALSE | cat_1 |
| 151 | PRC125 | 55 | T3 | a | 3.30 | 3 + 4 | Positive complex | Yes | 71.00 | FALSE | cat_2 |
| 152 | PRC126 | 72 | T3 | b | | 4 + 5 | Positive apex & circumferential & base | Yes | 56.00 | TRUE | unknown |
| 153 | PRC127 | 72 | T3 | b | | 4 + 5 | Positive apex & circumferential & base | Yes | 56.00 | TRUE | unknown |
| 154 | PRC128 | 70 | T3 | a | 4.70 | 4 + 3 | Positive circumferential | Yes | 60.00 | FALSE | cat_3 |
| 155 | PRC129 | 70 | T3 | a | 4.70 | 4 + 3 | Positive circumferential | Yes | 60.00 | FALSE | cat_3 |
| 156 | PRC12 | 63 | T3 | a | 13.70 | 4 + 3 | Positive circumferential | Yes | 26.00 | TRUE | cat_3 |
| 157 | PRC130 | 65 | T2 | c | 7.40 | 4 + 3 | Negative | No | 15.00 | TRUE | cat_2 |
| 158 | PRC133 | 72 | T2 | x | 11.10 | 3 + 4 | Positive circumferential | Unknown | 59.00 | FALSE | cat_2 |
| 159 | PRC134 | 72 | T2 | x | 11.10 | 3 + 4 | Positive circumferential | Unknown | 59.00 | FALSE | cat_2 |
| 160 | PRC135 | 71 | T2 | b | 6.30 | 4 + 3 | Negative | No | 57.00 | FALSE | cat_2 |
| 161 | PRC136 | 51 | T2 | c | 8.90 | 4 + 3 | Positive circumferential | No | 60.00 | FALSE | cat_2 |
| 162 | PRC137 | 64 | T2 | c | 6.10 | 3 + 4 | Positive apex | No | 51.00 | FALSE | cat_1 |
| 163 | PRC138 | 53 | T2 | c | 11.10 | 3 + 3 | Negative | No | 48.00 | FALSE | cat_2 |
| 164 | PRC139 | 53 | T2 | c | 11.10 | 3 + 3 | Negative | No | 48.00 | FALSE | cat_2 |
| 165 | PRC13 | 63 | T3 | b | 13.00 | 4 + 3 | Positive complex | Unknown | 9.00 | TRUE | cat_2 |
| 166 | PRC141 | 64 | T2 | c | 15.20 | 3 + 4 | Positive circumferential | No | 27.00 | FALSE | cat_2 |
| 167 | PRC142 | 60 | T3 | b | 8.00 | 4 + 5 | Positive circumferential | Yes | 6.00 | TRUE | cat_3 |
| 168 | PRC143 | 68 | T2 | c | 7.10 | 3 + 4 | Negative | No | 61.00 | FALSE | cat_1 |
| 169 | PRC144 | 61 | T2 | c | 7.80 | 3 + 4 | Negative | No | 23.00 | TRUE | cat_1 |
| 170 | PRC145 | 66 | T2 | c | 6.10 | 3 + 4 | | No | 63.00 | FALSE | cat_1 |
| 171 | PRC146 | 63 | T2 | c | 5.60 | 3 + 4 | Negative | No | 55.00 | FALSE | cat_1 |
| 172 | PRC147 | 63 | T2 | c | 5.60 | 3 + 4 | Negative | No | 55.00 | FALSE | cat_1 |
| 173 | PRC148 | 66 | T2 | c | 6.70 | 3 + 4 | Positive apex | No | 66.00 | FALSE | cat_1 |
| 174 | PRC149 | 63 | T2 | c | 11.50 | 4 + 3 | Negative | No | 53.00 | FALSE | cat_2 |
| 175 | PRC14 | 53 | T2 | x | 8.00 | 3 + 3 | | Unknown | 108.00 | FALSE | normal |
| 176 | PRC150 | 50 | T2 | c | 4.40 | 3 + 4 | Negative | No | 61.00 | FALSE | cat_1 |
| 177 | PRC151 | 56 | T3 | a | 7.70 | 3 + 4 | Negative | Yes | 54.00 | FALSE | cat_2 |
| 178 | PRC152 | 58 | T2 | c | 9.60 | 3 + 3 | Negative | No | 72.00 | FALSE | cat_1 |
| 179 | PRC153 | 58 | T2 | c | 9.60 | 3 + 3 | Negative | No | 72.00 | FALSE | cat_1 |
| 180 | PRC154 | 69 | T2 | c | 4.53 | 3 + 4 | Positive apex | No | 7.00 | TRUE | cat_1 |
| 181 | PRC155 | 61 | T2 | c | 7.50 | 3 + 3 | Negative | Unknown | 70.00 | FALSE | cat_1 |
| 182 | PRC156 | 50 | T3 | a | 3.60 | 3 + 4 | | Yes | 44.00 | FALSE | cat_2 |
| 183 | PRC157 | 56 | T1 | c | 10.50 | 3 + 3 | Negative | No | 34.00 | FALSE | cat_2 |
| 184 | PRC158 | 55 | T3 | a | 7.00 | 4 + 5 | Positive circumferential | Yes | 44.00 | TRUE | cat_3 |
| 185 | PRC159 | 60 | T3 | a | 5.40 | 4 + 3 | Negative | Yes | 32.00 | FALSE | cat_3 |
| 186 | PRC15 | 50 | T3 | b | 16.20 | 3 + 4 | Positive apex & circumferential | Unknown | 4.00 | TRUE | normal |

-continued

| Row | Sample ID | Age_at_ Diagnosis | Path- ology_ Stage | Path- ology_ sub_stage | PSA_pre_ pros- tatectomy | Gleason_ Score | Margins | Extra_ Capsular_ Extension | BCR_ FreeTime_ months | BCR_ Event | ICGC_ category |
|---|---|---|---|---|---|---|---|---|---|---|---|
| 187 | PRC160 | 64 | T3 | b | 7.20 | 4 + 3 | Negative | No | 34.00 | FALSE | cat_2 |
| 188 | PRC161 | 55 | T3 | a | 7.00 | 4 + 5 | Positive circumferential | Yes | 44.00 | TRUE | cat_3 |
| 189 | PRC162 | 56 | T3 | b | 9.28 | 3 + 4 | Negative | Unknown | 15.00 | TRUE | cat_1 |
| 190 | PRC163 | 60 | T3 | b | 8.00 | 4 + 5 | Positive circumferential | Yes | 6.00 | TRUE | cat_3 |
| 191 | PRC164 | 62 | T2 | c | 17.40 | 3 + 4 | Negative | No | 65.00 | FALSE | cat_2 |
| 192 | PRC165 | 64 | T2 | c | 12.90 | 3 + 4 | | Unknown | 9.00 | TRUE | cat_2 |
| 193 | PRC166 | 55 | T2 | c | 12.40 | 3 + 4 | Positive circumferential | No | 73.00 | FALSE | cat_2 |
| 194 | PRC167 | 64 | T3 | a | 3.80 | 3 + 4 | Negative | Yes | 67.00 | FALSE | cat_2 |
| 195 | PRC168 | 59 | T2 | c | 8.70 | 3 + 3 | Negative | No | 39.00 | FALSE | cat_1 |
| 196 | PRC169 | 70 | T2 | c | 8.10 | 3 + 4 | Negative | No | 32.00 | FALSE | cat_1 |
| 197 | PRC16 | 67 | T3 | a | 16.00 | 3 + 3 | Positive complex | Yes | 66.00 | TRUE | normal |
| 198 | PRC17 | 49 | T3 | b | 7.50 | 3 + 4 | Positive apex & circumferential | Unknown | 17.00 | TRUE | cat_1 |
| 199 | PRC18 | 63 | T3 | b | 13.00 | 4 + 3 | Positive complex | Unknown | 9.00 | TRUE | cat_2 |
| 200 | PRC19 | 65 | T3 | b | 9.70 | 4 + 3 | Positive complex | Unknown | 45.00 | TRUE | cat_2 |
| 201 | PRC1 | 61 | T2 | c | 9.30 | 3 + 3 | Negative | No | 110.00 | FALSE | cat_1 |
| 202 | PRC20 | 65 | T2 | x | 9.80 | 3 + 4 | | | 56.00 | FALSE | cat_1 |
| 203 | PRC21 | 65 | T2 | x | 9.80 | 3 + 4 | | | 56.00 | FALSE | cat_1 |
| 204 | PRC22 | 57 | T2 | c | 7.10 | 3 + 4 | Positive apex | No | 83.00 | FALSE | cat_1 |
| 205 | PRC23 | 69 | T2 | x | 5.60 | 3 + 4 | Positive circumferential | Unknown | 80.00 | FALSE | cat_1 |
| 206 | PRC24 | 56 | T2 | a | 7.90 | 3 + 3 | Positive complex | No | 92.00 | FALSE | cat_1 |
| 207 | PRC25 | 58 | T2 | c | 5.60 | 3 + 3 | Positive apex & circumferential | No | 19.00 | TRUE | cat_1 |
| 208 | PRC26 | 52 | T2 | c | 3.40 | 3 + 3 | Negative | No | 94.00 | FALSE | cat_1 |
| 209 | PRC27 | 56 | T3 | b | 8.00 | 3 + 3 | Positive complex | No | 98.00 | FALSE | cat_1 |
| 210 | PRC28 | 48 | T2 | c | 3.70 | 3 + 3 | Positive complex | Unknown | 31.00 | TRUE | cat_1 |
| 211 | PRC29 | 64 | T2 | x | 5.60 | 3 + 4 | Positive complex | Unknown | 90.00 | FALSE | cat_1 |
| 212 | PRC2 | 53 | T2 | x | 8.00 | 3 + 3 | | Unknown | 108.00 | FALSE | cat_1 |
| 213 | PRC30 | 58 | T2 | x | 4.10 | 3 + 3 | Positive circumferential | No | 93.00 | FALSE | cat_1 |
| 214 | PRC31 | 56 | T2 | a | 12.80 | 3 + 3 | Negative | No | 108.00 | FALSE | cat_2 |
| 215 | PRC32 | 52 | T2 | x | 6.10 | 3 + 3 | Positive complex | No | 91.00 | FALSE | cat_1 |
| 216 | PRC34 | 56 | T2 | x | 4.50 | 3 + 3 | Positive apex & circumferential | Unknown | 129.00 | FALSE | cat_1 |
| 217 | PRC35 | 56 | T2 | x | 4.50 | 3 + 3 | Positive apex & circumferential | Unknown | 129.00 | FALSE | cat_1 |
| 218 | PRC36 | 56 | T2 | a | 7.90 | 3 + 3 | Positive complex | No | 92.00 | FALSE | cat_1 |
| 219 | PRC38 | 55 | T2 | c | 5.70 | 3 + 3 | Positive base | Unknown | 89.00 | FALSE | cat_1 |
| 220 | PRC39 | 62 | T3 | b | 22.30 | 3 + 4 | Positive apex | No | 84.00 | FALSE | cat_3 |
| 221 | PRC3 | 50 | T3 | b | 16.20 | 3 + 4 | Positive apex & circumferential | Unknown | 4.00 | TRUE | cat_2 |
| 222 | PRC40 | 61 | T2 | c | 9.30 | 3 + 3 | Negative | No | 110.00 | FALSE | cat_1 |
| 223 | PRC42 | 68 | T2 | x | 9.80 | 3 + 3 | Positive circumferential | Unknown | 39.00 | TRUE | cat_1 |
| 224 | PRC45 | 56 | T2 | a | 12.80 | 3 + 3 | Negative | No | 108.00 | FALSE | cat_2 |
| 225 | PRC4 | 54 | T3 | a | 11.40 | 3 + 3 | Negative | Yes | 123.00 | FALSE | cat_2 |
| 226 | PRC5 | 41 | T2 | x | 4.00 | 3 + 3 | Negative | Unknown | 74.00 | FALSE | cat_1 |
| 227 | PRC6 | 67 | T3 | a | 16.00 | 3 + 3 | Positive complex | Yes | 66.00 | TRUE | cat_2 |
| 228 | PRC7 | 68 | T2 | x | 9.80 | 3 + 3 | Positive circumferential | Unknown | 39.00 | TRUE | cat_1 |
| 229 | PRC8 | 67 | T3 | a | 16.00 | 3 + 3 | Positive complex | Yes | 66.00 | TRUE | cat_2 |
| 230 | PRC9 | 67 | T2 | c | 13.90 | 4 + 5 | Negative | No | 11.00 | TRUE | cat_3 |
| 231 | ST1 | 72 | T3 | b | | 4 + 5 | Positive apex & circumferential & base | Yes | 56.00 | TRUE | unknown |
| 232 | ST2 | 63 | T2 | b | 4.78 | 3 + 4 | Positive circumferential | No | 67.00 | FALSE | cat_1 |
| 233 | ST3 | 63 | T2 | c | 5.00 | 3 + 3 | Negative | No | 60.00 | FALSE | cat_1 |
| 234 | ST4 | 60 | T2 | c | 16.90 | 3 + 4 | Positive circumferential | No | 69.00 | FALSE | cat_2 |
| 235 | ST5 | 64 | T3 | b | 7.20 | 4 + 3 | Negative | No | 34.00 | FALSE | normal |

REFERENCES

1. D'Amico, A. V., Moul, J., Carroll, P. R. & Sun, L. Cancer-specific mortality after surgery or radiation for patients with clinically localized prostate cancer managed during the prostate-specific antigen era. *J. Clin. Oncol.* 21, 2163-2172 (2003).
2. Buyyounouski, M. K., Pickles, T. & Kestin, L. L. Validating the interval to biochemical failure for the identification of potentially lethal prostate cancer. *J. Clin. Oncol.* 30, 1857-1863 (2012).
3. Draisma, G. et al. Lead time and overdiagnosis in prostate-specific antigen screening: importance of methods and context. *J. Natl. Cancer Inst.* 101, 374-383 (2009).
4. Etzioni, R., Gulati, R., Mallinger, L. & Mandelblatt, J. Influence of study features and methods on overdiagnosis estimates in breast and prostate cancer screening. *Ann. Intern. Med.* 158, 831-838 (2013).
5. Sorlie, T. et al. Repeated observation of breast tumor subtypes in independent gene expression data sets. *Proc. Natl. Acad. Sci. U.S.A.* 100, 8418-8423 (2003).
6. Taylor, B. S. et al. Integrative genomic profiling of human prostate cancer. *Cancer Cell* 18, 11-22 (2010).
7. Ross-Adams, H. et al. Integration of copy number and transcriptomics provides risk stratification in prostate cancer: A discovery and validation cohort study. *EBio Medicine* 2, 1133-1144 (2015).
8. Carrivick, L. et al. Identification of prognostic signatures in breast cancer microarray data using Bayesian techniques. *J R Soc Interface* 3, 367-381 (2006).
9. Glinsky, G. V., Glinskii, A. B., Stephenson, A. J., Hoffman, R. M. & Gerald, W. L. Gene expression profiling predicts clinical outcome of prostate cancer. *J. Clin. Invest.* 113, 913-923 (2004).
10. Erho, N. et al. Discovery and validation of a prostate cancer genomic classifier that predicts early metastasis following radical prostatectomy. *PLoS ONE* 8, e66855 (2013).
11. Cuzick, J. et al. Prognostic value of an RNA expression signature derived from cell cycle proliferation genes in patients with prostate cancer: a retrospective study. *Lancet Oncol.* 12, 245-255 (2011).
12. Ramos-Montoya, A. et al. HES6 drives a critical AR transcriptional programme to induce castration-resistant prostate cancer through activation of an E2F1-mediated cell cycle network. *EMBO Molecular Medicine* n/a-n/a (2014). doi:10.1002/emmm.201303581
13. Tomlins, S. A. et al. Characterization of 1577 primary prostate cancers reveals novel biological and clinicopathologic insights into molecular subtypes. *Eur. Urol.* 68, 555-567 (2015).
14. You, S. et al. Integrated classification of prostate cancer reveals a novel luminal subtype with poor outcome. *Cancer Res.* (2016). doi:10.1158/0008-5472.CAN-16-0902
15. Blei, D. M., Ng, A. Y. & Jordan, M. I. Latent dirichlet allocation. *the Journal of machine Learning research* (2003).
16. Boutros, P. C. et al. Spatial genomic heterogeneity within localized, multifocal prostate cancer. *Nat. Genet.* (2015). doi:10.1038/ng.3315
17. Clark, J. et al. Complex patterns of ETS gene alteration arise during cancer development in the human prostate. *Oncogene* 27, 1993-2003 (2008).
18. Cooper, C. S. et al. Analysis of the genetic phylogeny of multifocal prostate cancer identifies multiple independent clonal expansions in neoplastic and morphologically normal prostate tissue. *Nat. Genet.* 47, 367-372 (2015).
19. Svensson, M. A. et al. Testing mutual exclusivity of ETS rearranged prostate cancer. *Lab. Invest.* 91, 404-412 (2011).
20. Cancer Genome Atlas Research Network. The Molecular Taxonomy of Primary Prostate Cancer. *Cell* 163, 1011-1025 (2015).
21. Olmos, D. et al. Prognostic value of blood mRNA expression signatures in castration-resistant prostate cancer: a prospective, two-stage study. *Lancet Oncol.* 13, 1114-1124 (2012).
22. Klein, E. A., Yousefi, K., Haddad, Z., Choeurng, V. & Buerki, C. A genomic classifier improves prediction of metastatic disease within 5 years after surgery in node-negative high-risk prostate cancer patients managed by . . . *Eur. Urol.* (2015).
23. Stephenson, A. J. et al. Integration of gene expression profiling and clinical variables to predict prostate carcinoma recurrence after radical prostatectomy. *Cancer* 104, 290-298 (2005).
24. Ramaswamy, S., Ross, K. N., Lander, E. S. & Golub, T. R. A molecular signature of metastasis in primary solid tumors. *Nat. Genet.* 33, 49-54 (2003).
25. Klein, E. A. et al. A 17-gene assay to predict prostate cancer aggressiveness in the context of Gleason grade heterogeneity, tumor multifocality, and biopsy undersampling. *Eur. Urol.* 66, 550-560 (2014).
26. Tomlins, S. A. et al. Recurrent fusion of TMPRSS2 and ETS transcription factor genes in prostate cancer. *Science* 310, 644-648 (2005).
27. Weischenfeldt, J. et al. Integrative genomic analyses reveal an androgen-driven somatic alteration landscape in early-onset prostate cancer. *Cancer Cell* 23, 159-170 (2013).
28. Park, K. et al. TMPRSS2:ERG Gene Fusion Predicts Subsequent Detection of Prostate Cancer in Patients With High-Grade Prostatic Intraepithelial Neoplasia. *J. Clin. Oncol.* 32, 206-211 (2014).
29. Friedl, P., Locker, J., Sahai, E. & Segall, J. E. Classifying collective cancer cell invasion. *Nat. Cell Biol.* 14, 777-783 (2012).
30. Schröder, F. H. et al. Screening and prostate cancer mortality: results of the European Randomised Study of Screening for Prostate Cancer (ERSPC) at 13 years of follow-up. *Lancet* 384, 2027-2035 (2014).
31. Warren, A. Y. et al. Method for sampling tissue for research which preserves pathological data in radical prostatectomy. *Prostate* 73, 194-202 (2013).
32. Jhavar, S. et al. Detection of TMPRSS2-ERG translocations in human prostate cancer by expression profiling using GeneChip Human Exon 1.0 ST arrays. *J Mol Diagn* 10, 50-57 (2008).
33. Irizarry, R. A. et al. Exploration, normalization, and summaries of high density oligonucleotide array probe level data. *Biostatistics* 4, 249-264 (2003).
34. Johnson, W. E., Li, C. & Rabinovic, A. Adjusting batch effects in microarray expression data using empirical Bayes methods. *Biostatistics* (2007).
35. Rogers, S., Girolami, M., Campbell, C. & Breitling, R. The latent process decomposition of cDNA microarray data sets. *IEEE/ACM Trans Comput Biol Bioinform* 2, 143-156 (2005).
36. Ritchie, M. E. et al. limma powers differential expression analyses for RNA-sequencing and microarray studies. *Nucleic Acids Res.* 43, e47 (2015).
37. Friedman, J., Hastie, T. & Tibshirani, R. Regularization paths for generalized linear models via coordinate descent. *Journal of statistical software* (2010).
38. Breiman, L. Random forests. *Machine learning* (2001).
39. Liaw, A. & Wiener, M. Classification and regression by randomForest. *R news* (2002).

We gratefully acknowledge the support of the Institute of Cancer Research and also the University of Cambridge for supplying the CancerMap data.

The invention claimed is:
1. A method of predicting prostate cancer progression, comprising:
   a) determining the expression status of at least 50 genes selected from the group consisting of: TGM4, RLN1, ORM1, OLFM4, OR51E2, SERPINB11, CRISP3, TDRD1, SLC14A1, IGJ, ERG, GDEP, TMEFF2, CST1, LTF, AMACR, SERPINA3, NEFH, ACSM1, OR51E1, MT1G, ANKRD36B, LOC100510059, PLA2G2A, TARP, REXO1L1, ANPEP, HLA-DRB5, PLA2G7, NCAPD3, OR51F2, SPINK1, RCN1, CP, SMU1, ACTC1, AGR2, SLC26A4, IGKC, MYBPC1, NPY, PI15, SLC22A3, PIGR, MME, RBPMS, HLA-DRB1, FOLH1, LUZP2, MSMB, GSTT1, MMP7, ODZ1, ACTB, SPON2, SLC38A11, FOS, OR51T1, HLA-DMB, KRT15, ITGA8, CXADR, LYZ, CEACAM20, C8orf4, DPP4, PGC, C15orf21, CHORDC1, LRRN1, MT1M, EPHA6, PDE11A, TMSB15A, LYPLA1, FOSB, F5, C15orf48, MIPEP, HSD17B6, SLPI, CD38, MMP23B, OR51A7, CFB, CCL2, POTEM, TPMT, FAM3B, FLRT3, C7, NTN4, FAM36A, CNTNAP2, SC4MOL, CH17-189H20.1, TRGC2, RAP1B, SLC4A4, LCE2D, EGR1, MT1L,

SCUBE2, FAM55D, PDK4, CXCL13, CACNA1D, GPR160, CPM, PTGS2, TSPAN8, BMP5, GOLGA8A, OR4N2, FAM135A, DYNLL1, DSC3, C4orf3, HIST1H2BK, LCN2, STEAP4, RPS27L, TRPM8, ID2, LUM, EDNRB, PGM5, SFRP4, STEAP1, FADS2, CXCL11, CWH43, SNRPN, GPR110, THBS1, APOD, HPGD, LEPREL1, LCE1D, GSTM5, SLC30A4, SEMA3D, CACNA2D1, GPR116, C7orf63, FAM198B, SCD, NR4A2, ARG2, ZNF385B, RGS1, DNAH5, NPR3, RAB3B, CHRDL1, ZNF208, MBOAT2, ATF3, ST6GAL1, GDF15, ANXA1, FOLH1, C4B, ELOVL2, GSTM1, GLIPR1, C3, MYO6, ORM2, RAET1L, PCDHB3, C1orf150, ALOX15B, LSAMP, SLC15A2, PCP4, MCCC2, GCNT1, C5orf23, SCGB1D2, CXCL2, AFF3, ATP8A2, PRIM2, ADAMTSL1, NELL2, RPS4Y1, CD24, GOLGA6L9, ZFP36, TRIB1, BNIP3, KL, PDE5A, DCN, LDHB, PCDHB5, ACADL, ZNF99, CPNE4, CCDC144B, SLC26A2, CYP1B1, SELE, CLDN1, KRT13, SFRP2, SLC25A33, HSD17B11, HSD17B13, UGT2B4, CTGF, SCIN, C10orf81, CYR61, PRUNE2, IFI6, MYH11, PPP1R3C, KCNH8, ZNF615, ERV3, F3, TTN, LYRM5, FMOD, NEXN, IL28A, FHL1, CXCL10, SPOCK1, GSTP1, OAT, HIST2H2BF, ACSM3, GLB1L3, SLC5A1, OR4N4, MAOB, BZW1, GENSCAN00000007309, IFI44L, KRT5, SCN7A, GOLM1, HIST4H4, IL7R, CSGAL-NACT1, A2M, LRRC9, ARHGEF38, ACSL5, SGK1, TMEM45B, AHNAK2, NEDD8, GREB1, UBQLN4, SDHC, TCEAL2, SLC18A2, HIST1H2BE, RARRES1, PLN, OGN, GPR110, CLGN, NIPAL3, ACTG2, RCAN3, KLK11, HMGCS2, EML5, EDIL3, PIGH, GLYATL1, ATP1B1, GJA1, PLA1A, MPPED2, AMD1, EMP1, PRR16, CNN1, GHR, ALDH1A1, TRIM29, IFNA17, TAS2R4, SEPP1, GREM1, RASD1, C1S, CLSTN2, DMXL1, HIST1H2BC, NRG4, ARL17A, GRPR, PART1, CYP3A5, KCNC2, SERPINE1, SLC6A14, EIF4A1, MYOF, PHOSPHO2, GCNT2, AOX1, CCDC80, ATP2B4, UGDH, GSTM2, MEIS2, RGS2, PRKG2, FIBIN, FDXACB1, SOD2, SEPT7, PTPRC, GABRP, CBWD3, TOR1AIP2, CXCR4, OR51L1, SLC12A2, AGAP11, SLC27A2, AZGP1, VCAN, ERAP2, KRT17, SLC2A12, CCL4, RPF2, SLC45A3, SEC11C, IFIT1, PAK1IP1, HIST1H3C, ERRFI1, ADAMTS1, TRIM36, FLNA, CCND2, IFIT3, FN1, PRY, HSPB8, CD177, TP63, IFI44, COL12A1, EDNRA, PCDHB2, HLA-DRA, TUBA3E, ASPN, FAM127A, DMD, DHRS7, ANO7, MEIS1, TSPAN1, CNTN1, TRIM22, GSTA2, SORBS1, GPR81, CSRP1, C3orf14, FGFR2, SNAI2, CALCRL, MON1B, PVRL3, VGLL3, SULF1, LIFR, SH3RF1, C12orf75, GNPTAB, CALM2, KLF6, C7orf58, RDH11, NR4A1, RWDD4, ABCC4, ZNF91, GABRE, SLC16A1, DEGS1, CLDN8, HAS2, ODC1, REEP3, LYRM4, PPFIA2, PGM3, ZDHHC8P1, C6orf72, HIST1H2BD, TES, PDE8B, DNAJB4, RGS5, EPHA3, COX7A2, MT1H, HIST2H2BE, TGFB3, VEGFA, CRISPLD2, TFF1, LOC100128816, SYT1, CPE, TRPC4, RAB27A, CD69, RPL17, PSCA, ATRNL1, MYOCD, MS4A8B, TNS1, BAMBI, IGF1, RALGAPA1, S100A10, PMS2CL, MMP2, SLC8A1, OAS2, ARRDC3, AMY2B, SPARCL1, IQGAP2, ACAD8, LPAR3, HIGD2A, NUCB2, HLA-DPA1, SLITRK6, TPM2, REPS2, EAF2, CAV1, PRUNE2, TMEM178, MFAP4, SYNM, EFEMP1, RND3, SCNN1A, B3GNT5, LMOD1, UBC, LMO3, LOX, NFIL3, C11orf92, C11orf48, BCAP29, EPCAM, PTGDS, A5B5, TUBA1B, SERHL, ITGA5, SPARC, LOC286161, NAALADL2, TMPRSS2, SERPINF1, EPHA7, SDAD1, SOX14, RPL35, HSPA1B, MSN, MTRF1L, PTN, CAMKK2, RBM7, OR52H1, C1R, CHRNA2, MRPL41, PROM1, LPAR6, SAMHD1, SCNN1G, DNAJC10, MOXD1, HIST1H2BG, ID1, and SEMA3C in a sample obtained from a patient to provide a patient expression profile, wherein the expression level of the at least 50 genes selected from the group consisting of TGM4, RLN1, ORM1, OLFM4, OR51E2, SERPINB11, CRISP3, TDRD1, SLC14A1, IGJ, ERG, GDEP, TMEFF2, CST1, LTF, AMACR, SERPINA3, NEFH, ACSM1, OR51E1, MT1G, ANKRD36B, LOC100510059, PLA2G2A, TARP, REXO1L1, ANPEP, HLA-DRB5, PLA2G7, NCAPD3, OR51F2, SPINK1, RCN1, CP, SMU1, ACTC1, AGR2, SLC26A4, IGKC, MYBPC1, NPY, PI15, SLC22A3, PIGR, MME, RBPMS, HLA-DRB1, FOLH1, LUZP2, MSMB, GSTT1, MMP7, ODZ1, ACTB, SPON2, SLC38A11, FOS, OR51T1, HLA-DMB, KRT15, ITGA8, CXADR, LYZ, CEACAM20, C8orf4, DPP4, PGC, C15orf21, CHORDC1, LRRN1, MT1M, EPHA6, PDE11A, TMSB15A, LYPLA1, FOSB, F5, C15orf48, MIPEP, HSD17B6, SLPI, CD38, MMP23B, OR51A7, CFB, CCL2, POTEM, TPMT, FAM3B, FLRT3, C7, NTN4, FAM36A, CNTNAP2, SC4MOL, CH17-189H20.1, TRGC2, RAP1B, SLC4A4, LCE2D, EGR1, MT1L, SCUBE2, FAM55D, PDK4, CXCL13, CACNA1D, GPR160, CPM, PTGS2, TSPAN8, BMP5, GOLGA8A, OR4N2, FAM135A, DYNLL1, DSC3, C4orf3, HIST1H2BK, LCN2, STEAP4, RPS27L, TRPM8, ID2, LUM, EDNRB, PGM5, SFRP4, STEAP1, FADS2, CXCL11, CWH43, SNRPN, GPR110, THBS1, APOD, HPGD, LEPREL1, LCE1D, GSTM5, SLC30A4, SEMA3D, CACNA2D1, GPR116, C7orf63, FAM198B, SCD, NR4A2, ARG2, ZNF385B, RGS1, DNAH5, NPR3, RAB3B, CHRDL1, ZNF208, MBOAT2, ATF3, ST6GAL1, GDF15, ANXA1, FOLH1, C4B, ELOVL2, GSTM1, GLIPR1, C3, MYO6, ORM2, RAET1L, PCDHB3, C1orf150, ALOX15B, LSAMP, SLC15A2, PCP4, MCCC2, GCNT1, C5orf23, SCGB1D2, CXCL2, AFF3, ATP8A2, PRIM2, ADAMTSL1, NELL2, RPS4Y1, CD24, GOLGA6L9, ZFP36, TRIB1, BNIP3, KL, PDE5A, DCN, LDHB, PCDHB5, ACADL, ZNF99, CPNE4, CCDC144B, SLC26A2, CYP1B1, SELE, CLDN1, KRT13, SFRP2, SLC25A33, HSD17B11, HSD17B13, UGT2B4, CTGF, SCIN, C10orf81, CYR61, PRUNE2, IFI6, MYH11, PPP1R3C, KCNH8, ZNF615, ERV3, F3, TTN, LYRM5, FMOD, NEXN, IL28A, FHL1, CXCL10, SPOCK1, GSTP1, OAT, HIST2H2BF, ACSM3, GLB1L3, SLC5A1, OR4N4, MAOB, BZW1, GENSCAN00000007309, IFI44L, KRT5, SCN7A, GOLM1, HIST4H4, IL7R, CSGAL-NACT1, A2M, LRRC9, ARHGEF38, ACSL5, SGK1, TMEM45B, AHNAK2, NEDD8, GREB1, UBQLN4, SDHC, TCEAL2, SLC18A2, HIST1H2BE, RARRES1, PLN, OGN, GPR110, CLGN, NIPAL3, ACTG2, RCAN3, KLK11, HMGCS2, EML5, EDIL3, PIGH, GLYATL1, ATP1B1, GJA1, PLA1A, MPPED2, AMD1, EMP1, PRR16, CNN1, GHR, ALDH1A1, TRIM29, IFNA17, TAS2R4, SEPP1, GREM1, RASD1, C1S, CLSTN2, DMXL1, HIST1H2BC, NRG4, ARL17A, GRPR, PART1, CYP3A5, KCNC2, SERPINE1, SLC6A14, EIF4A1, MYOF, PHOSPHO2, GCNT2, AOX1, CCDC80, ATP2B4, UGDH, GSTM2, MEIS2, RGS2, PRKG2, FIBIN, FDXACB1, SOD2, SEPT7, PTPRC, GABRP, CBWD3, TOR1AIP2, CXCR4, OR51L1, SLC12A2, AGAP11, SLC27A2, AZGP1, VCAN, ERAP2, KRT17, SLC2A12, CCL4, RPF2, SLC45A3, SEC11C, IFIT1, PAK1IP1, HIST1H3C, ERRFI1, ADAMTS1, TRIM36, FLNA, CCND2, IFIT3, FN1, PRY, HSPB8, CD177, TP63, IFI44, COL12A1, EDNRA, PCDHB2, HLA-DRA, TUBA3E, ASPN, FAM127A, DMD, DHRS7, ANO7, MEIS1, TSPAN1, CNTN1, TRIM22, GSTA2, SORBS1, GPR81, CSRP1, C3orf14, FGFR2, SNAI2, CALCRL, MON1B, PVRL3, VGLL3, SULF1, LIFR, SH3RF1, C12orf75, GNPTAB, CALM2, KLF6, C7orf58, RDH11, NR4A1, RWDD4, ABCC4, ZNF91, GABRE, SLC16A1, DEGS1, CLDN8, HAS2, ODC1, REEP3, LYRM4, PPFIA2, PGM3, ZDHHC8P1, C6orf72, HIST1H2BD, TES, PDE8B, DNAJB4, RGS5, EPHA3, COX7A2, MT1H, HIST2H2BE, TGFB3, VEGFA, CRISPLD2, TFF1, LOC100128816, SYT1, CPE, TRPC4, RAB27A, CD69, RPL17, PSCA, ATRNL1, MYOCD, MS4A8B, TNS1, BAMBI, IGF1, RALGAPA1, S100A10, PMS2CL, MMP2, SLC8A1, OAS2, ARRDC3, AMY2B, SPARCL1, IQGAP2, ACAD8, LPAR3, HIGD2A, NUCB2, HLA-DPA1, SLITRK6, TPM2, REPS2, EAF2, CAV1, PRUNE2, TMEM178, MFAP4, SYNM, EFEMP1, RND3, SCNN1A, B3GNT5, LMOD1, UBC, LMO3, LOX, NFIL3, C11orf92, C11orf48, BCAP29, EPCAM, PTGDS, ASB5, TUBA1B, SERHL, ITGA5, SPARC, LOC286161, NAALADL2, TMPRSS2, SERPINF1, EPHA7, SDAD1, SOX14, RPL35, HSPA1B, MSN, MTRF1L, PTN, CAMKK2, RBM7, OR52H1, C1R, CHRNA2, MRPL41, PROM1, LPAR6, SAMHD1, SCNN1G, DNAJC10, MOXD1, HIST1H2BG, ID1, and SEMA3C are known to vary across prostate cancers;

b) conducting a Latent Process Decomposition (LPD) analysis on the patient expression profile and a reference dataset for the same at least 50 genes selected from the group consisting of TGM4, RLN1, ORM1, OLFM4, OR51E2, SERPINB11, CRISP3, TDRD1, SLC14A1, IGJ, ERG, GDEP, TMEFF2, CST1, LTF, AMACR, SERPINA3, NEFH, ACSM1, OR51E1, MT1G, ANKRD36B, LOC100510059, PLA2G2A, TARP, REXO1L1, ANPEP, HLA-DRB5, PLA2G7, NCAPD3, OR51F2, SPINK1, RCN1, CP, SMU1, ACTC1, AGR2, SLC26A4, IGKC, MYBPC1, NPY, PI15, SLC22A3, PIGR, MME, RBPMS, HLA-DRB1, FOLH1, LUZP2, MSMB, GSTT1, MMP7, ODZ1, ACTB, SPON2, SLC38A11, FOS, OR51T1, HLA-DMB, KRT15, ITGA8, CXADR, LYZ, CEACAM20, C8orf4, DPP4, PGC, C15orf21, CHORDC1, LRRN1, MT1M, EPHA6, PDE11A, TMSB15A, LYPLA1, FOSB, F5, C15orf48, MIPEP, HSD17B6, SLPI, CD38, MMP23B, OR51A7, CFB, CCL2, POTEM, TPMT, FAM3B, FLRT3, C7, NTN4, FAM36A, CNTNAP2, SC4MOL, CH17-189H20.1, TRGC2, RAP1B, SLC4A4, LCE2D, EGR1, MT1L, SCUBE2, FAM55D, PDK4, CXCL13, CACNA1D, GPR160, CPM, PTGS2, TSPAN8, BMP5, GOLGA8A, OR4N2, FAM135A, DYNLL1, DSC3, C4orf3, HIST1H2BK, LCN2, STEAP4, RPS27L, TRPM8, ID2, LUM, EDNRB, PGM5, SFRP4, STEAP1, FADS2, CXCL11, CWH43, SNRPN, GPR110, THBS1, APOD, HPGD, LEPREL1, LCE1D, GSTM5, SLC30A4, SEMA3D, CACNA2D1, GPR116, C7orf63, FAM198B, SCD, NR4A2, ARG2, ZNF385B, RGS1, DNAH5, NPR3, RAB3B, CHRDL1, ZNF208, MBOAT2, ATF3, ST6GAL1, GDF15, ANXA1, FOLH1, C4B, ELOVL2, GSTM1, GLIPR1, C3, MYO6, ORM2, RAET1L, PCDHB3, C1orf150, ALOX15B, LSAMP, SLC15A2, PCP4, MCCC2, GCNT1, C5orf23, SCGB1D2, CXCL2, AFF3, ATP8A2, PRIM2, ADAMTSL1, NELL2, RPS4Y1, CD24, GOLGA6L9, ZFP36, TRIB1, BNIP3, KL, PDE5A, DCN, LDHB, PCDHB5, ACADL, ZNF99, CPNE4, CCDC144B, SLC26A2, CYP1B1, SELE, CLDN1, KRT13, SFRP2, SLC25A33, HSD17B11, HSD17B13, UGT2B4, CTGF, SCIN, C10orf81, CYR61, PRUNE2, IFI6, MYH11, PPP1R3C, KCNH8, ZNF615, ERV3, F3, TTN, LYRM5, FMOD, NEXN, IL28A, FHL1, CXCL10, SPOCK1, GSTP1, OAT, HIST2H2BF, ACSM3, GLB1L3, SLC5A1, OR4N4, MAOB, BZW1, GENSCAN00000007309, IFI44L, KRT5, SCN7A, GOLM1, HIST4H4, IL7R, CSGALNACT1, A2M, LRRC9, ARHGEF38, ACSL5, SGK1, TMEM45B, AHNAK2, NEDD8, GREB1, UBQLN4, SDHC, TCEAL2, SLC18A2, HIST1H2BE, RARRES1, PLN, OGN, GPR110, CLGN, NIPAL3, ACTG2, RCAN3, KLK11, HMGCS2, EML5, EDIL3, PIGH, GLYATL1, ATP1B1, GJA1, PLA1A, MPPED2, AMD1, EMP1, PRR16, CNN1, GHR, ALDH1A1, TRIM29, IFNA17, TAS2R4, SEPP1, GREM1, RASD1, C1S, CLSTN2, DMXL1, HIST1H2BC, NRG4, ARL17A, GRPR, PART1, CYP3A5, KCNC2, SERPINE1, SLC6A14, EIF4A1, MYOF, PHOSPHO2, GCNT2, AOX1, CCDC80, ATP2B4, UGDH, GSTM2, MEIS2, RGS2, PRKG2, FIBIN, FDXACB1, SOD2, SEPT7, PTPRC, GABRP, CBWD3, TOR1AIP2, CXCR4, OR51L1, SLC12A2, AGAP11, SLC27A2, AZGP1, VCAN, ERAP2, KRT17, SLC2A12, CCL4, RPF2, SLC45A3, SEC11C, IFIT1, PAK1IP1, HIST1H3C, ERRFI1, ADAMTS1, TRIM36, FLNA, CCND2, IFIT3, FN1, PRY, HSPB8, CD177, TP63, IFI44, COL12A1, EDNRA, PCDHB2, HLA-DRA, TUBA3E, ASPN, FAM127A, DMD, DHRS7, ANO7, MEIS1, TSPAN1, CNTN1, TRIM22, GSTA2, SORBS1, GPR81, CSRP1, C3orf14, FGFR2, SNAI2, CALCRL, MON1B, PVRL3, VGLL3, SULF1, LIFR, SH3RF1, C12orf75, GNPTAB, CALM2, KLF6, C7orf58, RDH11, NR4A1, RWDD4, ABCC4, ZNF91, GABRE, SLC16A1, DEGS1, CLDN8, HAS2, ODC1, REEP3, LYRM4, PPFIA2, PGM3, ZDHHC8P1, C6orf72, HIST1H2BD, TES, PDE8B, DNAJB4, RGS5, EPHA3, COX7A2, MT1H, HIST2H2BE, TGFB3, VEGFA, CRISPLD2, TFF1, LOC100128816, SYT1, CPE, TRPC4, RAB27A, CD69, RPL17, PSCA, ATRNL1, MYOCD, MS4A8B, TNS1, BAMBI, IGF1, RALGAPA1, S100A10, PMS2CL, MMP2, SLC8A1, OAS2, ARRDC3, AMY2B, SPARCL1, IQGAP2, ACAD8, LPAR3, HIGD2A, NUCB2, HLA-DPA1, SLITRK6, TPM2, REPS2, EAF2, CAV1, PRUNE2, TMEM178, MFAP4, SYNM, EFEMP1, RND3, SCNN1A, B3GNT5, LMOD1, UBC, LMO3, LOX, NFIL3, C11orf92, C11orf48, BCAP29, EPCAM, PTGDS, ASB5, TUBA1B, SERHL, ITGA5, SPARC, LOC286161, NAALADL2, TMPRSS2, SERPINF1, EPHA7, SDAD1, SOX14, RPL35, HSPA1B, MSN, MTRF1L, PTN, CAMKK2, RBM7, OR52H1, C1R, CHRNA2, MRPL41, PROM1, LPAR6, SAMHD1, SCNN1G, DNAJC10, MOXD1, HIST1H2BG, ID1, and SEMA3C from different patients;

c) optionally repeating the analysis step b) multiple times; and d) predicting prostate cancer progression, wherein:

the LPD analysis organises individual patient expression profiles into groups; and for each expression profile, the LPD analysis determines a continuous contribution (pi) of each group to the overall expression profile for each patient expression profile with DESNT processes contributing to poor prognosis and non-DESNT contributing to non-poor prognosis.

2. The method of claim 1, wherein step a) comprises determining the expression status of 500 genes selected from the group consisting of TGM4, RLN1, ORM1, OLFM4, OR51E2, SERPINB11, CRISP3, TDRD1, SLC14A1, IGJ, ERG, GDEP, TMEFF2, CST1, LTF, AMACR, SERPINA3, NEFH, ACSM1, OR51E1, MT1G, ANKRD36B, LOC100510059, PLA2G2A, TARP, REXO1L1, ANPEP, HLA-DRB5, PLA2G7, NCAPD3, OR51F2, SPINK1, RCN1, CP, SMU1, ACTC1, AGR2, SLC26A4, IGKC, MYBPC1, NPY, PI15, SLC22A3, PIGR, MME, RBPMS, HLA-DRB1, FOLH1, LUZP2, MSMB, GSTT1, MMP7, ODZ1, ACTB, SPON2, SLC38A11, FOS, OR51T1, HLA-DMB, KRT15, ITGA8, CXADR, LYZ, CEACAM20, C8orf4, DPP4, PGC, C15orf21, CHORDC1, LRRN1, MT1M, EPHA6, PDE11A, TMSB15A, LYPLA1, FOSB, F5, C15orf48, MIPEP, HSD17B6, SLPI, CD38, MMP23B, OR51A7, CFB, CCL2, POTEM, TPMT, FAM3B, FLRT3, C7, NTN4, FAM36A, CNTNAP2, SC4MOL, CH17-189H20.1, TRGC2, RAP1B, SLC4A4, LCE2D, EGR1, MT1L, SCUBE2, FAM55D, PDK4, CXCL13, CACNA1D, GPR160, CPM, PTGS2, TSPAN8, BMP5, GOLGA8A, OR4N2, FAM135A, DYNLL1, DSC3, C4orf3, HIST1H2BK, LCN2, STEAP4, RPS27L, TRPM8, ID2, LUM, EDNRB, PGM5, SFRP4, STEAP1, FADS2, CXCL11, CWH43, SNRPN, GPR110, THBS1, APOD, HPGD, LEPREL1, LCE1D, GSTM5, SLC30A4, SEMA3D, CACNA2D1, GPR116, C7orf63, FAM198B, SCD, NR4A2, ARG2, ZNF385B, RGS1, DNAH5, NPR3, RAB3B, CHRDL1, ZNF208, MBOAT2, ATF3, ST6GAL1, GDF15, ANXA1, FOLH1, C4B, ELOVL2, GSTM1, GLIPR1, C3, MYO6, ORM2, RAET1L, PCDHB3, C1orf150, ALOX15B, LSAMP, SLC15A2, PCP4, MCCC2, GCNT1, C5orf23, SCGB1D2, CXCL2, AFF3, ATP8A2, PRIM2, ADAMTSL1, NELL2, RPS4Y1, CD24, GOLGA6L9, ZFP36, TRIB1, BNIP3, KL, PDE5A, DCN, LDHB, PCDHB5, ACADL, ZNF99, CPNE4, CCDC144B, SLC26A2, CYP1B1, SELE, CLDN1, KRT13, SFRP2, SLC25A33, HSD17B11, HSD17B13, UGT2B4, CTGF, SCIN, C10orf81, CYR61, PRUNE2, IFI6, MYH11, PPP1R3C, KCNH8, ZNF615, ERV3, F3, TTN, LYRM5, FMOD, NEXN, IL28A, FHL1, CXCL10, SPOCK1, GSTP1, OAT, HIST2H2BF, ACSM3, GLB1L3, SLC5A1, OR4N4, MAOB, BZW1, GENSCAN00000007309, IFI44L, KRT5, SCN7A, GOLM1, HIST4H4, IL7R, CSGALNACT1, A2M, LRRC9, ARHGEF38, ACSL5, SGK1, TMEM45B, AHNAK2, NEDD8, GREB1, UBQLN4, SDHC, TCEAL2, SLC18A2, HIST1H2BE, RARRES1, PLN, OGN, GPR110, CLGN, NIPAL3, ACTG2, RCAN3, KLK11, HMGCS2, EML5, EDIL3, PIGH, GLYATL1, ATP1B1, GJA1, PLA1A, MPPED2, AMD1, EMP1, PRR16, CNN1, GHR, ALDH1A1, TRIM29, IFNA17, TAS2R4, SEPP1, GREM1, RASD1, C1S, CLSTN2, DMXL1, HIST1H2BC, NRG4, ARL17A, GRPR, PART1, CYP3A5, KCNC2, SERPINE1, SLC6A14, EIF4A1, MYOF, PHOSPHO2, GCNT2, AOX1, CCDC80, ATP2B4, UGDH, GSTM2, MEIS2, RGS2, PRKG2, FIBIN, FDXACB1, SOD2, SEPT7, PTPRC, GABRP, CBWD3, TOR1AIP2, CXCR4, OR51L1, SLC12A2, AGAP11, SLC27A2, AZGP1, VCAN, ERAP2, KRT17, SLC2A12, CCL4, RPF2, SLC45A3, SEC11C, IFIT1, PAK1IP1, HIST1H3C, ERRFI1, ADAMTS1, TRIM36, FLNA, CCND2, IFIT3, FN1, PRY, HSPB8, CD177, TP63, IFI44, COL12A1, EDNRA, PCDHB2, HLA-DRA, TUBA3E, ASPN, FAM127A, DMD, DHRS7, ANO7, MEIS1, TSPAN1, CNTN1, TRIM22, GSTA2, SORBS1, GPR81, CSRP1, C3orf14, FGFR2, SNAI2, CALCRL, MON1B, PVRL3, VGLL3, SULF1, LIFR, SH3RF1, C12orf75, GNPTAB, CALM2, KLF6, C7orf58, RDH11, NR4A1, RWDD4, ABCC4, ZNF91, GABRE, SLC16A1, DEGS1, CLDN8, HAS2, ODC1, REEP3, LYRM4, PPFIA2, PGM3, ZDHHC8P1, C6orf72, HIST1H2BD, TES, PDE8B, DNAJB4, RGS5, EPHA3, COX7A2, MT1H, HIST2H2BE, TGFB3, VEGFA, CRISPLD2, TFF1, LOC100128816, SYT1, CPE, TRPC4, RAB27A, CD69, RPL17, PSCA, ATRNL1, MYOCD, MS4A8B, TNS1, BAMBI, IGF1, RALGAPA1, S100A10, PMS2CL, MMP2, SLC8A1, OAS2, ARRDC3, AMY2B, SPARCL1, IQGAP2, ACAD8, LPAR3, HIGD2A, NUCB2, HLA-DPA1, SLITRK6, TPM2, REPS2, EAF2, CAV1, PRUNE2, TMEM178, MFAP4, SYNM, EFEMP1, RND3, SCNN1A, B3GNT5, LMOD1, UBC, LMO3, LOX, NFIL3, C11orf92, C11orf48, BCAP29, EPCAM, PTGDS, ASB5, TUBA1B, SERHL, ITGA5, SPARC, LOC286161, NAALADL2, TMPRSS2, SERPINF1, EPHA7, SDAD1, SOX14, RPL35, HSPA1B, MSN, MTRF1L, PTN, CAMKK2, RBM7, OR52H1, C1R, CHRNA2, MRPL41, PROM1, LPAR6, SAMHD1, SCNN1G, DNAJC10, MOXD1, HIST1H2BG, ID1, and SEMA3C.

3. The method of claim 1, wherein:

a) prostate cancer progression in the patient is predicted according to the contribution (pi) of a poor prognosis (DESNT) group to the overall patient expression profile, wherein the higher the contribution of a poor prognosis (DESNT) group to the overall patient expression profile, the worse the predicted outcome;

b) the patient expression profile is assigned to an individual group according to the group that contributes the most to the overall expression profile;

c) prostate cancer progression is predicted when the contribution of the poor prognosis (DESNT) group to the overall expression profile is greater than the contribution of any other single group to the overall expression profile;

d) prostate cancer progression is predicted according to the contribution of the poor prognosis (DESNT) group to the overall expression profile and according to the stage of the patient's tumour, the Gleason score of the patient and/or PSA score of the patient;

e) cancer progression is predicted when the $p_i$ value for a poor prognosis (DESNT) group for the patient cancer sample is at least 0.1, at least 0.2, at least 0.3, at least 0.4 or at least 0.5;

f) only one group is assigned poor prognosis (DESNT) status;

g) cancer progression is predicted when the patient sample is grouped with poor prognosis (DESNT) cancers from the reference dataset or datasets;

h) the LPD analysis is carried out multiple times and cancer progression is predicted when the patient sample groups with poor prognosis (DESNT) cancers from the reference dataset or datasets in at least 60% of runs of the LPD analysis;
i) step b) is repeated at least 2, at least 3, at least 5, at least 20 times, at least 50 times or at least 100 times;
j) a different random seed is used for each clustering analysis;
k) determining the expression status of the plurality of genes comprises determining the level of expression of the plurality of genes;
l) the method further comprises normalising the patent expression profile to the reference dataset prior to conducting the statistical analysis;
m) the genes of step a) are selected from the group consisting of TGM4, RLN1, ORM1, OLFM4, OR51E2, SERPINB11, CRISP3, TDRD1, SLC14A1, IGJ, ERG, GDEP, TMEFF2, CST1, LTF, AMACR, SERPINA3, NEFH, ACSM1, OR51E1, MT1G, ANKRD36B, LOC100510059, PLA2G2A, TARP, REXO1L1, ANPEP, HLA-DRB5, PLA2G7, NCAPD3, OR51F2, SPINK1, RCN1, CP, SMU1, ACTC1, AGR2, SLC26A4, IGKC, MYBPC1, NPY, PI15, SLC22A3, PIGR, MME, RBPMS, HLA-DRB1, FOLH1, LUZP2, MSMB, GSTT1, MMP7, ODZ1, ACTB, SPON2, SLC38A11, FOS, OR51T1, HLA-DMB, KRT15, ITGA8, CXADR, LYZ, CEACAM20, C8orf4, DPP4, PGC, C15orf21, CHORDC1, LRRN1, MT1M, EPHA6, PDE11A, TMSB15A, LYPLA1, FOSB, F5, C15orf48, MIPEP, HSD17B6, SLPI, CD38, MMP23B, OR51A7, CFB, CCL2, POTEM, TPMT, FAM3B, FLRT3, C7, NTN4, FAM36A, CNTNAP2, SC4MOL, CH17-189H20.1, TRGC2, RAP1B, SLC4A4, LCE2D, EGR1, MT1L, SCUBE2, FAM55D, PDK4, CXCL13, CACNA1D, GPR160, CPM, PTGS2, TSPAN8, BMP5, GOLGA8A, OR4N2, FAM135A, DYNLL1, DSC3, C4orf3, HIST1H2BK, LCN2, STEAP4, RPS27L, TRPM8, ID2, LUM, EDNRB, PGM5, SFRP4, STEAP1, FADS2, CXCL11, CWH43, SNRPN, GPR110, THBS1, APOD, HPGD, LEPREL1, LCE1D, GSTM5, SLC30A4, SEMA3D, CACNA2D1, GPR116, C7orf63, FAM198B, SCD, NR4A2, ARG2, ZNF385B, RGS1, DNAH5, NPR3, RAB3B, CHRDL1, ZNF208, MBOAT2, ATF3, ST6GAL1, GDF15, ANXA1, FOLH1, C4B, ELOVL2, GSTM1, GLIPR1, C3, MYO6, ORM2, RAET1L, PCDHB3, C1orf150, ALOX15B, LSAMP, SLC15A2, PCP4, MCCC2, GCNT1, C5orf23, SCGB1D2, CXCL2, AFF3, ATP8A2, PRIM2, ADAMTSL1, NELL2, RPS4Y1, CD24, GOLGA6L9, ZFP36, TRIB1, BNIP3, KL, PDE5A, DCN, LDHB, PCDHB5, ACADL, ZNF99, CPNE4, CCDC144B, SLC26A2, CYP1B1, SELE, CLDN1, KRT13, SFRP2, SLC25A33, HSD17B11, HSD17B13, UGT2B4, CTGF, SCIN, C10orf81, CYR61, PRUNE2, IFI6, MYH11, PPP1R3C, KCNH8, ZNF615, ERV3, F3, TTN, LYRM5, FMOD, NEXN, IL28A, FHL1, CXCL10, SPOCK1, GSTP1, OAT, HIST2H2BF, ACSM3, GLB1L3, SLC5A1, OR4N4, MAOB, BZW1, GENSCAN00000007309, IFI44L, KRT5, SCN7A, GOLM1, HIST4H4, IL7R, CSGALNACT1, A2M, LRRC9, ARHGEF38, ACSL5, SGK1, TMEM45B, AHNAK2, NEDD8, GREB1, UBQLN4, SDHC, TCEAL2, SLC18A2, HIST1H2BE, RARRES1, PLN, OGN, GPR110, CLGN, NIPAL3, ACTG2, RCAN3, KLK11, HMGCS2, EML5, EDIL3, PIGH, GLYATL1, ATP1B1, GJA1, PLA1A, MPPED2, AMD1, EMP1, PRR16, CNN1, GHR, ALDH1A1, TRIM29, IFNA17, TAS2R4, SEPP1, GREM1, RASD1, C1S, CLSTN2, DMXL1, HIST1H2BC, NRG4, ARL17A, GRPR, PART1, CYP3A5, KCNC2, SERPINE1, SLC6A14, EIF4A1, MYOF, PHOSPHO2, GCNT2, AOX1, CCDC80, ATP2B4, UGDH, GSTM2, MEIS2, RGS2, PRKG2, FIBIN, FDXACB1, SOD2, SEPT7, PTPRC, GABRP, CBWD3, TOR1AIP2, CXCR4, OR51L1, SLC12A2, AGAP11, SLC27A2, AZGP1, VCAN, ERAP2, KRT17, SLC2A12, CCL4, RPF2, SLC45A3, SEC11C, IFIT1, PAK1IP1, HIST1H3C, ERRFI1, ADAMTS1, TRIM36, FLNA, CCND2, IFIT3, FN1, PRY, HSPB8, CD177, TP63, IFI44, COL12A1, EDNRA, PCDHB2, HLA-DRA, TUBA3E, ASPN, FAM127A, DMD, DHRS7, ANO7, MEIS1, TSPAN1, CNTN1, TRIM22, GSTA2, SORBS1, GPR81, CSRP1, C3orf14, FGFR2, SNAI2, CALCRL, MON1B, PVRL3, VGLL3, SULF1, LIFR, SH3RF1, C12orf75, GNPTAB, CALM2, KLF6, C7orf58, RDH11, NR4A1, RWDD4, ABCC4, ZNF91, GABRE, SLC16A1, DEGS1, CLDN8, HAS2, ODC1, REEP3, LYRM4, PPFIA2, PGM3, ZDHHC8P1, C6orf72, HIST1H2BD, TES, PDE8B, DNAJB4, RGS5, EPHA3, COX7A2, MT1H, HIST2H2BE, TGFB3, VEGFA, CRISPLD2, TFF1, LOC100128816, SYT1, CPE, TRPC4, RAB27A, CD69, RPL17, PSCA, ATRNL1, MYOCD, MS4A8B, TNS1, BAMBI, IGF1, RALGAPA1, S100A10, PMS2CL, MMP2, SLC8A1, OAS2, ARRDC3, AMY2B, SPARCL1, IQGAP2, ACAD8, LPAR3, HIGD2A, NUCB2, HLA-DPA1, SLITRK6, TPM2, REPS2, EAF2, CAV1, PRUNE2, TMEM178, MFAP4, SYNM, EFEMP1, RND3, SCNN1A, B3GNT5, LMOD1, UBC, LMO3, LOX, NFIL3, C11orf92, C11orf48, BCAP29, EPCAM, PTGDS, ASB5, TUBA1B, SERHL, ITGA5, SPARC, LOC286161, NAALADL2, TMPRSS2, SERPINF1, EPHA7, SDAD1, SOX14, RPL35, HSPA1B, MSN, MTRF1L, PTN, CAMKK2, RBM7, OR52H1, C1R, CHRNA2, MRPL41, PROM1, LPAR6, SAMHD1, SCNN1G, DNAJC10, MOXD1, HIST1H2BG, ID1, and SEMA3C;
n) step a) comprises determining the expression status of at least 1000 genes;
o) step a) comprises determining the expression status of at least 50 genes selected from the group consisting of TGM4, RLN1, ORM1, OLFM4, OR51E2, SERPINB11, CRISP3, TDRD1, SLC14A1, IGJ, ERG, GDEP, TMEFF2, CST1, LTF, AMACR, SERPINA3, NEFH, ACSM1, OR51E1, MT1G, ANKRD36B, LOC100510059, PLA2G2A, TARP, REXO1L1, ANPEP, HLA-DRB5, PLA2G7, NCAPD3, OR51F2, SPINK1, RCN1, CP, SMU1, ACTC1, AGR2, SLC26A4, IGKC, MYBPC1, NPY, PI15, SLC22A3, PIGR, MME, RBPMS, HLA-DRB1, FOLH1, LUZP2, MSMB, GSTT1, MMP7, ODZ1, ACTB, SPON2, SLC38A11, FOS, OR51T1, HLA-DMB, KRT15, ITGA8, CXADR, LYZ, CEACAM20, C8orf4, DPP4, PGC, C15orf21, CHORDC1, LRRN1, MT1M, EPHA6, PDE11A, TMSB15A, LYPLA1, FOSB, F5, C15orf48, MIPEP, HSD17B6, SLPI, CD38, MMP23B, OR51A7, CFB, CCL2, POTEM, TPMT, FAM3B, FLRT3, C7, NTN4, FAM36A, CNTNAP2, SC4MOL, CH17-189H20.1, TRGC2, RAP1B, SLC4A4, LCE2D, EGR1, MT1L, SCUBE2, FAM55D, PDK4, CXCL13, CACNA1D, GPR160, CPM, PTGS2, TSPAN8, BMP5, GOLGA8A, OR4N2, FAM135A, DYNLL1, DSC3, C4orf3, HIST1H2BK, LCN2, STEAP4, RPS27L, TRPM8, ID2, LUM, EDNRB, PGM5, SFRP4, STEAP1, FADS2, CXCL11, CWH43, SNRPN, GPR110, THBS1, APOD, HPGD, LEPREL1, LCE1D, GSTM5, SLC30A4, SEMA3D, CACNA2D1, GPR116, C7orf63, FAM198B, SCD, NR4A2, ARG2, ZNF385B, RGS1, DNAH5, NPR3, RAB3B, CHRDL1, ZNF208, MBOAT2, ATF3, ST6GAL1, GDF15, ANXA1, FOLH1, C4B, ELOVL2, GSTM1, GLIPR1, C3, MYO6, ORM2, RAET1L, PCDHB3, C1orf150, ALOX15B, LSAMP, SLC15A2, PCP4, MCCC2, GCNT1, C5orf23, SCGB1D2, CXCL2, AFF3, ATP8A2, PRIM2, ADAMTSL1, NELL2, RPS4Y1, CD24, GOLGA6L9, ZFP36, TRIB1, BNIP3, KL, PDE5A, DCN, LDHB, PCDHB5, ACADL, ZNF99, CPNE4, CCDC144B, SLC26A2, CYP1B1, SELE, CLDN1, KRT13, SFRP2, SLC25A33, HSD17B11, HSD17B13, UGT2B4, CTGF, SCIN, C10orf81, CYR61, PRUNE2, IFI6, MYH11, PPP1R3C, KCNH8, ZNF615, ERV3, F3, TTN, LYRM5, FMOD, NEXN, IL28A, FHL1, CXCL10, SPOCK1, GSTP1, OAT, HIST2H2BF, ACSM3, GLB1L3, SLC5A1, OR4N4, MAOB, BZW1, GENSCAN00000007309, IFI44L, KRT5, SCN7A, GOLM1, HIST4H4, IL7R, CSGALNACT1, A2M, LRRC9, ARHGEF38, ACSL5, SGK1, TMEM45B, AHNAK2, NEDD8, GREB1, UBQLN4, SDHC, TCEAL2, SLC18A2, HIST1H2BE, RARRES1, PLN, OGN, GPR110, CLGN, NIPAL3, ACTG2, RCAN3, KLK11, HMGCS2, EML5, EDIL3, PIGH, GLYATL1, ATP1B1, GJA1, PLA1A, MPPED2, AMD1, EMP1, PRR16, CNN1, GHR, ALDH1A1, TRIM29, IFNA17, TAS2R4, SEPP1, GREM1, RASD1, C1S, CLSTN2, DMXL1, HIST1H2BC, NRG4, ARL17A, GRPR, PART1, CYP3A5, KCNC2, SERPINE1, SLC6A14, EIF4A1, MYOF, PHOSPHO2, GCNT2, AOX1, CCDC80, ATP2B4, UGDH, GSTM2, MEIS2, RGS2, PRKG2, FIBIN, FDXACB1, SOD2, SEPT7, PTPRC, GABRP, CBWD3, TOR1AIP2, CXCR4, OR51L1, SLC12A2, AGAP11, SLC27A2, AZGP1, VCAN, ERAP2, KRT17, SLC2A12, CCL4, RPF2, SLC45A3, SEC11C, IFIT1, PAK1IP1, HIST1H3C, ERRFI1, ADAMTS1, TRIM36, FLNA, CCND2, IFIT3, FN1, PRY, HSPB8, CD177, TP63, IFI44, COL12A1, EDNRA, PCDHB2, HLA-DRA, TUBA3E, ASPN, FAM127A, DMD, DHRS7, ANO7, MEIS1, TSPAN1, CNTN1, TRIM22, GSTA2, SORBS1, GPR81, CSRP1, C3orf14, FGFR2, SNAI2, CALCRL, MON1B, PVRL3, VGLL3, SULF1, LIFR, SH3RF1, C12orf75, GNPTAB, CALM2, KLF6, C7orf58, RDH11, NR4A1, RWDD4, ABCC4, ZNF91, GABRE, SLC16A1, DEGS1, CLDN8, HAS2, ODC1, REEP3, LYRM4, PPFIA2, PGM3, ZDHHC8P1, C6orf72, HIST1H2BD, TES, PDE8B, DNAJB4, RGS5, EPHA3, COX7A2, MT1H, HIST2H2BE, TGFB3, VEGFA, CRISPLD2, TFF1, LOC100128816, SYT1, CPE, TRPC4, RAB27A, CD69, RPL17, PSCA, ATRNL1, MYOCD, MS4A8B, TNS1, BAMBI, IGF1, RALGAPA1, S100A10, PMS2CL, MMP2, SLC8A1, OAS2, ARRDC3, AMY2B, SPARCL1, IQGAP2, ACAD8, LPAR3, HIGD2A, NUCB2, HLA-DPA1, SLITRK6, TPM2, REPS2, EAF2, CAV1, PRUNE2, TMEM178, MFAP4, SYNM, EFEMP1, RND3, SCNN1A, B3GNT5, LMOD1, UBC, LMO3, LOX, NFIL3, C11orf92, C11orf48, BCAP29, EPCAM, PTGDS, ASB5, TUBA1B, SERHL, ITGA5, SPARC, LOC286161, NAALADL2, TMPRSS2, SERPINF1, EPHA7, SDAD1, SOX14, RPL35, HSPA1B, MSN, MTRF1L, PTN, CAMKK2, RBM7, OR52H1, C1R, CHRNA2, MRPL41, PROM1, LPAR6, SAMHD1, SCNN1G, DNAJC10, MOXD1, HIST1H2BG, ID1, and SEMA3C;

p) the method further comprises a step of selecting a sub-set of genes whose expression status has been determined for statistical analysis, optionally wherein the expression status of the each of the genes in the subset of genes is known to vary across cancer patient samples;

q) the method further comprises assigning a unique label to the patient expression profile prior to statistical analysis;

r) the prostate cancer progression (DESNT) status of each of the expression profiles in the reference dataset is known; or s) the patient expression profile is combined with at least 2 reference datasets prior to statistical analysis.

4. The method according to claim 1, wherein:
a) the sample is a urine sample, a semen sample, a prostatic exudate sample, or any sample containing macromolecules or cells originating in the prostate, a whole blood sample, a serum sample, saliva, or a biopsy, optionally wherein the sample is a prostate biopsy, prostatectomy or TURP sample;
b) the method is carried out on at least 2, at least 3, at least 3 or at least 5 samples, optionally wherein the method is conducted on the multiple patient samples concurrently; and/or
c) the dataset or datasets comprise a plurality of tumour or patient expression profiles, optionally wherein the datasets each comprise at least 20, at least 50, at least 100, at least 200, at least 300, at least 400 or at least 500 patient or tumour expression profiles, and further optionally wherein:
   i) the patient or tumour expression profiles comprise information on the expression status of at least 10, at least 40, at least 100, at least 500, at least 1000, at least 1500, at least 2000, at least 5000 or at least 10000 genes; or
   ii) wherein the patient or tumour expression profiles comprise information on the levels of expression of at least 10, at least 40, at least 100, at least 500, at least 1000, at least 1500, at least 2000, at least 5000 or at least 10000 genes.

* * * * *